(12) United States Patent
Bouchez et al.

(10) Patent No.: US 12,338,292 B2
(45) Date of Patent: Jun. 24, 2025

(54) CD47-CD38 BISPECIFIC ANTIBODIES

(71) Applicant: IGI Therapeutics SA, La Chaux-de-Fonds (CH)

(72) Inventors: Laure Bouchez, La Chaux-de-Fonds (CH); Blandine Pouleau, La Chaux-de-Fonds (CH); Marie-Agnes Doucey, La Chaux-de-Fonds (CH); Elie Dheilly, La Chaux-de-Fonds (CH); Stanislas Blein, La Chaux-de-Fonds (CH); Cian Stutz, La Chaux-de-Fonds (CH); Carole Estoppey, La Chaux-de-Fonds (CH); Jeremy Loyau, La Chaux-de-Fonds (CH); Thierry Monney, La Chaux-de-Fonds (CH); Camille Grandclement, La Chaux-de-Fonds (CH); Stefano Sammicheli, La Chaux-de-Fonds (CH)

(73) Assignee: IGI Therapeutics SA, La Chaux-de-Fonds (CH)

( * ) Notice: Subject to any disclaimer, the term of this patent is extended or adjusted under 35 U.S.C. 154(b) by 0 days.

(21) Appl. No.: 17/478,706

(22) Filed: Sep. 17, 2021

(65) Prior Publication Data
US 2022/0089767 A1   Mar. 24, 2022

(30) Foreign Application Priority Data
Sep. 18, 2020  (EP) .................................... 20197033

(51) Int. Cl.
*C07K 16/28* (2006.01)
*A61P 35/02* (2006.01)
*C07K 16/46* (2006.01)

(52) U.S. Cl.
CPC .......... *C07K 16/2896* (2013.01); *A61P 35/02* (2018.01); *C07K 16/468* (2013.01); *C07K 2317/31* (2013.01)

(58) Field of Classification Search
CPC .............. C07K 16/2896; C07K 16/468; C07K 2317/31; A61P 35/02
See application file for complete search history.

(56) References Cited

U.S. PATENT DOCUMENTS

2017/0355756 A1* 12/2017 Julien ..................... A61P 25/00
2021/0317230 A1  10/2021 Lv et al.

FOREIGN PATENT DOCUMENTS

| WO | WO-9311161 A1 | 6/1993 |
| WO | WO-9413804 A1 | 6/1994 |

(Continued)

OTHER PUBLICATIONS

Kussie, Paul H., "A Single Engineered Amino Acid Substitution Changes Antibody Fine Specificity", 1994, Journal of Immunology 152(1): pp. 146-152. (Year: 1994).*

(Continued)

*Primary Examiner* — Aurora M Fontainhas
*Assistant Examiner* — Selam Berhane
(74) *Attorney, Agent, or Firm* — Sterne, Kessler, Goldstein & Fox PLLC

(57) ABSTRACT

Novel bispecific heterodimeric immunoglobulins that target both a component of the human CD47 antigen and human CD38 antigen are provided and in particular those comprising an anti-CD38 heavy chain variable region and a light chain variable region and an anti-CD47 heavy chain variable region and a light chain variable region. The present invention also relates to the use of this novel class of bispecific heterodimeric immunoglobulins to treat autoimmune and (Continued)

Figure 1:
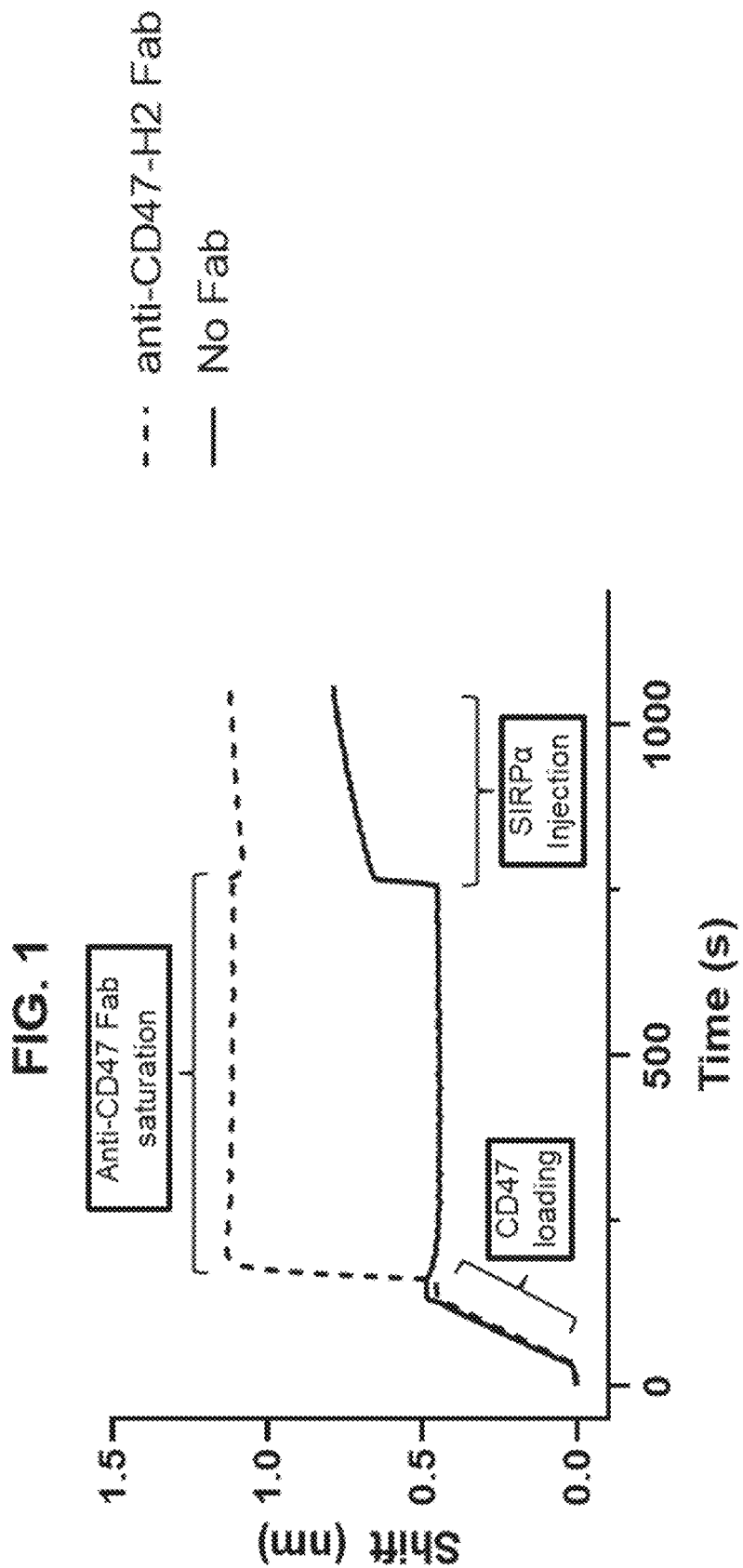

proliferative diseases and in particular cancers such as hematologic malignancies and solid tumors.

12 Claims, 62 Drawing Sheets

Specification includes a Sequence Listing.

(56) References Cited

FOREIGN PATENT DOCUMENTS

| WO | WO-9951642 | A1 | 10/1999 | |
|---|---|---|---|---|
| WO | WO-2008068048 | A2 * | 6/2008 | ............ A61P 31/10 |
| WO | WO-2011104604 | A2 | 9/2011 | |
| WO | WO-2012131555 | A2 | 10/2012 | |
| WO | WO-2012135345 | A1 | 10/2012 | |
| WO | WO-2017180913 | A2 | 10/2017 | |
| WO | WO-2020098672 | A1 | 5/2020 | |
| WO | WO-2022058539 | A1 | 3/2022 | |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

Chao et al. "The CD47-SIRPalpha pathway in cancer immune evasion and potential therapeutic implications", 2012, Current Opinion in Immunology: 24(2): pp. 225-232. (Year: 2012).*

Zuch de Zafra et al. "Targeting multiple myeloma with AMG 424, a novel anti-CD38/CD3 bispecific T-cell-recruiting antibody optimized for cytotoxicity and cytokine release", 2019, Clinical Cancer Research: 25: pp. 3921-3933. (Year: 2019).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Anderson, K.C., et al., "Clinically Relevant End Points and New Drug Approvals for Myeloma," Leukemia, 22(2):231-239, Nature Publishing Group, England (Feb. 2008).

Bird, R.E., et al., "Single-chain Antigen-binding Proteins," Science 242(4877):423-426, Association for the Advancement of Science, United States (Oct. 1988).

Bluemel, C., et al., "Epitope distance to the target cell membrane and antigen size determine the potency of T cell-mediated lysis by BiTE antibodies specific for a large melanoma surface antigen," Cancer Immunol Immunother 59, 1197-1209, Springer Link, Germany (Mar. 2010).

Bommel, P.E.V., et al., "CD20-selective Inhibition of CD47-SIRPα "Don't Eat Me" Signaling With a Bispecific Antibody-Derivative Enhances the Anticancer Activity of Daratumumab, Alemtuzumab, and Obinutuzumab," Oncoimmunology e1386361-2, Taylor & Francis, United States (Oct. 2017).

Chao, M.P., et al., "Anti-CD47 Antibody Synergizes With Rituximab to Promote Phagocytosis and Eradicate Non-Hodgkin Lymphoma," Cell, 142(5):699-713, Cell Press, United States (Sep. 2010).

Chothia, C. and Lesk, A.M., "Canonical Structures for the Hypervariable Regions of Immunoglobulins," Journal of Molecular Biology 196(4):901-917, Elsevier, England (Aug. 1987).

Chothia, C., et al., "Conformations of Immunoglobulin Hypervariable Regions," Nature 342(6252):877-883, Nature Publishing Group, England (Dec. 1989).

Coloma, M.J. and Morrison, S.L., "Design and Production of Novel Tetravalent Bispecific Antibodies," Nature Biotechnology 15(2):159-163, Nature America Publishing, United States (Feb. 1997).

Frankel, S.R., et al., "Targeting T Cells to Tumor Cells using Bispecific Antibodies," Current Opinion in Chemical Biology 17(3) 385-92, Elsevier, England (Jun. 2013).

Hinton, P.R., et al., "An Engineered Human IgG1 Antibody with Longer Serum Half-Life," Journal of Immunology 176(1):346-356, American Association of Immunologists, United States (2006).

Holliger, P., et al., "Diabodies: Small Bivalent and Bispecific Antibody Fragments," Proceedings of the National Academy of Sciences of the United States of America 90(14):6444-6448, National Academy of Sciences, United States (Jul. 1993).

Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences of the United States of America 85(16):5879-5883, National Academy of Sciences, United States (Aug. 1988).

Kabat, E.A. et al., Sequences of Proteins of Immunological Interest, Fifth Edition, vol. 1, pp. iii-xi, 103, 310, U.S. Department of Health and Human Services, Public Health Services, National Institute of Health, NIH Publication No. 91-3242, United States (1991).

Kalim, M., et al., "Intracellular Trafficking of New Anticancer Therapeutics Antibody drug Conjugates," Drug Design, Development and Therapy 11:2265-2276, Dove Press Limited, New Zealand (Aug. 2017).

Lazar, G.A., et al., "Engineered Antibody Fc Variants with Enhanced Effector Function," Proceedings of the National Academy of Sciences USA 103(11):4005-4010, National Academy of Sciences, United States (2006).

Lefranc, M.P., et al., "Imgt Unique Numbering for Immunoglobulin and T Cell Receptor Variable Domains and Ig Superfamily V like Domains," Developmental and Comparative Immunology 27(1) 55-77, Elsevier Science, United States (Jan. 2003).

MacCallum, R.M., et al., "Antibody-antigen Interactions: Contact Analysis and Binding Site Topography," Journal of Molecular Biology 262(5):732-745, Academic Press, England (Oct. 1996).

Martin, A.C.R., "Protein Sequence and Structure Analysis of Antibody Variable Domains," Chapter 3 in Antibody Engineering, vol. 2, Second Edition, pp. 33-51, Roland Kontermann and Stefan Dübel (eds), Springer-Verlag Berlin Heidelberg. (2010).

Martin, W.L., et al., "Crystal Structure at 2.8 A of an FcRn/Heterodimeric Fc Complex: Mechanism of pH-Dependent Binding," Molecular Cell 7(4):867-877, Cell Press, United States (2001).

Masui, S., et al., "An Efficient System to Establish Multiple Embryonic Stem Cell Lines Carrying an Inducible Expression Unit," Nucleic Acids Research 33(4) e43, Oxford University Press, England (Mar. 2005).

May, C., et al., "Advances in Bispecific Biotherapeutics for the Treatment of Cancer," Biochemical Pharmacology 84(9):1105-1112, Elsevier Science, England (Nov. 2012).

Nie, S., et al., "Biology Drives the Discovery of Bispecific Antibodies as Innovative Therapeutics," Antibody Therapeutics 3(1):18-62, Oxford University Press, United States (Feb. 2020).

Niwa, H., et al., "Efficient Selection for High-Expression Transfectants With a Novel Eukaryotic Vector," Gene 108(2) 193-9, Elsevier/North-Holland, Netherlands (Dec. 1991).

Ollier, R., et al., "Single-Step Protein A and Protein G Avidity Purification Methods to Support Bispecific Antibody Discovery and Development," mAbs 11(8):1464-1478, Taylor and Francis, United States (Dec. 2019).

Padlan, E.A., et al., "Identification of Specificity-Determining Residues in Antibodies," FASEB Journal 9(1):133-139, Federation of American Societies for Experimental Biology, United States (Jan. 1995).

Parslow, A.C., et al., "Antibody-Drug Conjugates for Cancer Therapy," Biomedicines 4(3):14, MDPI AG, Switzerland (Jul. 2016).

Richards, J.O., et al, "Optimization of Antibody Binding to FcgammaRIIa Enhances Macrophage Phagocytosis of Tumor Cells," Molecular Cancer Therapeutics 7(8):2517-2527, American Association for Cancer Research, United States (2008).

Scott, J.L., et al., "Characterization of a Novel Membrane Glycoprotein Involved in Platelet Activation," The Journal of Biological Chemistry 264(23):13475-13482, Elsevier Inc, United States (Aug. 1989).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to

(56) References Cited

OTHER PUBLICATIONS the Fc gamma R," The Journal of Biological Chemistry 276(9):6591-6604, American Society for Biochemistry and Molecular Biology, United States (Mar. 2001).
Sikic, B.I., et al., "First-in-human, First-in-class Phase I Trial of the Anti-CD47 Antibody Hu5F9-G4 in Patients With Advanced Cancers," Journal of Clinical Oncology 37(12):946-953, American Society of Clinical Oncology, United States (Apr. 2019).
Skegro, D., et al., "Immunoglobulin Domain Interface Exchange as a Platform Technology for the Generation of Fc Heterodimers and Bispecific Antibodies," The Journal of Biological Chemistry 292(23) 9745-9759, Elsevier, United States (Jun. 2017).
Smith, E.J., et al., "A Novel, Native-Format Bispecific Antibody Triggering T-Cell Killing of B-cells is Robustly Active in Mouse Tumor Models and Cynomolgus Monkeys," Scientific Reports 5:17943, Nature Publishing Group, England (Dec. 2015).
Sondergeld, P., et al., "Monoclonal Antibodies in Myeloma," Clinical Advances in Hematology and Oncology 13(9):599-609, Millennium Medical Pub, United States (Sep. 2015).
Sonneveld, P. and Broijl, A., "Treatment of Relapsed and Refractory Multiple Myeloma," Haematologica 101(4):396-406, Ferrata Storti Foundation, Italy (Apr. 2016).
Stutz, C. and Blein, S., "A Single Mutation Increases Heavy-chain Heterodimer Assembly of Bispecific Antibodies by Inducing Structural Disorder in One Homodimer Species," The Journal of Biological Chemistry 295(28):9392-9408, Elsevier, United States (Jul. 2020).
Tai, Y., et al., "Anti-CS1 Humanized Monoclonal Antibody Huluc63 Inhibits Myeloma Cell Adhesion and Induces Antibody-dependent Cellular Cytotoxicity in the Bone Marrow Milieu," Blood 112(4):1329-1337, Elsevier, United States (Aug. 2008).
Tandon, N., et al., "Monoclonal Antibodies for the Treatment of Multiple Myeloma—A New Paradigm," Oncology & Hematology Review 11(2):115-121 (2015).
Thompson, J.D., et al., "Clustal W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, England (Nov. 1994).
Tomlinson, I. and Holliger, P., "[28] Methods for Generating Multivalent and Bispecific Antibody Fragments," Methods in Enzymology 326:461-479, Academic Press, United States (2000).
Vogiatzi, F., et al., "Co-Targeting of CD38 and CD47 in T Cell Acute Lymphoblastic Leukemia," Blood 136(Supplement 1):39-40, ASH Publications, United States (Nov. 2020).
Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).
Willingham, S.B., et al., "The CD47-Signal Regulatory Protein Alpha (SIRPa) Interaction is a Therapeutic Target for Human Solid Tumors," Proceedings of the National Academy of Sciences of the United States of America 109(17):6662-6667, National Academy of Sciences, United States (Apr. 2012).
Yu, T., et al., "Novel Anti-CD38 Humanized mAb SG003 Possessed Enhanced Cytotoxicity in Lymphoma Than Daratumumab via Antibody-dependent Cell-mediated Cytotoxicity," BMC Biotechnology 19(1):28, BioMed Central, England (May 2019).
Boyd-Kirkup, J., et al., "HMBD004, a Novel Anti-CD47xCD33 Bispecific Antibody Displays Potent Anti-Tumor Effects in Pre-Clinical Models of AML," Blood 130(1):1378, American Society of Hematology, United States (2017).
Demichelis-Gomez, R., et al., "Bispecific Antibodies in Hematologic Malignancies: When, to Whom, and How Should Be Best Used?" Curr. Oncol. Rep. 21(2):17, Current Science, Inc., United States (Feb. 2019).
Dheilly, E., et al., "Selective Blockade of the Ubiquitous Checkpoint Receptor CD47 Is Enabled by Dual-Targeting Bispecific Antibodies," Mol. Ther. 25(2):523-533, Cell Press, United States (2017).
Ferrero, E., et al., "Characterization and phylogenetic epitope mapping of CD38 Adpr cyclase in the cynomolgus macaque," BMC Immunol. 5(1):21, BioMed Central, United Kingdom (2004).
Guy, D.G., et al., "Bispecific Antibodies for the Treatment of Acute Myeloid Leukemia," Curr. Hematol. Malig. Rep. 13(6):417-425, Springer Science + Business Media, United States (Oct. 2018).
Labrijn, A.F., et al., "Bispecific antibodies: a mechanistic review of the pipeline," Nat. Rev. Drug Discov. 18(8):585-608, Nature Publishing Group, Germany (Jun. 2019).
Li., H., et al., "Highlights of 2019 Protein Engineering Summit (PEGS) in Boston, USA: Advancing Antibody-Based Cancer Therapies to the Clinic," Antib. Ther. 2(4):79-87, Oxford Academic Press, United Kingdom (Sep. 2019).
Moore, G.L., et al., "A robust heterodimeric Fc platform engineered for efficient development of bispecific antibodies of multiple formats," Methods 154:38-50, Elsevier, Netherlands (Feb. 2019).
Piccione, E.C., et al., "A bispecific antibody targeting CD47 and CD20 selectively binds and eliminates dual antigen expressing lymphoma cells," MAbs. 7(5):946-956, Taylor & Francis, United Kingdom (2015).
Sun, J., et al., "Targeting CD47 as a Novel Immunotherapy for Multiple Myeloma," Cancers 12(2):305, MDPI, Switzerland (Jan. 2020).
Suurs, F.V., et al., "A review of bispecific antibodies and antibody constructs in oncology and clinical challenges," Pharmacol. Therap. 201:103-119, Elsevier, Netherlands (Apr. 2019).
Van De Donk, N.W., et al., "CD38 Antibodies in Multiple Myeloma: Mechanisms of Action and Modes of Resistance," Front. Immunol. 9:2134, Frontiers Media S.A., Switzerland (Sep. 2018).
Zuch De Zafra, C.L., et al., "Targeting Multiple Myeloma with AMG 424, a Novel Anti-CD38/CD3 Bispecific T-cell-recruiting Antibody Optimized for Cytotoxicity and Cytokine Release," Clin. Cancer Res. 25(13):3921-3933, American Association for Cancer Research, United States (2019).
International Search Report and Written Opinion for International Application No. PCT/EP2021/075687, mailed Jan. 4, 2022, European Patent Office, Netherlands, 23 pages.

\* cited by examiner

FIG. 14A
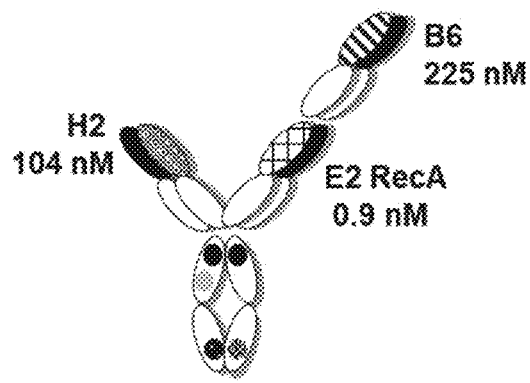
BEAT 38/47-48
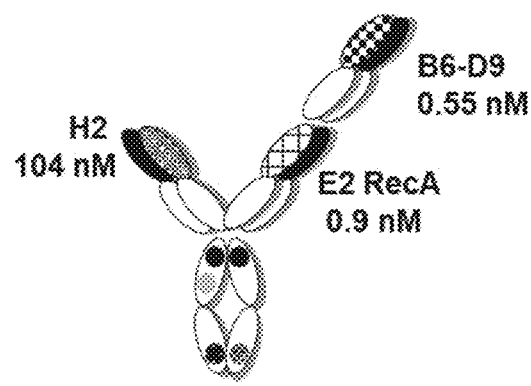
BEAT 38/47-60
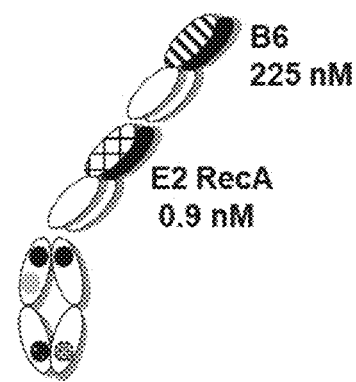
Monoarm 38-59
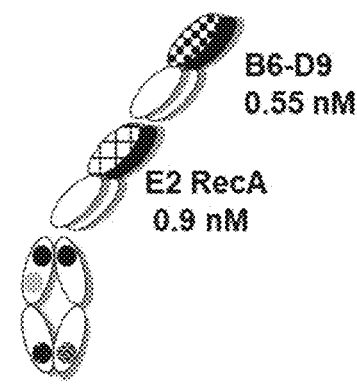
Monoarm 38-79
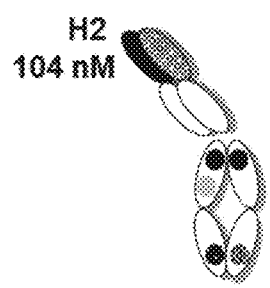
Monoarm 47-54

FIG. 16D
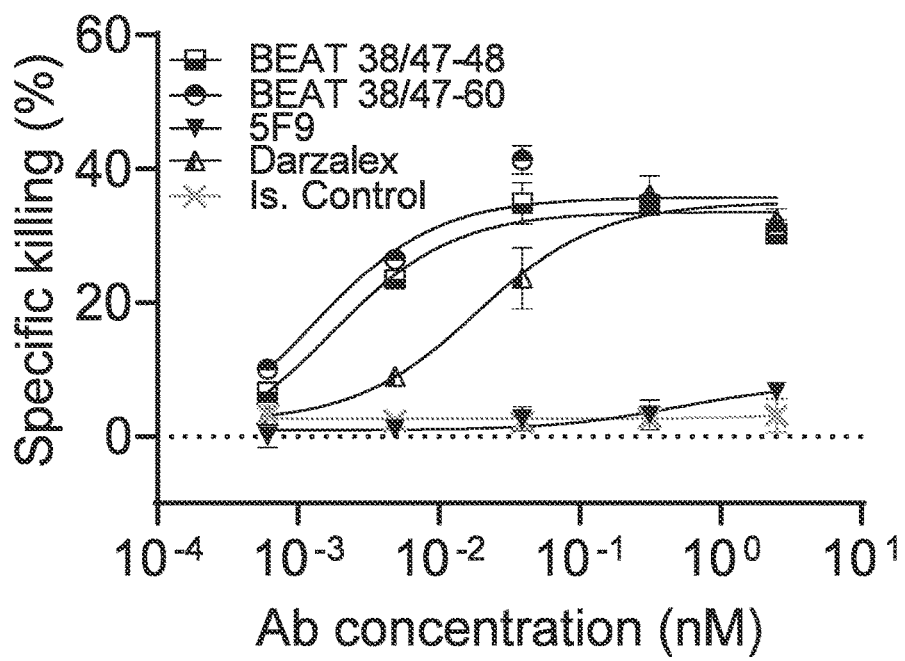
FIG. 16E
FIG. 16F
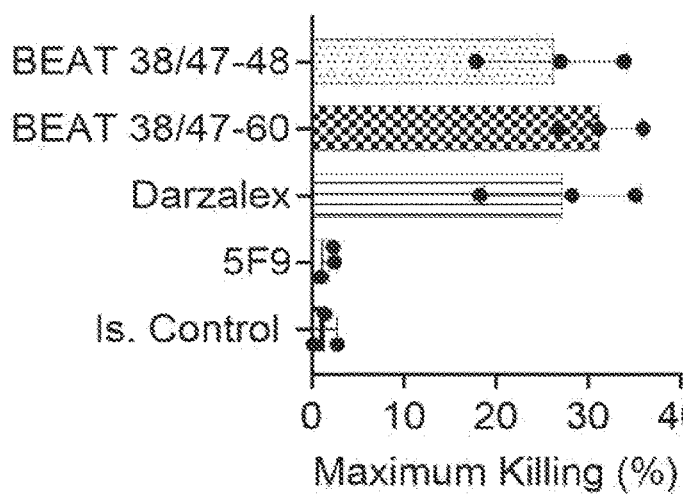
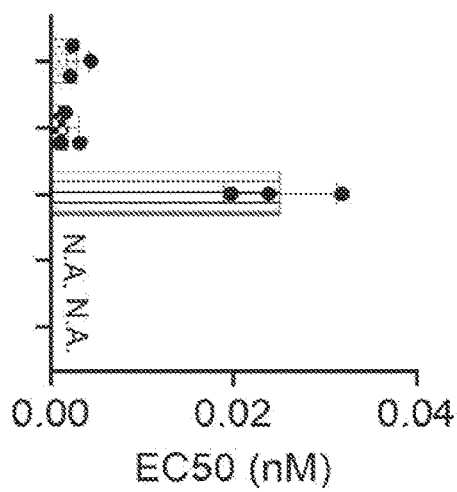

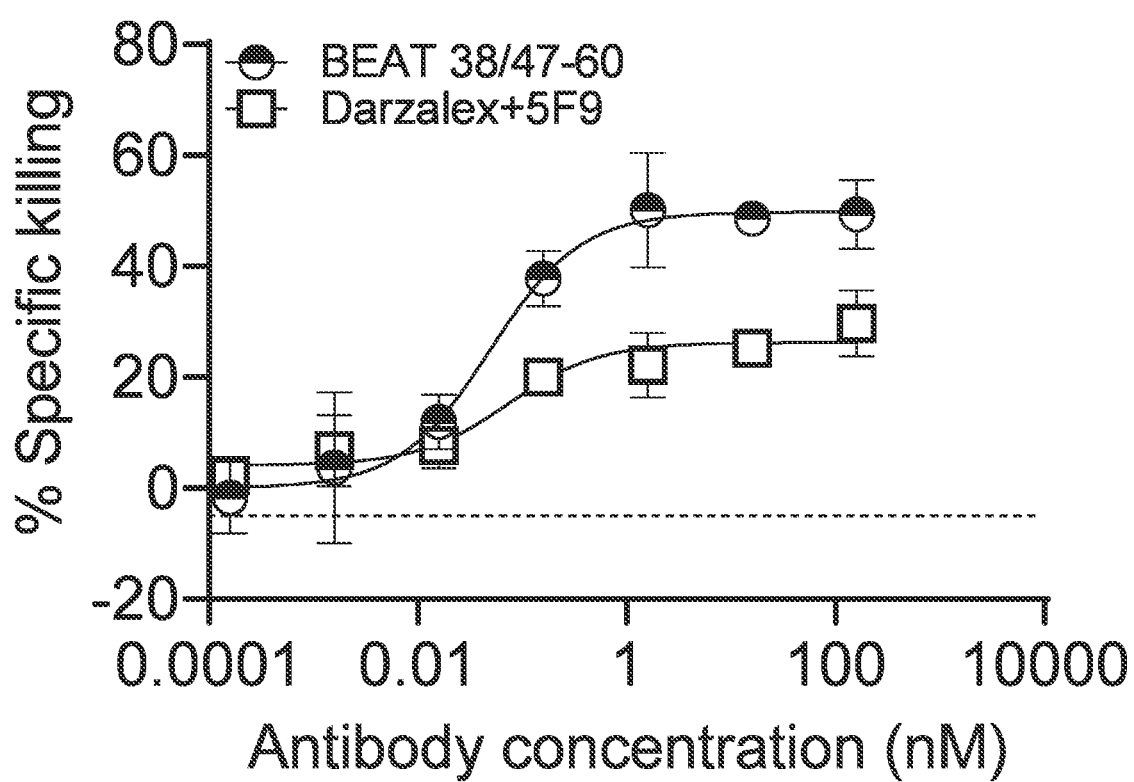

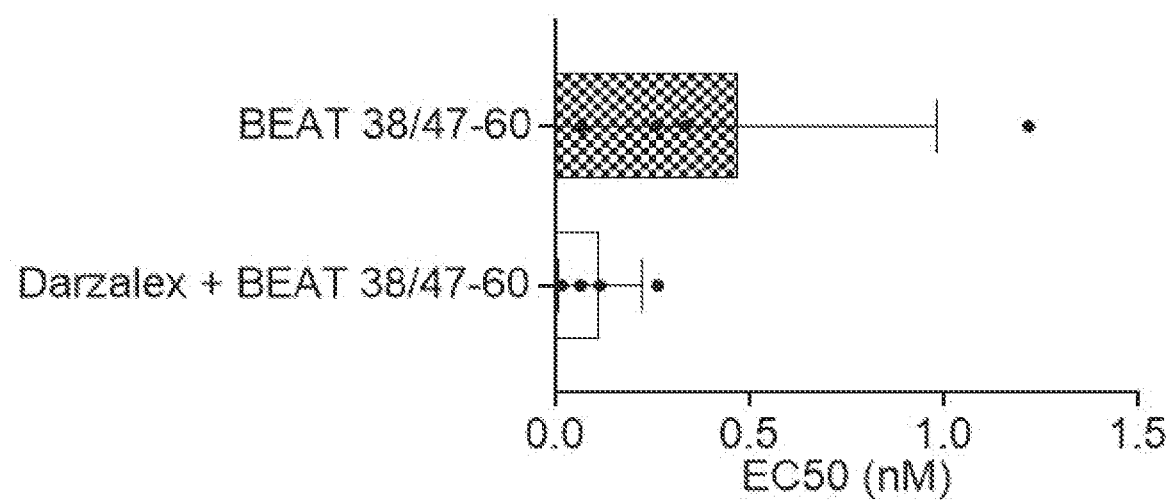
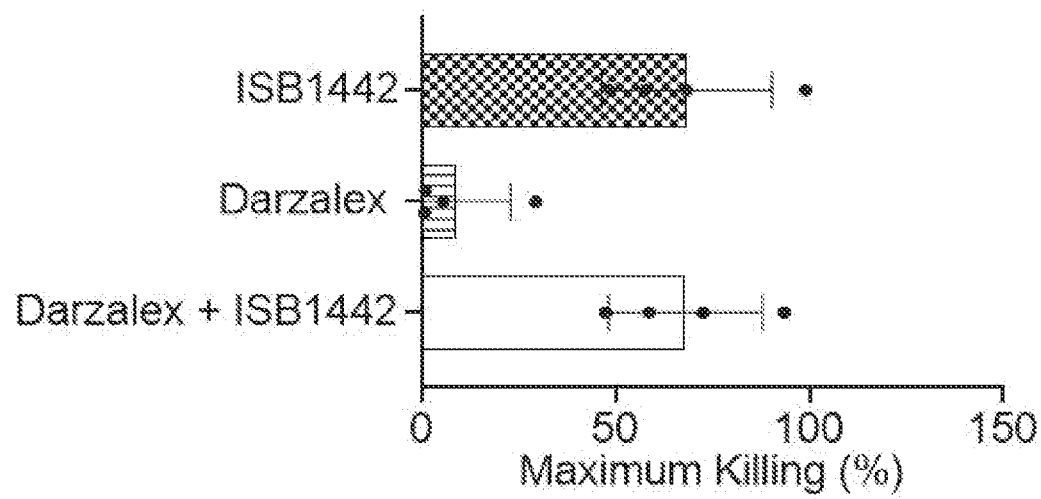

CD47-CD38 BISPECIFIC ANTIBODIES

CROSS REFERENCE TO RELATED APPLICATIONS

This application claims priority to EP Application No. 20197033.2, filed Sep. 18, 2020, the contents of which are incorporated herein by reference in their entirety.

REFERENCE TO A SEQUENCE LISTING SUBMITTED ELECTRONICALLY VIA EFS-WEB

The content of the electronically submitted sequence listing (Name 3305_0360001_Seqlisting_ST25; Size: 354, 820 bytes; and Date of Creation: Sep. 17, 2021) is incorporated herein by reference in its entirety.

FIELD OF THE INVENTION

The present invention relates to novel bispecific heterodimeric immunoglobulins that target both a component of the human CD47 antigen and human CD38 antigen. More specifically, the present invention relates to an anti-CD38 heavy chain variable region and a light chain variable region and an anti-CD47 heavy chain variable region and a light chain variable region. The present invention also relates to the use of this novel class of bispecific heterodimeric immunoglobulins to treat autoimmune and proliferative diseases and in particular cancers such as hematologic malignancies and solid tumors.

BACKGROUND OF THE INVENTION

Multiple myeloma is a neoplastic plasma-cell disorder characterized by clonal proliferation of malignant plasma cells in the bone marrow (BM) microenvironment, monoclonal protein in the blood or urine and associated organ dysfunction. Multiple myeloma accounts for 1-2% of all new cancer diagnoses and approximately 20% of all deaths from blood malignancies. The disease is slightly more common in males and African-Americans. Multiple myeloma remains an incurable cancer, although recent improved understanding of pathogenesis of myeloma has led to the development of new treatments and improved survival.

The diagnosis of multiple myeloma requires the presence of one or more myeloma defining events (MDE) in addition to evidence of either 10% or more clonal plasma cells on BM examination or a biopsy-proven plasmacytoma. MDE include so-called CRAB (hypercalcemia, renal failure, anemia, or lytic bone lesions) features as well as three specific biomarkers: clonal BM plasma cells >60%, serum free light chain (sFLC) ratio >100 (provided involved sFLC level is >100 mg/L), and more than 1 focal lesion on magnetic resonance imaging (MRI). Several genetic abnormalities that occur in tumor plasma cells play major roles in the pathogenesis of myeloma and determine disease prognosis.

The uncontrolled growth of myeloma cells has many consequences, including skeletal destruction, BM failure, increased plasma volume and viscosity, suppression of normal immunoglobulin production, and renal impairment.

Symptomatic (active) disease should be treated immediately, whereas asymptomatic (smoldering) myeloma requires only clinical observation, since early treatment with conventional chemotherapy has shown no clear benefit yet. Investigational trials are currently evaluating the ability of immunomodulatory drugs to delay the progression from asymptomatic to symptomatic myeloma. For active myeloma, current data support the initiation of induction therapy regimens including thalidomide, lenalidomide, and/or bortezomib followed by autologous hematopoietic stem-cell transplantation (HSCT) after major disease response for patients who can tolerate auto-HSCT conditioning regimens. Considerations of physiologic age, which may differ from chronologic age, and the presence of coexisting conditions drive decisions of treatment choice and drug dose. For example, less intensive approaches are desirable for patients with significant comorbidities, including cardiopulmonary or hepatic impairment, limiting treatment-related mortality and mitigating risk of treatment interruption.

Treatment of relapsed/refractory multiple myeloma presents a special therapeutic challenge, due to the heterogeneity of disease at relapse and the absence of clear biological based recommendations regarding the choice of salvage therapies at various time points of disease progression. With increasing recognition of the inherent clonal heterogeneity and genomic instability of the plasma cells influencing both inherent and acquired therapeutic resistance, the identification of the optimal choice and sequence of therapies has become critical. New agents have gained approval by United States (US) Food and Drug Administration (FDA) for relapsed/refractory myeloma in recent years, adding to the complexity of these decisions, including proteasome inhibitors (carfilzomib and ixazomib), the thalidomide derivative pomalidomide, and the histone deacetylase inhibitor panobinostat. Other molecularly targeted therapies directed at specific cell signaling pathways, as well as survival and proliferation controls (including PI3K/AKT/mTOR inhibitors, Hsp90 inhibitors, cyclin-dependent kinase inhibitors, kinesin spindle protein inhibitors) are currently in development. Despite advances in the management of multiple myeloma, relapse is inevitable in almost all patients. Recurrence of myeloma is typically more aggressive with each relapse, leading to the development of treatment refractory-disease, which is associated with a shorter survival. Thus, additional treatment options are needed.

Antibodies that target two different antigens within the same molecule offer an immunotherapeutic treatment strategy for numerous malignancies. The largest class of immune effector cell redirecting antibodies has been shown to mediate T cell redirection both in pre-clinical and clinical investigations (May C et al., (2012) Biochem Pharmacol, 84(9): 1105-12; Frankel S R & Baeuerle P A, (2013) Curr Opin Chem Biol, 17(3): 385-92; Nie et al., (2020) Antibody Therapeutics, 3(1), 17-62). All effector cell retargeting bispecific antibodies or fragments thereof are engineered to have at least two antigen binding sites wherein one site binds a surface antigen on a target cell and the other site binds an effector cell surface antigen.

Nevertheless, improvements in effector cell redirecting antibody-based therapeutics are still needed, particularly relating to the therapeutic window. The therapeutic window is defined as the range in concentration of a drug that exerts therapeutic efficacy with no or limited toxicity observed. (Handbook of Pharmacogenomics and Stratified Medicine, 2014). The aim of any therapy is to reach a dose where efficacy is seen in all patients, with no or manageable side effects in any of the patients (Principles of Clinical Pharmacology (Third Edition), 2012). To broaden a bispecific antibody's therapeutic window, the concentration of a drug that gives half-maximal therapeutic response (EC50) can be decreased (improved efficacy), and/or the concentration that exerts toxic effects can be increased (improved on-target specificity).

Aiming to target a larger therapeutic window in comparison to other approved or candidate medicines for CD38-overexpressing cancers, such as multiple myeloma, the inventors have set out to provide improved effector cell redirecting antibody-based therapeutics, that specifically act on the tumor cells. Nevertheless, while it has been shown that monoclonal antibodies that binds CD38, such as dararumumab, may be used in combination with CD47-blocking scFv genetically fused in tandem to a CD20-targeting scFv to enhance phagocytosis of cancer cells by blocking the CD47/SIRPα signal (van Bommel, P. E. et al. (2017) CD20-selective inhibition of CD47-SIRPα "don't eat me" signaling with a bispecific antibody-derivative enhances the anticancer activity of daratumumab, alemtuzumab and obinutuzumab. ONCOIMMUNOLOGY, vol. 7, no. 2, 1-8), the possibility to block the CD47-SIRPα interaction selectively in CD38 expressing cancer cells, still remains an unmet need.

DETAILED DESCRIPTION

The present invention relates to a bispecific antibody comprising at least two binding portions, at least one of which binds to human CD38 and at least one of which binds to human CD47.

The present invention also relates to a bispecific antibody comprising at least one binding portion which binds to human CD47 and at least two binding portions which bind to human CD38.

The present invention also relates to a bispecific antibody comprising at least one binding portion which binds to human CD47 and at least two binding portions which bind to human CD38, wherein the at least two CD38 binding portions are monoparatopic.

The present invention also relates to a bispecific antibody comprising at least one binding portion which binds to human CD47 and at least two binding portions which bind to human CD38, wherein the at least two CD38 binding portions are biparatopic.

The present invention also relates to a bispecific antibody comprising at least two binding portions, at least one of which binds to human CD38 and at least one of which binds to human CD47, wherein at least one of the binding portions which binds to human CD47 can also bind to cynomologus CD47.

The present invention also relates to a bispecific antibody comprising at least two binding portions, at least one of which binds to human CD38 and at least one of which binds to human CD47, wherein at least one of the binding portions which binds to human CD38 can also bind to cynomologus CD38.

The present invention also relates to the bispecific antibody above for use as a medicament.

More in particular, for use in treating multiple myeloma, acute lymphoblastic leukemia, chronic lymphocytic leukemia, acute myeloid leukemia, lymphoma, breast cancer such as Her2+ breast cancer, prostate cancer, cervival cancer, germinal center B-cell lympohoma or B-cell acute lymphoblastic leukemia, Chronic lymphocytic leukemia (CLL), Myelodisplastic syndrome (MDS), Non-Hodgkin lymphoma, diffuse large B-cell lymphoma, non small cell lung cancer (NSCLC), Hepatocellular carcinoma (HCC), Highgrade serous ovarian carcinoma, peritoneal cancer.

According to one aspect of the present invention, the disclosed bispecific antibody comprises at least one binding portion which binds to human CD38 comprising a CDR set selected from the group comprising: SEQ ID NO: 103, SEQ ID NO: 163, SEQ ID NO: 223; SEQ ID NO: 117, SEQ ID NO: 177, SEQ ID NO: 237; SEQ ID NO: 121; SEQ ID NO: 181, SEQ ID NO: 241.

According to another aspect of the present invention, the disclosed bispecific antibody comprises at least one binding portion which binds to human CD47 comprising a CDR set comprising: SEQ ID NO: 75, SEQ ID NO: 135, SEQ ID NO: 195.

In certain embodiments, the bispecific antibody according to the present invention comprises a Fc region.

In particular, said Fc region is a variant which comprises at least one amino acid modification relative to the Fc region of the parent antibody, whereas the antibody comprising the variant Fc region exhibits altered effector function compared to the parent antibody.

In certain embodiments, the bispecific antibody according to the present invention comprises at least one binding portion which binds to human CD47 that has an affinity to human CD47 lower than the affinity of at least one binding portion which binds to human CD38 has to human CD38.

The present invention also relates to an epitope on the human CD38 extracellular domain which is bound by the bispecific antibody disclosed herein.

The present invention also relates to an epitope on the human CD47 extracellular domain which is bound by the bispecific antibody disclosed herein.

The present invention also relates to an isolated nucleic acid encoding the bispecific antibody disclosed herein.

The present invention also relates to a vector comprising an isolated nucleic acid encoding the bispecific antibody disclosed herein.

The present invention also relates to a host cell comprising an isolated nucleic add encoding the bispecific antibody disclosed herein or a vector comprising an isolated nucleic add encoding the bispecific antibody disclosed herein.

The present invention also relates to a composition comprising the bispecific antibody according to the present invention and a pharmaceutically acceptable carrier, and to said composition further comprising another pharmaceutically active agent.

The present invention also relates to an immunoconjugate comprising the bispecific antibody according to the present invention linked to a therapeutic agent.

As utilized in accordance with the present disclosure, the following terms, unless otherwise indicated, shall be understood to have the following meanings. Unless otherwise required by context, singular terms shall include pluralities and plural terms shall include the singular. As used in this specification and the appended claims, the singular forms "a", "an" and "the" include plural referents unless the content clearly dictates otherwise. Thus, for example, reference to "a molecule" optionally includes a combination of two or more such molecules, and the like.

It is understood that aspects and embodiments of the present disclosure described herein include "comprising," "consisting," and "consisting essentially of aspects and embodiments.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

The term "antibody" as referred to herein includes whole antibodies and any antigen binding fragments or single chains thereof. Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain (VH) and three constant domains (CH1, CH2, and CH3), wherein the VH domain is at the amino-terminus of the polypeptide and the CH3 domain is at the carboxyl-terminus, and a full-length light chain immunoglobulin polypeptide includes a variable domain (VL) and a constant domain (CL), wherein the VL domain is at the amino-terminus of the polypeptide and the CL domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al, SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, J. Mol Biol. 196: 901-17; Chothia et al, 1989, Nature 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, FASEB J. 9: 133-39; MacCallum, 1996, J. Mol. Biol. 262(5): 732-45; and Lefranc, 2003, Dev. Comp. Immunol. 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," In Antibody Engineering, Vol. 2. Kontermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, Nucleic Acids Res. 22: 4673-80. Molecular models are conventionally used to correctly delineate framework and CDR regions and thus correct the sequence-based assignments. All such alternative definitions are encompassed by the current invention and the sequences provided in this specification are not intended to exclude alternatively defined CDR sequences which may only comprise a portion of the CDR sequences provided in the sequence listing The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins. Fc molecules are made up of monomeric polypeptides that can be linked into dimeric or multimeric forms by covalent {i.e., disulfide bonds) and non-covalent association. The number of intermolecular disulfide bonds between monomeric subunits of native Fc molecules ranges from 1 to 4 depending on class {e.g., IgG, IgA, and IgE) or subclass {e.g., IgG1, IgG2, IgG3, IgA1, IgGA2, and IgG4). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the VH and CH1 domains of one heavy chain, wherein the VH-CH1 heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a CH1 domain.

A F(ab') fragment typically includes one light chain and a portion of one heavy chain that contains more of the constant region (between the CH1 and CH2 domains), such that an interchain disulfide bond can be formed between two heavy chains to form a F(ab')2 molecule.

The term "binding protein" as used herein refers to a non-naturally occurring or recombinant or engineered molecule, such as non-naturally occurring or recombinant or engineered antibody, that specifically binds to at least one target antigen, e.g., a CD38 polypeptide, or a CD47 polypeptide of the present disclosure.

A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen. A target antigen may have one or more epitopes. With respect to each target antigen recognized by a binding protein, the binding protein is capable of competing with an intact antibody that recognizes the target antigen. The antigen is bound by a binding protein, such as an antibody, via an antigen binding site, also referred herein as "binding portion" or "binding domain".

"CD38" is cluster of differentiation 38 polypeptide, a glycoprotein found on the surface of many immune cells. In some embodiments, a binding protein of the present disclosure binds the extracellular domain of one or more CD38 polypeptide. Exemplary CD38 extracellular domain polypeptide sequences include, but are not limited to, the extracellular domain of human CD38 (e.g., as represented by SEQ ID NO: 5) and the extracellular domain of cynomolgus monkey CD38 (e.g., as represented by SEQ ID NO: 6).

"CD47" is cluster of differentiation 47, a transmembrane protein that in humans is encoded by the CD47 gene. CD47 belongs to the immunoglobulin superfamily, it partners with membrane integrins and also binds the ligands thrombospondin-1 (TSP-1) and signal-regulatory protein alpha (SIRPα). CD47 acts as a don't eat me signal to macrophages of the immune system. Human CD47 is encoded by SEQ ID NO: 7 and cynomolgus monkey CD47 is encoded by SEQ ID NO: 8.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets. In some embodiments, a bispecific binding protein binds to two different antigens. In some embodiments, a bispecific binding protein binds to two different epitopes on the same antigen.

The term "bivalent binding protein" refers to a binding protein that has two antigen binding sites.

The term "trispecific binding protein" refers to a binding protein that specifically binds to three different antigen targets. In some embodiments, a trispecific binding protein binds to three different antigens. In some embodiments, a trispecific binding protein binds to one, two, or three different epitopes on the same antigen.

The term "trivalent binding protein" refers to a binding protein that has three binding sites. In particular embodiments the trivalent binding protein can bind to one antigen target (i.e. monospecific trivalent binding protein"). In other embodiments, the trivalent binding protein can bind to two antigen targets (i.e. bispecific trivalent binding protein"). In other embodiments, the trivalent binding protein can bind to three antigen targets (i.e. trispecific trivalent binding protein"). In a more particular embodiment, the trivalent binding protein that bind to two antigen targets comprises a binding portion that binds to a first antigen target and two binding portions that bind to the same epitope of a second antigen target; such binding protein is referred to as "monoparatopic". In another more particular embodiment, the trivalent binding protein that bind to two antigen targets comprises a binding portion that binds to a first antigen target and two binding portions that bind to two distinct epitopes of a second antigen target; such binding protein is referred to as "biparatopic". An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present {i.e., on a molar basis it is more abundant than any other individual species in the composition). In some embodiments, a substantially purified fraction is a composition wherein the species comprises at least about 50%) (on a molar basis) of all macromolecular species present. In other embodiments, a substantially pure composition will comprise more than about 80%>, 85%>, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

A nucleic acid k "isolated" or "substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g. F. Ausubel, et al., ed. (1987) Current Protocols in Molecular Biology, Greene Publishing and Wiley Interscience, New York. A nucleic acid of the invention can be, for example, DNA or RNA and may or may not contain intron sequences.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $<10^8 M$, more preferably when the equilibrium dissociation constant is $<10^9 M$, and most preferably when the dissociation constant is $<10^{10} M$.

The dissociation constant (KD) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (GE). Surface plasmon analysis can also be performed by immobilizing the analyte (binding protein on a biosensor matrix) and presenting the ligand (target antigen). The term "KD," as used herein refers to the dissociation constant of the interaction between a particular binding protein and a target antigen.

The term "binds to" as used herein in reference to a binding protein refers to the ability of a binding protein or an antigen-binding fragment thereof to bind to an antigen containing an epitope with an Kd of at least about $1\times10^6 M$, $1\times10^7 M$, $1\times10^8 M$, $1\times10^9 M$, $1\times10^{10} M$, $1\times10^{11} M$, $1\times10^{12} M$, or more, and/or to bind to an epitope with an affinity that is at least two-fold greater than its affinity for a nonspecific antigen. In some embodiments, a binding protein of the present disclosure binds to two or more antigens, e.g., a human and a cynomologus monkey CD38 polypeptide.

In some embodiments, an antigen binding domain and/or binding protein of the present disclosure "cross reacts" with human and cynomolgus monkey CD38 polypeptides, e.g., CD38 extracellular domains, such as SEQ ID NO: 295 (human CD38 isoform 28907-1), SEQ ID NO: 294 (human CD38 isoform 28907-2), SEQ ID NO: 296 (human CD38 isoform 28907-E) and SEQ ID NO:6 (cynomolgus monkey CD38). In some embodiments, a binding protein or antigen-binding fragment thereof cross-reacts with human CD47 (e.g., SEQ ID NO: 300 (human CD47 isoform OA3-323), SEQ ID NO: 301 (human CD47 isoform OA3-293), SEQ ID NO: 302 (human CD47 isoform OA3-305), and SEQ ID NO: 303 (human CD47 isoform OA3-312)) and cynomolgus monkey CD47. A binding protein binding to antigen 1 is "cross-reactive" to antigen 2 when the EC50S are in a similar range for both antigens.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as σ-,α-disubstituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, 0-phosphoserine, N-acetyl serine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
(1) hydrophobic: Met, Ala, Val, Leu, He, Phe, Trp, Tyr, Pro;
(2) polar hydrophilic: Arg, Asn, Asp, Gin, Glu, His, Lys, Ser, Thr;
(3) aliphatic: Ala, Gly, He, Leu, Val, Pro;
(4) aliphatic hydrophobic: Ala, He, Leu, Val, Pro;
(5) neutral hydrophilic: Cys, Ser, Thr, Asn, Gin;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects.

The terms "treatment" or "treat" as used herein refer to both therapeutic treatment and prophylactic or preventative measures. Those in need of treatment include those having a disorder as well as those prone to have the disorder or those in which the disorder is to be prevented. In particular embodiments, binding proteins can be used to treat humans with cancer, or humans susceptible to cancer, or ameliorate cancer in a human subject. The binding proteins can also be used to prevent cancer in a human patient. In particular embodiments, the cancer is multiple myeloma, acute lymphoblastic leukemia, chronic lymphocytic leukemia, acute myeloid leukemia, lymphoma, breast cancer such as Her2+ breast cancer, prostate cancer, cervival cancer, germinal center B-cell lympohoma or B-cell acute lymphoblastic leukemia, Chronic lymphocytic leukemia (CLL), Non-Hodgkin lymphoma, diffuse large B-cell lymphoma, non small cell lung cancer (NSCLC), Hepatocellular carcinoma (HCC), High-grade serous ovarian carcinoma, peritoneal cancer.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding protein.

Anti-CD38 Binding Proteins

Certain aspects of the present disclosure relate to binding proteins that comprise an antigen binding site that binds a CD38 polypeptide {e.g., human and cynomolgus monkey CD38 polypeptides). In some embodiments, the binding proteins are monospecific and/or monovalent, bispecific and/or bivalent, trispecific and/or trivalent, or multispecific and/or multivalent.

A variety of features of exemplary monospecific, bispecific, or trispecific binding proteins are described herein. For example, in some embodiments, a binding protein or antigen-binding fragment thereof cross-reacts with human CD38 (e.g., SEQ ID NO: 295 (human CD38 isoform 28907-1), SEQ ID NO: 294 (human CD38 isoform 28907-2), SEQ ID NO: 296 (human CD38 isoform 28907-E)) and cynomolgus monkey CD38. In some embodiments, a binding protein induces apoptosis of a CD38+ cell.

In some embodiments, the binding protein is bivalent and/or bispecific. In some embodiments, the binding protein is multivalent, such as trivalent or tetravalent. In some embodiments, at least one of the antigen binding sites binds a CD38 polypeptide (e.g., the extracellular domain of human and/or cynomolgus monkey CD38 polypeptides).

In any of the bispecific binding proteins described supra, the target antigen other than CD38 can be any of the following exemplary antigen targets: A2AR, APRIL, ATPDase, BAFF, BAFFR, BCMA, BIYS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-Ia), CCL4 (also known as MIP-Ib), CCL5 (also known as RANTES), CCL7 (also known as MCP-3), CCL8 (also known as mcp-2), CCL11 (also known as eotaxin), CCL15 (also known as MIP-Id), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CCR7, CD19, CD20, CD23 (also known as FCER2, a receptor for IgE), CD24, CD27, CD28, CD38, CD39, CD40, CD47, CD48, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, GPRCSD, Her2, HHLA2, HMGB1, HVEM, ICOSLG, IDO, IFNa, IgE, IGF1R, IL2Rbeta, IL1, IL1RAP, ILILIA, IL1B, IL1F10, IL2, IL4, IL4Ra, IL5, IL5R, IL6, IL7, IL7Ra, IL8, IL9, RAP, IL9R, IL10, rILI0, IL12, IL13, IL13RaI, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, KG2D, NTPDase-1, OX40, OX40L, PD-1H, platelet receptor, PROM1, S152, SISP1, SLC, SPG64, ST2 (also known as a receptor for IL33), STEAP2, Syk kinase, TACT, TDO, T14, TIGIT, TIM3, TLR, TLR2, TLR4, TLR5, TLR9, TMEF1, TNFa, TFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1), XCL1 and XCL2. In some embodiments, one or more of the above antigen targets are human antigen targets.

In any of the bispecific binding proteins described supra, any linker or combination of linkers described herein may be used.

In certain particular embodiments, the present invention relates to a bispecific antibody comprising at least one binding portion which binds to human CD38 comprising a CDR set selected from the group comprising: SEQ ID NO: 80, SEQ ID NO: 140, SEQ ID NO: 200; SEQ ID NO: 81, SEQ ID NO: 141, SEQ ID NO: 201; SEQ ID NO: 82, SEQ ID NO: 142, SEQ ID NO: 202; SEQ ID NO: 83, SEQ ID NO: 143, SEQ ID NO: 203; SEQ ID NO: 84, SEQ ID NO: 144, SEQ ID NO: 204; SEQ ID NO: 85, SEQ ID NO: 145, SEQ ID NO: 205; SEQ ID NO: 86, SEQ ID NO: 146, SEQ ID NO: 206; SEQ ID NO: 87, SEQ ID NO: 147, SEQ ID NO: 207, SEQ ID NO: 88, SEQ ID NO: 148, SEQ ID NO: 208; SEQ ID NO: 89, SEQ ID NO: 149, SEQ ID NO: 209; SEQ ID NO: 90, SEQ ID NO: 150, SEQ ID NO: 210; SEQ ID NO: 91, SEQ ID NO: 151, SEQ ID NO: 211; SEQ ID NO: 92, SEQ ID NO: 152, SEQ ID NO: 212; SEQ ID NO: 93, SEQ ID NO: 153, SEQ ID NO: 213; SEQ ID NO: 94, SEQ ID NO: 154, SEQ ID NO: 214; SEQ ID NO: 95, SEQ ID NO: 155, SEQ ID NO: 215; SEQ ID NO: 96, SEQ ID NO: 156, SEQ ID NO: 216; SEQ ID NO: 97, SEQ ID NO: 157, SEQ ID NO: 217; SEQ ID NO: 98, SEQ ID NO: 158, SEQ ID NO: 218; SEQ ID NO: 99, SEQ ID NO: 159, SEQ ID NO: 219; SEQ ID NO: 100, SEQ ID NO: 160, SEQ ID NO: 220; SEQ ID NO: 101, SEQ ID NO: 161, SEQ ID NO: 221; SEQ ID NO: 102, SEQ ID NO: 162, SEQ ID NO: 222; SEQ ID NO: 103, SEQ ID NO: 163, SEQ ID NO: 223; SEQ ID NO: 104, SEQ ID NO: 164, SEQ ID NO: 224; SEQ ID NO: 105, SEQ ID NO: 165, SEQ ID NO: 225; SEQ ID NO: 106, SEQ ID NO: 166, SEQ ID NO: 226; SEQ ID NO: 107, SEQ ID NO: 167, SEQ ID NO: 227; SEQ ID NO: 108, SEQ ID NO: 168, SEQ ID NO: 228; SEQ ID NO: 109, SEQ ID NO: 169, SEQ ID NO: 229; SEQ ID NO: 110, SEQ ID NO: 170, SEQ ID NO: 230; SEQ ID NO: 111, SEQ ID NO: 171, SEQ ID NO: 231; SEQ ID NO: 112, SEQ ID NO: 172, SEQ ID NO: 232; SEQ ID NO: 113, SEQ ID NO: 173, SEQ ID NO: 233; SEQ ID NO: 114, SEQ ID NO: 174, SEQ ID NO: 234; SEQ ID NO: 115, SEQ ID NO: 176, SEQ ID NO: 235; SEQ ID NO: 116, SEQ ID NO: 175, SEQ ID NO: 236; SEQ ID NO: 117, SEQ ID NO: 177, SEQ ID NO: 237; SEQ ID NO: 118, SEQ ID NO: 178, SEQ ID NO: 238; SEQ ID NO: 119, SEQ ID NO: 179, SEQ ID NO: 239; SEQ ID NO: 120, SEQ ID NO: 180, SEQ ID NO: 240; SEQ ID NO: 121; SEQ ID NO: 181, SEQ ID NO: 241; SEQ ID NO: 122, SEQ ID NO: 182, SEQ ID NO: 242; SEQ ID NO: 123, SEQ ID NO: 183, SEQ ID NO: 243; SEQ ID NO: 124, SEQ ID NO: 184, SEQ ID NO: 244; SEQ ID NO: 125, SEQ ID NO: 185, SEQ ID NO: 245; SEQ ID NO: 126, SEQ ID NO: 186, SEQ ID NO: 246; SEQ ID NO: 127, SEQ ID NO: 187, SEQ ID NO: 247; SEQ ID NO: 128, SEQ ID NO: 188, SEQ ID NO: 248; SEQ ID NO: 129, SEQ ID NO: 189, SEQ ID NO: 249; SEQ ID NO: 130, SEQ ID NO: 190, SEQ ID NO: 250. In a preferred embodiment, the bispecific antibody according to the present invention comprises at least one binding portion which binds to human CD38 comprising a CDR set selected from the group comprising SEQ ID NO: 112, SEQ ID NO: 172, SEQ ID NO: 232; SEQ ID NO: 115, SEQ ID NO: 176, SEQ ID NO: 235; SEQ ID NO: 117, SEQ ID NO: 177, SEQ ID NO: 237; SEQ ID NO: 103, SEQ ID NO: 163, SEQ ID NO: 223, and SEQ ID NO: 121; SEQ ID NO: 181, SEQ ID NO: 241.

Anti-CD47 Binding Proteins

Certain aspects of the present disclosure relate to binding proteins that comprise an antigen binding site that binds a CD47 polypeptide (e.g., human and cynomolgus monkey CD47 polypeptides). In some embodiments, the binding proteins are monospecific and/or monovalent, bispecific and/or bivalent, trispecific and/or trivalent, or multispecific and/or multivalent.

A variety of features of exemplary monospecific, bispecific, or trispecific binding proteins are described herein. For example, in some embodiments, a binding protein or antigen-binding fragment thereof cross-reacts with human CD47 (e.g., SEQ ID NO: 300 (human CD47 isoform OA3-323), SEQ ID NO: 301 (human CD47 isoform OA3-293), SEQ ID NO: 302 (human CD47 isoform OA3-305), and SEQ ID NO: 303 (human CD47 isoform OA3-312)) and cynomolgus monkey CD47.

In some embodiments, the binding protein is bivalent and/or bispecific. In some embodiments, the binding protein is multivalent, such as trivalent or tetravalent. In some embodiments, at least one of the antigen binding sites binds a CD47 polypeptide (e.g., the extracellular domain of human and/or cynomolgus monkey CD47 polypeptides).

In any of the bispecific binding proteins described supra, the target antigen other than CD47 can be any of the following exemplary antigen targets: A2AR, APRIL, ATP-Dase, BAFF, BAFFR, BCMA, BIYS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-Ia), CCL4 (also known as MIP-Ib), CCL5 (also known as RANTES), CCL7 (also known as MCP-3), CCL8 (also known as mcp-2), CCL11 (also known as eotaxin), CCL15 (also known as MIP-Id), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CCR7, CD19, CD20, CD23 (also known as FCER2, a receptor for IgE), CD24, CD27, CD28, CD38, CD39, CD40, CD47, CD48, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, GPRCSD, Her2, HHLA2, HMGB1, HVEM, ICOSLG, IDO, IFNa, IgE, IGF1R, IL2Rbeta, IL1, IL1RAP, ILILIA, IL1B, IL1F10, IL2, IL4, IL4Ra, IL5, IL5R, IL6, IL7, IL7Ra, IL8, IL9, RAP, IL9R, IL10, rILI0, IL12, IL13, IL13RaI, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, KG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1), XCL1 and XCL2. In some embodiments, one or more of the above antigen targets are human antigen targets.

In certain particular embodiments, the present invention relates to a bispecific antibody comprising a binding portion which binds to human CD47 comprising a CDR set selected from the group comprising: SEQ ID NO: 71, SEQ ID NO: 131, SEQ ID NO: 191; SEQ ID NO: 72, SEQ ID NO: 132, SEQ ID NO: 192; SEQ ID NO: 73, SEQ ID NO: 133, SEQ ID NO: 193; SEQ ID NO: 74, SEQ ID NO: 134, SEQ ID NO: 194; SEQ ID NO: 75, SEQ ID NO: 135, SEQ ID NO: 195; SEQ ID NO: 76, SEQ ID NO: 136, SEQ ID NO: 196; SEQ ID NO: 77, SEQ ID NO: 137, SEQ ID NO: 197; SEQ ID NO: 78, SEQ ID NO: 138, SEQ ID NO: 198; SEQ ID NO: 79, SEQ ID NO: 139, SEQ ID NO: 199; SEQ ID NO: 80, SEQ ID NO: 140, SEQ ID NO: 200; SEQ ID NO: 81, SEQ ID NO: 141, SEQ ID NO: 201. In a preferred embodiment, the bispecific antibody according to the present invention comprises a binding portion which binds to human CD47 comprising a CDR set comprising SEQ ID NO: 75, SEQ ID NO: 135, SEQ ID NO: 195.

Bispecific Anti-CD47 and Anti-CD38 Proteins

The present invention relates to a bispecific antibody comprising at least two binding portions, at least one of which binds to human CD38 and at least one of which binds to human CD47.

In particular the at least one binding portion which binds to human CD38 comprises a CDR set selected from the group comprising: SEQ ID NO: 80, SEQ ID NO: 140, SEQ ID NO: 200; SEQ ID NO: 81, SEQ ID NO: 141, SEQ ID NO: 201; SEQ ID NO: 82, SEQ ID NO: 142, SEQ ID NO: 202; SEQ ID NO: 83, SEQ ID NO: 143, SEQ ID NO: 203; SEQ ID NO: 84, SEQ ID NO: 144, SEQ ID NO: 204; SEQ ID NO: 85, SEQ ID NO: 145, SEQ ID NO: 205; SEQ ID NO: 86, SEQ ID NO: 146, SEQ ID NO: 206; SEQ ID NO: 87, SEQ ID NO: 147, SEQ ID NO: 207, SEQ ID NO: 88, SEQ ID NO: 148, SEQ ID NO: 208; SEQ ID NO: 89, SEQ ID NO: 149, SEQ ID NO: 209; SEQ ID NO: 90, SEQ ID NO: 150, SEQ ID NO: 210; SEQ ID NO: 91, SEQ ID NO: 151, SEQ ID NO: 211; SEQ ID NO: 92, SEQ ID NO: 152, SEQ ID NO: 212; SEQ ID NO: 93, SEQ ID NO: 153, SEQ ID NO: 213; SEQ ID NO: 94, SEQ ID NO: 154, SEQ ID NO: 214; SEQ ID NO: 95, SEQ ID NO: 155, SEQ ID NO: 215; SEQ ID NO: 96, SEQ ID NO: 156, SEQ ID NO: 216; SEQ ID NO: 97, SEQ ID NO: 157, SEQ ID NO: 217; SEQ ID NO: 98, SEQ ID NO: 158, SEQ ID NO: 218; SEQ ID NO: 99, SEQ ID NO: 159, SEQ ID NO: 219; SEQ ID NO: 100, SEQ ID NO: 160, SEQ ID NO: 220; SEQ ID NO: 101, SEQ ID NO: 161, SEQ ID NO: 221; SEQ ID NO: 102, SEQ ID NO: 162, SEQ ID NO: 222; SEQ ID NO: 103, SEQ ID NO: 163, SEQ ID NO: 223; SEQ ID NO: 104, SEQ ID NO: 164, SEQ ID NO: 224; SEQ ID NO: 105, SEQ ID NO: 165, SEQ ID NO: 225; SEQ ID NO: 106, SEQ ID NO: 166, SEQ ID NO: 226; SEQ ID NO: 107, SEQ ID NO: 167, SEQ ID NO: 227; SEQ ID NO: 108, SEQ ID NO: 168, SEQ ID NO: 228; SEQ ID NO: 109, SEQ ID NO: 169, SEQ ID NO: 229; SEQ ID NO: 110, SEQ ID NO: 170, SEQ ID NO: 230; SEQ ID NO: 111, SEQ ID NO: 171, SEQ ID NO: 231; SEQ ID NO: 112, SEQ ID NO: 172, SEQ ID NO: 232; SEQ ID NO: 113, SEQ ID NO: 173, SEQ ID NO: 233, SEQ ID NO: 114, SEQ ID NO: 174, SEQ ID NO: 234; SEQ ID NO: 115, SEQ ID NO: 176, SEQ ID NO: 235; SEQ ID NO: 116, SEQ ID NO: 175, SEQ ID NO: 236; SEQ ID NO: 117, SEQ ID NO: 177, SEQ ID NO: 237; SEQ ID NO: 118, SEQ ID NO: 178, SEQ ID NO: 238; SEQ ID NO: 119, SEQ ID NO: 179, SEQ ID NO: 239; SEQ ID NO: 120, SEQ ID NO: 180, SEQ ID NO: 240; SEQ ID NO: 121; SEQ ID NO: 181, SEQ ID NO: 241; SEQ ID NO: 122, SEQ ID NO: 182, SEQ ID NO: 242; SEQ ID NO: 123, SEQ ID NO: 183, SEQ ID NO: 243; SEQ ID NO: 124, SEQ ID NO: 184, SEQ ID NO: 244; SEQ ID NO: 125, SEQ ID NO: 185, SEQ ID NO: 245; SEQ ID NO: 126, SEQ ID NO: 186, SEQ ID NO: 246; SEQ ID NO: 127, SEQ ID NO: 187, SEQ ID NO: 247; SEQ ID NO: 128, SEQ ID NO: 188, SEQ ID NO: 248; SEQ ID NO: 129, SEQ ID NO: 189, SEQ ID NO: 249; SEQ ID NO: 130, SEQ ID NO: 190, SEQ ID NO: 250; and the at least one binding portion which binds to human CD47 comprises a CDR set selected from the group comprising: SEQ ID NO: 71, SEQ ID NO: 131, SEQ ID NO: 191; SEQ ID NO: 72, SEQ ID NO: 132, SEQ ID NO: 192; SEQ ID NO: 73, SEQ ID NO: 133, SEQ ID NO: 193; SEQ ID NO: 74, SEQ ID NO: 134, SEQ ID NO: 194; SEQ ID NO: 75, SEQ ID NO: 135, SEQ ID NO: 195; SEQ ID NO: 76, SEQ ID NO: 136, SEQ ID NO: 196; SEQ ID NO: 77, SEQ ID NO: 137, SEQ ID NO: 197; SEQ ID NO: 78, SEQ ID NO: 138, SEQ ID NO: 198; SEQ ID NO: 79, SEQ ID NO: 139, SEQ ID NO: 199; SEQ ID NO: 80, SEQ ID NO: 140, SEQ ID NO: 200; SEQ ID NO: 81, SEQ ID NO: 141, SEQ ID NO: 201.

More specifically, the at least one binding portion which binds to human CD38 comprises a CDR set selected from the group comprising: SEQ ID NO: 112, SEQ ID NO: 172, SEQ ID NO: 232; SEQ ID NO: 115, SEQ ID NO: 176, SEQ ID NO: 235; SEQ ID NO: 117, SEQ ID NO: 177, SEQ ID NO: 237; SEQ ID NO: 103, SEQ ID NO: 163, SEQ ID NO: 223, and SEQ ID NO: 121; SEQ ID NO: 181, SEQ ID NO: 241; and the at least one binding portion which binds to human CD47 comprises a CDR set comprising SEQ ID NO: 75, SEQ ID NO: 135, SEQ ID NO: 195. Even more specifically, the at least one binding portion which binds to human CD38 comprises a CDR set comprising SEQ ID NO: 117, SEQ ID NO: 177, SEQ ID NO: 237; and the at least one binding portion which binds to human CD47 comprises a CDR set selected from the group comprising set comprising SEQ ID NO: 75, SEQ ID NO: 135, SEQ ID NO: 195.

In exemplary embodiments, the present invention relates to bispecific antibodies comprising at least one binding portion which binds to human CD47 and at least two binding portions which bind to human CD38. The at least one binding portion which binds to human CD47 may comprise any of the CDRs set described above and in paragraph "Anti-CD47 Binding Proteins". The at least two binding portions which bind to human CD38 may comprise any of the CDRs set described above and in paragraph "Anti-CD38 Binding Proteins".

In certain embodiments, the at least two CD38 binding portions are monoparatopic, i.e. they bind to the same epitope of their antigen target. In other embodiments, the at least two CD38 binding portions are biparatopic, i.e. they bind to different epitopes their antigen target. In particular, the antibody according to certain embodiments of the present invention comprises at least two binding portions which binds to human CD38: one Fc proximal binding portion which binds to a first epitope of human CD38, and one Fc distal binding portion which binds to a second epitope of human CD38. In particular embodiments, at least one of the at least two binding portions which binds to human CD38 comprises a CDR set selected from the group comprising SEQ ID NO: 112, SEQ ID NO: 172, SEQ ID NO: 232; SEQ ID NO: 115, SEQ ID NO: 176, SEQ ID NO: 235; SEQ ID NO: 117, SEQ ID NO: 177, SEQ ID NO: 237; SEQ ID NO: 103, SEQ ID NO: 163, SEQ ID NO: 223, and SEQ ID NO: 121; SEQ ID NO: 181, SEQ ID NO: 241. In more specific embodiments, at least one of the at least two binding portions which binds to human CD38 comprises a CDR set selected form the group comprising SEQ ID NO: 103, SEQ ID NO: 163, SEQ ID NO: 223, and SEQ ID NO: 121; SEQ ID NO: 181, SEQ ID NO: 241; and at least one of the at least two binding portions which binds to human CD38 comprises the CDR set SEQ ID NO: 117, SEQ ID NO: 177, SEQ ID NO: 237. In a preferred embodiment, the Fc proximal binding portion which binds to a first epitope of human CD38 comprises a CDR set selected from the group comprising SEQ ID NO: 103, SEQ ID NO: 163, SEQ ID NO: 223, and SEQ ID NO: 121; SEQ ID NO: 181, SEQ ID NO: 241; and the Fc distal binding portion which binds to a second epitope of human CD38 comprises the CDR set SEQ ID NO: 117, SEQ ID NO: 177, SEQ ID NO: 237. In a more preferred embodiment, the Fc proximal binding portion which binds to a first epitope of human CD38 comprises a CDR set selected form the group comprising SEQ ID NO: 103, SEQ ID NO: 163, SEQ ID NO: 223, and SEQ ID NO: 121; SEQ ID NO: 181, SEQ ID NO: 241; the Fc distal binding portion which binds to a second epitope of human CD38 comprises the CDR set SEQ ID NO: 117, SEQ ID NO: 177, SEQ ID NO: 237; further the bispecific antibody described above comprises at least one binding portion which binds to human CD47 comprising a CDR set comprising SEQ ID NO: 75, SEQ ID NO: 135, SEQ ID NO: 195. Preferably, the bispecific antibody of the present invention comprises at least one binding portion which binds to human CD38 comprises a CDR set comprising SEQ ID NO: 117, SEQ ID NO: 177, SEQ ID NO: 237, at least a second binding portion which binds to human CD38 comprises a CDR set selected from the group comprising SEQ ID NO: 103, SEQ ID NO: 163, SEQ ID NO: 223, and SEQ ID NO: 121; SEQ ID NO: 181, SEQ ID NO: 241; and at least one binding portion which binds to human CD47 comprising a CDR set comprising SEQ ID NO: 75, SEQ ID NO: 135, SEQ ID NO: 195.

In certain embodiments of the present invention, the bispecific antibody is a full-length antibody, wherein the at least one binding portion which binds to human CD38 and/or the at least one of binding portion which binds to human CD47 is a Fab region. The term "Fab" or "Fab region" or "Fab domain" as used herein includes the polypeptides that comprise the VH, CH1, VL, and CL immunoglobulin domains. Fab may refer to this region in isolation, or this region in the context of a full-length antibody or antibody fragment. The present invention also provides an antibody fragment that binds to a human CD38 or to a human Cd47. Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward E S et al., (1989)

Nature, 341: 544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird R E et al., (1988) Science 242: 423-426; Huston J S et al., (1988) Proc. Natl. Acad. Sci. USA, 85: 5879-83), (vii) bispecific single chain Fv dimers (PCT/US92/09965), (viii) "diabodies" or "triabodies", multivalent or multispecific fragments constructed by gene fusion Tomlinson I & Hollinger P (2000) Methods Enzymol. 326: 461-79; WO94/13804; Holliger P et al., (1993) Proc. Natl. Acad. Sci. USA, 90: 6444-48) and (ix) scFv genetically fused to the same or a different antibody (Coloma M J & Morrison S L (1997) Nature Biotechnology, 15(2): 159-163).

In certain embodiments the bispecific antibody of the present invention comprises at least one binding portion which binds to human CD47 and it is a Fab comprising and amino acid sequence selected from the group comprising SEQ ID NOs: 11, 12, 13, 14, 15, 16, 17, 18, 19, 20, 21, 299; in a particular embodiment the Fab which binds to human CD47 comprises a VH chain with a G65S mutation (Kabat numbering), in more particular embodiments the Fab which binds to human CD47 comprises an amino acid sequence of SEQ ID NO: 15 or 299. In a preferred embodiment, the bispecific antibody of the present invention comprises at least a Fab which binds to human CD47 having SEQ ID NO: 15 and comprising a VH chain with a G65S mutation (Kabat numbering), in particular the bispecific antibody of the present invention comprises at least a Fab which binds to human CD47 comprising an amino acid sequence of SEQ ID NO: 299. In certain embodiments the bispecific antibody of the present invention comprises at least one binding portion which binds to human CD38 and is a Fab comprising and amino acid sequence selected from the group comprising SEQ ID NOs: 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70. Preferably the amino acid sequence of the Fab which binds to human CD38 is selected from the group comprising SEQ ID NOs: 43, 52, 55, 57 and 61.

In particular embodiments of the present invention, the bispecific antibody is constructed using the BEAT® heavy chain (Hc) heterodimerization technology previously described (Skegro et al., (2017) J Biol Chem 292(23): 9745-9759 and Stutz et al., (2020) J Biol Chem 295(28): 9392-9408, WO2012131555), wherein the BEAT(A) chain, also referred herein to as BEAT(A), and the BEAT (B) chain, also referred herein to as BEAT(B). More specifically, the BEAT (A) Hc encompasses a VH domain with mutation G65S (Kabat numbering) a CH1 γ1 region, a γ1 hinge region, a γ1 CH2 region, and a γ3 based BEAT (A) CH3 domain assembled with a common light chain (cLc). BEAT (B) Hc encompasses a VH domain, a CH1 γ1 region, a γ1 hinge region, a γ1 CH2 region, and a γ1 based BEAT (B) CH3 domain assembled with a cLc. According to the present invention the BEAT(A) heavy chain (Hc) comprises an amino acid sequence selected from the group comprising SEQ ID NOs: 259, 274, 276, 280, 281, 283, 285 and 278; the BEAT(B) Hc comprises an amino acid sequence selected from the group comprising SEQ ID NOs: 260, 261, 262, 275, 277, 279, 282, 284, 286, 287, 288, 289, 290, 291, 292 and 293. The cLc comprises an amino acid sequence of SEQ ID NO: 10. In preferred embodiments the bispecific antibody according to the present invention comprises a BEAT (A) chain comprising the amino acid sequence of SEQ ID NO: 259, a BEAT(B) chain comprising the amino acid sequence of SEQ ID NO: 260, and a cLc comprising the amino acid sequence of SEQ ID NO: 10; or a BEAT(A) chain comprising the amino acid sequence of SEQ ID NO: 259, a BEAT(B) chain comprising the amino acid sequence of SEQ ID NO: 261, and a cLc comprising the amino acid sequence of SEQ ID NO: 10; or a BEAT(A) chain comprising the amino acid sequence of SEQ ID NO: 259, a BEAT(B) chain comprising the amino acid sequence of SEQ ID NO: 262, and a cLc comprising the amino acid sequence of SEQ ID NO: 10; a BEAT(A) chain comprising the amino acid sequence of SEQ ID NO: 274, a BEAT(B) chain comprising the amino acid sequence of SEQ ID NO: 275, and a cLc comprising the amino acid sequence of SEQ ID NO: 10; or a BEAT(A) chain comprising the amino acid sequence of SEQ ID NO: 276, a BEAT(B) chain comprising the amino acid sequence of SEQ ID NO: 277, and a cLc comprising the amino acid sequence of SEQ ID NO: 10; or a BEAT(A) chain comprising the amino acid sequence of SEQ ID NO: 278, a BEAT(B) chain comprising the amino acid sequence of SEQ ID NO: 279, and a cLc comprising the amino acid sequence of SEQ ID NO: 10; or a BEAT(A) chain comprising the amino acid sequence of SEQ ID NO: 280, a BEAT(B) chain comprising the amino acid sequence of SEQ ID NO: 277, and a cLc comprising the amino acid sequence of SEQ ID NO: 10; or a BEAT(A) chain comprising the amino acid sequence of SEQ ID NO: 281, a BEAT(B) chain comprising the amino acid sequence of SEQ ID NO: 282, and a cLc comprising the amino acid sequence of SEQ ID NO: 10; or a BEAT(A) chain comprising the amino acid sequence of SEQ ID NO: 283, a BEAT(B) chain comprising the amino acid sequence of SEQ ID NO: 284, and a cLc comprising the amino acid sequence of SEQ ID NO: 10; or a BEAT(A) chain comprising the amino acid sequence of SEQ ID NO: 285, a BEAT(B) chain comprising the amino acid sequence of SEQ ID NO: 286, and a cLc comprising the amino acid sequence of SEQ ID NO: 10; or a BEAT(A) chain comprising the amino acid sequence of SEQ ID NO: 281, a BEAT(B) chain comprising the amino acid sequence of SEQ ID NO: 287, and a cLc comprising the amino acid sequence of SEQ ID NO: 10; or a BEAT(A) chain comprising the amino acid sequence of SEQ ID NO: 278, a BEAT(B) chain comprising the amino acid sequence of SEQ ID NO: 288, and a cLc comprising the amino acid sequence of SEQ ID NO: 10; or a BEAT(A) chain comprising the amino acid sequence of SEQ ID NO: 281, a BEAT(B) chain comprising the amino acid sequence of SEQ ID NO: 290, and a cLc comprising the amino acid sequence of SEQ ID NO: 10; or a BEAT(A) chain comprising the amino acid sequence of SEQ ID NO: 278, a BEAT(B) chain comprising the amino acid sequence of SEQ ID NO: 291, and a cLc comprising the amino acid sequence of SEQ ID NO: 10; or a BEAT(A) chain comprising the amino acid sequence of SEQ ID NO: 280, a BEAT(B) chain comprising the amino acid sequence of SEQ ID NO: 292, and a cLc comprising the amino acid sequence of SEQ ID NO: 10; or a BEAT(A) chain comprising the amino acid sequence of SEQ ID NO: 280, a BEAT(B) chain comprising the amino acid sequence of SEQ ID NO: 293, and a cLc comprising the amino acid sequence of SEQ ID NO: 10. In preferred embodiments, the bispecific antibody disclosed herein comprises a BAET(A) chain that binds to CD47 and comprises the amino acid sequence of SEQ ID NO: 280; a BEAT(B) chain that binds to CD38 and comprises an amino acid sequence of SEQ ID NOs: 292 or 293, more preferably the amino acid sequence of SEQ ID NO: 293; and a cLc comprising the amino acid sequence of SEQ ID NO: 10.

In certain aspects the present invention discloses a bispecific antibody comprising at least two binding portions, at least one of which binds to human CD38 and at least one of which binds to human CD47 wherein the at least one binding portion which binds to human CD47 has an affinity to human CD47 lower than the affinity that the at least one binding portion which binds to human CD38 has against human CD38. In particular, the at least one binding portion which binds to human CD47 has an affinity to human CD47 of about 1000 nM or less, or about 900 nM or less, or about 800 nM or less, or about 850 nM or less, or about 700 nM or less, or about 600 nM or less, or about 500 nM or less, or about 400 nM or less, or about 300 nM or less, 200 nM or less, or of about 150 nM or less, or of about 140 or less, or of about 130 nM or less, or of about 120 nM or less, preferably of about 110 nM or less, more preferably of 105 nM or less, for instance of about 104 nM; or preferably between about 700 nM and about 1000 nM, more preferably between about 798 nM and about 958 nM, more preferably about 878.3 nM. In particular, the at least one binding portion which binds to human CD38 has an affinity to human CD38 of about 100 nM or less, or of about 50 nM or less, or of about 30 or less, or of about 20 or less, or of about 10 or less, preferably of about 10 nM or less, of about 9 nM or less, of about 8 nM or less, of about 7 nM or less, of about 6 nM or less, of about 5 nM or less, of about 4 nM or less, of about 3 nM or less, of about 2 nM or less, preferably of about 1 nM or less, for instance of about 16.22 nM, about 17.6 nM, about 6.13 nM, about 2.3 nM, about 3.5 nM, about 0.55 nM, about 0.9 nM.

The present invention also discloses bispecific antibodies comprising at least one binding portion which binds to human CD47 and at least two binding portions which bind to human CD38, particular biparatopic bispecific antibodies wherein the affinity of the Fc proximal binding portion to a first epitope of human CD38 is about the same, or the same or different than the affinity of the Fc distal binding portion to a second epitope of human CD38.

Nucleic Acids

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins described herein. In some embodiments, the isolated nucleic acid molecules comprise a sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical.

Certain aspects of the present disclosure relate to kits of polynucleotides. In some embodiments, one or more of the polynucleotides is a vector {e.g., an expression vector). The kits may find use, inter alia, in producing one or more of the binding proteins described herein, e.g., a bi-, or trispecific binding protein of the present disclosure. In some embodiments, the kit comprises one, two, three, or four polynucleotides.

In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2): 193-9, 1991), the phosphogly cerate kinase (PGK)-promoter, a tetracycline-inducible promoter (Masui et al., Nucleic Acids Res. 33:e43, 2005), the lac system, the tip system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, a-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art and can be used to transfect any cell of interest.

Other aspects of the present disclosure relate to a vector system comprising one or more vectors encoding a first, second, third, and fourth polypeptide chain of any of the binding proteins described herein. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the vector system comprises a first vector encoding the first and third polypeptide chains of the binding protein, and a second vector encoding the second and fourth polypeptide chains of the binding protein. In some embodiments, the vector system comprises a first vector encoding the first and fourth polypeptide chains of the binding protein, and a second vector encoding the second and third polypeptide chains of the binding protein. In some embodiments, the vector system comprises a first vector encoding the first, second, third, and fourth polypeptide chains of the binding protein. The one or more vectors of the vector system may be any of the vectors described herein. In some embodiments, the one or more vectors are expression vectors.

Isolated Host Cells

Other aspects of the present disclosure relate to an isolated host cell comprising one or more isolated polynucleotides, polynucleotide kits, vectors, and/or vector systems described herein. In some embodiments, the host cell is a bacterial cell (e.g., a E. coli cell). In some embodiments, the host cell is a yeast cell (e.g., an S. cerevisiae cell). In some embodiments, the host cell is an insect cell. Examples of insect host cells may include, for example, Drosophila cells (e.g., S2 cells), Trichoplusia ni cells (e.g., High Five™ cells), and Spodoptera frugiperda cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), Expi293TM cells, CHO cells, baby hamster kidney cells (e.g., BHK, ATCC CCL 10), mouse Sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding protein; and b) isolating the binding protein from the host cell. Methods of culturing host cells under conditions to express a protein are well known to one of ordinary skill in the art. Methods of isolating proteins from cultured host cells are well known to one of ordinary skill in the art, including, for example, by affinity chromatography (e.g., two step affinity chromatography comprising protein A affinity chromatography followed by size exclusion chromatography).

In some embodiments, a binding protein of the present disclosure is purified by protein A affinity chromatography.

Linkers

In some embodiments, the linkers L1, L2, L3 and L4 range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. L1, L2, L3 and L4 in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues; a peptide with five glycine residues; a peptide with six glycine residues; a peptide with seven glycine residues; and a peptide with eight glycine residues. Other combinations of amino acid residues may be used such as the peptide GGGT (SEQ IS NO: 297), or the GGGGS, or repetitions of said peptides, such as the peptide GGGGS GGGGS GGGGS (SEQ ID NO: 298). In a preferred embodiment, the linker has an amino acid sequence of SEQ ID NO: 298.

The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345 and International Application No. PCT/US2017/027488.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

Fc Regions and Constant Domains

The present invention also relates to a bispecific antibody comprising an Fc region. In some embodiments, a binding protein of the present disclosure comprises an antibody fragment, including but not limited to antibody F(ab), F(ab') 2, Fab'-SH, Fv, or scFv fragments. In some embodiments, a binding protein of the present disclosure comprises an antibody fragment, including but not limited to antibody F(ab), F(ab')2, Fab'-SH, Fv, or scFv fragments, comprising an Fc region.

In some embodiments, a binding protein of the present disclosure comprises a full-length antibody heavy chain or a polypeptide chain comprising an Fc region. In some embodiments, the Fc region is a human Fc region, e.g., a human IgG1, IgG2, IgG3, or IgG4 Fc region. In some embodiments, the Fc region includes an antibody hinge, CH1, CH2, CH3, and optionally CH4 domains. In some embodiments, the Fc region is a human IgG1 Fc region. In some embodiments, the Fc region is a human IgG4 Fc region. In some embodiments, the Fc region includes one or more of the mutations described herein.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "parent antibody" or "parent immunoglobulin" as used herein includes an unmodified antibody that is subsequently modified to generate a variant. Said parent antibody may be a naturally occurring antibody, a non-naturally occurring antibody, or a variant or engineered version of a naturally occurring antibody. Parent antibody may refer to the antibody itself, compositions that comprise the parent antibody, or the amino acid sequence that encodes it. In preferred embodiments of the present invention, the parent antibody comprises an Fc region. More specifically, the Fc region of the parent antibody according to the present invention is a human IgG1, IgG2, IgG3, or IgG4 Fc region; in some embodiments the Fc region of the parent antibody according to the present invention is a modified or not modified IgG1 Fc region.

In certain aspects, the bispecific antibody of the present invention comprises a variant Fc region which comprises at least one amino acid modification relative to the Fc region of the parent antibody, whereas the antibody comprising the variant Fc region exhibits altered effector function compared to the parent antibody. More specifically the CH2 domain of the Fc region comprises at least one amino acid modification.

In particular embodiments of the present invention, the bispecific antibody is constructed using the BEAT® heavy chain (Hc) heterodimerization technology previously described (Skegro et al., (2017) J Biol Chem 292(23): 9745-9759 and Stutz et al., (2020) J Biol Chem 295(28): 9392-9408, WO2012131555), wherein the BEAT(A) chain, also referred herein to as BEAT(A), and the BEAT (B) chain, also referred herein to as BEAT(B), have been engineered to as to increase the Fc effector function. More specifically the CH2 domain of the Fc region has been engineered so as to comprise at least one amino acid modification. More specifically BEAT(A) comprises one or more substitutions at a position selected from the group comprising: 324, 334, 269, 298, 239, 332 and 333; and BEAT(B) comprises one or more substitutions at a position selected from the group comprising: 324, 334, 269, 298, 239, 332 and 333; preferably comprising 324, 334, 269, 289, 298, 333. Even more specifically BEAT(A) comprises one or more substitutions selected from the group comprising: S324N, K334E, K334A, E269D, S298A, S239D, I332E and E333A; and BEAT(B) comprises one or more substitutions at a position selected from the group comprising: S324N, K334E, K334A, E269D, S289A, K334A, E333A. In certain particular embodiments, BEAT(A) comprises a set of mutations selected from the group comprising: S324N; or S324N and K334E; or E269D, S298A, S324N and K334A; or S239D, I332E and S324N; or E269D, S298A, S324N and E334A; or S298A, S324N and E333A; or S298A, S324N and K334A; or S324N, S298A, E269D and E333A; or S324N, S298A, E269D and K334A. In other particular embodiments, BEAT(B) comprises a set of mutations selected from the group comprising: S324N; or S324N and K334E; or E269D, S298A, S324N and K334A; or S239D, I332E and S324N; or E269D; or E269D, S298A, S324N and E334A; or S298A, S324N and E333A; or S298A, S324N and K334A; or S324N, S298A, E269D and E333A; or S324N, S298A, E269D and K334A. In certain preferred embodiments, BEAT(A) and BEAT(B) comprises the mutation S324N; or the mutations S324N and K334E; or the mutations E269D, S298A, S324N and K334A; or the mutations E269D, S298A, S324N and E334A; or the mutations S298A, S324N and E333A; or the mutations S298A, S324N and K334A; or the mutations S324N and K334E. In particularly preferred embodiments, BEAT(A) comprises the mutations S239D, I332E and S324N, and BEAT(B) comprises the mutation S324N.

In some embodiments, the Fc region comprises one or more mutations that reduce or eliminate Fc receptor binding and/or effector function of the Fc region (e.g., Fc receptor-mediated antibody-dependent cellular phagocytosis (ADCP), complement-dependent cytotoxicity (CDC), and/or antibody-dependent cellular cytotoxicity (ADCC)).

In some embodiments, the Fc region is a human IgG1 Fc region comprising one or more amino acid substitutions at positions corresponding to positions 234, 235, and/or 329 of human IgG1 according to EU Index. In some embodiments, the amino acid substitutions are L234A, L235A, and/or P329A. In some embodiments, the Fc region is a human IgG1 Fc region comprising amino acid substitutions at positions corresponding to positions 298, 299, and/or 300 of human IgG1 according to EU Index. In some embodiments, the amino acid substitutions are S298N, T299A, and/or Y300S.

In some embodiments, the Fc region is a human IgG4 Fc region comprising one or more mutations that reduce or eliminate FcγI and/or FcγII binding. In some embodiments, the Fc region is a human IgG4 Fc region comprising one or more mutations that reduce or eliminate FcγI and/or FcγII binding but do not affect FcRn binding. In some embodiments, the Fc region is a human IgG4 Fc region comprising amino acid substitutions at positions corresponding to positions 228 and/or 409 of human IgG4 according to EU Index. In some embodiments, the amino acid substitutions are S228P and/or R409K. In some embodiments, the Fc region is a human IgG4 Fc region comprising amino acid substitutions at positions corresponding to positions 234 and/or 235 of human IgG4 according to EU Index. In some embodiments, the amino acid substitutions are F234A and/or L235A. In some embodiments, the Fc region is a human IgG4 Fc region comprising amino acid substitutions at positions corresponding to positions 228, 234, 235, and/or 409 of human IgG4 according to EU Index. In some embodiments, the amino acid substitutions are S228P, F234A, L235A, and/or R409K. In some embodiments, the Fc region is a human IgG4 Fc region comprising amino acid substitutions at positions corresponding to positions 233-236 of human IgG4 according to EU Index. In some embodiments, the amino acid substitutions are E233P, F234V, L235A, and a deletion at 236. In some embodiments, the Fc region is a human IgG4 Fc region comprising amino acid mutations at substitutions corresponding to positions 228, 233-236, and/or 409 of human IgG4 according to EU Index. In some embodiments, the amino acid mutations are S228P; E233P, F234V, L235A, and a deletion at 236; and/or R409K.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) Sci. Rep. 5: 17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region CH2 and CH3 immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and hole mutations and one or more mutations to improve purification. In some embodiments, the first and/or second Fc regions are human IgG1 Fc regions. In some embodiments, the first and/or second Fc regions are human IgG4 Fc regions.

To improve the yields of some binding proteins (e.g., bispecific or trispecific binding proteins), the CH domains can be altered by the BEAT technology which is described in detail with several examples in and in International Publication No. WO2012131555.

In some embodiments, a binding protein of the present disclosure comprises one or more mutations to improve serum half-life (See e.g., Hinton, P R. et al. (2006) J. Immunol. 176(I):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to CH1, the first Fc region comprising an immunoglobulin hinge region and CH2 and CH3 immunoglobulin heavy chain constant domains; wherein the third polypeptide chain further comprises a second Fc region linked to CH1, the second Fc region comprising an immunoglobulin hinge region and CH2 and CH3 immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235A. In some embodiments, the second polypeptide chain further comprises a first Fc region linked to CH1, the first Fc region comprising an immunoglobulin hinge region and CH2 and CH3 immunoglobulin heavy chain constant domains; wherein the third polypeptide chain further comprises a second Fc region linked to CH1, the second Fc region comprising an immunoglobulin hinge region and CH2 and CH3 immunoglobulin heavy chain constant domains; wherein the first and second Fc regions are human IgG1 Fc regions; and wherein the first and the second Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG4 Fc regions, and the Fc regions each comprise amino acid substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A.

In some embodiments, a binding protein of the present disclosure comprises knob and hole mutations and one or more mutations to reduce effector function. In some embodiments, the first and/or second Fc regions are human IgG1 Fc regions. In some embodiments, the first and/or second Fc regions are human IgG4 Fc regions. For further description of Fc mutations at position 329, see, e.g., Shields, R. L. et al. (2001) J. Biol. Chem. 276:6591-6604 and WO 1999051642.

Application of the Binding Protein

The binding proteins can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

For diagnostic applications, in certain embodiments, binding proteins can be labeled with a detectable moiety. The detectable moiety can be any one that is capable of producing, either directly or indirectly, a detectable signal. For example, the detectable moiety can be a radioisotope, such as 3H, 14C, 32P, 35S, 125I, 99Tc, U1In, or 67Ga; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, preferably into the bloodstream, and the presence and location of the labeled antibody in the host assayed. The binding protein can be labeled with any moiety that is detectable in an animal, whether by nuclear magnetic resonance, radiology, or other detection means known in the art.

For clinical or research applications, in certain embodiments, binding proteins can be conjugated to a cytotoxic agent. A variety of antibodies coupled to cytotoxic agents {i.e., antibody-drug conjugates) have been used to target cytotoxic payloads to specific tumor cells. Cytotoxic agents and linkers that conjugate the agents to an antibody are known in the art; see, e.g., Parslow, A. C. et al. (2016) Biomedicines 4: 14 and Kalim, M. et al. (2017) Drug Des. Devel. Ther. 11:2265-2276.

The disclosure also relates to a kit comprising a binding protein and other reagents useful for detecting target antigen levels in biological samples. Such reagents can include a detectable label, blocking serum, positive and negative control samples, and detection reagents. In some embodiments, the kit comprises a composition comprising any binding protein, polynucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper pierceable by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, a binding protein of the present disclosure is administered to a patient in need thereof for the treatment or prevention of cancer. In some embodiments, the present disclosure relates to a method of preventing and/or treating a proliferative disease or disorder (e.g., cancer). In some embodiments, the method comprises administering to a patient a therapeutically effective amount of the heterodimeric antibody, or pharmaceutical compositions related thereto, described herein. In some embodiments, the present disclosure relates to uses of the heterodimeric antibody, or pharmaceutical compositions related thereto, described herein for preventing and/or treating a proliferative disease or disorder (e.g., cancer) in a patient in need thereof. In some embodiments, the present disclosure relates to the heterodimeric antibody, or pharmaceutical compositions related thereto, described herein for use in the manufacture of a medicament for preventing and/or treating a proliferative disease or disorder (e.g., cancer) in a patient in need thereof. In some embodiments, the patient is a human. In some embodiments, the binding protein comprises one antigen binding site that binds a T-cell surface protein and another antigen binding site that binds the extracellular domain of a human CD38 polypeptide. In some embodiments, the binding protein comprises an antigen binding site that binds the extracellular domain of a human CD38 polypeptide and an antigen binding site that binds a human CD47 polypeptide.

In some embodiments, cells of the cancer express a human CD38 1 polypeptide on their cell surface (e.g., comprising the amino acid sequence of SEQ ID NO: 1). In some embodiments, cells of the cancer express a human CD38 isoform SEQ ID NO: 295 (human CD38 isoform 28907-1), SEQ ID NO: 294 (human CD38 isoform 28907-2), SEQ ID NO: 296 (human CD38 isoform 28907-E). In some embodiments, the patient is selected for treatment on the basis that the cells of the cancer express a human CD38 isoform SEQ ID NO: 295 (human CD38 isoform 28907-1), SEQ ID NO: 294 (human CD38 isoform 28907-2), SEQ ID NO: 296 (human CD38 isoform 28907-E).

In certain embodiments, the cancer is selected from the group comprising: for use in treating multiple myeloma, acute lymphoblastic leukemia, chronic lymphocytic leukemia, acute myeloid leukemia, lymphoma, breast cancer such as Her2+ breast cancer, prostate cancer, cervical cancer, germinal center B-cell lymphoma or B-cell acute lymphoblastic leukemia, Chronic lymphocytic leukemia (CLL), Myelodisplastic syndrome (MDS), Non-Hodgkin lymphoma, diffuse large B-cell lymphoma, non small cell lung cancer (NSCLC), Hepatocellular carcinoma (HCC), High-grade serous ovarian carcinoma, peritoneal cancer. In a specific embodiment the cancer is multiple myeloma. Anti-CD38 antibodies have been tested for the treatment of multiple myeloma, such as Daratumumab, also called herein Darzalex® and isatuximab. However, while multiple myeloma is considered treatable, relapse is inevitable in almost all patients, leading to the development of treatment-refractory disease. In some embodiments, the cancer is relapsed or refractory multiple myeloma. In some embodiments, the patient has been treated with a prior multiple myeloma treatment. In some embodiments, a binding protein of the present disclosure is administered to the patient as a 1st, 2nd, or 3rd line treatment for multiple myeloma.

In certain embodiments, the bispecific antibody according to the present invention which has at least one binding portion that binds to CD47 allows blocking the interaction between CD47 and SIRPα, avoiding the transmission of a "Don't eat me" signal due to CD47-SIRPα interaction, which inhibits macrophages phagocytosis. An exemplary clinical benchmark monoclonal antibody which binds to CD47 is Magrolimab, also called herein 5F9. In the present invention the terms "Magrolimab" and "5F9" are used interchangeably. In certain embodiments the tested molecule is a "59F-like" (also called herein "Magrolimab-like") antibody which is the same as the clinical Magrolimab molecule but it is produced in house. In the present invention the terms "Magrolimab", "5F9", "59F-like" and "Magrolimab-like" are interchangeable. More in particular the bispecific antibody comprising at least two binding portions, at least one of which binds to human CD38 and at least one of which binds to human CD47, blocks the CD47-SIRPα interaction and therefore the "Don't eat me" signal selectively in CD38 expressing cells.

In certain embodiments, the bispecific antibody according to the present invention shows higher binding to CD38 high tumor cell lines (such as Daudi, Raji, KMS-12-PE) as compared to benchmark Darzalex and 5F9, in vitro. In other embodiments the bispecific antibody according to the present invention shows higher binding to CD38 low tumor cell lines (NCI-H929 and KMS-12-BM) as compared to Darzalex. In certain embodiments, the bispecific antibodies according to the present invention show a comparable efficiency as that of 5F9 at inducing phagocytosis of both $CD38^{high}$ or $CD38^{low}$ expressing tumor cells, in vitro. In certain embodiments, the bispecific antibodies according to the present invention show higher tumor cells killing by CDC as compared to Darzalex, in vitro. In certain embodiments, the bispecific antibodies according to the present invention show comparable killing by ADCC of $CD38^{high}$ or $CD38^{low}$ expressing tumor cells as that induced by Darzalex and on $CD38^{low}$ expressing tumor cells higher potency, in vitro. In certain embodiments, the bispecific antibodies according to the present invention show higher potency as compared to the combination of Darzalex and 5F9, in vitro.

Binding Protein Therapeutic Compositions and Administration Thereof

Therapeutic or pharmaceutical compositions comprising binding proteins are within the scope of the disclosure. Such therapeutic or pharmaceutical compositions can comprise a therapeutically effective amount of a binding protein, or binding protein-drug conjugate, in admixture with a pharmaceutically or physiologically acceptable formulation agent selected for suitability with the mode of administration. Acceptable formulation materials preferably are non-toxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles.

Other exemplary pharmaceutical compositions comprise Tris buffer of about pH 7.0-8.5, or acetate buffer of about pH 4.0-5.5, which can further include sorbitol or a suitable substitute. In one embodiment of the disclosure, binding protein compositions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

The pharmaceutical compositions of the disclosure can be selected for parenteral delivery or subcutaneous. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polygly colic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry powder for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

The disclosure also provides a method of treating multiple myeloma in a subject in need thereof. The method employs a heterodimeric antibody that co-engages CD47 and CD38 in such a manner so as to transiently connect malignant cells with T cells, thereby inducing T cell mediated killing of the bound malignant cell. The method described herein utilizes a heterodimeric antibody that binds CD47 and CD38 in such a manner so as to maximize destruction of target cells while reducing unwanted side effects (e.g., uncontrolled cytokine release).

Therapeutic Regimen

The heterodimeric antibody is administered to a subject in need thereof, e.g., a human subject suffering from multiple myeloma, such as relapsed/refractory multiple myeloma. Relapsed myeloma is characterized as a recurrence of disease after prior response. Examples of laboratory and radiological criteria signaling the disease include, but are not limited to, >25% increase of the serum or urine monoclonal protein (M-protein) or >25% difference between involved and uninvolved serum free light chains from nadir, respectively, or the development of new plasmacytomas or hypercalciemia. Sonneveld et al., Haematologica. 2016 April; 101(4): 396-406.

In non-secretory disease patients, relapse is characterized by an increase of the bone marrow plasma cells. A signal for relapsed disease also is characterized by the appearance or reappearance of one or more CRAB criteria or a rapid and consistent biochemical relapse. Refractory myeloma is myeloma that is not responsive to treatment. Relapsed/refractory multiple myeloma refers to the disease which becomes non-responsive or progressive on therapy or within 60 days of the last treatment in patients who previously achieved at least a minimal response on previous therapy. Sonneveld, supra; Anderson et al., Leukemia. 2008; 22(2): 231-239.

The method of the disclosure comprises administering to the subject a dose of about 0.05 mg to about 200 mg of the heterodimeric antibody. The dose is, in various embodiments, about 0.5 mg to about 200 mg, about 0.5 to about 150 mg, about 1 mg to about 150 mg, about 10 mg to about 100 mg, about 10 mg to about 200 mg, about 4 mg to about 200 mg, about 12 mg to about 200 mg, about 12 mg to about 100 mg, about 36 mg to about 200 mg, about 36 mg to about 100 mg, or about 100 mg to about 200 mg. In various aspects of the method, the dose administered to the subject is about 0.05 mg, about 0.15 mg, about 0.45 mg, about 1.35 mg, about 4 mg, about 12 mg, about 36 mg, about 100 mg, or about 200 mg.

In alternative aspects, a single dose of heterodimeric antibody is at least about 0.05 mg, at least about 0.15 mg, at least about 0.45 mg, at least about 1.35 mg, at least about 4 mg, at least about 12 mg, at least about 36 mg, or at least about 100 mg. In various aspects, a single dose of heterodimeric antibody is no more than about 200 mg (e.g., no more than about 100 mg or no more than about 36 mg). It will be appreciated that a single dose may be administered via multiple administrations (i.e., a divided dose), such that the multiple administrations combine to the dose recited herein. For example, multiple administrations (e.g., two or more injections) combine to be at least about 0.05 mg, at least about 0.15 mg, at least about 0.45 mg, at least about 1.35 mg, at least about 4 mg, at least about 12 mg, at least about 36 mg, or at least about 100 mg. In various aspects, the multiple administrations of a single dose of heterodimeric antibody combine to be no more than about 200 mg (e.g., no more than about 100 mg or no more than about 36 mg).

In various aspects of the method, the dose is adjusted over the course of treatment. For example, the subject is administered an initial dose at one or more administrations, and a higher dose is used in one or more subsequent administrations. Put another way, the disclosure contemplates increasing the dose of heterodimeric antibody at least once over the course of treatment. Alternatively, the dose may be decreased over the course of treatment, such that amount of heterodimeric antibody is reduced as treatment progresses.

The disclosure contemplates a method wherein multiple (i.e., two or more) doses of the heterodimeric antibody are administered over the course of a treatment period. The individual doses may be administered at any interval, such as once a week, twice a week, three times a week, four times a week, or five times a week. Individual doses may be administered every two weeks, every three weeks, or every four weeks. In other words, in some aspects, a waiting period of at two weeks passes between heterodimeric antibody administrations to the subject. The waiting period between administrations of the doses need not be consistent over the course of the treatment period. In other words, the interval between doses can be adjusted over the course of treatment. In some aspects, the method comprises administering two doses of heterodimeric antibody per week to the subject in the first and second weeks of treatment (i.e., twice a week for weeks 1 and 2), administering one dose of heterodimeric antibody per week to the subject in the third and fourth weeks of treatment (i.e., once a week for weeks 3 and 4), and administering one dose of heterodimeric antibody every two weeks starting in week 5 through the end of treatment (i.e., there is a waiting period of two weeks between doses starting in week 5 through the end of treatment). While not wishing to be bound to any particular theory, the shorter interval between doses for the first administrations (e.g., two doses per week) promotes rapid target cell clearance. Increasing the interval between doses as set forth herein maintains cell clearance while minimizing unwanted side effects associated with immunotherapy.

Alternatively, in various aspects, the method comprises administering one dose of heterodimeric antibody per week for weeks 1~4 of treatment, and optionally administering one dose of the heterodimeric antibody every two weeks starting in week 5 through the end of treatment.

The multiple doses of heterodimeric antibody are administered over treatment period of, e.g., three months to about 18 months, or about three months to about 12 months, or about three months to about nine months, or about three months to about six months, or about three months to about eight months, or about six months to about 18 months, or about six months to about 12 months, or about eight months to about 12 months, or about six months to about eight months, or about eight months to about 12 months (e.g., about eight months). Optionally, the multiple (i.e., two or more) doses of the heterodimeric antibody are administered over a treatment period of about 12 weeks to about 52 weeks, or about 12 weeks to about 36 weeks, or about 24 weeks to about 32 weeks, with doses administered twice a week, once a week, once every two weeks, or once every four weeks.

By "treating" multiple myeloma is meant achievement of any positive therapeutic response with respect to the disease. For example, a positive therapeutic response includes one or more of the following improvements in the disease: (1) a reduction in the number of neoplastic cells; (2) an increase in neoplastic cell death; (3) inhibition of neoplastic cell survival; (4) reduction in paraprotein production by tumor cells; (5) inhibition (i.e., slowing to some extent, preferably halting) of tumor growth; (6) an increased patient survival rate; and (7) some relief from one or more symptoms associated with the disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation. A complete therapeutic response (i.e., absence of clinically detectable disease with normalization of any previously abnormal radiographic studies, bone marrow, and cerebrospinal fluid (CSF) or abnormal monoclonal protein) is not required; any degree of improvement is contemplated. Various additional parameters associated with disease treatment and improvement are set forth in the Examples.

The heterodimeric antibody may be administered via any suitable means to the subject, e.g., via intravenous, intraarterial, intralymphatic, intrathecal, intracerebral, intraperitoneal, intracerobrospinal, intradermal, subcutaneous, intraarticular, intrasynovial, oral, topical, or inhalation routes. For example, the heterodimeric antibody may be administered via intravenous administration as a bolus or by continuous infusion over a period of time. In various aspects, the method comprises administering the heterodimeric antibody via intravenous infusion over a period of about 30 minutes to about four hours. Optionally, the time for infusion is decreased in subsequent administrations. For example, in one embodiment, the first dose of heterodimeric antibody is administered over a period of about four hours, and subsequent doses are administered over a period of two hours or less. In this regard, the first dose of heterodimeric antibody is optionally administered over a period of about four hours, the second dose of heterodimeric antibody is optionally administered over a period of about two hours, and subsequent doses are optionally administered over a period of about 30 minutes.

In some instances, the subject has previously been treated for multiple myeloma. For example, the subject may have previously been administered an immunomodulatory drug (thalidomide, lenalidomide, pomalidomide), a proteasome inhibitor (such as pomalidomide, bortezomib, or carfilzomib), dexamethasone, doxorubicin, or combinations thereof.

Optionally, the subject was previously treated with an anti-CD38 monospecific antibody, such as daratumumab (DARZALEX®). In various embodiments, the subject is relapsed or refractory with prior anti-CD38 monospecific antibody treatment. When the patient has been treated with anti-CD38 monospecific antibody, the initial dose of the heterodimeric antibody is preferably administered following a wash-out period sufficient to reduce systemic concentration of the anti-CD38 monospecific antibody to 0.2 pg/ml or less. Put another way, the method comprises a waiting period between the previous administration of anti-CD38 monospecific antibody and administration of the heterodimeric antibody. In various embodiments, the method comprises ceasing treatment with the anti-CD38 monospecific antibody for at least 12 weeks (e.g., about 13 to about 15 weeks) prior to administering an initial dose of the heterodimeric antibody.

Co-Therapy

Optionally, the heterodimeric antibody is part of a therapeutic regimen that comprises administration of one or more other therapeutic agents, radiation therapy, stem cell transplantation, and the like.

The method of the disclosure optionally further comprises administering dexamethasone to the subject. The dexamethasone may be administered by any route, such as the routes described here. Preferably, the dexamethasone is administered intravenously or orally. When the dexamethasone is administered intravenously, it is optionally administered to the subject within one hour prior to administration of the heterodimeric antibody. The dexamethasone is optionally administered in an amount of about 8 mg or about 4 mg.

In various embodiments, the method of the disclosure further comprises administering a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib, CEP-18770, MG132, peptide vinyl sulfones, peptide epoxyketones (such as epoxomicin and carfilzomib), beta-lactone inhibitors (such as lactacystin, MLN 519, NPI-0052, Salinosporamide A), compounds that create dithiocarbamate complexes with metals (such as Disulfiram), and certain antioxidants (such as Epigallocatechin-3-gallate, catechin-3-gallate, and Salinosporamide A); NF-kB inhibitors, including inhibitors of IKB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

The therapeutic regimen may comprise administration of other antibody therapeutics, such as elotuzumab (a humanized monoclonal against SLAMF7; Tai et al., Blood, 2008; 112:1329-37); daratumumab, MOR202, and isatuximab that target CD38; nBT062-SMCC-DMI, nBT062-SPDB-DM4, and nBT062-SPP-DMI that target CD138; lucatumumab (also known as HCD122) and dacetuzumab (also known as SGN-40) that target CD40; Lorvotuzumab which targets CD56. For a review of antibody therapeutics for the treatment of multiple myeloma, see, e.g., Tandon et al., Oncology & Hematology Review, 2015; 11(2):115-21, and Sondergeld et al., Clinical Advances in Hematology & Oncology, 2015; 13(9), 599, both incorporated by reference.

In some embodiments, the heterodimeric antibody is administered prior to, concurrent with, or after treatment with Velcade® (bortezomib), Thalomid™ (thalidomide), Aredia™ (pamidronate), or Zometa™ (zoledronic acid).

All cited references are herein expressly incorporated by reference in their entirety. Whereas particular embodiments of the invention have been described above for purposes of illustration, it will be appreciated by those skilled in the art that numerous variations of the details may be made without departing from the invention as described in the appended claims.

FIGURES

FIG. 1. Blocking of the human CD47/human SIRPα interaction upon binding of anti-CD47-H2 Fab to human CD47 assessed by Octet Bio-Layer Interferometry. Biotinylated human CD47-avi-his protein was loaded on a streptavidin SA Biosensor. Anti-CD47-H2 Fab was injected over immobilized human CD47 at 1 µM in kinetic buffer to reach saturation of the surface. Then, a pre-mixed solution of anti-CD47 Fab at 1 µM and human SIRPα at 2 µM final concentration was injected over saturated surface. Plot shows binding to the sensor tip as a wavelength shift (in nm; Y axis) vs. time (X axis). Curves are labelled by Fab clone name.

Figure 2:
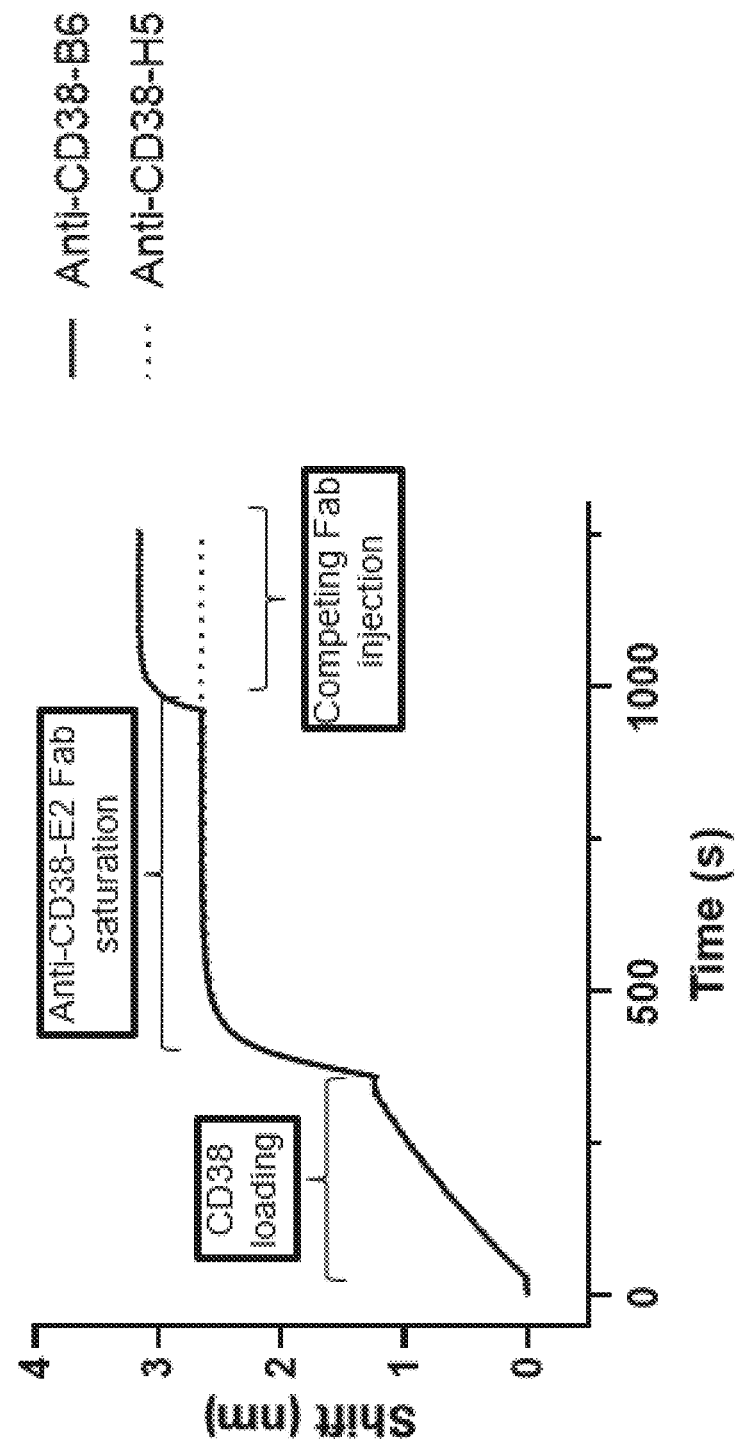

FIG. 2. Epitope binning of anti-CD38-E2 and anti-CD38-B6 clones to human CD38 using Octet Bio-Layer Interferometry Biotinylated human CD38-avi-his protein was loaded on a streptavidin SA Biosensor. Anti-CD38-E2 Fab was injected over immobilized human CD38 at 200 nM in kinetic buffer to reach saturation of the surface. Then, a pre-mixed solution of anti-CD38-E2 Fab and anti-CD38-B6 Fab at 200 nM final concentration each was injected over saturated surface. Same experimental procedure was performed using anti-CD38-H5 Fab instead of anti-CD38-B6 Fab, as competing control. Plot shows binding to the sensor tip as a wavelength shift (in nm; Y axis) vs. time (X axis). Curves are labelled by competing Fab clone name.

Figure 3:
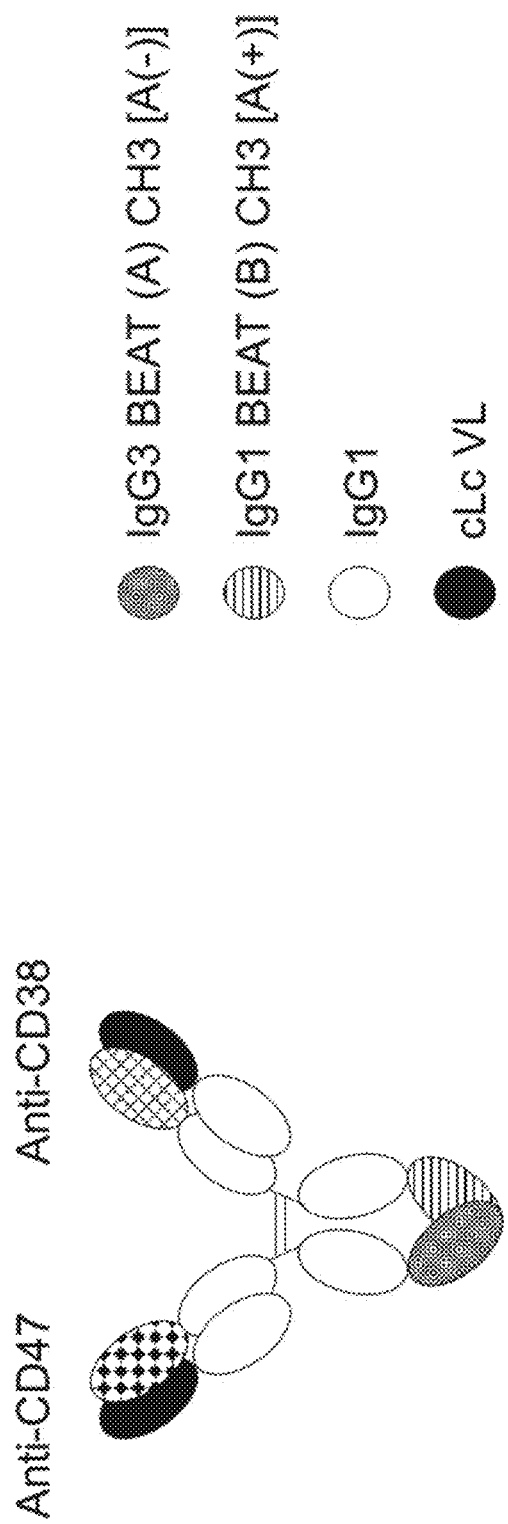

FIG. 3. Schematic drawing of a BEAT CD38/CD47 bispecific antibody. A(−) means no PA binding site while A(+) means a PA binding site is present.

Figure 4:
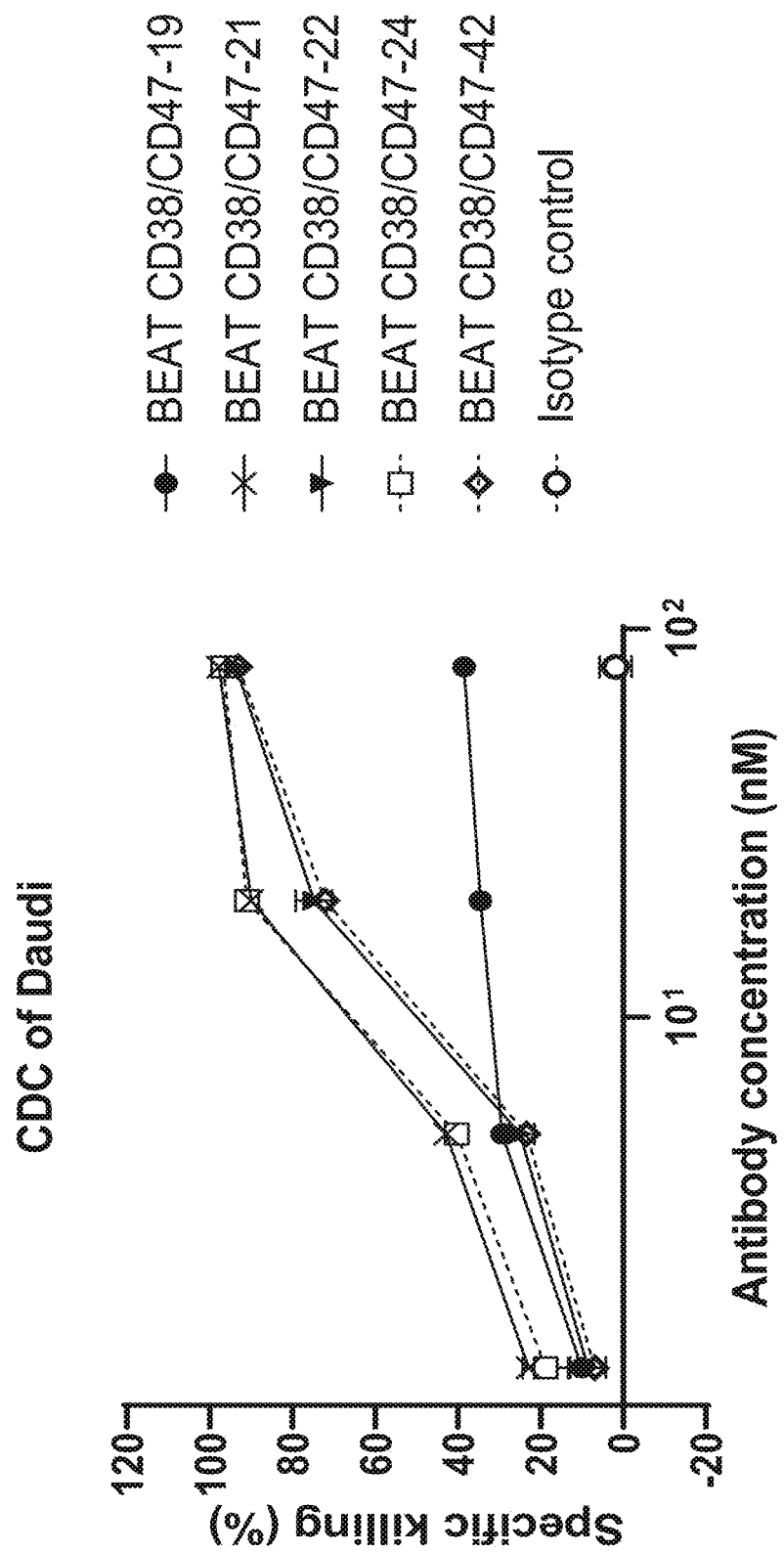

FIG. 4. CDC assay on Daudi cells comparing Fc engineered variants to the non-enhanced control.

Figure 5:
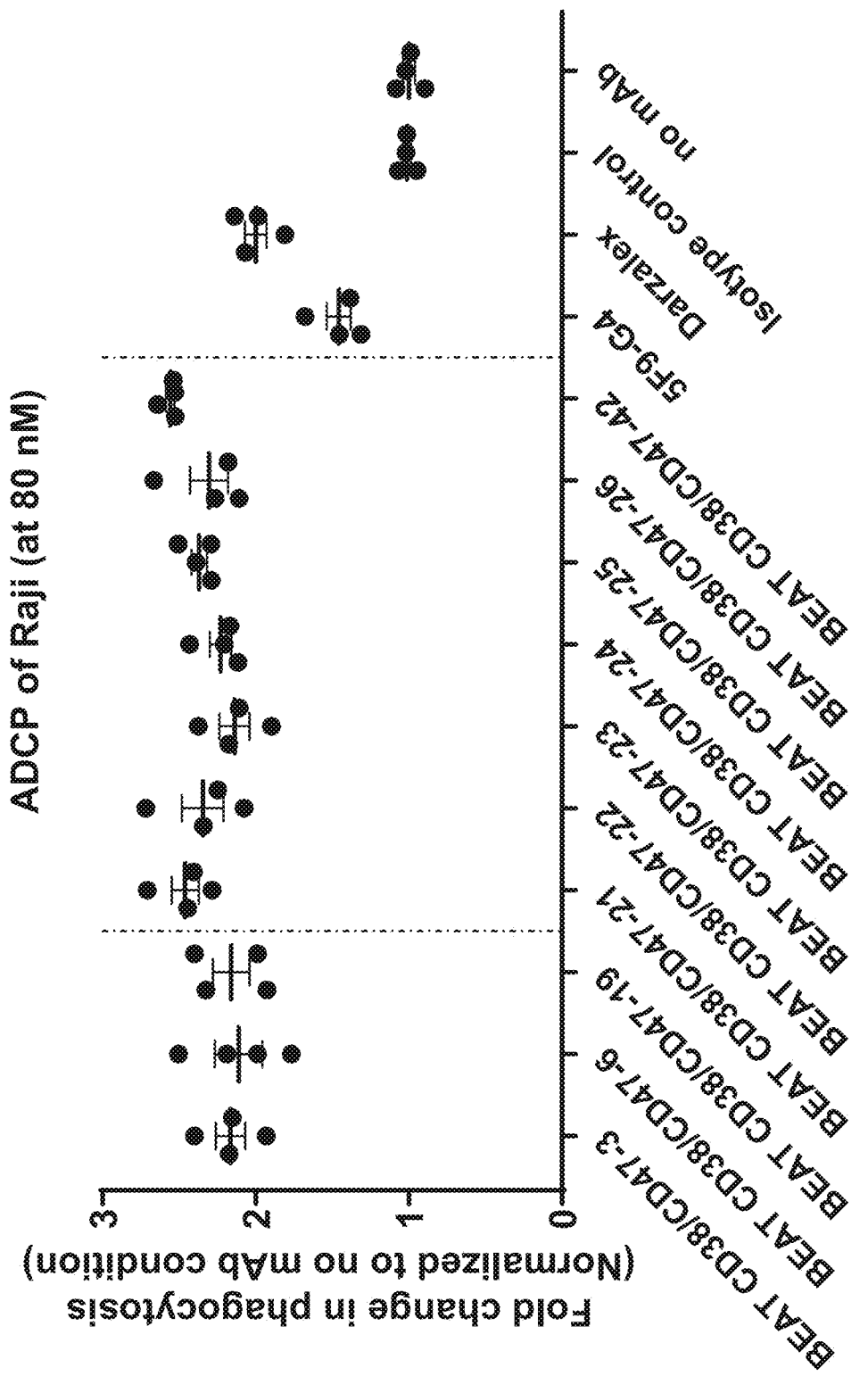

FIG. 5. ADCP assay on Raji cells comparing Fc engineered variants to the non-enhanced control. A horizontal line is drawn through the average fold change in phagocytosis for non-enhanced BEAT CD38/CD47-19 to visualize the impact of Fc engineering on ADCP potency.

Figure 6:
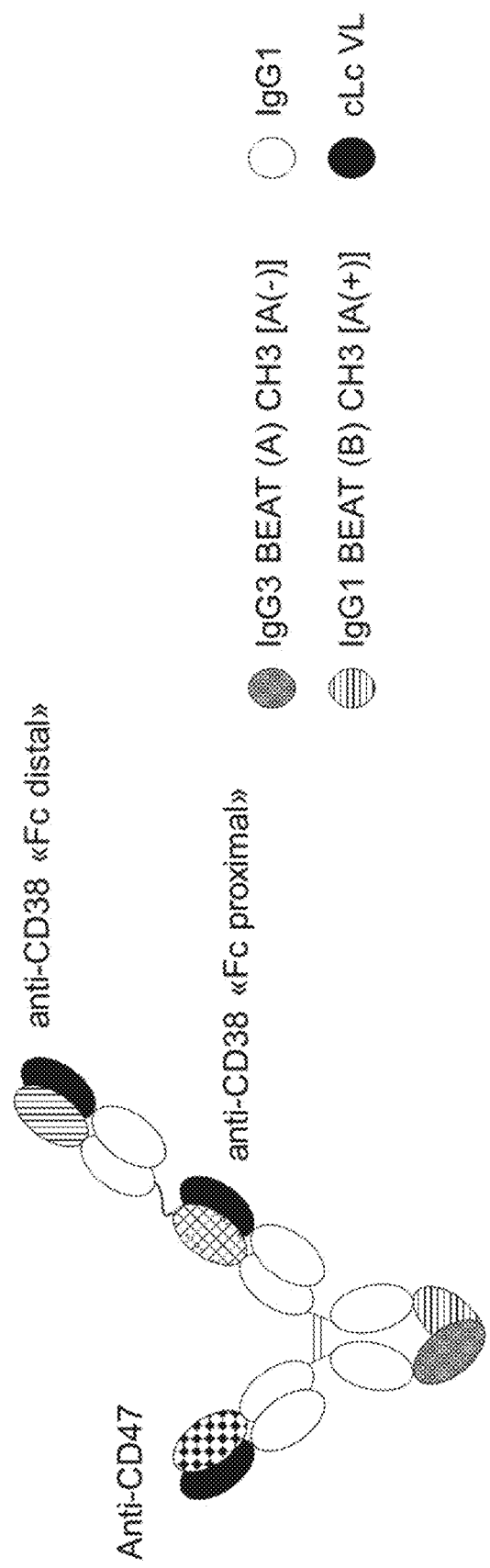

FIG. 6. Schematic drawing of a "2+1" BEAT CD38/CD47 bispecific antibody. "2+1" BEAT bispecific antibodies were engineered analogously to those in the "1+1" format. The "Fc distal" anti-CD38 Fab domain was fused to the N-terminus of the VH domain of the "Fc proximal" anti-CD38 Fab.

Figure 7:
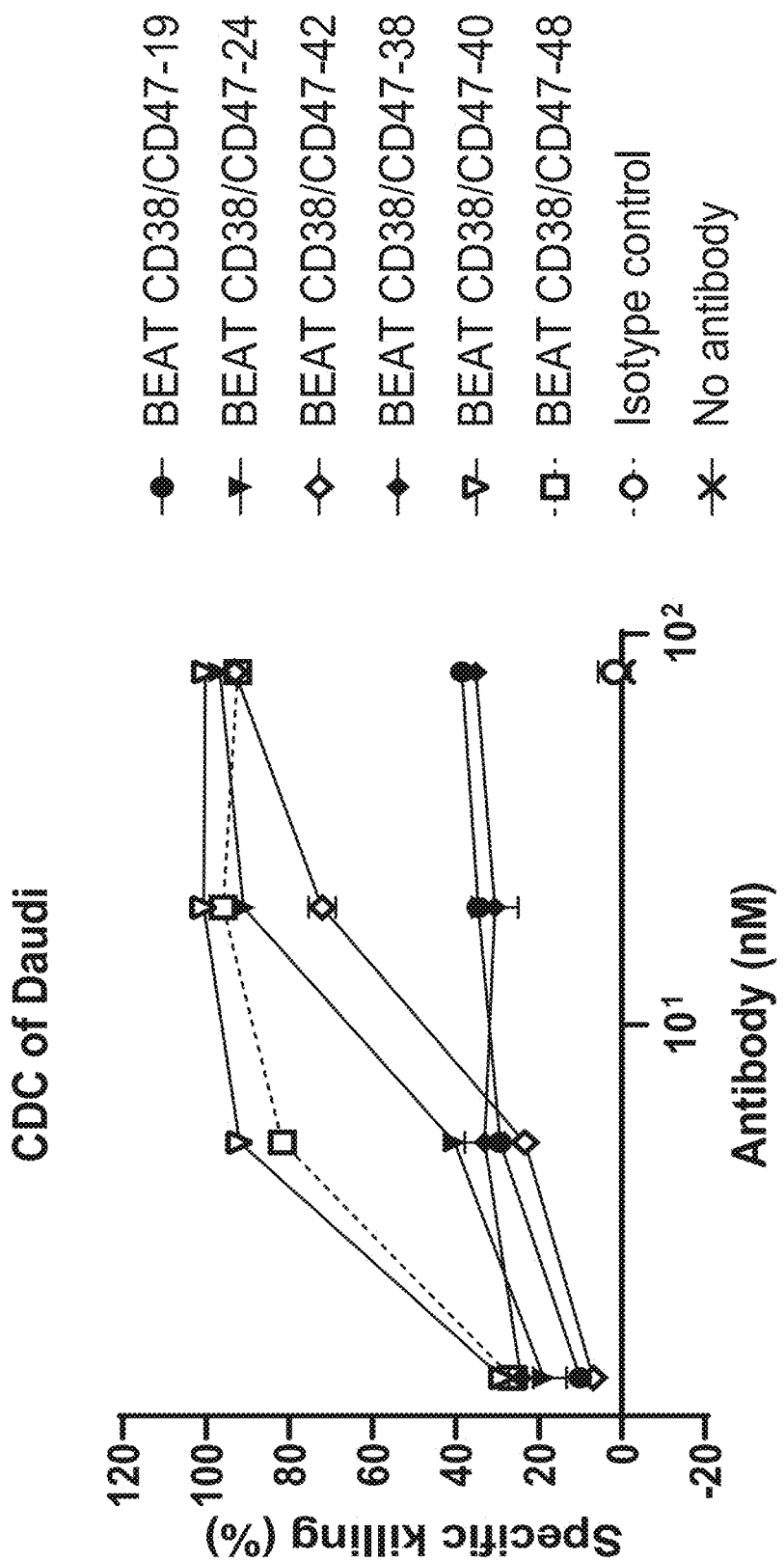

FIG. 7. CDC assay on Daudi cells comparing CD38/CD47 BEAT antibodies in the "2+1" and "1+1" formats.

Figure 8:
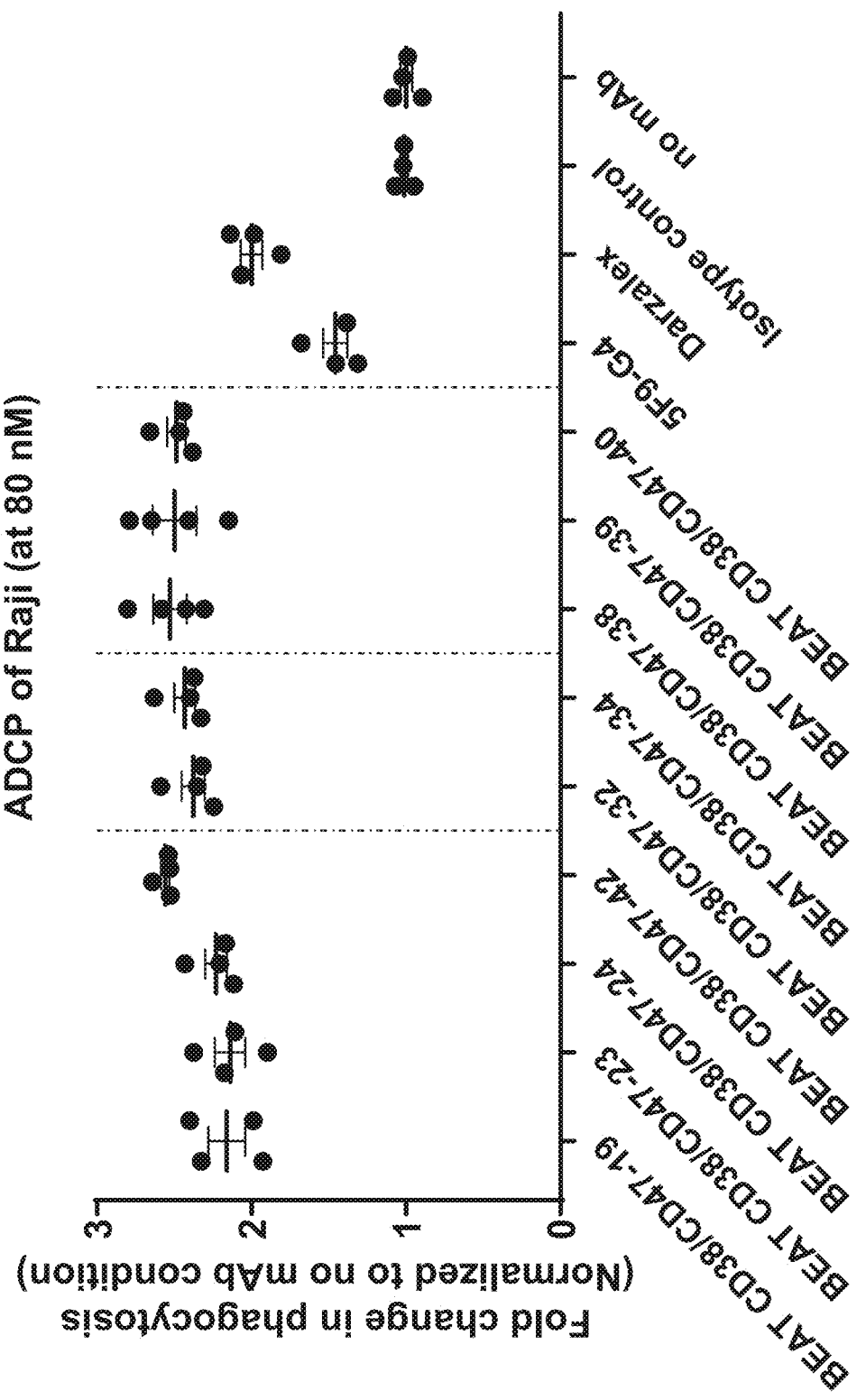

FIG. 8. ADCP assay on Raji cells comparing CD38/CD47 BEAT antibodies in the "2+1" and "1+1" formats. A horizontal line is drawn through the average fold change in phagocytosis for non-enhanced "1+1" BEAT CD38/CD47-19 to visualize the impact of the "2+1" format and Fc engineering on ADCP potency.

FIG. 9. (A) CDC assay comparing BEAT CD38/CD47-42, -48 and -60. FIG. 9. (B) ADCC assay comparing BEAT CD38/CD47-42, -48, and -60. FIG. 9. (C) ADCP assay comparing BEAT CD38/CD47-42, -48, and -60.

FIG. 10. (A) Thermostability analysis of CD38/CD47-42 bispecific antibodies by DSC. FIG. 10. (B) Thermostability analysis of BEAT CD38/CD47-48 bispecific antibodies by DSC. FIG. 10. (C) Thermostability analysis of BEAT CD38/CD47-60 bispecific antibodies by DSC.

FIG. 11. (A) Binding of BEAT CD38/47-48 and 60 was evaluated by flow cytometry on a panel of Daudi cells. FIG. 11. (B) Binding of BEAT CD38/47-48 and 60 was evaluated by flow cytometry on Raji cells. FIG. 11. (C) Binding of BEAT CD38/47-48 and 60 was evaluated by flow cytometry on a panel of multiple myeloma cells, KMS-12-PE. FIG. 11. (D) Binding of BEAT CD38/47-48 and 60 was evaluated by flow cytometry on a panel of multiple NCI-H929 cells. FIG. 11. (E) Binding of BEAT CD38/47-48 and 60 was evaluated by flow cytometry on a panel of multiple KMS-12-BM cells. BEAT CD38/47-48 and BEAT CD38/47-60 show superior dose dependent binding to tumor cell lines with different level of CD38 and CD47 expression as compared to benchmarks.

FIG. 12. (A) BEAT CD38/47-48 and BEAT CD38/47-60 block CD47/SIRPα interaction comparable to high affinity anti-CD47 antibody benchmark, isotype control background displayed as a dotted line. FIG. 12. (B) Cumulative analysis of Maximal CD47/SIRPα inhibition. FIG. 12. (C) Cumulative analysis of EC50.

FIG. 13. (A) ADCP assay performed with CD38$^{high}$ (Daudi) tumor cells. Mean of duplicates +/−Standard Deviations (SD). FIG. 13. (B) Cumulative analysis of Maximum phagocytosis in multiple experiments with Daudi tumor cells. FIG. 13. (C) Cumulative analysis of EC50 in multiple experiments with Daudi tumor cells. FIG. 13. (D) ADCP assay performed with CD38$^{low}$ (KMS12-BM) tumor cells. Mean of duplicates+1-Standard Deviations (SD). FIG. 13. (E) Cumulative analysis of Maximum phagocytosis in multiple experiments with KMS12-BM tumor cells. FIG. 13. (F) Cumulative analysis of EC50 in multiple experiments with KMS12-BM tumor cells. Mean of n=9 experiments +/−SD is represented. When killing curves do not reach comparable maximal level, comparing EC50 is not applicable (NA).

FIG. 14. (A) Schematic of molecules structures and Fab arms affinities. FIG. 14. (B) Cumulative analysis of Maximum phagocytosis in multiple experiments of KMS12-BM tumor cells. FIG. 14. (C) Cumulative analysis of EC50 in multiple experiments of KMS12-BM tumor cells. Mean of n=7 experiments +/−SD is represented.

FIG. 15. (A) CDC assay performed with CD38$^{high}$ expressing tumor cells (Daudi). Mean of duplicates is represented here +/−Standard Deviations (SD). FIG. 15. (B) Cumulative analysis of Maximum killing in multiple experiments. FIG. 15. (C) Cumulative analysis of EC50 in multiple experiments. Mean of n=5 experiments +/−SD is represented. When killing curves do not reach comparable maximal level, comparing EC50 is not applicable (NA).

FIG. 16. (A) ADCC assay performed with CD38$^{high}$ (Raji) tumor cells. Mean of duplicates+/−Standard Deviations (SD). FIG. 16. (B) Cumulative analysis of ADCC Maximum killing in multiple +---experiments in Raji tumor cells. FIG. 16. (C) Cumulative analysis of ADCC EC50 in multiple experiments in Raji tumor cells. FIG. 16. (D) ADCC assay performed with CD38$^{low-int}$ (NCI-H929) tumor cells. FIG. 16. (E) Cumulative analysis of ADCC Maximum killing in multiple experiments in NCI-H929 tumor cells. FIG. 16. (F) Cumulative analysis of ADCC EC50 in multiple experiments in NCI-H929 tumor cells. Mean of n=3 experiments +/−SD is represented. When killing curves do not reach comparable maximal level, comparing EC50 is not applicable (NA).

FIG. 17. (A) Schematic of an MMoAK assay performed with CD38$^{low-int}$ (NCI-H929) tumor cells. ADCC=antibody dependent cell cytotoxicity; ADCP=antibody dependent cell phagocytosis; CDC=complement dependent cytotoxicity. FIG. 17. (B) A representative curve of tumor cell killing by MMoAK. Mean of duplicates+/−Standard Deviations (SD). FIG. 17. (C) Cumulative analysis of Maximal killing in multiple experiments using CD38$^{low-int}$ (NCI-H929) as target cells. FIG. 17. (D) Cumulative analysis of EC50 in multiple experiments using CD38$^{low-int}$ (NCI-H929) as target cells. Mean of n=9 experiments +/−SD is represented. When killing curves do not reach comparable maximal level, comparing EC50 is not applicable (NA).

FIG. 18. (A) Cumulative analysis of Maximal killing in an MMoAK assay performed in multiple experiments using CD38$^{low-int}$ (NCI-H929) in the presence of 5 million/ml of RBCs as antigen sink. FIG. 18. (B) Cumulative analysis of Maximal killing in multiple experiments using CD38$^{low-int}$ (NCI-H929) in the presence of 5 million/ml of 2.8 ng/ml of sCD38 as antigen sink. FIG. 18. (C) Cumulative analysis of EC50 in multiple experiments using CD38$^{low-low}$ (NCI-H929) in the presence of 5 million/ml of RBCs as antigen sink. FIG. 18. (D) Cumulative analysis of EC50 in multiple experiments using CD38$^{low-int}$ (NCI-H929) in the presence of 5 million/ml of 2.8 ng/ml of sCD38 as antigen sink. Mean of n=3-5 experiments +/−SD is represented. Statistics: paired T-test. NS=not significant RBCs=Red Blood Cells; sCD38=soluble CD38.

FIG. 19. (A) Representative curve of MMoAK assay performed with CD38$^{low-int}$ (NCI-H929) tumor cells. FIG. 19. (B) Cumulative analysis of EC50 in multiple experiments. FIG. 19. (C) Maximum killing in multiple experiments. When killing curves do not reach comparable maximal level, comparing EC50 is not applicable (NA).

FIG. 20. (A) Representative experiment showing binding of Darzalex (AF647 conjugated in Raji-CD47KO cells. FIG. 20. (B) Representative experiment showing binding of BEAT 38/47-60 (AF488 conjugated) in Raji-CD47KO cells. FIG. 20. (C) Representative experiment showing binding of a mix of conjugated Darzalex and BEAT 38/47-60 in Raji-CD47KO cells. FIG. 20. (D) Percentage of competition with BEAT 38/47-60 (AF488 conjugated) mediated by Control antibody (Cntrl IgG1), Darzalex or BEAT 38/47-60 purified antibodies in Raji-CD47KO cells.

FIG. 21. (A) ADCP assay performed with $CD38^{high}$ (Daudi) tumor cells. FIG. 21. (B) Cumulative analysis of EC50 in multiple experiments with Daudi tumor cells. FIG. 21. (C) Cumulative analysis of Maximum phagocytosis in multiple experiments with Daudi tumor cells. FIG. 21. (D) ADCP assay performed with $CD38^{low}$ (KMS12-BM) tumor cells. FIG. 21. (E) Cumulative analyses of EC50 in multiple experiments with KMS12-BM tumor cells. FIG. 21. (F) Cumulative analysis of Maximum phagocytosis in multiple experiments with KMS12-BM tumor cells. FIG. 21. (G) ADCC assay performed with $CD38^{high}$ (Raji) tumor cells. FIG. 21. (H) Cumulative analysis of EC50 in multiple experiments with Raji tumor cells. FIG. 21. (I) Cumulative analysis of Maximum killing in multiple experiments with Raji tumor cells. FIG. 21. (J) ADCC assay performed with $CD38^{low-int}$ (NCI-H929) tumor cells. FIG. 21. (K) Cumulative analysis of EC50 in multiple experiments with NCI-H929 tumor cells. FIG. 21. (L) Cumulative analysis of Maximum killing in multiple experiments with NCI-H929 tumor cells. FIG. 21. (M) CDC assay performed with $CD38^{high}$ expressing tumor cells (Daudi). FIG. 21. (N) Cumulative analysis of EC50 in multiple experiments with Daudi tumor cells. FIG. 21. (O) Cumulative analysis of Maximum killing in multiple experiments with Daudi tumor cells. Mean of duplicates is represented in all representative curves graphs +/−Standard Deviations.

FIG. 22. (A) Representative nonlinear sigmoidal regression binding curves (Relative Geometric Mean Fluorescence Intensity) in human healthy donor RBCs analyzed by flow cytometry (n=6). FIG. 22. (B) Hemagglutination as measured by Coombs assay (n=6). Extent of agglutination was scored after centrifugation from 0 (no agglutination) to 4 (complete agglutination). FIG. 22. (C) Induction of RBCs depletion evaluated in-house using a hematology analyzer (Sigma 5H). FIG. 22. (D) Hemolysis quantified by measuring the absorbance of hemoglobin in plasma at 414 nm using spectrometry. Results were normalized in GraphPad Prism software to no antibody treatment condition (negative control) and triton X-100 (positive control). FIG. 22. (E) Platelet aggregation relative to LeoA1 positive control analyzed by flow cytometry.

FIG. 23. (A) Representative nonlinear sigmoidal regression binding curves (Relative Geometric Mean Fluorescence Intensity) in human healthy donor analyzed by flow cytometry upon gating of cell types as CD8+ T cells. FIG. 23. (B) Representative nonlinear sigmoidal regression binding curves (Relative Geometric Mean Fluorescence Intensity) in human healthy donor analyzed by flow cytometry upon gating of cell types as CD4+ T cells. FIG. 23. (C) Representative nonlinear sigmoidal regression binding curves (Relative Geometric Mean Fluorescence Intensity) in human healthy donor analyzed by flow cytometry upon gating of cell types as B cells. FIG. 23. (D) Representative nonlinear sigmoidal regression binding curves (Relative Geometric Mean Fluorescence Intensity) in human healthy donor analyzed by flow cytometry upon gating of cell types as Granulocytes. FIG. 23. (E) Representative nonlinear sigmoidal regression binding curves (Relative Geometric Mean Fluorescence Intensity) in human healthy donor analyzed by flow cytometry upon gating of cell types as Myeloid cells. Binding was evaluated on six different donors.

FIG. 24. (A) Tumor growth (+/−SEM) over time in mice xenografted subcutaneously with Raji tumors (n=5 mice/group) and treated with PBS (black), BEAT CD38/47-48 at 10 mg/kg (dark grey), BEAT CD38/47-48 at 1 mg/kg (grey), BEAT CD38/47-48 at 0.1 mg/kg (light grey). Treatments were administered when tumor reached around 100 mm3. FIG. 24. (B) Tumor volume (+/−SEM) at day 27. Raj_9 study.

FIG. 25. (A) Tumor growth (+/−SEM) over time in mice xenografted subcutaneously with Raji tumors (n=5 mice/group) and treated with PBS (black), BEAT CD38/47-60 at 10 mg/kg (dark grey), BEAT CD38/47-60 at 1 mg/kg (grey), BEAT CD38/47-60 at 0.1 mg/kg (light grey). Treatments were administered when tumor reached around 100 mm3. FIG. 25. (B) Tumor volume (+/−SEM) at day 27. Raj_9 study.

FIG. 26. (A) Tumor growth (+/−SEM) over time in mice xenografted subcutaneously with Raji tumors (n=10 mice/group; 5 mice were used for ex vivo studies after day 15) and treated with PBS (black), BEAT CD38/47-48 at 10 mg/kg (dark grey), BEAT CD38/47-59 at 10 mg/kg (grey) and Darzalex (square-dotted lines). Treatments were administered when tumor reached around 100 mm3. FIG. 26. (B) Tumor volume (+/−SEM) at day 36. Statistical analysis performed: one-way analysis of variance (ANOVA) followed by Dunnett's post hoc for multiple comparisons. $P<0.05$ was considered as statistically significant. Level of significance is represented by asterisks. Raj_10 study.

FIG. 27. (A) Tumor growth (+/−SEM) over time in mice xenografted subcutaneously with Raji tumors (n=10 mice/group; 5 mice were used for ex vivo studies after day 15) and treated with PBS (black), BEAT CD38/47-60 at 10 mg/kg (dark grey), BEAT CD38/47-79 at 10 mg/kg (grey) and Darzalex (square-dotted lines). Treatments were administered when tumor reached around 100 mm3. FIG. 27. (B) Tumor volume (+/−SEM) at day 36. Statistical analysis performed: one-way analysis of variance (ANOVA) followed by Dunnett's post hoc for multiple comparisons. $P<0.05$ was considered as statistically significant. Level of significance is represented by asterisks. Raj_10 study.

FIG. 28. (A) Tumor growth (+/−SEM) over time in mice xenografted subcutaneously with Raji tumors (n=10 mice/group; 5 mice were used for ex vivo studies after day 15) and treated with PBS (black), BEAT CD38/47-48 at 10 mg/kg (dark grey), BEAT CD38/47-60 at 10 mg/kg (grey) and Darzalex (square-dotted lines). Treatments were administered when tumor reached around 100 mm3. FIG. 28. (B) Tumor volume (+/−SEM) at day 36. Statistical analysis performed: one-way analysis of variance (ANOVA) followed by Dunnett's post hoc for multiple comparisons. $P<0.05$ was considered as statistically significant. Level of significance is represented by asterisks. Raj_10 study.

FIG. 29. (A) IL-1b levels in tumors. 16 days after the xenograft, 5 animals per group were sacrificed. Mice serum and tumors were harvested and analyzed ex vivo by Luminex. BEAT CD38/CD47-48 and BEAT CD38/CD47-60 showed a trend of IL-1b decrease level in the tumors. FIG. 29. (B) MHCII+macrophages in tumors harvested and analyzed ex vivo by FACS. BEAT CD38/CD47-60 showed a significant decrease of MHCII+macrophages in the tumors. Statistical analysis performed: one-way analysis of variance (ANOVA) followed by Dunnett's post hoc for multiple comparisons. P<0.05 was considered as statistically significant. Level of significance is represented by asterisks. Raj_10 study.

Figure 30A:
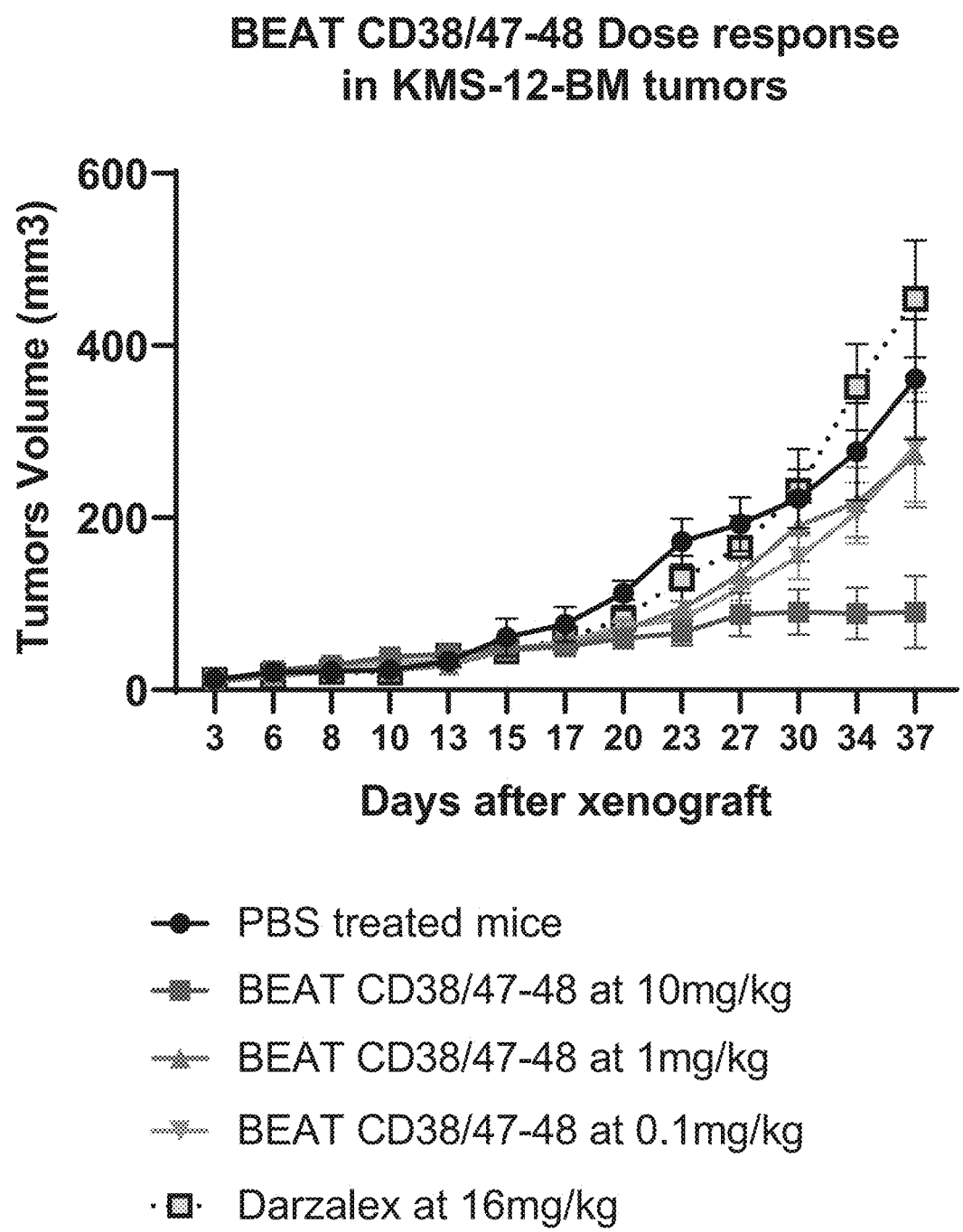

FIG. 30. (A) Tumor growth (+/−SEM) over time in mice xenografted subcutaneously with KMS-12-BM tumors (n=5 mice/group) and treated with PBS (black), BEAT CD38/47-48 at 10 mg/kg (dark grey), BEAT CD38/47-48 at 1 mg/kg (grey), BEAT CD38/47-48 at 0.1 mg/kg (light grey) and Darzalex (square-dotted lines). Treatments were administered when tumor reached around 100 mm3. FIG. 30. (B) Tumor growth since randomization (ΔT) (+/−SEM) at day 37. Statistical analysis performed: one-way analysis of variance (ANOVA) followed by Dunnett's post hoc for multiple comparisons. P<0.05 was considered as statistically significant. Level of significance is represented by asterisks. KMS_7 study.

Figure 31A:
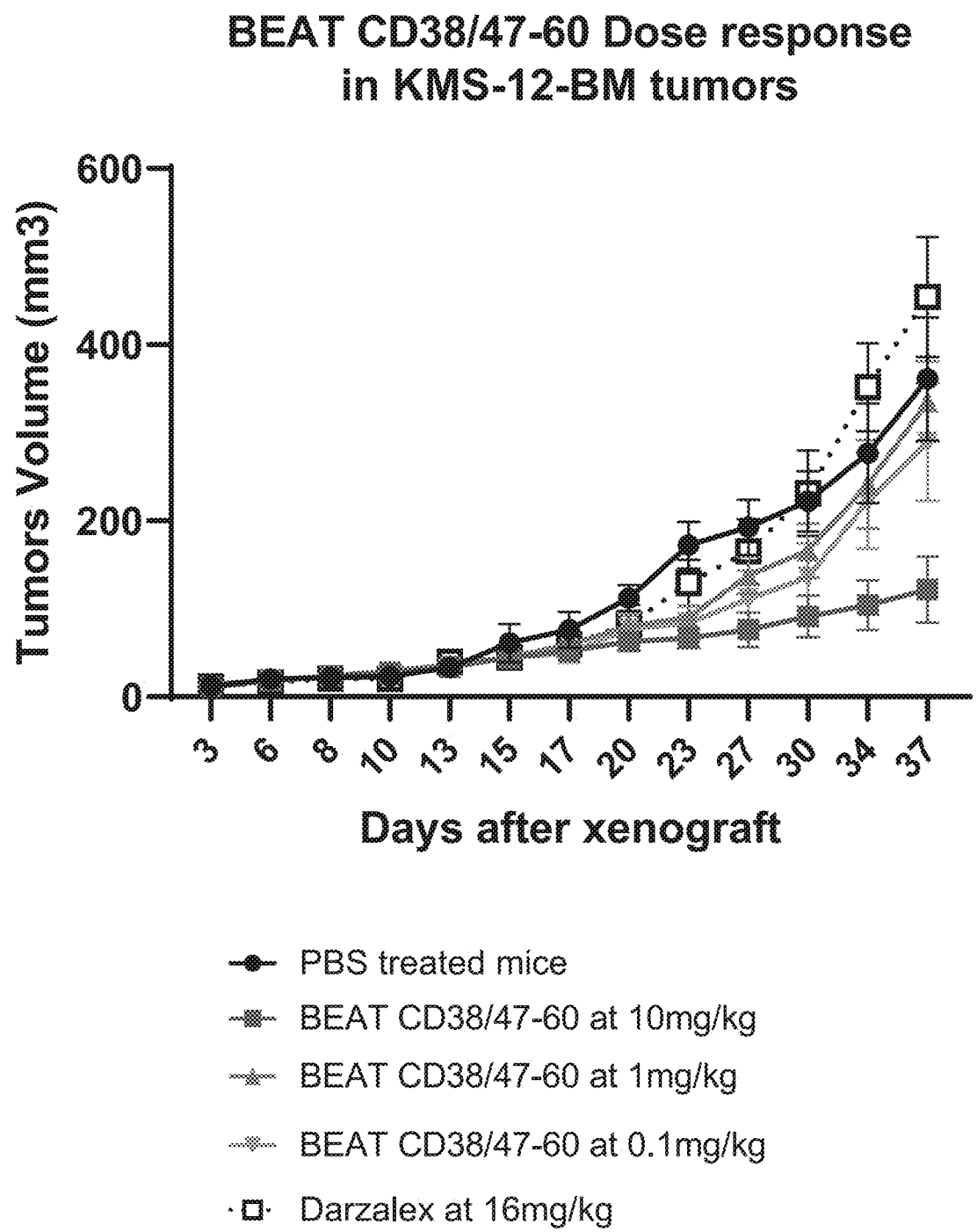

FIG. 31. (A) Tumor growth (+/−SEM) over time in mice xenografted subcutaneously with KMS-12-BM tumors (n=5 mice/group) and treated with PBS (black), BEAT CD38/47-60 at 10 mg/kg (dark grey), BEAT CD38/47-60 at 1 mg/kg (grey), BEAT CD38/47-60 at 0.1 mg/kg (light grey) and Darzalex (square-dotted lines). Treatments were administered when tumor reached around 100 mm3. FIG. 31. (B) Tumor growth since randomization (ΔT) (+/−SEM) at day 37. Statistical analysis performed: one-way analysis of variance (ANOVA) followed by Dunnett's post hoc for multiple comparisons. P<0.05 was considered as statistically significant. Level of significance is represented by asterisks. KMS_7 study.

EXAMPLE 1: GENERATION OF ANTI-CD47 ANTIBODIES

Material and Methods

Recombinant Antigens

Human codon-optimized sequences encoding the full-length human CD47 (UniProt accession no: 008722; SEQ ID NO: 7) and full-length cynomolgus monkey CD47 (accession no: A0A2K5x412, SEQ ID NO: 8) were synthetized by Twist Biosciences (San Francisco, USA). The soluble extracellular regions of human CD47 (residues 19 to 141; SEQ ID NO: 3) and cynomolgus monkey CD47 (residues 19 to 141; SEQ ID NO: 4) were cloned in a modified pcDNA™3.1 plasmid (ThermoFisher Scientific, catalog NO: V79020) to generate a protein with a C-terminal Avitag™ (Avidity LLC) followed by a 10-His tag with a Gly$_3$ linker sequence between the two tags (abbreviated human CD47-ECD-Avi-His and cynomolgus CD47-ECD-Avi-His). For both human and cynomolgus monkey proteins, the cysteine located at position 33 was mutated to a serine in order to prevent multimerization. The expression vector was carrying the murine VJ2C leader peptide to drive product secretion as well as the OriP sequence. For protein expression, the plasmids coding for human CD47-ECD-Avi-His and cynomolgus CD47-ECD-Avi-His (residues 19 to 141; SEQ ID NO: 3 and SEQ ID NO: 4, respectively) and a non-coding plasmid were co-transfected into suspension-adapted HEK293-EBNA cells (ATCC-LGL standards; Cat. No: CRL-10852) using Polyethyleneimine (PEI; Polysciences). Briefly, cells were prepared at 8 million cells per ml in RPMI 1640 (Biowest) supplemented with 0.1% Pluronic F-68 (Gibco). Cells were then transfected with a DNA-PEI mixture at 37° C. Four hours post-transfection, the cell culture was diluted 1:1 in EX-CELL® 293 (Sigma Aldrich) supplemented with Phenol Red and 4 mM L-Glutamine and incubated for 5 days with orbital shaking at 37° C., 5% CO2 and 80% humidity. Post-expression, clarified supernatants were prepared by centrifugation and filtration, pH was adjusted at 7.4 (4° C.) using 1 M sodium hydroxide. Ni-Sepharose Excell beads (GE Healthcare) were added to the clarified supernatant and incubated overnight at 4° C. under gentle agitation. Next, the mixtures were loaded on Econo-Columns (Bio-Rad Laboratories) for gravity-flow purification. The beads were first washed in 1×PBS, pH 7.4 (10 CV), then 1×PBS supplemented with 20 mM imidazole (10 CV) and the proteins were eluted, either with a single elution step at 500 mM imidazole (9×1 CV) or following a step-elution protocol using, sequentially, 1×PBS, pH 7.4 supplemented with 40 mM (9×1 CV), 80 mM (11×1 CV), 250 mM (5×1 CV) and 500 mM (3×1 CV) imidazole. Fractions were pooled and dialyzed twice against 1×PBS, pH 7.4 at 4° C. Protein quality was assessed by SDS-PAGE, SE-HPLC, endotoxin measurement and SPR as described above. Human and cynomolgus monkey CD47-ECD-Avi-His tagged fusion proteins as described herein have SEQ ID NO: 3 and 4, respectively.

Human codon-optimized sequence encoding the full-length human SIRPα (UniProt accession no: P78324-2) was synthetized by Twist Bioscience. The soluble extracellular regions of human SIRPα (residues 31 to 352; SEQ ID NO: 9) was cloned in a modified pcDNA™3.1 plasmid (ThermoFisher Scientific, catalog NO: V79020) to generate a protein with a C-terminal Avitag™ (Avidity LLC) followed by a 10-His tag with a Gly$_3$ linker sequence between the two tags (abbreviated human SIRPα-ECD-Avi-His). The expression vector was carrying the murine VJ2C leader peptide to drive product secretion as well as the OriP sequence. For protein expression, the plasmids coding for human SIRPα-ECD-Avi-His (residues 31 to 352; SEQ ID NO: 9) and a non-coding plasmid were co-transfected into suspension-adapted HEK293-EBNA cells (ATCC-LGL standards; Cat. No: CRL-10852) using Polyethyleneimine (PEI; Polysciences) as described above. Post expression, Ni-Sepharose Excell beads (GE Healthcare) were added to the clarified supernatant and incubated overnight at 4° C. under gentle agitation. Next, the mixtures were loaded on Econo-Columns (Bio-Rad Laboratories) for gravity-flow purification. The beads were first washed in 1×PBS, pH 7.4 (10 CV), then 1×PBS supplemented with 20 mM imidazole (10 CV) and the proteins were eluted with a single elution step at 500 mM imidazole (6×2 CV). Buffer exchange to 1×PBS, pH 7.4 was performed on PD-10 columns (GE). Protein quality was assessed by SDS-PAGE, SE-HPLC, endotoxin measurement and SPR as described above. Human SIRPα-ECD-Avi-His tagged fusion proteins as described herein have SEQ ID NO: 9.

Recombinant Cell Lines

The human codon-optimized sequences of the full-length human CD47 (UniProt sequence ID 008722; residues 1-323; SEQ ID NO: 7) and full-length cynomolgus monkey CD47 (accession number A0A2K5x412; residues 1-323; SEQ ID NO: 8) were cloned in a modified pcDNA™3.1 plasmid (ThermoFisher Scientific, catalog NO: V79020). The vector also contained the enhanced Green Fluorescent Protein (eGFP) and puromycin resistance genes (with intercalated intraribosomal entry sites (IRES) elements). For protein expression, the aforementioned plasmids were transfected into suspension-adapted CHO-S cells (cGMP banked, Invitrogen, Cat.-NO:A1136401) using Polyethyleneimine (PEI; Polysciences). Briefly, cells were prepared at 2 million cells per ml in CD CHO (Gibco). Cells were then transfected with a DNA-PEI mixture at 37° C. Four hours post-transfection, the cell culture was diluted 1:1 PowerCHO 2 (Lonza) supplemented with 4 mM L-Glutamine and incubated with orbital shaking at 37° C., 5% CO2 and 80% humidity. The expression of the target antigens was assessed by monitoring the expression of the eGFP reporter protein with a fluorescence microscope. Human and cynomolgus monkey CD47 proteins as described herein have SEQ ID NO: 7 and 8, respectively.

Library Generation

The library used herein was from synthetic origin with a diversity restricted to the heavy chain (CDR-H1, CDR-H2 and CDR-H3) and a fixed VK3-15/JK1 light chain (SEQ ID NO: 10). The library contained 4 different sub libraries based on VH1-69, VH3-23, VH3-15 and VH3-53 antibody germlines. CDRs have been randomized using Trimer oligonucleotides. Primers used for diversifying CDR-H1 and CDR-H2 were designed for each sub libraries and encoded germline-specific naturally occurring diversity at Kabat residues 27-35 and 50-58, respectively. CDR-H3 has been randomized using a pool of oligonucleotides encoding 15 CDR-H3 lengths (6-20) and length-specific naturally occurring diversity at Kabat residues 95-102. Diversified scFv fragments have been pooled to mimic natural CDR-H3 length distribution and cloned into the pNGLEN (in-house modified pUC119 phagemid vector) and the resulting ligation reaction electroporated into *E. coli* TG1 cells. Each sub-library had diversity between $1.2 \times 10^{10}$ and $1.7 \times 10^{10}$, the four sub-libraries reached a total diversity of $5.6 \times 10^{10}$.

Library Selection

Each sub-library were either selected individually or as a pool. The first panning strategy consisted in two rounds of selection using recombinant human CD47 protein followed by 2 rounds using cynomolgus monkey CD47-expressing CHO cells. The second panning strategy consisted in one round of selection using recombinant human CD47 protein followed by 3 rounds using human CD47-expressing CHO cells. The third panning strategy consisted in one round of selection using human CD47-expressing CHO cells followed by 3 rounds using recombinant human CD47 protein.

For the panning strategies using recombinant proteins, purified phage particles ($10^{12}$ plaque-forming units) and magnetic Dynabeads™ MyOne™ Streptavidin C1 beads (Invitrogen, catalog NO: 65002) were blocked with phosphate buffered saline (PBS) containing 3% (w/v) skimmed milk (3% MPBS) for 1 h at room temperature (RT). Phages were deselected against pre-blocked beads for 1 h at RT. Deselected phages were incubated with 100 nM of biotinylated recombinant human CD47-avi-his protein produced in house (SEQ ID NO: 3) for 2 h at RT. Antigen bound phages were captured on streptavidin beads for 30 min at RT and beads were washed five times with PBS containing 0.1% (v/v) Tween (PBS-Tween 0.1%) and twice with PBS. Phages were eluted with 100 mM triethylamine for 10 min at RT and neutralized using Tris-HCl 1 M pH 8. Eluted phages were used to infect 10 ml of exponentially growing *E. coli* TG1 cells. Infected cells were grown in 2YT medium for 1 h at 37° C. and 100 rotation per minute (RPM), then spread on 2YTAG (2TY medium supplemented with 100 µg/ml ampicillin and 2% glucose) agar plates and incubated overnight (ON) at 30° C. Colonies were scrapped off the plates into 10 ml of 2YT and 15% glycerol (v/v) was added for storage at −80° C. TG1 cells from glycerol stocks were grown at 37° C. and 240 RPM in 2YTAG medium until OD at 600 nm reached 0.5. Cells were then superinfected with the M13K07 helper phage using a multiplicity of infection (MOI) of 10 for 1 h at 37° C. and 100 RPM. Culture medium was then changed for 2YTAK (2YT medium supplemented with 100 µg/ml ampicillin and 50 µg/ml kanamycin) and cells were further cultured ON at 30° C. and 280 RPM. The next day, 10 µl of phage containing cell-free supernatant were used for the subsequent round of selection.

For the panning strategies using CHO cells, purified phage particles were blocked with phosphate buffered saline (PBS) containing 3% (w/v) Bovine Serum Albumin (PBS/BSA 3%) for 1 h at RT. $2 \times 10^{7}$ non-transfected CHO cells and $2 \times 10^{7}$ CHO cells transiently expressing human CD47 protein (SEQ ID NO: 7) or cynomolgus monkey CD47 protein (SEQ ID NO: 8) were blocked with PBS/BSA 3% supplemented with 0.1% azide to avoid receptor internalization for 1 h at RT. Phage were deselected against non-transfected cells for 1 h at RT. The deselected phages were then incubated with the transfected cells for 2 h at RT. In order to remove non-specific phages, cells were washed four times with PBS-Tween 0.1% and twice with PBS. Phages were eluted with citric acid 76 mM, pH 2.0 for 10 min at RT and neutralized using Tris-HCl 1 M pH 8. Eluted phages were used to infect 10 ml of exponentially growing *E. coli* TG1 cells. Phage amplification was performed as described above.

scFv Screening by SPR

Surface Plasmon Resonance (SPR) analysis was used to confirm specific binding activity of the scFv clones. Measurements were performed on a Biacore 2000 instrument (Biacore, GE Healthcare) using the Biacore 2000 Control Software v3.2 at room temperature and analyzed with the Biacore T200 Evaluation Software (v3.1) from the same manufacturer. Recombinant human CD47-avi-his protein produced in house (SEQ ID NO: 3) and recombinant cynomolgus monkey CD47-avi-his protein produced in house (SEQ ID NO: 4) were individually diluted to a final concentration of 200 nM in acetate buffer pH 4.5 (Biacore, GE Healthcare, catalog NO: BR100350) and subsequently immobilized on flow-path 2 and 3 respectively, to a level of about one 1500 resonance units (abbreviated RU) on CM5 Sensor Chips (Biacore, GE Healthcare, catalog NO: BR100012) using an amine coupling kit (Biacore, GE Healthcare, catalog NO: BR100050). Flow-path 4 was similarly immobilized with an irrelevant protein. HBS-EP (Biacore, GE Healthcare, catalog NO: BR100188) was used as running buffer. Filtered periplasmic extracts were injected directly on the covalently coupled human CD47 and cynomolgus CD47 CM5 Sensor Chip. Samples were injected on the flow-path 1, 2, 3 and 4 (flow-path 1 being used as reference) at a 30 µl/min flow rate for 3 min, followed by a dissociation time of 3 min in running buffer. After each binding event, surface was regenerated with 10 mM Glycine pH 1.5 solution (Biacore, GE Healthcare, catalog NO: BR100354) injected for 1 min at 30 µl/min. Each measurement included zero-concentration samples as well as irrelevant scFv periplasmic extracts for referencing and specificity, respectively.

scFv Screening by Flow Cytometry

The binding of scFv clones to CHO cells transiently expressing human CD47 protein (SEQ ID NO: 7) was assessed by flow cytometry. Individual *E. coli* colonies from the third or fourth round of selection were picked and grown in 2TY medium supplemented with 100 µg/ml ampicillin and 0.1% glucose in 96-well deepwell plates. scFv expression was induced by addition of 0.02 mM of IPTG and incubation ON at 30° C. and 250 RPM. Cells were centrifuged and periplasmic extracts were obtained by resuspending the bacterial pellets in TES buffer (50 mM Tris-HCl pH 8; 1 mM EDTA pH 8; 20% sucrose) followed by incubation on ice for 30 min. Cellular debris were removed by centrifugation, and the scFv containing supernatants were used in flow cytometry experiment. CD47-expressing and non-transfected CHO cells were seeded at a density of $10^5$ cells/well in microtiter plates. Next, the plates were centrifuged to remove the cell supernatant and 100 µl of periplasmic extract previously diluted 1:1 in PBS containing 3% (w/v) bovine serum albumin (PBS-BSA 3%) was added to each well and the plates further incubated for 30 min at 4° C. Cells were then washed with PBS-BSA 3% and incubated with a biotin-chicken anti-c-Myc antibody (*Gallus* Immunotech catalog NO: ACMYC-B) diluted at 1:200 in PBS-BSA 3% for 30 min at 4° C. Next, cells were washed with PBS-BSA 3% and incubated with streptavidin APC (eBioscience, catalog NO: 17-4317) diluted at 1:100 in PBS-BSA 3% for 30 min at 4° C. Finally, cell fluorescence was measured using a FACSCalibur flow cytometer (BD biosciences).

Fab Expression cDNAs encoding the different antibody constant regions were gene synthetized by GENEART AG (Regensburg, Germany) and modified using standard molecular biology techniques. PCR products were digested with appropriate DNA restriction enzymes, purified and ligated in modified pcDNA3.1 plasmids (Invitrogen) which carried a CMV promoter and a bovine hormone poly-adenylation (poly(A)). The expression vectors also carried oriP, which is the origin of plasmid replication of Epstein-Barr virus, and the murine VJ2C leader peptide for secretion of the encoded polypeptide chain. For reformatting scFv library clones into human IgG1 Fab fragments, each scFv clone in its phage library vector was used to amplify its individual VH cDNAs by PCR, next the VH PCR product was cloned in the modified pcDNA 3.1 vector described above upstream of a cDNA encoding a human IgG1 heavy chain CH1 domain, whereas the fixed VK3-15/JK1 light chain (SEQ ID NO: 10) was cloned in the modified pcDNA 3.1 vector described above upstream of a cDNA encoding a human kappa constant light chain domain.

For Fab expression, equal quantities of heavy chain and light chain vectors were co-transfected into suspension-adapted HEK293-EBNA cells (ATCC, cat no CRL-10852) using PEI. Typically, cells were prepared at 8 million cells per ml in RPMI supplemented with 0.1% Pluronic F-68. Cells were then transfected with a DNA-PEI mixture. Four hours post-transfection, the cell culture was diluted 1:1 in EX-CELL® 293 supplemented with Phenol Red and 4 mM L-Glutamine and incubated for 5 days with orbital shaking at 37° C., 5% CO2 and 80% humidity. Cell-free culture supernatants containing the recombinant proteins were prepared by centrifugation followed by filtration, and used for further purification. Fab proteins were purified using CaptureSelect™ IgG-CH1 Affinity Matrix (ThermoScientific, catalog NO: 194320050). Affinity resin was added to the filtered culture supernatants and incubated ON at 4° C. with gentle mixing. The next day, resin beads were collected into Poly-Prep columns (Bio-Rad Laboratories), washed with PBS, and the recombinant proteins eluted with an acidic buffer (typically glycine 0.1 M pH 3). After neutralization with 1/10 volume of Tris-HCl pH 8, preparations were buffer-exchanged into PBS.

Fab Binding Affinities for CD47

Surface plasmon resonance (SPR) was used to measure the binding affinities of the Fab fragments for human and cynomolgus monkey CD47. Affinities were measured on a Biacore T200 instrument (Biacore, GE Healthcare) at 25° C. and analyzed with the Biacore T200 Evaluation Software (v3.1). Measurements were performed on Series S CM5 Sensor Chips (Biacore, GE Healthcare, catalog NO: BR100530) using recombinant human CD47-avi-his and recombinant cynomolgus monkey CD47-avi-his proteins produced in house (SEQ ID NO: 3 and SEQ ID NO: 4, respectively). Recombinant human CD47 protein and recombinant cynomolgus monkey CD47 protein were covalently immobilized to around 50 RU on flow-path 2 and flow-path 4 respectively of the Sensor Chip surface using a commercially available amine coupling kit (Biacore, GE Healthcare, catalog NO: BR100050). Fab fragments were injected in single cycle kinetic at different concentrations ranging from 15.6 to 2000 nM, in HBS-EP+ buffer (Biacore, GE Healthcare, catalog NO: BR100669) at a flow rate of 30 µl/min for 3 min on flow-path 1, 2, 3 and 4 (flow-path 1 and 3 being used as reference). Dissociation was monitored for 5 min. After each cycle, the Series S CM5 Sensor Chip surface coated with recombinant CD47 proteins was regenerated with 30 µl of 10 mM Glycine pH 1.5 (Biacore, GE Healthcare, catalog NO: BR100354). Experimental data were processed using the 1:1 Langmuir kinetic fitting model. Measurements included zero-concentration samples for referencing. Chi$^2$, U- and residual values were used to evaluate the quality of a fit between the experimental data and individual binding models.

CD47/SIRPα Blocking Assay

The ability of the Fab fragments to block the interaction between human CD47 and human SIRPα was assessed by Bio-Layer Interferometry (BLI). Measurements were done on an OctetRED96e instrument (ForteBio) and analyzed using the Data Analysis HT version 11.1 software (Octet, ForteBio). Biotinylated recombinant human CD47-avi-his protein produced in house (SEQ ID NO: 3) was loaded at 1 µg/ml in kinetic buffer (ForteBio, catalog NO: 18-1105) on a streptavidin SA Biosensor (ForteBio, catalog NO: 15-5019) for 100 sec. Streptavidin biosensor coated with biotinylated human CD47 antigen was dipped into a solution of 1 µM of Fab for 10 min to achieve saturation of the CD47 coated surface, followed by a successive dip into a mixed solution of 1 µM of Fab 1 and 2 µM of recombinant human SIRPα protein produced in house (SEQ ID NO: 9) for 5 min. All steps were performed at 25° C. and 1000 RPM shaking. Fresh streptavidin biosensors were coated with biotinylated human CD47 protein before each cycle.

Results and Conclusions

ScFv clones showing specific binding to recombinant human CD47 protein and to recombinant cynomolgus monkey CD47 protein by SPR, as well as, for those tested, showing specific binding to CD47-expressing CHO cells, were sequenced and unique sequences were reformatted in Fab fragment for further characterization. Biochemical characterization included assessment of binding affinities and functional assessment was performed using human CD47/SIRPα blocking assays.

Fab Binding Affinities for CD47

Twenty one Fab clones showed binding affinities to human and cynomolgus monkey CD47 with an equilibrium dissociation constant (KD) below 2 µM as determined by SPR. Clone anti-CD47-UCP01-H2, hereafter also referred to as anti-CD47-H2, showed affinities to human CD47 of 104 nM and to cynomolgus monkey CD47 of 142 nM. Heavy chain sequence identification numbers and binding affinities of the mentioned clones are reported in Table 1.

TABLE 1

Overview of the developed Fab clones and their relative affinity to human and cynomolgus monkey CD47.

| Clone name | Clone heavy chain SEQ ID NO | Human CD47 KD (nM) | Cynomolgus monkey CD47 KD (nM) |
|---|---|---|---|
| anti-CD47-UCP01-A1 FAB | SEQ ID NO: 11 | 292 | 15.9 |
| anti-CD47-UCP01-G1 FAB | SEQ ID NO: 12 | 136 | 214 |
| anti-CD47-UCP01-A2 FAB | SEQ ID NO: 13 | 822 | 1070 |
| anti-CD47-UCP01-G2 FAB | SEQ ID NO: 14 | 183 | 190 |
| anti-CD47-UCP01-H2 FAB | SEQ ID NO: 15 | 878.3 | 939.3 |
| anti-CD47-UCP01-A3 FAB | SEQ ID NO: 16 | 1170 | 1260 |
| anti-CD47-UCP01-B3 FAB | SEQ ID NO: 17 | 316 | 340 |
| anti-CD47-UCP02-C1 FAB | SEQ ID NO: 18 | 193 | 113 |
| anti-CD47-UCP02-C2 FAB | SEQ ID NO: 19 | 1100 | 1230 |
| anti-CD47-UCP02-B3 FAB | SEQ ID NO: 20 | 1010 | 1120 |
| anti-CD47-UCP02-H3 FAB | SEQ ID NO: 21 | 455 | 17.8 |

CD47/SIRPα Blocking Assay

Fab fragments were tested at blocking the interaction between human CD47 and human SIRPα using Bio-Layer Interferometry. All developed Fab fragments tested to block the interaction between human CD47 and human SIRPα. Blocking of the interaction between recombinant human CD47 protein and recombinant human SIRPα protein with clone anti-CD47-H2 is illustrated in FIG. 1.

EXAMPLE 2: GENERATION OF ANTI-CD38 ANTIBODIES

Material and Methods

Recombinant Target Antigens cDNA for human and cynomolgus monkey CD38 were obtained from Source Biosciences (Erwin-Negelein-Haus, Germany, Cat. NO: IRAU37D11, 4309086), their extracellular regions (UniProt accession No: P28907 residues 43-300 and Uniprot accession No: Q5VAN0, residues 43-301 (residue 44 was deleted), respectively) were PCR amplified and cloned into an in-house expression vector derived from pcDNA3.1 (Invitrogen AG). This expression vector encompassed a Kozak sequence and a start codon followed by the murine IgGκ light chain leader peptide at the 5' end and a 6-His-tag at the 3' end of its multiple cloning site. The soluble extracellular region of human CD38 (residues 43 to 300, SEQ ID NO: 1) and cynomolgus monkey CD38 (residues 43-301, SEQ ID NO: 2) fused to a 6-His-tag were expressed as follows. Briefly, one volume of RPMI 1640 medium (PAA Laboratories) containing HEK cells, 0.1% pluronic acid (Invitrogen AG), expression vector and polyethylenimine (JetPEI®, Polyplus-transfection, Illkirch, France) was incubated in a shake flask at 37° C., 5% $CO_2$ and 80% humidity. One volume of Ex-Cell 293 medium supplemented with 6 mM glutamine was added to the mixture after 4 hours and incubation continued further for a total of 5 days. Post production, clarified supernatant was obtained by centrifugation and filtrated using 0.2 μm filters, pH was adjusted at 7.4 (4° C.) using Tris 1 M pH 8.7. Ni-Sepharose Excell beads (GE Healthcare) were added to the clarified supernatant and incubated overnight at 4° C. under agitation. The solution was loaded on an Econo-Column (Bio-Rad Laboratories) for gravity-flow purification. The beads were subsequently washed with 1×PBS, pH 7.4 (1 or 2×10 CV) and 1×PBS, pH 7.4 supplemented with 20 mM imidazole (10 CV). The protein was, depending on the batch, either eluted with 1×PBS, pH 7.4 supplemented with 500 mM imidazole or eluted by increasing stepwise the concentration in imidazole (40 mM, 80 mM and 250 mM imidazole). Fractions of interest were pooled and dialyzed twice against 1×PBS, pH 7.4 at 4° C. The protein was concentrated and sterile-filtered using 0.22 μm filters. Protein quality was assessed by SDS-PAGE, SE-HPLC, endotoxin measurement and ELISA. Briefly, SE-HPLC was performed using a Tosoh Bioscience TSKgel G3000SWxl column (catalog NO: 08541, Tosoh Bioscience) at room temperature with 0.1 M sodium phosphate buffer, 0.15 M sodium chloride, pH 6.8 as eluent at 1 ml/min flow rate, on a Waters Alliance 2695 HPLC system with a Waters 2998 PDA detector (Waters), monitoring at 214 nm and 280 nm. The Multi-Cartridge System Endosafe-MCS from Charles River utilizing a Limulus amebocyte lysate (LAL)-based assay was used to confirm a bacterial endotoxin level inferior to 0.5 EU/mg. These proteins are referred herein as human CD38-C-His and cyno CD38-C-His and are described as SEQ ID NO: 1 and SEQ ID NO: 2, respectively.

Recombinant Cell Lines

The human codon-optimized sequences of the full-length human CD38 (UniProt sequence ID P28907; residues 1-300; SEQ ID NO: 5), of the full-length cynomolgus monkey CD38 (accession number: Q5VAN0; residues 1-301; SEQ ID NO: 6) were cloned in a modified pcDNA™3.1 plasmid (ThermoFisher Scientific, catalog NO: V79020). Transfection and protein expression were done in suspension-adapted CHO-S cells (cGMP banked, Invitrogen, Cat.-NO: A1136401) as described in Example 1. Human and cynomolgus monkey CD38 proteins as described herein have SEQ ID NO: 5 and 6, respectively.

Library Selection

The selections have been performed as described in the Example 1 with the following modifications. The first panning strategy consisted in three rounds of selection using biotinylated recombinant human CD38 protein (Acrobiosystems, catalog NO: CD8-H82E7). The second panning strategy consisted in two rounds of selection using biotinylated recombinant human CD38 protein followed by two rounds using CHO cells transiently expressing human CD38 protein (SEQ ID NO: 5) or cynomolgus monkey CD38 protein (SEQ ID NO: 6).

scFv Screening by SPR

Surface Plasmon Resonance (SPR) analysis was used to confirm specific binding activity of the scFv clones. Measurements were performed on a Biacore 2000 instrument (Biacore, GE Healthcare) using the Biacore 2000 Control Software v3.2 at room temperature and analyzed with the Biacore T200 Evaluation Software (v3.1) from the same manufacturer. Commercially available recombinant human CD38 protein (Acrobiosystems, catalog NO: CD8-H224) and recombinant cynomolgus monkey CD38 protein (R&D Systems, catalog NO: 9834-AC-050), or recombinant human CD38 extracellular domain (ECD)-C-his (SEQ ID NO: 1) and recombinant cynomolgus CD38-ECD-C-his (SEQ ID NO: 2) proteins produced in house were individually diluted to a final concentration of 200 nM in acetate buffer pH 4.5 (Biacore, GE Healthcare, catalog NO: BR100350) and subsequently immobilized on flow-path 2 and 3 respectively, to a level of about one 1500 resonance units (abbreviated RU) on CM5 Sensor Chips (Biacore, GE Healthcare, catalog NO: BR100012) using an amine coupling kit (Biacore, GE Healthcare, catalog NO: BR100050). Flow-path 4 was similarly immobilized with commercially available recombinant mouse CD38 protein (Creative Biomart, catalog NO: CD38-3112M) or with an irrelevant antigen. HBS-EP (Biacore, GE Healthcare, catalog NO:

BR100188) was used as running buffer. Filtered periplasmic extracts were injected directly on the covalently coupled human CD38-his and cynomolgus CD38-his CM5 Sensor Chip. Samples were injected on the flow-path 1, 2, 3 and 4 (flow-path 1 being used as reference) at a 30 µl/min flow rate for 3 min, followed by a dissociation time of 5 min in running buffer. After each binding event, surface was regenerated with 10 mM Glycine pH 1.5 solution (Biacore, GE Healthcare, catalog NO: BR100354) injected for 1 min at 30 µl/min. Each measurement included zero-concentration samples as well as irrelevant scFv periplasmic extracts for referencing and specificity, respectively.

scFv Screening by Flow Cytometry

The binding of scFv clones to CHO cells transiently expressing human CD38 protein (SEQ ID NO: 5) was assessed by flow cytometry as described in Example 1.

Fab Binding Affinities for CD38

Human IgG1 Fab fragments were expressed and purified as described in Example 1. Surface plasmon resonance (SPR) was used to measure the binding affinities of the Fab fragments for human and cynomolgus monkey CD38. Affinities were measured on a Biacore T200 instrument (Biacore, GE Healthcare) at 25° C. and analyzed with the Biacore T200 Evaluation Software (v3.1). Measurements to human CD38 were performed on Series S Sensor Chips SA (Biacore, GE Healthcare, catalog NO: BR100531) or on Series S BiotinCAPture Chips (Biacore, GE Healthcare, catalog NO: 28920234) using commercially available recombinant biotinylated human CD38 Avitag™, His Tag (Acrobiosystems, catalog NO: CD8-H82E7). Measurements to cynomologus monkey CD38 were performed on Series S CM5 sensor chips (Biacore, GE Healthcare, catalog NO: BR100530) previously immobilized with anti-histidin antibody (Biacore, GE Healthcare, catalog NO: 28995056) using recombinant cynomolgus monkey CD38-ECD-C-his protein produced in house (SEQ ID NO: 2).

The affinities to human and cynomolgus monkey CD38 were assessed by immobilizing CD38 and using Fab fragments as analyte. Biotinylated recombinant human CD38 protein was immobilized to around 160 RU on flow-path 2 of a Series S Sensor Chip SA or to around 100 RU on flow-path 2 of a Series S BiotinCAPture Chip and recombinant cynomolgus monkey CD38-his protein was immobilized to around 50-100 RU on flow-path 2 of a Series S CM5 Sensor Chip previously coated with anti-histidin antibody. Fab fragments were injected in single cycle kinetic at different concentrations ranging from 7.8 to 2000 nM, in HBS-EP+ buffer (Biacore, GE Healthcare, catalog NO: BR100669) at a flow rate of 30 µl/min for 3 min on flow-path 1 and 2 (flow-path 1 being used as reference). Dissociation was monitored for 5 min. After each cycle, the Series S Sensor Chip SA coated with biotinylated recombinant human CD38 protein surface was regenerated with 60 µl of 10 mM Glycine pH1.5 (Biacore, GE Healthcare, catalog NO: BR100354) while Series S BiotinCAPture Chip and Series S CM5 Sensor Chip coated with anti-histidin antibody surfaces were regenerated using regeneration solution provided with BiotinCAPture kit (Biacore, GE Healthcare, catalog NO: 28920234) and His Capture kit (Biacore, GE Healthcare, catalog NO: 28995056) respectively. Experimental data were processed using the 1:1 Langmuir kinetic fitting model. Measurements included zero-concentration samples for referencing. Chi', U- and residual values were used to evaluate the quality of a fit between the experimental data and individual binding models Epitope Binning Epitope binning of Fab fragments on human CD38 was assessed using Bio-Layer Interferometry (BLI). Measurements were done on an OctetRED96e instrument (ForteBio) and analyzed using the Data Analysis HT version 11.1 software (Octet, ForteBio). Biotinylated human CD38-avi-his protein (Acrobiosystems, catalog NO: CD8-H82E7) was loaded at 1 µg/ml in kinetic buffer (ForteBio, catalog NO: 18-1105) on a streptavidin SA Biosensor (ForteBio, catalog NO: 15-5019) for 5 min. Streptavidin biosensor coated with biotinylated human CD38 antigen was dipped into a solution of 200 nM of Fab 1 (saturating Fab) for 10 min, followed by a successive dip into a mixed solution of 200 nM of Fab 1 and 200 nM of Fab 2 (competing Fab) for 5 min. All steps were performed at 25° C. and 1000 RPM shaking. Fresh streptavidin biosensors were coated with biotinylated human CD38 before each cycle.

Results and Conclusions

ScFv clones showing specific binding to both recombinant human CD38 and recombinant cynomolgus monkey CD38 proteins by SPR as well as specific binding to human CD38 CHO cells were sequenced and unique sequences showing the best binding profiles on SPR were reformatted in Fab fragment for binding affinity measurement.

Fab Binding Affinities to CD38

Thirty-five Fab clones showed binding affinities to recombinant human and cynomolgus monkey CD38 proteins with an equilibrium dissociation constant (KD) below 10 µM as determined by SPR. Clone anti-CD38-UCP01-E2, hereafter also referred to as anti-CD38-E2 (heavy chain SEQ ID NO: 28) showed affinities to human CD38 and cynomologus monkey CD38 of 110 nM and 89 nM respectively. Clone anti-CD38-UCP03-B6, hereafter also referred to as anti-CD38-B6 (heavy chain SEQ ID NO: 43) showed affinities to human CD38 and cynomolgus monkey CD38 of 225 nM and 829 nM respectively. Heavy chain sequence identification numbers and binding affinities of the mentioned clones are reported in Table 2.

TABLE 2

Overview of the developed Fab clones and their relative affinity to human and cynomolgus monkey CD38. NB = no detectable binding; NT = not tested.

| Clone name | Clone heavy chain SEQ ID NO | Human CD38 KD (nM) | Cynomolgus monkey CD38 KD (nM) |
|---|---|---|---|
| Anti-CD38-UCP01-B1 Fab | SEQ ID NO: 22 | 193 | 102 |
| Anti-CD38-UCP01-D1 Fab | SEQ ID NO: 23 | 666 | NB |
| Anti-CD38-UCP01-F1 Fab | SEQ ID NO: 24 | 429 | 393 |
| Anti-CD38-UCP01-G1 Fab | SEQ ID NO: 25 | 1124 | 283 |
| Anti-CD38-UCP01-H1 Fab | SEQ ID NO: 26 | 437 | 352 |
| Anti-CD38-UCP01-C2 Fab | SEQ ID NO: 27 | 85.3 | 53.5 |
| Anti-CD38-UCP01-E2 Fab | SEQ ID NO: 28 | 110 | 88.9 |
| Anti-CD38-UCP02-A7 Fab | SEQ ID NO: 29 | 71.14 | low binding |
| Anti-CD38-UCP02-B1 Fab | SEQ ID NO: 30 | 595 | low binding |
| Anti-CD38-UCP02-B7 Fab | SEQ ID NO: 31 | 1709 | NT |
| Anti-CD38-UCP02-C3 Fab | SEQ ID NO: 32 | 305.1 | 187.7 |
| Anti-CD38-UCP02-D1 Fab | SEQ ID NO: 33 | 132.9 | 78 |
| Anti-CD38-UCP02-D5 Fab | SEQ ID NO: 34 | 192 | 33.5 |
| Anti-CD38-UCP02-E5 Fab | SEQ ID NO: 35 | 0.03 | low binding |
| Anti-CD38-UCP02-F2 Fab | SEQ ID NO: 36 | 14.16 | 13.96 |
| Anti-CD38-UCP02-F5 Fab | SEQ ID NO: 37 | 71.08 | 55.22 |
| Anti-CD38-UCP02-F6 Fab | SEQ ID NO: 38 | 389.2 | low binding |
| Anti-CD38-UCP02-H1 Fab | SEQ ID NO: 39 | 153.9 | 2.7 |
| Anti-CD38-UCP03-B3 Fab | SEQ ID NO: 40 | 115 | 170 |
| Anti-CD38-UCP03-C3 Fab | SEQ ID NO: 41 | 117 | 465 |

TABLE 2-continued

Overview of the developed Fab clones and their relative affinity to human and cynomolgus monkey CD38. NB = no detectable binding; NT = not tested.

| Clone name | Clone heavy chain SEQ ID NO | Human CD38 KD (nM) | Cynomolgus monkey CD38 KD (nM) |
|---|---|---|---|
| Anti-CD38-UCP03-H5 Fab | SEQ ID NO: 42 | 141.6 | 111 |
| Anti-CD38-UCP03-B6 Fab | SEQ ID NO: 43 | 225 | 829 |
| Anti-CD38-UCP03-E3 Fab | SEQ ID NO: 44 | 300 | 195 |
| Anti-CD38-UCP03-A6 Fab | SEQ ID NO: 45 | 410 | 525 |
| Anti-CD38-UCP03-B1 Fab | SEQ ID NO: 46 | 882 | 462 |
| Anti-CD38-UCP03-C2 Fab | SEQ ID NO: 47 | 1388 | 628 |
| Anti-CD38-UCP03-H2 Fab | SEQ ID NO: 48 | 1850 | 672 |
| Anti-CD38-UCP03-H3 Fab | SEQ ID NO: 49 | 810 | 178 |

Epitope Binning

To assess competition of anti-CD38 clones on CD38, epitope binning assay using anti-CD38 Fab fragments and recombinant human CD38 protein was performed using Octet Bio-Layer Interferometry. FIG. 2 shows that anti-CD38-E2 and anti-CD38-B6 clones do not compete with each other and thereby do not recognize overlapping epitopes on CD38.

EXAMPLE 3: OPTIMIZATION OF ANTI-CD38-E2 AND ANTI-CD38-B6

Material and Methods

Recombinant Target Antigens

Recombinant human CD38-ECD-C-his protein (SEQ ID NO: 1), hereafter also referred to as recombinant human CD38 protein, and recombinant cynomolgus monkey CD38-ECD-C-his protein (SEQ ID NO: 2), hereafter also referred to as recombinant cynomolgus monkey CD38 protein, were produced in house as described in Example 2.

Library Generation and Selection

Five affinity maturation libraries were generated for both anti-CD38-E2 (SEQ ID NO: 28) and anti-CD38-B6 (SEQ ID NO: 43) clones by introducing diversity in CDRs' heavy chain. CDR-H1, CDR-H2 and CDR-H3 were randomized using degenerated NNK codon oligonucleotides (wherein N is any of the four deoxyribonucleotides and K is G or T) at Kabat residues 27-35, 50-58, 95-101 minus 2, respectively. Each library was generated using a pool of overlapping oligonucleotides containing 5 consecutive degenerated codons. CDR-H1 and CDR-H2 were also diversified using Trimer oligonucleotide at position Kabat 27-35 and 50-58 respectively. The resulting five library PCR products were cloned into the pNGLEN (in-house modified pUC119 phagemid vector) and the resulting ligation reaction electroporated into E. coli TG1 cells. Transformed cells were spread on 2YTAG plates and incubated ON at 30° C. Colonies were scrapped off the plates into 10 ml of 2YT medium and 15% glycerol (final concentration) was added for storage at −80° C. Phages were produced and purified by two precipitations steps with one-third v/v of 20% PEG-6000, 2.5 M NaCl and resuspended in PBS.

Phage display selections were performed using recombinant proteins as described in Example 1 with the following modifications. Deselected phage were incubated with 50 nM, 5 nM and 0.5 nM of biotinylated recombinant human CD38 protein (Acrobiosystems, catalog NO: CD8-H82E7) for round 1, round 2 and round 3, respectively. After 1 h incubation, 1 µM of recombinant human CD38 protein produced in house (non-biotinylated, SEQ ID NO: 1) was added for 3 h at RT during rounds 2 and 3.

Affinity Screening by SPR

SPR analysis was used to confirm specific binding activity of the new scFv clones and rank the positive clones according to their binding profile. Measurements were performed as described in Example 2 with the following modifications. Measurements were performed on a Biacore T200 instrument (Biacore, GE Healthcare) at 25° C. and analyzed with the Biacore T200 Evaluation Software (v3.1). Commercially available recombinant human CD38 protein (Acrobiosystems, catalog NO: CD8-H224) was diluted to a final concentration of 200 nM in acetate buffer pH 4.5 (Biacore, GE Healthcare, catalog NO: BR100350) and subsequently immobilized on flow-path 2 to a level of about 1300 RU on a Series S CM5 sensor CHIP (Biacore, GE Healthcare, catalog NO: BR100530) using an amine coupling kit (Biacore, GE Healthcare, catalog NO: BR100050). Filtered periplasmic extracts were injected directly on the covalently coupled human CD38 CM5 Sensor Chip on the flow-path 1 and 2 (flow-path 1 being used as reference). Dissociation in HBS-EP+ buffer was monitored for 10 min. The scFv clones showing the best binding profiles were reformatted in Fab fragments as described in Example 1.

Fab Binding Affinities to CD3

Affinities of the Fab to human CD38 using Fab as analyte were performed on Series S BiotinCAPture Chips (Biacore, GE Healthcare, catalog NO: 28920234) using commercially available recombinant biotinylated human CD38 Avitag™, His Tag (Acrobiosystems, catalog NO: CD8-H82E7) as described in Example 2, with Fab injection concentrations ranging from 1.95 nM to 500 nM. Measurements to cynomolgus monkey CD38 using Fab as analyte were performed on Series S CM5 Sensor Chips (Biacore, GE Healthcare, catalog NO: BR100530) previously immobilized with anti-histidin antibody (Biacore, GE Healthcare, catalog NO: 28995056) using recombinant cynomolgus monkey CD38-ECD-C-his protein produced in house (SEQ ID NO: 2) as described in Example 2, with Fab injection concentrations ranging from 1.48 nM to 120 nM.

Affinities of the Fab to human and cynomolgus CD38 using the Fab as ligand were measured on a Biacore T200 instrument (Biacore, GE Healthcare) at 25° C. and analyzed with the Biacore T200 Evaluation Software (v3.1). Measurements were performed on Series S CM5 Sensor Chips (Biacore T200, Biacore, GE Healthcare, catalog NO: BR100530) coupled with anti-human Fab antibodies using a commercial kit (Human Fab Capture Kit, Biacore, GE Healthcare, catalog NO: 28958325). SPR measurements were performed with recombinant human CD38 protein or recombinant cynomolgus monkey CD38 protein produced in house (SEQ ID NO: 1 and SEQ ID NO: 2, respectively). The affinities to human and cynomolgus monkey CD38 were assessed by immobilizing Fab fragments and using human or cynomolgus monkey CD38 protein as analyte. Around 50-200 RU of Fab was captured on flow-path 2 of a Series S CM5 Sensor Chip coupled with anti-human Fab antibodies. Human or cynomolgus monkey CD38 was injected in multi cycle kinetic at different concentrations ranging from 0.2 to 100 nM, in HBS-EP+ buffer (Biacore, GE Healthcare, catalog NO: BR100669) at a flow rate of 30 µl/min for 5 min on flow-path 1 and 2 (flow-path 1 being used as reference). Dissociation was monitored for 10 min. After each cycle, the surface was regenerated with 60 µl of regeneration solution provided with Human Fab Capture Kit (Biacore, GE Healthcare, catalog NO: 28958325). Experimental data were processed using the 1:1 Langmuir kinetic fitting model. Measurements included zero-concentration samples for referencing. Chi', U- and residual values were used to evaluate the quality of a fit between the experimental data and individual binding models.

Results and Conclusions

Affinity maturation of anti-CD38-E2 clone (heavy chain SEQ ID NO: 28) and of anti-CD38-B6 clone (heavy chain SEQ ID NO: 43) involved diversification of CDR-H1 (Kabat positions 27-35), CDR-H2 (Kabat positions 50-58) and CDR-H3 (Kabat positions 95-101 minus 2) in five individual libraries. ScFv clones having a slower off-rate than their respective parental clone (anti-CD38-E2 or anti-CD38-B6) as measured by SPR were isolated. ScFv clones were reformatted and expressed as Fab fragments and affinities to human and cynomolgus CD38 were measured by SPR. From this assessment, selected mutations originating from the CDR-H1 and CDR-H2 libraries were combined for further off-rate improvement; one clone referred to as Fab clone anti-CD38-E2-RecA (SEQ ID NO: 57) had the highest affinities to human and cynomolgus monkey CD38 with KD measured at 0.9 nM and 3.7 nM respectively using Fab as ligand. Clones anti-CD38-E2-UCP02-F3 (SEQ ID NO: 52), hereafter also referred to as anti-CD38-E2-F3, and anti-CD38-E2-UCP02-F8 (SEQ ID NO: 55), hereafter also referred to as anti-CD38-E2-F8, showed affinities to human CD38 of 3.5 nM and 17.6 nM respectively and to cynomologus monkey CD38 of 2.4 nM and 24.5 nM respectively, measured using the Fabs as analyte. One clone referred to as Fab clone anti-CD38-B6-D9 (SEQ ID NO: 61) showed highest increase in affinity to human and cynomolgus CD38 from affinity maturation of anti-CD38-B6, with KD values measured at 2.3 nM and 5.2 nM respectively, using Fab as ligand and of 0.55 and 3.3 nM respectively, using Fab as analyte. Heavy chain sequence identification numbers and binding affinity of the mentioned clones to human and cynomolgus monkey CD38 are reported in Table 3.

TABLE 3

Overview of the developed Fab clones and their relative affinity to human and cynomolgus monkey CD38 measured with Fab as analyte and with Fab as ligand.
NB = no detectable binding; NT = not tested.

| Library | Clone name | Clone heavy chain SEQ ID NO | Human CD38 KD (nM), Fab as analyte | Cynomolgus monkey CD38 KD (nM), Fab as analyte | Human CD38 KD (nM), Fab as ligand | Cynomolgus monkey CD38 KD (nM), Fab as ligand |
|---|---|---|---|---|---|---|
| CDR-H1 | anti-CD38-E2-UCP01-A10 FAB | SEQ ID NO: 50 | 9.4 | 8.6 | 16.89 | NT |
| CDR-H2 | anti-CD38-E2-UCP02-E7 FAB | SEQ ID NO: 51 | 2.2 | 1.8 | 4.66 | NT |
| CDR-H2 | anti-CD38-E2-UCP02-F3 FAB | SEQ ID NO: 52 | 3.5 | 2.4 | 6.13 | NT |
| CDR-H2 | anti-CD38-E2-UCP02-D6 FAB | SEQ ID NO: 53 | 4.9 | 1.1 | 5.35 | NT |
| CDR-H2 | anti-CD38-E2-UCP02-G8 FAB | SEQ ID NO: 54 | 5.2 | 4.2 | 7.7 | NT |
| CDR-H2 | anti-CD38-E2-UCP02-F8 FAB | SEQ ID NO: 55 | 17.6 | 24.5 | 16.22 | NT |
| CDR-H2 | anti-CD38-E2-UCP02-A5 FAB | SEQ ID NO: 56 | 23.6 | 4.4 | 35.03 | NT |
| Combination | anti-CD38-420-E2-RecA FAB | SEQ ID NO: 57 | NT | NT | 0.9 | 3.7 |
| Combination | anti-CD38-420-E2-RecB FAB | SEQ ID NO: 58 | NT | NT | 1.6 | 4.4 |
| Combination | anti-CD38-420-E2-RecC FAB | SEQ ID NO: 59 | NT | NT | 1.3 | 3.9 |
| Combination | anti-CD38-420-E2-RecD FAB | SEQ ID NO: 60 | NT | NT | 6.7 | 22.1 |
| CDR-H1 | anti-CD38-B6-MP01-D9 FAB | SEQ ID NO: 61 | 0.55 | 3.33 | 2.3 | 5.2 |
| CDR-H1 | anti-CD38-B6-MP01-B4 FAB | SEQ ID NO: 62 | 11.9 | 45.4 | 51.6 | 167 |
| CDR-H1 | anti-CD38-B6-MP02-C1 FAB | SEQ ID NO: 63 | 12 | 67.2 | 97.7 | 333 |
| CDR-H1 | anti-CD38-B6-MP02-B10 FAB | SEQ ID NO: 64 | 20.1 | 81.2 | 108 | 528 |
| CDR-H1 | anti-CD38-B6-MP01-H3a FAB | SEQ ID NO: 65 | 28.3 | 120 | 89.4 | 389 |
| CDR-H1 | anti-CD38-B6-MP01-H3b FAB | SEQ ID NO: 66 | 28.9 | 130 | 171 | 330 |
| CDR-H1 | anti-CD38-B6-MP01-A4 FAB | SEQ ID NO: 67 | 84.9 | 229 | 227 | 828 |
| CDR-H1 | anti-CD38-B6-MP01-C2 FAB | SEQ ID NO: 68 | 209 | NT | 345 | NT |
| CDR-H1 | anti-CD38-B6-MP02-C2 FAB | SEQ ID NO: 69 | 101 | NT | 404 | 342 |
| CDR-H1 | anti-CD38-B6-MP02-G11 FAB | SEQ ID NO: 70 | 425 | 262 | 128 | 534 |

EXAMPLE 4: ENGINEERING CD38/CD47 BISPECIFIC ANTIBODIES

Material and Methods

Construction of Expression Vectors for Transient Mammalian Cell Expression cDNAs encoding the different polypeptide chains in part or in full were first gene synthetized by Twist Biosciences (San Francisco, USA) and modified using standard molecular biology techniques. PCR products were inserted in a modified pcDNA3.1 plasmid (Invitrogen AG, Zug, Switzerland) carrying a CMV promoter and a bovine hormone poly-adenylation signal (poly(A)) using standard molecular biology techniques. All polypeptide chains were independently cloned in an expression vector where secretion was driven by the murine IgGκ light chain leader peptide.

Expression of Antibodies in HEK-293-EBNA Cells

BEAT bispecific antibodies and control antibodies were expressed as follows unless otherwise indicated. For transient expression, equal quantities of each engineered chains vectors were co-transfected into suspension-adapted HEK293-EBNA cells (ATCC-LGL standards, Teddington, UK; Cat. No: CRL-10852) using polyethyleneimine (PEI; Polysciences). Typically, cells were prepared at 8 million cells per ml in RPMI 1640 (Biowest) supplemented with 0.1% Pluronic F-68 (Gibco). Cells were then transfected with a DNA-PEI mixture at 37° C. 4 hours post-transfection, the cell culture was diluted 1:1 in EX-CELL® 293 supplemented with Phenol Red or BalanCD HEK293 (Irvine Scientific) and 4 mM L-Glutamine and incubated for 5 days with orbital shaking at 37° C., 5% CO2 and 80% humidity. Cell-free culture supernatants containing the recombinant proteins were prepared by centrifugation followed by filtration, and used for further purification.

Purification of BEAT CD38/CD47 Bispecific Antibodies by Differential Protein A Affinity Chromatography Supernatants from HEK293-EBNA were optionally conditioned with 0.1 volume (V) of sodium phosphate 1 M, pH 6.0 prior purification or used directly without conditioning. KanCapA resin (KANEKA, Belgium) was added to conditioned supernatants. Mixtures were incubated overnight at 4° C. with stirring. After incubation, bound proteins were washed with 10 column volumes (CVs) of PBS pH 7.4, followed by 2 CVs of sodium acetate 170 mM, pH 5.0, then eluted in multiple steps of 50 mM sodium acetate, pH 4.3, 4.1 and/or pH 3.9 and neutralised with 0.1V of 1 M Tris-HCl pH 8.0. The elution fractions were dialyzed to PBS, pH 7.4, sterile-filtered and analyzed by SE-HPLC (TSKgel G3000SWXL, 5 µm, 7.8 mm×30 cm L, 5 µm particles and 250 Å pores (Cat No 08541, TOSOH BIOSCIENCE) at room temperature with 0.1 M sodium phosphate buffer, 0.15 M sodium chloride, pH 6.8 as eluent at 1 ml/min flow rate on HPLC Alliance 2695 (Waters) or Acquity Arc HPLC (Waters) with column heater and either UV/Vis detector (2487 or 2489 from Waters) or PDA detector (2996 or 2998 from Waters)) and SDS-PAGE (NuPAGE Bis-Tris 4-12% acrylamide, Invitrogen AG, Basel, Switzerland). The Multi-Cartridge System Endosafe-MCS from Charles River utilizing a Limulus amebocyte lysate (LAL)-based assay was used to confirm a bacterial endotoxin level inferior to 5 EU/mg. Typically, for purified antibodies the content of aggregated forms was lower than 5% and monodispersity by SE-HPLC was superior to 95%. Samples were further analysed for heterodimerization levels by reverse phase high performance liquid chromatography coupled to mass spectrometry (RP-HPLC-MS) as described below.

Heterodimerization Level Determination by RP-HPLC-MS

Samples were deglycosylated overnight with PNGase F. RP-HPLC-MS was performed on a Vanquish chromatography system (ThermoFisher Scientific) coupled to an extended mass range hybrid electrospray-quadrupole_Orbitrap mass spectrometer (QExactive Plus BioPharma, ThermoFisher Scientific). Purified proteins were injected on a polyphenyl reverse phase column (Bio BioResolve RP mAb 2.1×150 mm 450 Å, 2.7 µm column, Waters UK). Column temperature was set to 70° C. The mobile phase consisted of 0.08% formic acid and 0.02% trifluoroacetic acid in water (solvent A) and 0.08% formic acid and 0.02% trifluoroacetic acid in acetonitrile (solvent B). The proteins were loaded at 5% solvent B with a 0.4 ml/min flow rate. Elution was performed with a linear 30% to 38% gradient of solvent B. The mass spectrometer was operated in positive ion mode scanning the m/z 1500-5000 range with a resolution of 17500 at m/z 200. In-source collision energy was set to 60 eV to avoid TFA adducts. Acquired data was processed using the BioPharma Finder software (ThermoFisher Scientific). Peak detection was performed using the sliding window with deconvolution performed using the ReSpect® algorithm. Identifications were performed by comparing the measured masses with those calculated for the different expected species. Purity was assessed by integrating the areas of the extracted ion chromatograms for the detected protein species.

Results and Conclusion

Bispecific antigen-binding molecules that bind CD38 and CD47 were constructed using the BEAT® heavy chain (Hc) heterodimerization technology previously described (Skegro et al., (2017) J Biol Chem 292(23): 9745-9759 and Stutz et al., (2020) J Biol Chem 295(28): 9392-9408); such bispecific antigen-binding molecules are referred to herein as BEAT CD38/CD47. The anti-CD38 portion of the BEAT CD38/CD47 molecule is useful for targeting tumor cells that express CD38, and the anti-CD47 portion of the bispecific molecule is useful for blocking the CD47 mediated phagocytosis inhibition signal which is driven through the interaction of CD47 with SIRPα (Signal regulatory protein a) on immune cells (mainly macrophages, Willingham et al., (2012) Proc Natl Acad Sci USA 109(17): 6662-6667). The interaction of SIRPα with its ligand, CD47, a widely expressed transmembrane protein, transmits a "don't eat me" signal by initiating signalling cascades that ultimately inhibit phagocytosis. The presence of this inhibition signal allows cancer cells to escape in part macrophage mediated control mechanisms of the immune system. CD47 is expressed on most cell types and thus in order to avoid binding CD47 expressing cells that do not express CD38, a weak affinity for CD47 was deemed suitable, i.e. letting the anti-CD38 domain drive the binding to the target cells which subsequently allows binding of a proximal CD47 receptor on the same cell by avidity. Importantly, CD47 is expressed on red blood cells (RBC) and platelets that express CD38. Critical to the on-target specificity of the bispecific antibody is mitigating the crosslinking of RBCs as well as platelets by bridging of CD47 and CD38, which would be induced by a bispecific antibody construct with two high affinity binding arms. We envisaged a low affinity of the CD47 binding arm to minimize the binding to CD47 expressing cells that do not express CD38 and to avoid hemagglutination and platelet-aggregation, but to efficiently block the CD47-SIRPα interaction. Blocking of CD47 in combination with a high specificity for CD38 will therefore allow disabling CD47 mediated phagocytosis inhibition specifically for cancer cells expressing CD38. As a result, target cells will be susceptible to antibody-dependent cellular phagocytosis (ADCP). Further effector mechanisms, i.e. antibody-dependent cellular cytotoxicity (ADCC) and complement-dependent cytotoxicity (CDC), will contribute to the mechanism of action.

Bispecific antibodies comprising an anti-CD38-specific binding domain and an anti-CD47-specific binding domain were constructed using standard methodologies, wherein the anti-CD38 antigen binding domain and the anti-CD47 antigen binding domain each comprise different, distinct Hc variable regions (VH) paired with a common light chain (cLc) (FIG. 3). The cLc circumvents any possible light chain mispairing that is commonly observed when incorporating two different VH domains as well as two different cognate light chains in a bispecific antibody. Bispecific antibodies contained the heterodimeric BEAT Fc region (SEQ ID NOs: 257 and 258) and Hcs were engineered with different avidity for Protein A (PA), thereby allowing separation of homo- and heterodimer species as previously reported (Skegro et al., (2017) supra and Ollier et al., (2019) MAbs 11(8): 1464-1478). More specifically, the anti-CD47 arm of the hetero-dimeric immunoglobulin consisted of a BEAT (A) Hc encompassing a VH with mutation G65S (Kabat numbering) selected from Table 1 (anti-CD47-H2), a CH1 γ1 region, a γ1 hinge region, a γ1 CH2 region, and a γ3 based BEAT (A) CH3 domain assembled with a cLc (SEQ ID NO: 10). This Hc encompassed part of a human IgG3 Fc region and therefore had no binding to PA. However, since the Hc used herein had its VH domain originating from the VH3-subclass, the VH domain was mutated to include the G65S substitution, thereby removing any additional PA binding sites within the Hc (Ollier et al., (2019) supra). Importantly, a number of additional constructs not shown here, with alternative anti-CD47 VH domains with varying affinities, were designed and tested after which anti-CD47-H2 was deemed the most suitable. The anti-CD38 arm of the heterodimeric immunoglobulin consisted of a BEAT (B) Hc encompassing a VH domain selected from Table 3 (anti-CD38-E2-F3, anti-CD38-E2-F8 or anti-CD38-E2-RecA), a CH1 γ1 region, a γ1 hinge region, a γ1 CH2 region, and a γ1 based BEAT (B) CH3 domain assembled with a cLc. The bispecific antibodies resulting from the assembly of the BEAT (A) and BEAT (B) Hcs as well as the cLc are referred to herein as BEAT CD38/CD47-X where X is the construct number consisting of a particular set of variable domains (Table 4). Bispecific antibodies were transiently expressed in HEK and purified by differential PA chromatography. For all antibodies, monodispersity of >95% was observed by SE-HPLC with <1% homodimeric contaminants as determined by RP-HPLC-MS. Endotoxin levels were inferior to 5 EU/mg. BEAT CD38/CD47 bispecific antibodies were further tested for their biological activity below.

TABLE 4

List of BEAT CD38/CD47 bispecific antibody constructs with their associated SEQ ID NOs.

| Construct | BEAT (A) Hc | BEAT (B) Hc | cLc |
|---|---|---|---|
| BEAT CD38/CD47-3 | SEQ ID NO: 259 | SEQ ID NO: 260 | SEQ ID NO: 10 |
| BEAT CD38/CD47-6 | SEQ ID NO: 259 | SEQ ID NO: 261 | SEQ ID NO: 10 |
| BEAT CD38/CD47-19 | SEQ ID NO: 259 | SEQ ID NO: 262 | SEQ ID NO: 10 |

EXAMPLE 5: ENGINEERING ANTIBODIES WITH INCREASED EFFECTOR FUNCTION

Material and Methods

Cloning, Expression and Purification

Bispecific antibodies were produced in HEK293-EBNA cells as described above. BEAT CD38/CD47-60 as well as -42 and -48 used in assays described in FIGS. 9A, 9B, and 9C and after, were expressed in CHO-S cells. Engineered chains vectors and a vector encoding Epstein-Barr Virus (EBV) nuclear antigen-1 (EBNA-1) were co-transfected into CHO-S cells (cGMP banked, Invitrogen, Cat.-No.A1136401), using polyethyleneimine (PEI; Polysciences). Typically, cells were prepared at 8 million cells per ml in CD-CHO media (Gibco). Cells were then transfected with a DNA-PEI mixture at 37° C. Four hours post-transfection, the cell culture was diluted 1:1 in PowerCHO™ 2 (Lonza) supplemented with 4 mM L-Glutamine and incubated for 14 days with orbital shaking at 32° C., 5% CO2 and 80% humidity. Clarified cell culture supernatants containing the recombinant proteins were prepared by centrifugation followed by filtration. Purification of BEAT CD38/CD47 bispecific antibodies from supernatant was performed by differential PA chromatography as described above.

Trastuzumab control IgG1 antibody (SEQ ID NOs: 263 and 264) was expressed in HEK293-EBNA or CHO-S as described above and purified as follows: clarified cell culture supernatants containing the recombinant proteins were prepared by centrifugation followed by filtration. Supernatants were used directly without conditioning. CaptivA resin (Repligen, Waltham, USA) was added to supernatant and incubated overnight at 4° C. under constant agitation. After incubation, bound protein was washed with 10 column volumes (CV) of PBS pH 7.4, followed by an additional 10 CV of PBS pH 7.4. Protein was then eluted in multiple steps of 4 CV of 100 mM Glycine, pH 3.0 and neutralized with 0.1V of 1 M Tris-HCl pH 8.0.

For expression of the isotype control antibody (ABC IgG1, SEQ ID NOs: 265 and 266), equal quantities of each engineered chains vectors, and vectors encoding enhanced Green Fluorescent Protein (eGFP), puromycin N-acetyl-transferase (PAC) and neomycin resistance gene, were co-transfected into CHO-S cells (cGMP banked, Invitrogen, Cat.-No.A1136401), using linear polyethyleneimine (PEI) in Opti-MEM medium (ThermoFisher). Four hours post-transfection, the cell culture was diluted 1:1 in PowerCHO2 CD medium (Lonza) with 4 mM L-Glutamine. The following day, cells were diluted to 2×10e6 cells/ml and subcloned using limiting dilution (from 1:10 to 1:50) in 96-well plates (100 µl per well) in PowerCHO2 medium with 4 mM L-Glutamine supplemented with puromycin (5 µg/ml) and geneticine (200 µg/ml). Selection pressure was renewed after one week by addition of 100 µl of PowerCHO2 medium with 4 mM L-Glutamine and puromycin. The selection of stable clone was done 14 days post-transfection and based on the strength of the eGFP signal as judged by flow cytometry. Clones with the strongest eGFP expression were amplified. Stable CHO cell lines expressing ABC IgG1 antibody were subcultured in PowerCHO2 medium supplemented with 4 mM L-Glutamine, 5 µg/ml puromycin and 200 µg/ml geneticin in TubeSpin bioreactors (TPP), with orbital shaking at 200 RPM, at 37° C., 5% CO2 and 80% humidity. Purification was performed analogously to that of trastuzumab control IgG1 antibody described above. 5F9 IgG4 hinge-stabilized antibody, referred hereafter as 5F9-G4

(SEQ ID NOs: 267 and 268), was expressed in HEK293-EBNA as described above and purified as follows: clarified cell culture supernatants containing the recombinant proteins were prepared by centrifugation followed by filtration. KANEKA KanCapA™ resin (Kaneka) was added to supernatant and incubated overnight at 4° C. under constant agitation. After incubation, bound protein was washed with 1×PBS, pH 7.4 (1×10 CV) and eluted using a step-elution protocol with, sequentially, 50 mM sodium acetate pH 4.3, pH 4.1, pH 3.9 and glycine 0.1 M pH 3.5.

All purified samples were analysed by SDS-PAGE, SE-HPLC and optionally RP-HPLC-MS as described above.

Recombinant Human Neonatal Fc Receptor (FcRn) Extracellular Domain Avitag™-Poly-Histidine Tagged Fusion Protein The soluble extracellular regions of human FcRn (Uniprot accession No: P55899; residues 24-297; SEQ ID NO: 269) and the full-length Beta 2-microglobulin (B2M; Uniprot accession No: P61769, residues 1-119; SEQ ID NO: 270) were cloned as described above. B2M was cloned without any tag and FcRn was cloned to generate a protein with a C-terminal Avitag™ (Avidity LLC) followed by a 10-His tag with a gly$_3$ linker sequence between the two tags (abbreviated human SIRPα-ECD-Avi-His). The expression vector coding for human FcRn was carrying the murine VJ2C leader peptide to drive product secretion as well as the OriP sequence. The expression vector coding for human B2M was carrying the B2M native leader peptide. For the expression of the human FcRn/B2M complex, the plasmids coding for human FcRn-ECD-Avi-His and B2M were co-transfected into suspension-adapted HEK293-EBNA cells as described above. Post expression, Ni-Sepharose Excell beads (GE Healthcare) were added to the clarified supernatant and incubated overnight at 4° C. under gentle agitation. Next, the mixtures were loaded on Econo-Columns (Bio-Rad Laboratories) for gravity-flow purification. The beads were first washed in 1×PBS, 20 mM imidazole, pH 7.4 (10 CV), then 1×PBS supplemented with 40 mM imidazole, pH 7.4 (10 CV) and the protein was eluted using 1×PBS supplemented with 250 mM imidazole (1×1 CV and 5×2 CV). Buffer exchange to 20 mM sodium phosphate, 100 mM NaCl, pH 6.0 was performed on PD-10 columns (GE). Protein quality was assessed by SDS-PAGE, SE-HPLC, endotoxin measurement as described above. Human FcRn-ECD-Avi-His tagged fusion protein as described herein have SEQ ID NO: 269.

Recombinant Human Fcγ Receptors (FcγRs) Extracellular Domain Poly-Histidine Tagged Fusion Protein The extracellular regions of FcγR2a (UniProt accession No: P12318 residues 34-208), of FcγR2b (UniProt accession No: P31994 residues 46-217) and FcγR3a (Uniprot accession No: P08637, residues 17-193) were cloned as described above. The expression vector encompassed a Kozak sequence and a start codon followed by the murine IgGκ light chain leader peptide at the 5' end and a 6 or 10-His-tag at the 3' end of its multiple cloning site. The soluble extracellular regions of human FcγR2a, FcγR2b and FcγR3a fused to a 6 or 10-His-tag were expressed as described above. After expression and harvest, the clarified supernatant was supplemented with 20 mM imidazole and the pH adjusted at 7.4 before adding the resin, except for FcγR3a-ECD-His. The supernatant was incubated with the resin overnight. The next day, the flow through was collected by gravity flow and the resin was washed with 2×10 CVs of 1×PBS, 20 mM imidazole, pH 7.4 (FcγR2a-ECD-His and FcγR2b-ECD-His) or 10 CV of 1×PBS, pH 7.4, followed by a second wash step with 10 CVs of 1×PBS, 20 mM imidazole, pH 7.4 (for FcγR3a-ECD-His). The protein was eluted with 5×1 CV and 2×2 CVs of 1×PBS, 500 mM imidazole, pH 7.4 (FcγR2a-ECD-His and FcγR2b-ECD-His) or 8×1 CV of 1×PBS, 250 mM imidazole, pH 7.4 (FcγR3a-ECD-His). The purified protein was then dialyzed against 1×PBS, pH 7.4. Protein quality was assessed by SDS-PAGE, SE-H PLC, endotoxin measurement as described above. Human FcγR2a, FcγR2b and FcγR3a His tagged fusion proteins as described herein have SEQ ID NO: 271, SEQ ID NO: 272 and SEQ ID NO: 273, respectively.

FcγR1a Affinity Measurements by SPR

SPR analysis was used to measure the association and dissociation rate constants for the binding kinetics of the different bispecific antibodies using single cycle kinetics. The binding kinetics of antibodies were measured on a BIAcore 8K+ instrument (BIAcore-GE Healthcare Europe GmbH, Glattbrugg, Switzerland) at 25° C. and analysed with the Biacore Insight Evaluation software (version 2.0.15.12933, BIAcore-GE Healthcare Europe GmbH).

Measurements were performed on Series S CAP sensor chips (Cytiva Life Sciences, formerly GE Healthcare Europe GmbH, Cat. No: 28920234) coupled with Avi-Tagged FcγR1a (Acrobiosystems, Cat. No: FCA-H82E8) using a commercial Biotin CAPture Kit (Cytiva Life Sciences, formerly GE Healthcare Europe GmbH, Cat. No: 28920234) to a final level of 50-150 RU. Different dilutions of bispecific antibody candidates and trastuzumab control IgG1 (0, 1.2, 3.7, 11.1, 33.3, 100 nM) were injected over the sensor chip for 2 min at 30 µl/min. After ten minutes of dissociation, a CAP regeneration solution was injected for 2 min at 10 µl/min for regeneration followed by a two-minute stabilization period. Data (sensorgram: fc2-fc1) were fitted with a 1:1 Langmuir model without mass transfer using global fitting. Dissociation times were of at least 600 seconds. Measurements were performed in duplicate and included zero-concentration samples for referencing. Both Chi2 and residual values were used to evaluate the quality of a fit between the experimental data and individual binding models.

FcγRIIa, IIb, and IIIa Affinity Measurements by SPR

SPR analysis was used to measure the steady state affinity for the binding of the different bispecific antibodies. The steady state affinity of antibodies was measured on a BIAcore 8K+ instrument (BIAcore-GE Healthcare Europe GmbH, Glattbrugg, Switzerland) at 25° C. and analysed with the Biacore Insight Evaluation software (version 2.0.15.12933, BIAcore-GE Healthcare Europe GmbH).

Measurements were performed on Series S protein G sensor chips (Cytiva Life Sciences, formerly GE Healthcare Europe GmbH, Cat. No: 29179315). Bispecific candidate molecules and trastuzumab control IgG1 were captured to give a final Rmax of approximately 80-100 RU.

Different dilution of Fc-receptors IIa, IIb, and IIIa (0, 39, 78, 156, 312, 625, 1250, 2500, 5000 nM) were injected over the sensor chip for 2 minutes at a flow rate of 30 µl/min. After 2 min of dissociation, the next concentration of analyte was injected. The chip was regenerated at the end of a concentration series, 10 mM glycine pH 1.5 was injected for 1 min at a flow rate of 30 µl/min, followed by a 2 min stabilization period. Data (sensorgram: fc2-fc1) were fitted with a steady state affinity model using global fitting. Dissociation times were of at least 120 seconds. Measurements were performed in duplicate and included zero-concentration samples for referencing. Both Chi2 and residual values were used to evaluate the quality of a fit between the experimental data and individual binding models.

FcRn Affinity Measurements by SPR

SPR analysis was used to measure the steady state affinity of binding of the different bispecific antibodies. The steady state affinity of antibodies was measured on a BIAcore 8K+ instrument (BIAcore-GE Healthcare Europe GmbH, Glattbrugg, Switzerland) at 25° C. and analysed with the Biacore Insight Evaluation software (version 2.0.15.12933, BIAcore-GE Healthcare Europe GmbH).

Measurements were performed on Series S CAP sensor chips (Cytiva Life Sciences, formerly GE Healthcare Europe GmbH, Cat. No: 28920234) coupled with Avi-Tagged FcRn (Acrobiosystems, Cat. No: FCM-H82W2) using a commercial Biotin CAPture Kit (Cytiva Life Sciences, formerly GE Healthcare Europe GmbH, Cat. No: 28920234) to a final level of 50-150 RU. Different dilutions of bispecific antibody candidates trastuzumab control IgG1 (4, 12, 37, 111, 333 and 1000 nM) were injected over the chip for 2 min at a flow rate of 10 μl/min. Following 2 min dissociation, the chip was regenerated with an injection of HBS-EP+pH 8.5, followed by a stabilization period of 2 min. Data (sensorgram: fc2-fc1) were fitted with a steady state affinity model using global fitting. Measurements were performed in duplicate and included zero-concentration samples for referencing. Both Chi2 and residual values were used to evaluate the quality of a fit between the experimental data and individual binding models.

Alternatively (for BEAT CD38/CD47-60), measurements were performed on CM5 sensor chips (Cytiva Life Sciences, formerly GE Healthcare Europe GmbH, Cat. No: 29104988) coupled with a mixture of monoclonal antibodies that recognize kappa and lambda subtypes of human Fab light chains using a commercial Human Fab Capture kit (Cytiva Life Sciences, formerly, GE Healthcare Europe GmbH, Cat. No: 28958325). Antibody candidate molecules and trastuzumab control IgG1 were coupled to give a final RU of approximately 20 RU. Different dilutions of FcRn (0, 7.2, 15.6, 31.3, 62.5, 125, 250, 500, 1000 nM) were injected over the chip for 3 min at a flow rate of 30 μl/min. Following 10 min dissociation, the chip was regenerated with an injection of 10 mM glycine pH 2.0 for 2 min at a flow rate of 30 μl/min, followed by a stabilization period of 1 min. Data (sensorgram: fc2-fc1) were fitted with a steady state affinity model using global fitting. Dissociation times were of at least 600 seconds. Measurements were performed in duplicate and included zero-concentration samples for referencing. Both Chi2 and residual values were used to evaluate the quality of a fit between the experimental data and individual binding models.

Cell Culture

Raji (DSMZ, ACC-319) and Daudi (DSMZ, ACC-78) were cultured in RPM11640. Cell culture media were supplemented with 10% heat-inactivated fetal calf serum (BioWest, cat #S1816), L-Glutamine (Biowest, cat #X0550), 1 mM sodium pyruvate (Dutscher, cat #L064213), 1% Nonessential Amino Acid (Gibco, cat #11140-035), and 1% penicillin-streptomycin solution (Dutscher, cat #L0022). Medium was further supplemented with 1% HEPES (Dutscher, cat #L0180-100) for Raji and NCI-H929, and with 0.05 mM 2-mercaptoethanol (Gibco, cat #31350-010) for NCI-H929.

Complement-Dependent Cytotoxicity (CDC) Assay

Tumor cells were labelled with 5 μM calcein AM (ThermoFisher, cat #C1430) and plated in ultra-low attachment 96-well plates (Corning, cat #3474) with increasing concentration of test antibody and in presence of human serum (Sigma Aldrich, H4522) for 4 h30. Darzalex used here and in all other assays below was commercially obtained (conc perf 100 mg/5 ml, Janssen). Triton X-100 was used as a positive control for maximum tumor cell killing. After the completion of the assay, cells were centrifuged at 350 g for 5 minutes and cell supernatant was transferred in a 96 well plate with clear bottom. Tumor cell killing was measured by quantifying calcein released in the supernatant using Synergy plate reader. Specific killing percentage was calculated according to the formula [(release in test condition−spontaneous release)/(maximum release−spontaneous release)].

Macrophage Differentiation

PBMC were isolated by Ficoll gradient from fresh buffy coat. Human monocytes were subsequently isolated from PBMC using EasySep CD14+ monocytes isolation kit (Stemcell, cat #19359). Isolated monocytes were differentiated into macrophages by culturing them in complete medium containing 50 ng/mL M-CSF (Peprotech, cat #300-25) for 7 days.

Antibody-Dependent Cell Phagocytosis (ADCP) Assay

ADCP assay shown in FIG. 5 and FIG. 8 was performed as follows: differentiated macrophages were collected using Detachin (AMSBio, cat #T00-100). $5\times10^4$ macrophages were plated in a 96-well flat bottom plate and incubated for 2 h at 37° C. to let macrophages re-adhere. $1\times10^5$ Raji cells labelled with phRodo (Sartorius, cat #4649) following manufacturer's instructions were subsequently added to the plate (Effector: Target ratio 1:2) with 80 nM of test antibody. Plates were transferred into the IncuCyte cell analysis system (Sartorius) housed inside a cell incubator at 37° C. for 5 h. Two images per well were taken every 30 min using a 10× objective with red channel acquisition time set to 800 ms. Plates were analyzed using IncuCyte software. Phagocytosis was quantified as the area under the curve measured for phRodo signal over 5 h.

Assessment of Phagocytosis by Automated High Throughput Quantitative Microscopy

Figure 9A:
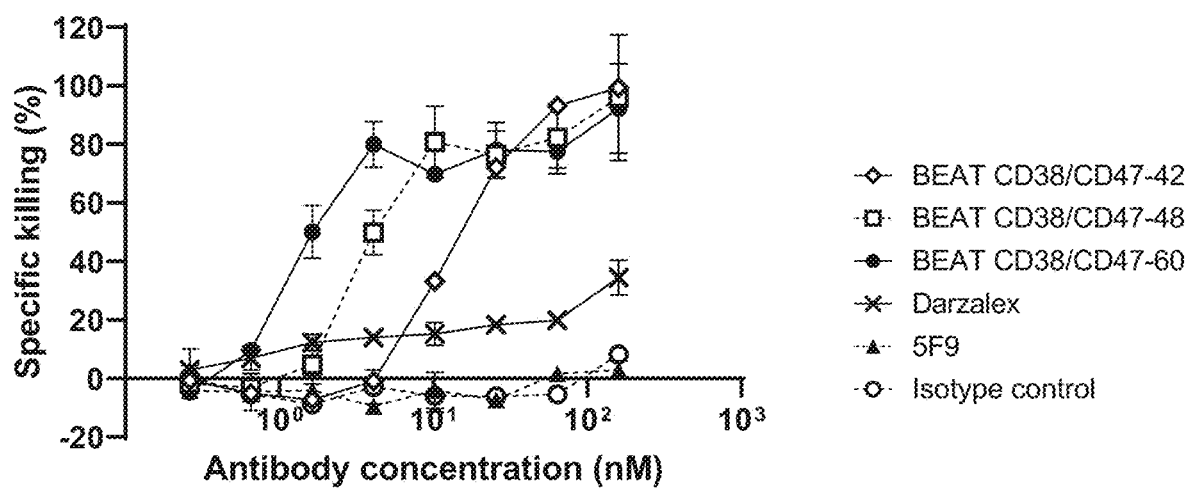
Figure 9B:
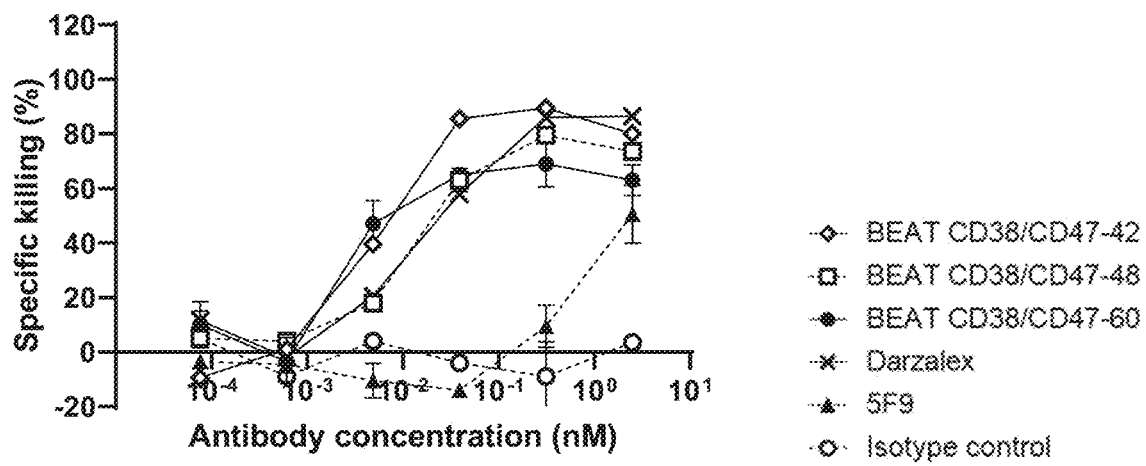
Figure 9C:
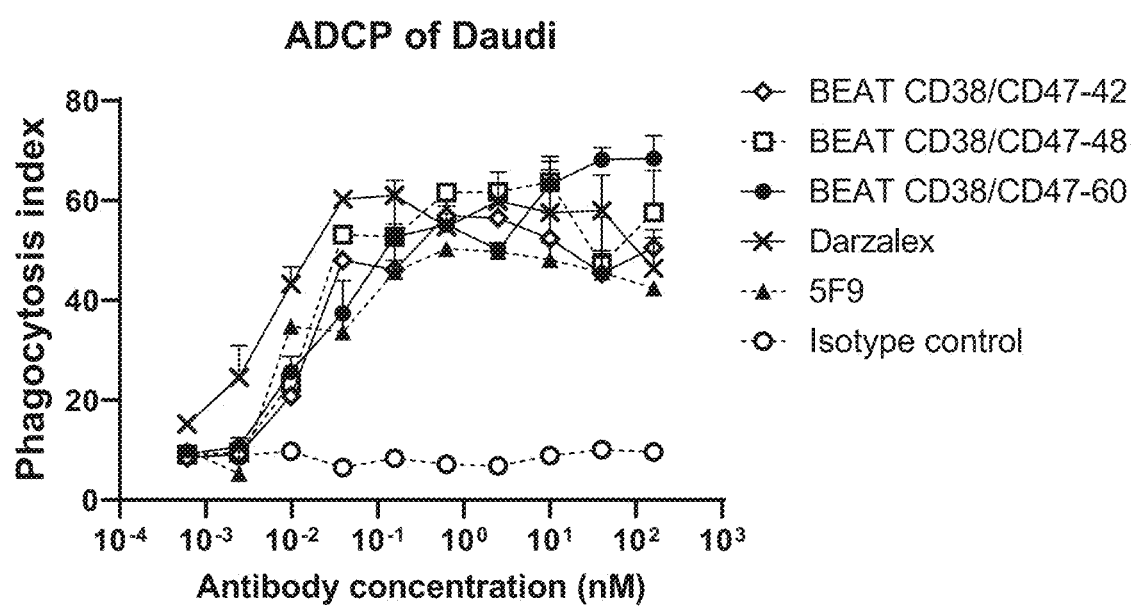

ADCP assay shown in FIG. 9C was performed as follows: $1.5\times10^4$ tumor cells labelled with 1 μg/mL pHrodo Red SE (Thermofisher, P36600) were plated with $3\times10^3$ monocytes-derived-macrophages stained with 2.5 μM Cell trace violet (Thermofisher, C34557) (effector: target ratio=5:1) in a 384-well clear-bottom plates (Corning, cat #3770). Increasing concentration of test antibody was subsequently added to the well, and incubated for 2 h30 at 37° C. Phagocytosis was then evaluated using CellInsightCX5 High Content Screening Platform (Thermofisher) and analyzed using HCS Studio Cell Analysis Software. Phagocytosis was quantified using image based analysis as the average number of pHrodo-bright tumor cells for 100 cell trace violet-positive macrophages.

Antibody-Dependent Cell Cytoxicity (ADCC) Assay

PBMC were isolated from fresh buffy coat by Ficoll gradient. NK cells were subsequently purified using NK cell isolation kit (Miltenyi, cat #130-092-657). Purified NK cells were then incubated with 100 U/mL recombinant human IL-2 (Novartis, cat #L03AC01) overnight at 37° C.

On the day of the experiment, $5\times10^4$ IL-2 stimulated NK cells were plated with $1\times10^4$ tumor cells (effector: target ratio=5:1) stained with 5 μM calcein AM (ThermoFisher, cat #C1430) in ultra-low attachment 96-well plates (Corning, cat #3474). Increasing concentration of test antibody was subsequently added to the well and incubated for 4 h30 at 37° C. After the completion of the assay, cells were centrifuged at 350 g for 5 minutes and resuspended in FACS Buffer containing Sytox dead cell stain (Thermofisher, cat #S11348). Samples were acquired using Cytoflex flow cytometer (Beckman Coulter) and analyzed using Flowjo (Tree Star). Viable tumor cells were identified as positive for calcein AM and negative for Sytox dead cell stain. Killing was quantified using the formula: 100−[(count in test condition)/(count in no antibody condition)].

Differential Scanning Calorimetry (DSC)

The thermal stabilities of antibodies were compared using calorimetric measurements. Calorimetric measurements were carried out on a VP-DSC differential scanning calorimeter or a MicroCal PEAQ-DSC differential scanning calorimeter (Malvern Instruments, UK). The cell volume was 0.128 ml, the heating rate was 1° C./min and the excess pressure was kept at 64 p.s.i. All protein fragments were used at a concentration of 1-2 mg/ml in PBS (pH 7.4). The molar heat capacity of each protein was estimated by comparison with duplicate samples containing identical buffer from which the protein had been omitted. The partial molar heat capacities and melting curves were analysed using standard procedures. Thermograms were baseline corrected and concentration normalized before being further analysed using a Non-Two State model in the manufacturer supplied software.

Forced Degradation

Antibodies were diluted to 0.5 mg/mL in PBS, sterile filtered and incubated at 40° C. for a period of 3 to 14 days and then stored at −80° C. until analysis. Following the incubation, samples were analysed by SDS-PAGE and SE-HPLC as described above.

Results and Conclusion

As discussed above, effector function is critical to the mode of action of BEAT CD38/CD47 bispecific antibodies. Mutations introduced in the Fc portion have previously been reported to increase the effector function of antibodies (e.g. Shields et al., (2001) J Biol Chem 276(9): 6591-6604, Lazar et al., (2006) Proc Natl Acad Sci USA 103(11): 4005-4010). Accordingly, the Fc region of BEAT CD38/CD47 bispecific antibodies was further engineered to enhance multiple modes of action as described below.

Antibody Variants with Enhanced Complement-Mediated Effector Function and Enhanced Antibody-Dependent Cellular Phagocytosis A number of variants of the BEAT Fc were designed with the goal of enhancing CDC as well as ADCP. Interaction of the Fc portion of a target bound antibody with C1q, the first subcomponent of the C1 complement, activates the complement pathway and ultimately induces CDC. Several combinations of amino acid substitutions in the C1q binding region of the CH2 domain of IgG1 antibodies have previously been reported to enhance CDC (WO2011104604). ADCP conversely, depends on the interaction of the antibody Fc with the Fc gamma receptors (FcγRs) on effector cells. These are expressed on macrophages and FcγRIIa in particular has been implicated in ADCP, with FcγRIa and FcγIIIa providing a lower but yet significant and complimentary contribution (Richards et al., (2008) Mol Cancer Ther 7(8): 2517-2527). A plethora of mutations introduced into the CH2 domains of IgG antibodies have previously been reported to increase the affinities to the FcγRs to varying extents and to modulate FcγR mediated effector function (Shields et al., (2001) supra, Lazar et al., (2006) supra).

Here we aimed at introducing a combination of amino acid substitutions into the CH2 domains of the heterodimeric BEAT Fc with the goal of enhancing CDC and ADCP mediated by BEAT CD38/CD47 bispecific antibodies in cooperation with macrophage enabling CD47-SIRPα blockade.

We previously reported substitution S324N as well as combinations of S324N with E269D and S298A to greatly increase complement-induced lysis of target cells by an IgG1 antibody. Notably, substitution S298A has also been reported to increase affinity to FcγRIIIa and can thus be considered for CDC as well as ADCP enhancement (Shields et al., (2001) supra). An important consideration to keep in mind when engineering ADCP enhancement in CD47 targeting antibodies, is the presence of CD47 as well as FcγRIIa on the cell surface of platelet cells. The concern would be that CD38/CD47 bispecific antibodies with strongly increased affinity for FcγRIIa could bind platelet cells via the Fc and by simultaneously interacting with CD47 could potentially induce cross-linking and aggregation of platelets, which would affect on-target specificity. To that extent, our engineering efforts were focused on increasing FcγRIIIa binding affinity, while limiting the increase in affinity to FcγRIIa. Taken together, the aim was to explore various levels of increases in affinity to the different FcγRs in cooperation with CDC enhancing mutations, with the goal of finding the optimal balance between killing potency and on-target specificity. Accordingly, various combinations of CDC enhancing mutations S324N, E269D and S298A, and FcγR affinity modulating mutations S298A, K334E, K334A, S239D and I332E, were introduced into BEAT CD38/CD47-19 resulting in constructs -21, -22, -24 and -42 (Table 5). Substitutions were generally introduced symmetrically into both heavy chains. Mutations S239D and I332E however, were introduced asymmetrically into the BEAT (A) Hc only, as symmetric engineering thereof abolished the expression of the BEAT bispecific antibodies.

TABLE 5

List of CD38/CD47 BEAT bispecific antibody constructs with effector function enhancing Fc mutations and their associated SEQ ID NOs.

| Construct | Fc mutations | BEAT (A) Hc | BEAT (B) Hc | cLc |
|---|---|---|---|---|
| BEAT CD38/CD47-19 | None | SEQ ID NO: 259 | SEQ ID NO: 262 | SEQ ID NO: 10 |
| BEAT CD38/CD47-21 | BEAT (A): S324N + K334E BEAT (B): S324N + K334E | SEQ ID NO: 274 | SEQ ID NO: 275 | SEQ ID NO: 10 |
| BEAT CD38/CD47-22 | BEAT (A): S324N BEAT (B): S324N | SEQ ID NO: 276 | SEQ ID NO: 277 | SEQ ID NO: 10 |
| BEAT CD38/CD47-24 | BEAT (A): E269D + S298A + S324N + K334A + BEAT (B): E269D + S298A + S324N + K334A | SEQ ID NO: 278 | SEQ ID NO: 279 | SEQ ID NO: 10 |
| BEAT CD38/CD47-42 | BEAT (A): S239D + I332E + S324N BEAT (B): S324N | SEQ ID NO: 280 | SEQ ID NO: 277 | SEQ ID NO: 10 |

Bispecific antibodies were produced and characterized as described above. Monodispersity of >95% was observed by SE-HPLC with <1% homodimeric contaminants as determined by RP-HPLC-MS. Endotoxin levels were inferior to 5 EU/mg. Their capacity to mediate CDC was assessed in a cell-based assay on Daudi cells. All further engineered variants showed superior CDC activity over the non-enhanced BEAT CD38/CD47-19, confirming that the mutations are functional in the context of the heterodimeric BEAT Fc, as they were in the context of wild-type IgG1 (FIG. 4). S324N alone (BEAT CD38/CD47-22) mediated most of the gain in CDC. Additional mutations K334E in BEAT CD38/CD47-21 and E269D+S298A+K334A in BEAT CD38/CD47-24 mediated minimal additional gain over S324N alone at lower antibody concentrations. S239D+I332E did not mediate any additional gain in CDC over S324N alone (BEAT CD38/CD47-42).

Next, the capacity to mediate ADCP was assessed for BEAT CD38/CD47 bispecific antibodies in a cell-based assay on Raji cells. Additional constructs to those in tables 4 and 5 were assessed, where further FcγR affinity modulation was explored (Table 6). Removal of substitution E269D from BEAT CD38/CD47-23 and -24 was assessed in constructs BEAT CD38/CD47-25 and -26 with the hypothesis that while E269D is beneficial for CDC it could potentially disturb interaction with FcγRs as previously observed for mutation E269A (Shields et al., (2000) supra). Constructs were produced and characterized as described above. Monodispersity of >95% was observed by SE-HPLC with <1% homodimeric contaminants as determined by RP-HPLC-MS. Endotoxin levels were inferior to 5 EU/mg.

TABLE 6

List of further CD38/CD47 BEAT bispecific antibody constructs with effector function enhancing Fc mutations and their associated SEQ ID NOs.

| Construct | Fc mutations | BEAT (A) Hc | BEAT (B) Hc | cLc |
|---|---|---|---|---|
| BEAT CD38/ CD47-23 | BEAT (A): E269D + S298A + S324N + E333A<br>BEAT (B): E269D + S298A + S324N + E333A | SEQ ID NO: 281 | SEQ ID NO: 282 | SEQ ID NO: 10 |
| BEAT CD38/ CD47-25 | BEAT (A): S298A + S324N + E333A<br>BEAT (B): S298A + S324N + E333A | SEQ ID NO: 283 | SEQ ID NO: 284 | SEQ ID NO: 10 |
| BEAT CD38/ CD47-26 | BEAT (A): S298A + S324N + K334A<br>BEAT (B): S298A + S324N + K334A | SEQ ID NO: 285 | SEQ ID NO: 286 | SEQ ID NO: 10 |

Non-enhanced antibodies BEAT CD38/CD47-3, -6 and -19, which all share the same anti-CD47 VH, showed similar levels of ADCP, regardless of the anti-CD38 affinity, which was lowest for construct-6 and highest for construct-19 (FIG. 5). Mutation K334E significantly enhanced ADCP for BEAT CD38/CD47-21. Removing substitution E269D mildly improved ADCP in BEAT CD38/CD47-25 and 26 over BEAT CD38/CD47-23 and -24. Mutations S239D+ I332E introduced in BEAT CD38/CD47-42 mediated the largest gain in ADCP potency over any other construct. FcγR affinities for favorable constructs were measured by SPR and compared to those of the trastuzumab control IgG1 (Table 7). Strongest FcγR affinities correlated with largest gain in ADCP potency.

TABLE 7

Modulation of FcγR affinities as measured by SPR.

| Construct | Fc mutations | Ia [fold gain in affinity vs control] | IIa [fold gain in affinity vs control] | IIb [fold gain in affinity vs control] | IIIa [fold gain in affinity vs control] |
|---|---|---|---|---|---|
| BEAT CD38/ CD47-21 | BEAT (A): S324N + K334E<br>BEAT (B): S324N + K334E | 1027 | 1 | 0.1 | 2 |

TABLE 7-continued

Modulation of FcγR affinities as measured by SPR.

| Construct | Fc mutations | Ia [fold gain in affinity vs control] | IIa [fold gain in affinity vs control] | IIb [fold gain in affinity vs control] | IIIa [fold gain in affinity vs control] |
|---|---|---|---|---|---|
| BEAT CD38/ CD47-42 | BEAT (A): S239D + I332E + S324N<br>BEAT (B): S324N | 3750 | 6 | 14 | 11 |

For T cell redirecting bispecific antibodies, Bluemel et al., (2010) Cancer Immunol Immunother 59(8): 1197-1209 showed that potency can be affected by the targeted epitope and thus by the geometrical arrangement created on the cell surface. Accordingly, we hypothesized that the geometrical positioning of the Fc upon target engagement will determine the efficiency of C1q binding and in turn the extent of complement activation. Furthermore, we postulated that similarly, the geometry and distances created between the BEAT CD38/CD47 bispecific antibody and the FcγRs on immune cells will affect the potency of effector function. To that end, we explored various binding epitopes in CD38 as well as the "2+1" antibody format. "2+1" BEAT bispecific antibodies have an additional Fab domain fused to a first Fab domain via a flexible linker, commonly a glycine-serine sequence (FIG. 6). The Fab domain that is located between the antibody Fc and the second Fab domain is termed the "Fc proximal" binding unit, while the Fab domain that is fused to the N-terminus of the VH of the "Fc proximal" Fab is termed the "Fc distal" binding unit. Analogously to the traditional BEAT antibody format described in FIG. 3, which is now termed the "1+1" format, light chain mispairing in the "2+1" architecture is avoided by use of a cLc, which essentially allows the addition of an unlimited number of different binding domains to a BEAT antibody. Consequently, the cLc allows the engineering of a BEAT CD38/CD47 bispecific antibody that has two anti-CD38 binding units with different VH sequences that bind two distinct epitopes in CD38, in addition to the VH domain that binds CD47. Such a construct is referred herein as a "2+1" biparatopic BEAT bispecific antibody. A biparatopic BEAT CD38/CD47 bispecific antibody may induce a different geometry of binding on the target cell as compared to an antibody in the "1+1" format or an antibody in the "2+1" format that is monoparatopic and has two identical anti-CD38 binding units, and this in turn may modulate effector function.

"2+1" BEAT bispecific antibodies were engineered analogously to those in the "1+1" format with the anti-CD47 BEAT (A) arm designed as those described above. The anti-CD38 arm of the heterodimeric immunoglobulin consisted of a BEAT (B) Hc encompassing a first VH domain selected from Table 3 (anti-CD38-E2-RecA or anti-CD38-B6), a CH1 γ1 region, a glycine-serine linker (GGGGSGGGGSGGGS), a second VH domain selected from Table 3 (anti-CD38-E2-RecA), a second CH1 γ1 region, a γ1 hinge region, a γ1 CH2 region, and a γ1 based BEAT (B) CH3 domain assembled with a cLc. "2+1" BEAT bispecific antibodies resulting from the assembly of the BEAT (A) and BEAT (B) Hcs as well as the cLc are listed in Table 8. Importantly, biparatopic "2+1" BEAT bispecific antibodies consisted of VH domains that targeted non-overlapping epitopes in CD38 and that could bind simultaneously (FIG. 2) (BEAT CD38/CD47-38, -39, -40 and -48). Contrariwise, monoparatopic "2+1" BEAT bispecific antibodies contained two copies of the same VH domain (BEAT CD38/CD47-32 and -34). "2+1" BEAT bispecific antibodies were expressed and purified as above. For all antibodies, monodispersity of >95% was observed by SE-HPLC with <1% homodimeric contaminants as determined by RP-HPLC-MS. Endotoxin levels were inferior to 5 EU/mg. BEAT CD38/CD47 bispecific antibodies were then further tested for their biological activity.

"2+1" BEAT bispecific antibodies did not further improve ADCP activity (BEAT CD38/CD47-39 and -40). A biparatopic construct with mutations S239D+I332E, which mediate the strongest increases in FcγR binding, was not yet available at the time the assay above was performed but was later shown in a subsequent assay to have further potentiated ADCP activity over the equivalent "1+1" construct (BEAT CD38/CD47-48 vs -42) (FIG. 9C). FcγR affinities for favourable constructs were measured by SPR and compared to those of trastuzumab control IgG1 (Table 9).

TABLE 8

List of CD38/CD47 "2 + 1" BEAT bispecific antibody constructs with and without effector function enhancing Fc mutations and their associated SEQ ID NOs.

| Construct | Fc mutations | CD38 engagement | BEAT (A) Hc | BEAT (B) Hc | cLc |
|---|---|---|---|---|---|
| BEAT CD38/CD47-32 | BEAT (A): E269D + S298A + S324N + E333A<br>BEAT (B): E269D + S298A + S324N + E333A | Monoparatopic | SEQ ID NO: 281 | SEQ ID NO: 287 | SEQ ID NO: 10 |
| BEAT CD38/CD47-34 | BEAT (A): E269D + S298A + S324N + K334A<br>BEAT (B): E269D + S298A + S324N + K334A | Monoparatopic | SEQ ID NO: 278 | SEQ ID NO: 288 | SEQ ID NO: 10 |
| BEAT CD38/CD47-38 | None | Biparatopic | SEQ ID NO: 259 | SEQ ID NO: 289 | SEQ ID NO: 10 |
| BEAT CD38/CD47-39 | BEAT (A): E269D + S298A + S324N +E333A<br>BEAT (B): E269D + S298A + S324N +E333A | Biparatopic | SEQ ID NO: 281 | SEQ ID NO: 290 | SEQ ID NO: 10 |
| BEAT CD38/CD47-40 | BEAT (A): E269D + S298A + S324N + K334A<br>BEAT (B): E269D + S298A + S324N +K334A | Biparatopic | SEQ ID NO: 278 | SEQ ID NO: 291 | SEQ ID NO: 10 |
| BEAT CD38/CD47-48 | BEAT (A): S239D + I332E + S324N<br>BEAT (B): S324N | Biparatopic | SEQ ID NO: 280 | SEQ ID NO: 292 | SEQ ID NO: 10 |

The capacity of "2+1" BEAT bispecific antibodies to mediate CDC compared to those in the "1+1" format was assessed in a cell-based assay on Daudi cells. Moving from the "1+1" format to the "2+1" format, in the context of an Fc that was not further engineered for effector function, did not improve CDC potency (BEAT CD38/CD47-19 vs -38) (FIG. 7). In the context of enhanced BEAT Fc however, the "2+1" architecture led to a gain in CDC activity at lower antibody concentrations over the equivalent antibody in the "1+1" format (BEAT CD38/CD47-40 and -48 vs -24 and -42). Next, "2+1" BEAT bispecific antibodies were compared for their capacity to induce ADCP in a cell based assay on Raji cells (FIG. 8). Monoparatopic "2+1" BEAT bispecific antibodies showed a gain in ADCP potency over their "1+1" counterparts (BEAT CD38/CD47-32 and -34 vs -23 and -24), however the level of phagocytosis could not match that of the most favorable "1+1" construct BEAT CD38/CD47-42. Intriguingly, biparatopic "2+1" BEAT bispecific antibodies showed significant gain in ADCP potency, even with a non-enhanced Fc (BEAT CD38/CD47-38), to levels of the most enhanced "1+1" construct BEAT CD38/CD47-42, confirming the hypothesis that the geometry of antibody binding on the cell surface impacts effector function and that biparatopic engagement positively affects ADCP potency. Mild increase in FcγR affinities in the context of biparatopic

TABLE 9

Modulation of FcγR affinities for "2 + 1" constructs as measured by SPR.

| Construct | Fc mutations | Ia [fold gain in affinity vs control] | IIa [fold gain in affinity vs control] | IIb [fold gain in affinity vs control] | IIIa [fold gain in affinity vs control] |
|---|---|---|---|---|---|
| BEAT CD38/CD47-48 | BEAT (A): S239D + I332E + S324N<br>BEAT (B): S324N | 864 | 7 | 16 | 10 |
| BEAT CD38/CD47-32 | BEAT (A): S324N + S298A + E269D + E333A<br>BEAT (B): S324N + S298A + E269D + E333A | 12 | 0.5 | 1 | 3 |
| BEAT CD38/CD47-40 | BEAT (A): S324N + S298A + E269D + K334A<br>BEAT (B): S324N + S298A + E269D + K334A | 4513 | 0.4 | 1 | 4 |
| BEAT CD38/CD47-34 | BEAT (A): S324N + S298A + E269D + K334A<br>BEAT (B): S324N + S298A + E269D + K334A | 874 | 0.4 | 1 | 4 |

Taken together, mutation S324N favorably affected CDC potency and the biparatopic "2+1" format further potentiated the same (FIG. 4 and FIG. 7). S239D+I332E introduced asymmetrically in the BEAT (B) heavy chain resulted in the strongest gain in ADCP activity, which was further enhanced by the biparatopic "2+1" architecture.

Construct BEAT CD38/CD47-48 which encompassed all of the aforementioned, was engineered with an "Fc distal" anti-CD38 binder of low affinity (anti-CD38-B6, SPR KD=225 nM). Affinity maturation of said binder (Table 3) allowed the engineering of an additional biparatopic "2+1" BEAT bispecific antibody with high affinity "Fc proximal" (anti-CD38-E2-RecA) and "Fc distal" (anti-CD38-B6-D9) anti-CD38 binding domains (BEAT CD38/CD47-60) (Table 10). BEAT CD38/CD47-60 as well as -42 and 48 were transiently expressed in CHO, purified and characterized as described above. Monodispersity of >95% was observed by SE-HPLC with <1% homodimeric contaminants as determined by RP-HPLC-MS. Endotoxin levels were inferior to 5 EU/mg.

TABLE 10

SEQ ID NOs for construct BEAT CD38/CD47-60.

| Construct | Fc mutations | CD38 engagement | BEAT (A) Hc | BEAT (B) Hc | cLc |
|---|---|---|---|---|---|
| BEAT CD38/ CD47-60 | BEAT (A): S239D + I332E + S324N BEAT (B): S324N | Biparatopic | SEQ ID NO: 280 | SEQ ID NO: 293 | SEQ ID NO: 10 |

Next, the capacity to induce CDC, ADCP as well as ADCC were assessed in cell based assays for construct BEAT CD38/CD47-60 compared to favorable candidates -42 and -48. Notably, BEAT CD38/CD47-60, which had a high affinity anti-CD38 binding domain in the "Fc distal" position, induced significantly more potent CDC than BEAT CD38/CD47-48 that had a low affinity anti-CD38 binding domain in the "Fc distal" position (FIG. 9A). ADCC was similar for all constructs (FIG. 9B) and ADCP of Daudi cells showed minimal gain for BEAT CD38/CD47-60 over -48 (FIG. 9C).

Biophysical Characterization of BEAT CD38/CD47 Bispecific Antibodies

Figure 10A:
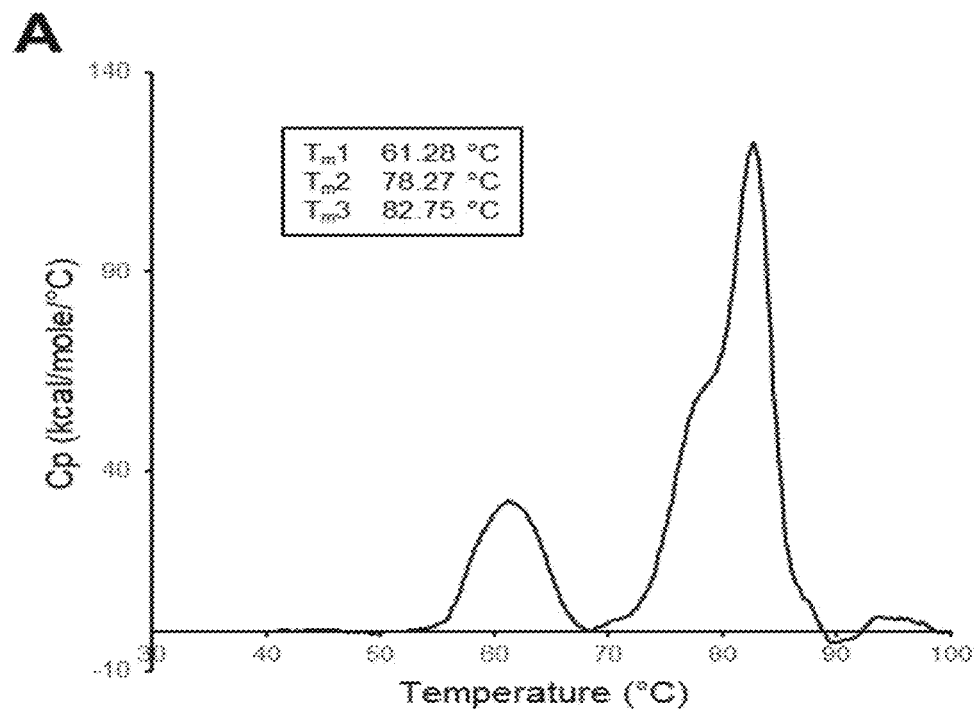
Figure 10B:
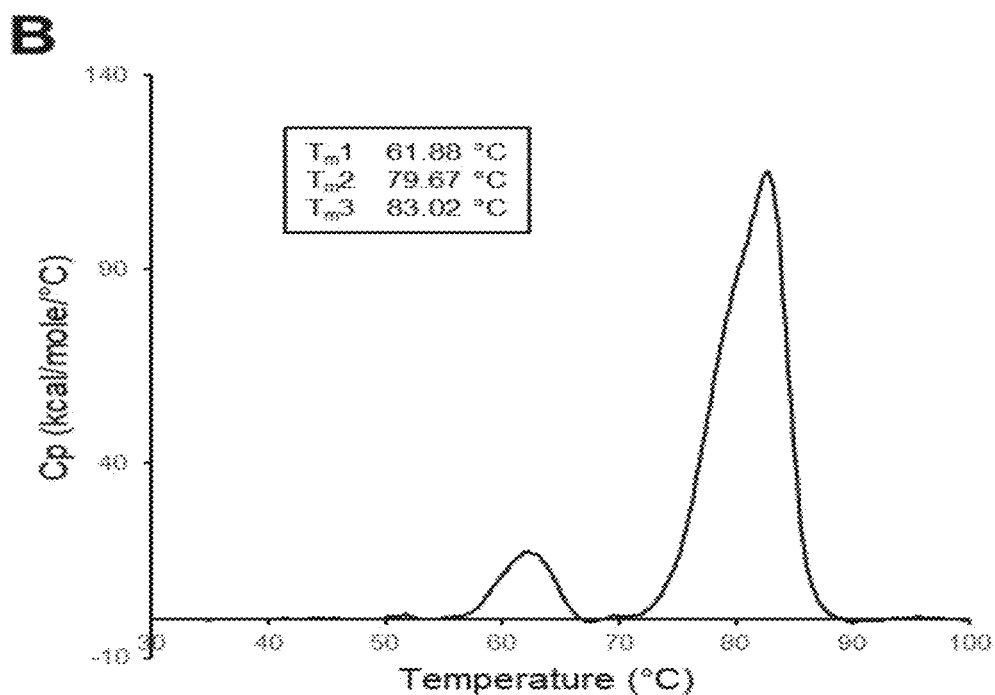
Figure 10C:
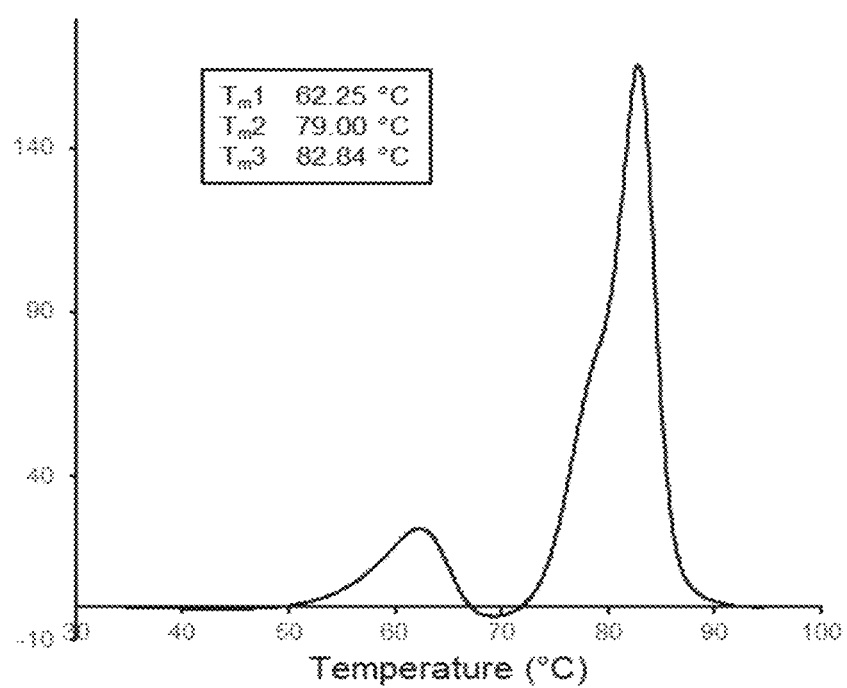
Figure 11A:
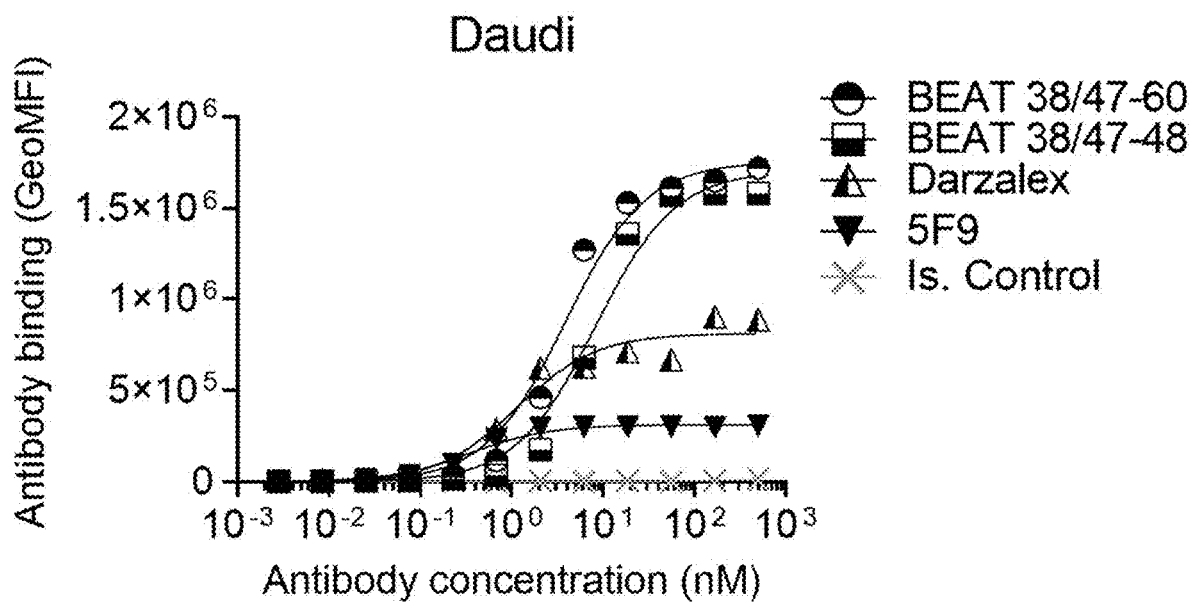
Figure 11B:
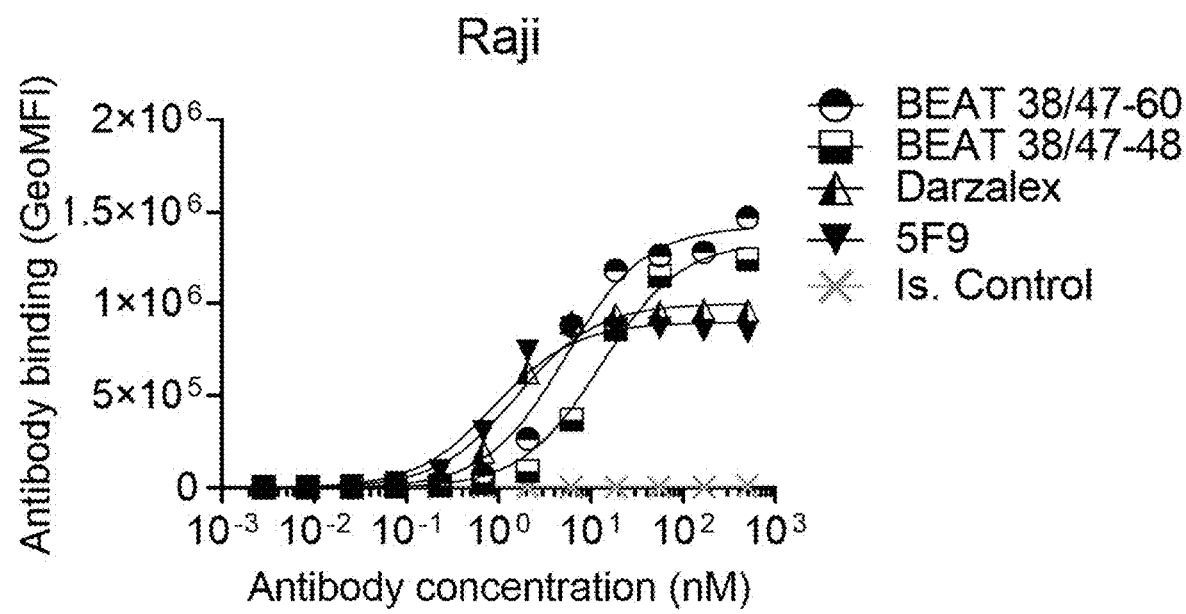
Figure 11C:
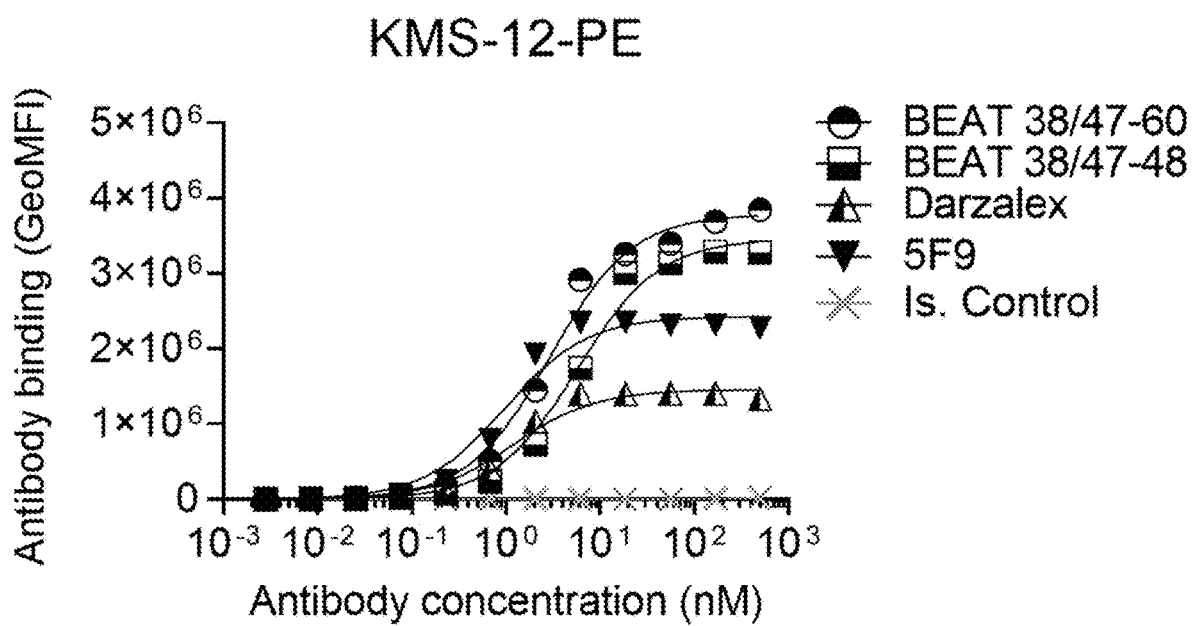
Figure 11D:
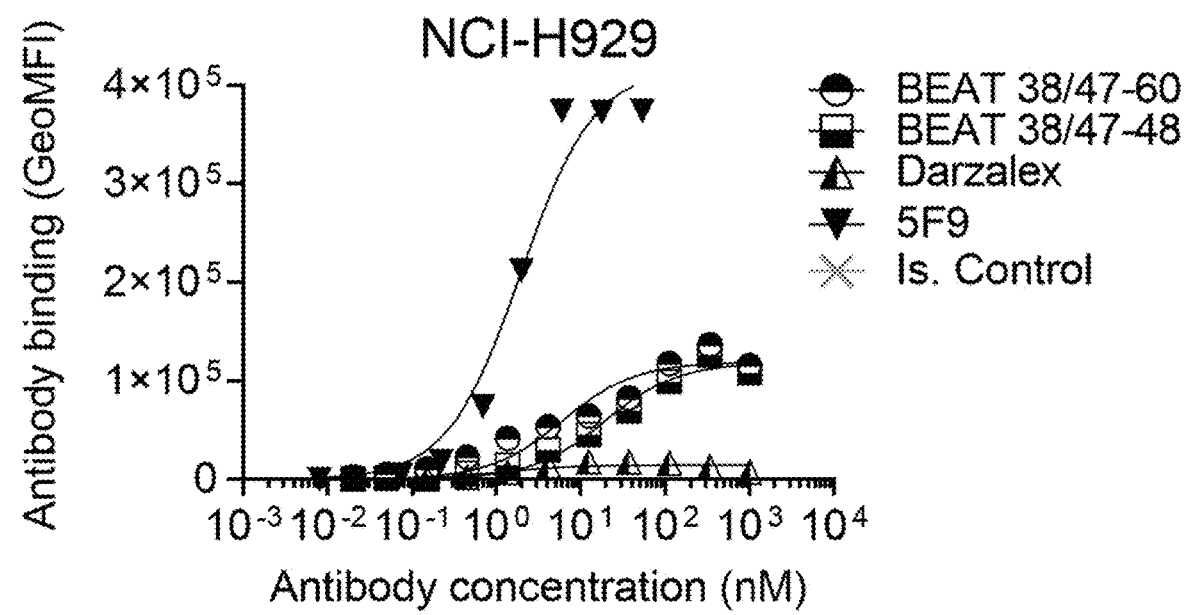
Figure 11E:
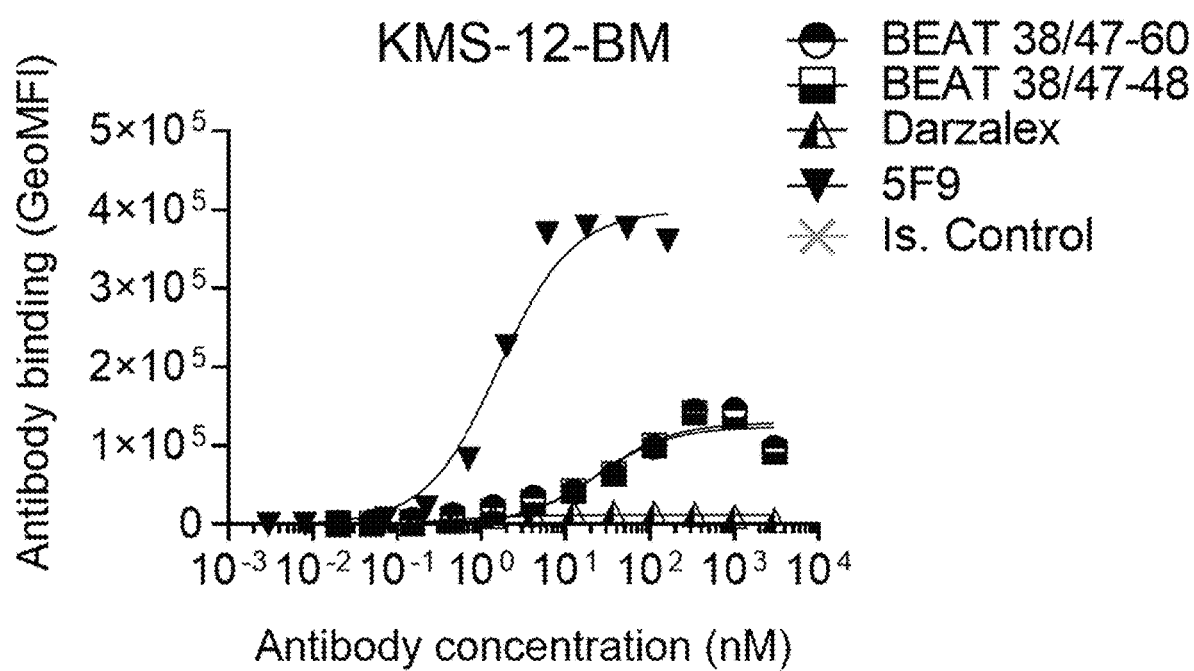

BEAT CD38/CD47 bispecific antibodies were further characterized by DSC to investigate the impact of effector function engineering in the Fc on thermal stability (Table 11). Corresponding thermograms for candidates BEAT CD38/CD47-42, -48 and -60 are depicted in FIGS. 10A, 10B and 10C, respectively. All BEAT Fcs with effector function enhancing mutations had reduced thermal stability compared to non-enhanced BEAT Fc. Mutations S239D+I332E had the strongest impact on thermal stability followed by K334E. Other combinations of mutations also reduced thermal stability but to a lesser extent.

TABLE 11

Summary of thermal transitions (Tm) observed by DSC for BEAT CD38/CD47 bispecific antibodies.

| Construct | Fc mutations | Tm1 [° C.] Fc | Tm2 [° C.] Fab 1 | Tm3 [° C.] Fab 2 |
|---|---|---|---|---|
| BEAT CD38/ CD47-3 | None | 69.5 | 83.5 | — |
| BEAT CD38/ CD47-21 | BEAT (A): S324N + K334E BEAT (B): S324N + K334E | 62.7 | 78.2 | 82.0 |
| BEAT CD38/ CD47-32 | BEAT (A): E269D + S298A + S324N + E333A BEAT (B): E269D + S298A + S324N + E333A | 64.2 | 77.6 | 81.9 |
| BEAT CD38/ CD47-34 | BEAT (A): E269D + S298A + S324N + K334A BEAT (B): E269D + S298A + S324N + K334A | 65.1/67.6 | 77.6 | 81.9 |
| BEAT CD38/ CD47-40 | BEAT (A): S324N + S298A + E269D + K334A BEAT (B): S324N + S298A + E269D + K334A | 64.7/67.5 | 79.1 | 82.4 |
| BEAT CD38/ CD47-42 | BEAT (A): S239D + I332E + S324N BEAT (B): S324N | 61.3 | 78.3 | 82.8 |
| BEAT CD38/ CD47-48 | BEAT (A): S239D + I332E + S324N BEAT (B): S324N | 61.9 | 79.7 | 83.0 |
| BEAT CD38/ CD47-60 | BEAT (A): S239D + I332E + S324N BEAT (B): S324N | 62.3 | 79.0 | 82.8 |

Given the reduced thermal stability of the enhanced BEAT Fcs, we further assessed the stability of the different variants in a 2 week forced degradation study at 40° C. Percent monodispersity as determined by SE-HPLC was unchanged after 2 weeks for the original BEAT Fc as well as for all of the tested enhanced BEAT Fc variants while that of trastuzumab control IgG1 was severely reduced (Table 12).

TABLE 12

Results of force degradation study performed on CD38/CD47 BEAT bispecific antibodies.

| Construct | t = 0 [% monodispersity] | t = 14, 4° C. [% monodispersity] | t = 3 d, 40° C. [% monodispersity] | t = 7 d, 40° C. [% monodispersity] | t = 14 d, 40° C. [% monodispersity] | Δ [% monodispersity] (t = 0) − (t = 14) |
|---|---|---|---|---|---|---|
| BEAT CD38/CD47-3 | 95.8 | 96.5 | 96.4 | 97.2 | 96.9 | 1.2 |
| BEAT CD38/CD47-21 | 98.8 | 99.5 | 98.8 | 99.0 | 99.2 | 0.3 |
| BEAT CD38/CD47-40 | 99.0 | 99.5 | 98.9 | 98.6 | 97.9 | −1.2 |
| BEAT CD38/CD47-42 | 98.6 | 99.0 | 98.6 | 98.6 | 98.6 | −0.0 |
| BEAT CD38/CD47-48 | 97.8 | 98.0 | 97.4 | 97.0 | 95.9 | −1.9 |
| Control IgG1 | 94.9 | 95.2 | 73.7 | 36.9 | 0 | −94.9 |

Next, we assessed whether engineering of enhanced BEAT Fc impacted binding of human neonatal Fc receptor (FcRn). FcRn binds at the interface between the CH2 and the CH3 domains and thus changes in the Fc could potentially modulate the binding affinity, which in turn could affect serum half-life (Martin et al., (2001) Mol Cell 7(4): 867-877). Affinities of enhanced BEAT Fc variants for FcRn were determined by SPR (Table 13). Binding of FcRn was not negatively impacted by further engineering of the BEAT Fc and KDs were in the range of what was measured for trastuzumab control IgG1.

TABLE 13

SPR measurements for BEAT CD38/CD47 binding to FcRn.

| Construct | Fc mutations | KD ratio [BEAT/ Control IgG1] |
|---|---|---|
| BEAT CD38/ CD47-21 | BEAT (A): S324N + K334E BEAT (B): S324N + K334E | 0.4 |
| BEAT CD38/ CD47-40 | BEAT (A): S324N + S298A + E269D + K334A BEAT (B): S324N + S298A + E269D + K334A | 0.3 |
| BEAT CD38/ CD47-42 | BEAT (A): S239D + I332E + S324N BEAT (B): S324N | 0.5 |
| BEAT CD38/ CD47-48 | BEAT (A): S239D + I332E + S324N BEAT (B): S324N | 0.2 |
| BEAT CD38/ CD47-60 | BEAT (A): S239D + I332E + S324N BEAT (B): S324N | 0.5 |

EXAMPLE 6: IN VITRO BIOLOGICAL CHARACTERIZATION OF BEAT CD38/47-48 AND BEAT CD38/47-60 CANDIDATES

Example 6.1: In Vitro Characterization of BEAT CD38/47-48 and 60 Binding Activity of Multiple Myeloma and Lymphoma Cell Lines Material and Methods Hundred thousand cells per well were plated in U-bottom 96-well plate (TPP) and centrifuged at 350 g for 5 minutes. Supernatants were discarded by flicking the plates and cell pellets were resuspended in 100 μl of a dose-response of primary purified antibodies. Cells were incubated for 30 minutes at 4° C. (dark). After two washing steps (350 g for 5 minutes), cells were stained with monoclonal mouse anti-Human IgG-Fc PE diluted at 1/200 in FACS Buffer for 30 minutes at 4° C. After a last washing step, cells were suspended in FACS buffer containing Sytox (1/2000) or Dapi (1/50000).

Flow-cytometric analysis was then performed with a Cytoflex (Beckman Coulter).

Data were analyzed using FlowJo software (BD): PE Geometric Mean of Fluorescence Intensities (geoMFI) of viable single cells for each sample were extracted. Since antibodies can display some non-specific binding to cells, a normalization was performed using the geoMFI of the Isotype control antibody (ABC-IgG1). The values of geoMFI from the control staining were subtracted to the geoMFI values of each molecule to generate the relative fluorescence intensity (RFI). All the KD values were calculated using the RFI. For some curves, geoMFI values at the highest concentration were excluded due to the observation of a hook effect.

For the KD calculation, a non-linear one site binding (hyperbola) regression was applied in Prism software (GraphPad) on the RFI values.

Results and Conclusions

Binding of BEAT CD38/47-48 and -60 was evaluated by flow cytometry on a panel of multiple myeloma (KMS-12-PE (FIG. 11C), KMS-12-BM (FIG. 11E), NCI-H929 (FIG. 11D)), and lymphoma (Raji (FIG. 11B), Daudi (FIG. 11 A)) cell lines expressing different level of CD38 and CD47. The rational for this assessment was to evaluate the Kd of BEAT 38/47-48 and -60 as well as to understand their binding to tumor cell lines as compared to anti-CD38 (DArzalex) or anti-CD47 (5F9-like, Magrolimab) monoclonal antibody binding.

BEAT CD38/47-48 and BEAT CD38/47-60 show higher binding to CD38 high tumor cell lines (Daudi, Raji, KMS-12-PE) as compared to benchmark Darzalex and 5F9. In addition, BEAT CD38/47-48 and BEAT CD38/47-60 show higher binding to CD38 low tumor cell lines (NCI-H929 and KMS-12-BM) as compared to Darzalex. Multiple myeloma cells in patients show several features of primary or acquired tumor escape mechanisms, including the upregulation of CD47 "do not eat me" signal and the downregulation of cell surface CD38 (in patients receiving Darzalex as standard of care for example). BEATs 38/47 are designed to overcome both these tumor escape mechanisms and improve the targeting of CD38 expressing tumor cells as compared to standard of care Darzalex. The present cell binding data suggest that co-targeting of CD38 and CD47 could allow for a better therapeutic window as compared to current benchmark, especially in CD38 low MM tumor cells.

Example 6.2: BEAT CD38/47-48 and BEAT CD38/47-60 Inhibition CD47-SIRPα Interactions Materials and Methods $10 \times 10^3$ Daudi cells labelled with 8 uM Hoescht (Thermofisher, cat #33342) were plated in 20 uL in a 384-well clear-bottom plates (Corning, cat #3770) and co-incubated with 20 uL of increasing concentration (from 0.00015 nM to 640 nM) of test antibody for 30 minutes at 4° C. In parallel, a mix of antibodies (detection mix) composed of 300 ng/mL SIRPα-mIgG1 Fc fusion protein (Accrobiosystem, cat #SIA-H52A8) and 2.5 ug/mL of Alexa Fluor 647-conjugated anti-mouse IgG Fc detection reagent (Jackson Immunoresearch, cat #115-605-205) was prepared in assay buffer (PBS+2.5% FBS+0.1% $NaN_3$) and incubated for 30 min at room temperature in the dark. The detection mix (20 uL) was added to the cells and incubated for 3 h at room temperature. Binding of recombinant SIRPα-Fc to tumor cells was quantified by image based analysis using CellInsight CX5 High Content Screening Platform (Thermo Fisher Scientific). CD47/SIRPα inhibition is shown as percentage of inhibition of the Detection Mix fluorescence signal.

Results and Conclusions

Figure 12A:
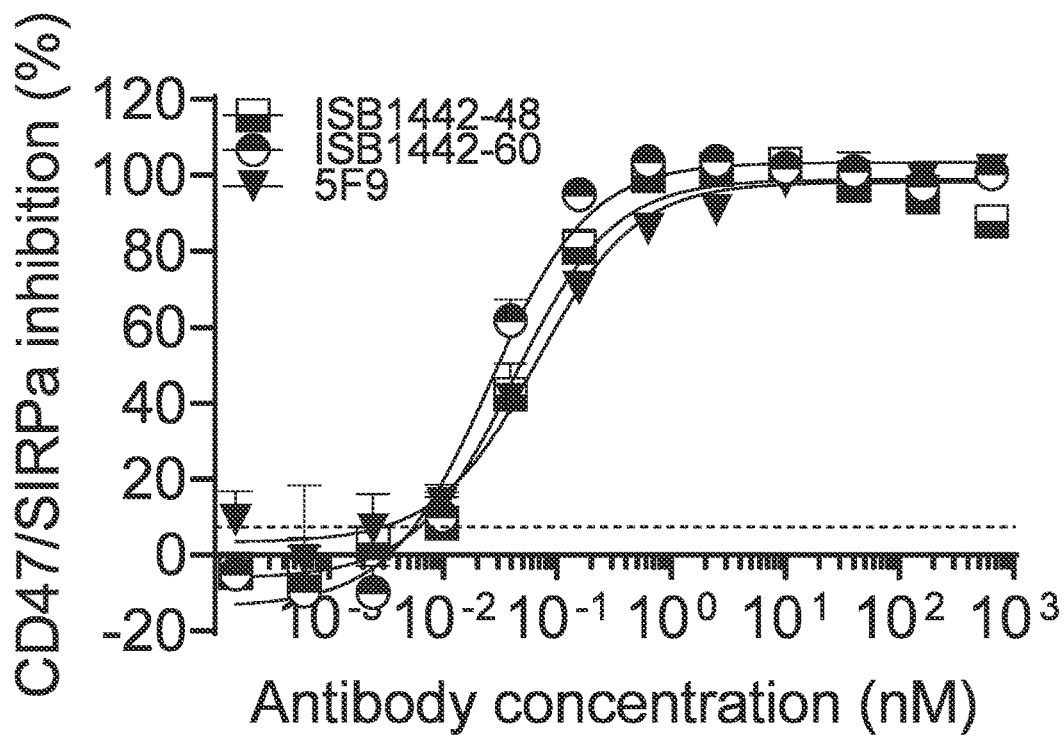
Figure 12B:
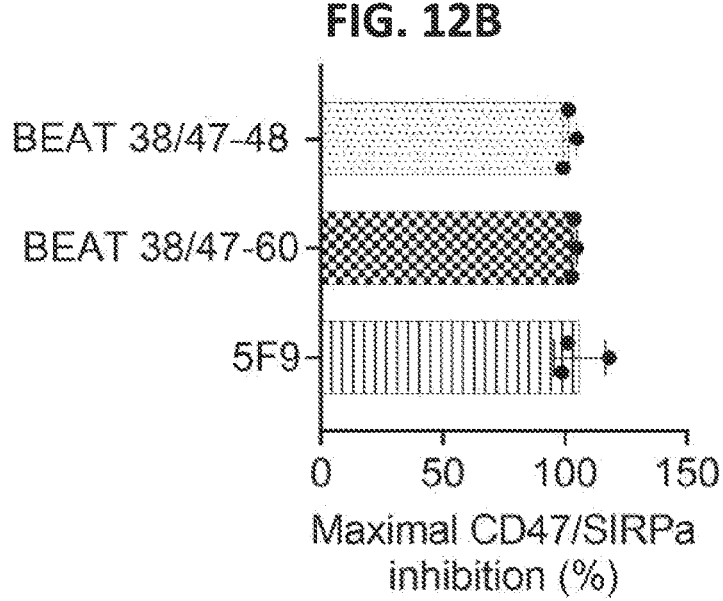
Figure 12C:
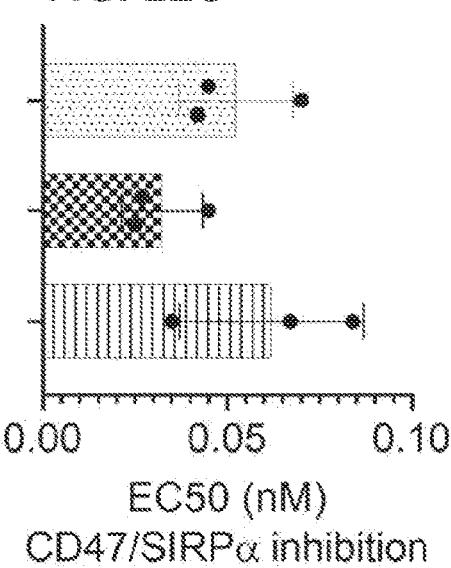

The ubiquitous immune checkpoint CD47 works as a "Don't eat me" signal inhibiting phagocytosis upon binding to its cognate receptor SIRPα expressed by macrophages. Tumor cells highjack this mechanism and overexpress CD47 as a mechanism of immune evasion to avoid phagocytosis. BEAT CD38/47-48 and BEAT CD38/47-60 are designed to selectively block CD47-SIRPα on CD38 expressing cells upon target-co-engagement and enhance antibody dependent cell phagocytosis. We therefore assessed using in vitro models and image based analysis, the efficacy of BEAT CD38/47-48 and BEAT CD38/47-60 to inhibit CD47/SIRPα interaction on CD38 positive tumor cells (FIGS. 12A, 12B, and 12C).

Despite low affinity for CD47, BEAT CD38/47-48 and BEAT CD38/47-60 show a potent inhibition of CD47/SIRPα interaction on Daudi cells. This is comparable to the ability of the high affinity anti-CD47 5F9 antibody to inhibit CD47/SIRPα interaction. Altogether the data suggest that combining a high affinity anti-CD38 binder allow for inhibition of CD47/SIRPα interaction even in the presence of a low affinity CD47 binder.

Example 6.3. BEAT38/47-48 and -60 Show Superior Killing of $CD38^{low}$ Expressing Tumor Cells Through Antibody Dependent Cell Phagocytosis (ADCP) as Compared to Clinical Benchmark Darzalex Material and Methods $1.5 \times 10^4$ tumor cells labelled with 1 μg/mL pH-rodo Red SE were plated with $3 \times 10^3$ monocytes-derived-macrophages stained with 2.5 μM Cell trace violet (effector: target ratio=5:1) in a 384-well clear-bottom plates. In some experiments, either 2.8 ng/ml sCD38 or 500 M/ml red blood cells were added to each well in order to assess the impact of CD38 and CD47 antigen-sink. Increasing concentration of test antibody was subsequently added to the well and incubated for 2 h30 at 37° C., 5% CO2. Phagocytosis was then evaluated using CellInsightCX5 High Content Screening Platform and analyzed using HCS Studio Cell Analysis Software. Phagocytosis was quantified using image-based analysis as the average number of pHrodo-bright tumor cells for 100 cell trace violet-positive macrophages.

Results and Conclusions

Tumor cells has evolved mechanisms to evade the recognition by the immune system, including hijacking CD47-SIRPα axis. Indeed, CD47 is overexpressed in MM patients where it is reported that nearly 100% of CD38 positive myeloma cells express CD47 at a high level. CD47 expression has been associated with disease progression and low response to therapies in both hematological malignancies and solid tumors.

CD47/SIRPα neutralizing molecules have shown anti-tumor activity against a wide range of tumor cell lines both in vitro and in vivo. In vitro, CD47/SIRPα blocking antibodies have been described to restore tumor cell phagocytosis and to potentiate antibody dependent cell phagocytosis initiated by tumor-targeting antibodies such as Rituximab or Trastuzumab. Several anti-CD47 targeting approaches have been developed both in preclinical and in clinical settings; the more prominent is the anti-CD47 antibody Hu5F9-G4, a monoclonal antibody with two high affinity anti-CD47 Fab arms with low/absent Fc function in an IgG4 format (herein referred to as 5F9). Owing to its low functionality IgG4 Fc portion, 5F9 primarily works in combination, as it is reported in clinical trials as combo partner synergizing with Rituximab in the treatments of Non-Hodgkin's Lymphomas. Differently for 5F9, BEAT CD38/47-48 and -60 enhances ADCP as a stand-alone molecule, by selectively blocking CD47-SIRPα interaction on CD38 expressing tumor cells while concomitantly activating phagocytosis through its Fc enhanced for effector functions, including enhanced ADCP. In addition, BEAT CD38/47-48 and -60 differentiates from MM standard of care Darzalex as it is predicted to potentiate ADCP activity against MM cells by targeting CD38 tumor cells and concomitantly CD47/SIRPα interactions. The ability of BEAT 38/47 top candidates to inhibit CD47/SIRPα interaction was assessed in vitro in a competitive binding assay using a SIRPα-Fc-fusion protein. Both BEAT 38/47-48 and -60 efficiently inhibited CD47/SIRPα interactions on tumor cells in vitro to a comparable extent of that mediated by 5F9 (Example 6.2).

Figure 13A:
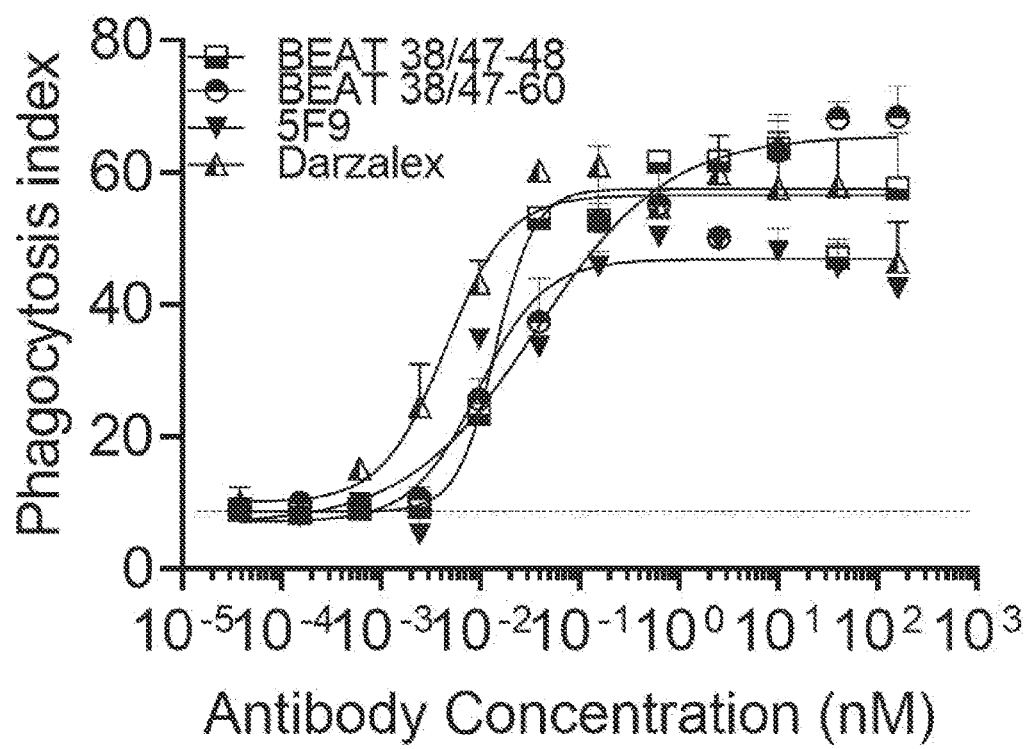
Figure 13B:
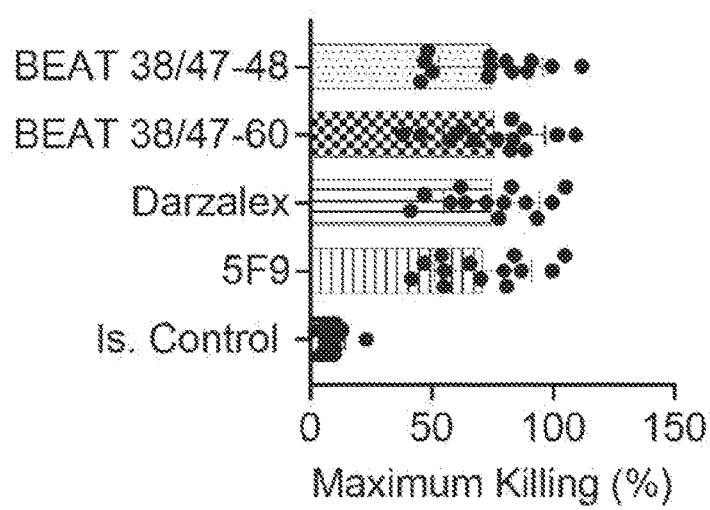
Figure 13C:
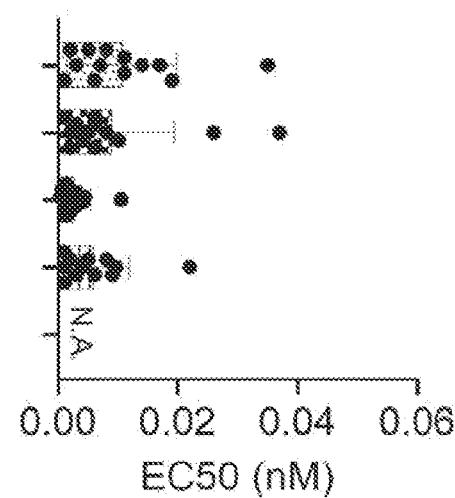
Figure 13D:
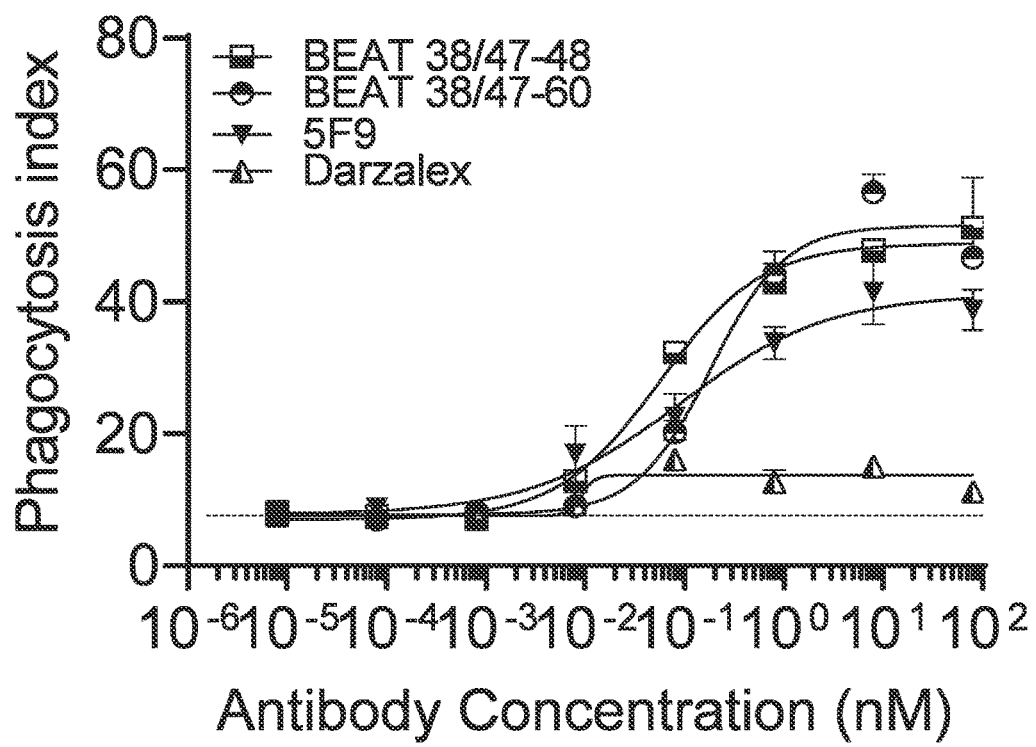
Figure 13E:
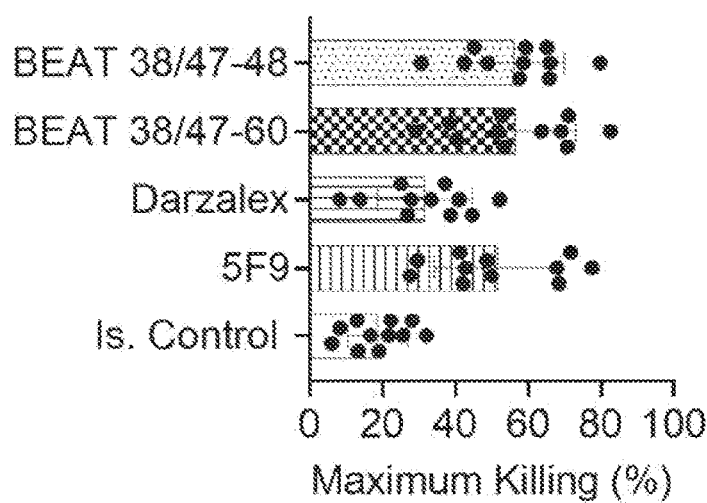
Figure 13F:
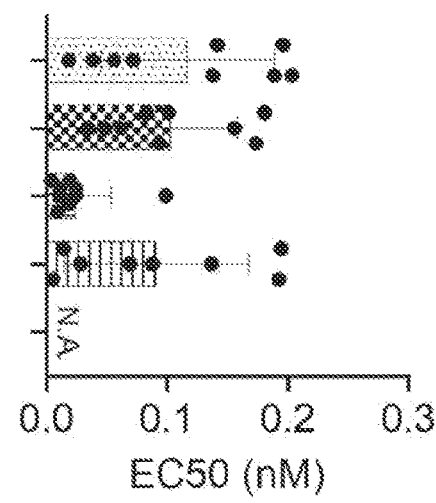

We assessed BEATs 38/47-48 and -60 ADCP potency against tumor cells as compared to clinical benchmarks 5F9 and Darzalex. Both BEAT 38/47-48 and -60 showed a comparable maximal level of phagocytosis induction of $CD38^{high}$ expressing tumor cells as that mediated by Darzalex (FIGS. 13A, 13B). Against $CD38^{high}$ expressing tumor cells, Darzalex showed a slightly higher albeit statistical significant potency as that of BEAT 38/47-48 and -60 measured by its lower EC50 value (FIG. 13C). On the contrary, on $CD38^{low}$ expressing tumor cells, both BEAT 38/47-48 and -60 induced a statistical significant higher phagocytosis of tumor cells (FIG. 13D), at a level that was twice the amount of that induced by Darzalex, as measured by their maximal phagocytosis index (FIG. 13E and Table 14). Albeit blocking CD47/SIRPα interaction with only one Fab arm of low affinity, Both BEAT 38/47-48 and -60 showed a comparable efficiency as that of 5F9 at inducing phagocytosis of both $CD38^{high}$ or CD38" expressing tumor cells (FIGS. 13A and 13D). This latter point is of high relevance as it suggests that lowering anti-CD47 affinity do not impact on tumor cell phagocytosis in the BEAT CD38/47 format when targeted on tumor cells via concomitantly having two anti-CD38 high affinity Fab arms. When comparing our internal clinical candidates BEAT 38/47-48 and -60, we found no differences in their potency as measured by both Maximal killing or EC50 in either $CD38^{high}$ or $CD38^{low}$ expressing tumor cells (FIGS. 13B, 13C, 13E, and 13F).

These data suggest that BEAT CD38/47 design allows for a comparable phagocytosis of tumor cells as that of 5F9, albeit drastically lowering the affinity to CD47 thereby potentially improving CD47 on target. Indeed, targeting CD47 can be challenging due to its ubiquitous expression; RBCs and platelets are among the cell types better characterized for the involvement of their clearance being dependent on CD47 expression. Therefore, a critical aspect in designing anti-CD47 therapies is mitigating the crosslinking of RBCs (or platelets) that are the main antigen sinks. As a matter of fact, due to its on-target binding to RBCs, 5F9 caused a dose-dependent anemia in 27-41% of NHL patients treated. In addition, BEAT CD38/47 format showed to induce higher potency against CD38" expressing tumor cells as that induced by standard of care Darzalex. Altogether our data suggest that both BEAT 38/47-48 and -60 have improved potency as compared to MM standard of care in the settings of low CD38 antigen availability while having a more favorable on target on RBCs as that reported by 5F9.

TABLE 14

Statistics values calculated in CD38$^{high}$ (Daudi)
or CD38$^{low}$ (KMS12-BM) tumor
cells using Tuckey's multiple comparison tests. NS = not significant.
When killing curves do not reach comparable maximal
level, comparing EC50 is not applicable (NA).

| Conditions | CD38$^{high}$ | | CD38$^{low}$ | |
|---|---|---|---|---|
| | Max Phagocytosis | EC50 | Max Phagocytosis | EC50 |
| BEAT 38/47-48 vs. Darzalex | NS | >0.001 | >0.001 | NA |
| BEAT 38/47-60 vs. Darzalex | NS | >0.05 | >0.01 | NA |
| BEAT 38/47-48 vs. 5F9 | NS | NS | NS | NS |
| BEAT 38/47-60 vs. 5F9 | NS | NS | NS | NS |
| Darzalex vs 5F9 | NS | >0.05 | >0.01 | NA |
| BEAT 38/47-60 vs. BEAT 38/47-48 | NS | NS | NS | NS |

Example 6.4: BEAT38/47-48 and -60 Show Superior Killing of CD38$^{low}$ Expressing Tumor Cells as Compared to Mono Arm Anti-CD47

Material and Methods

Experiments performed as described in paragraph "Material and methods" of Example 6.3.

Results and Conclusions

Figure 14B:
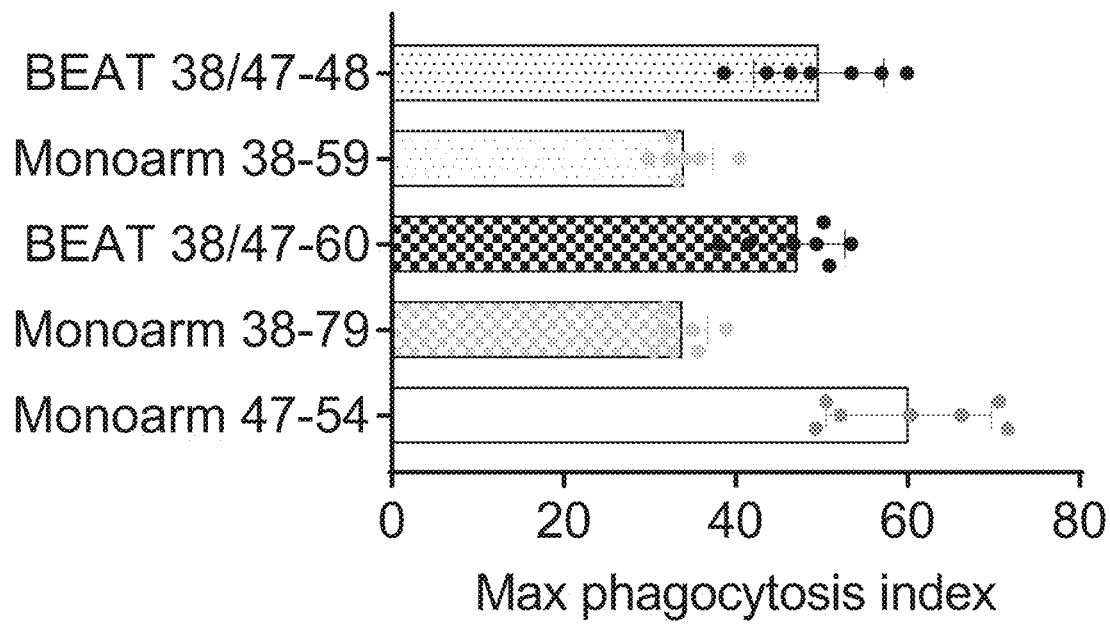
Figure 14C:
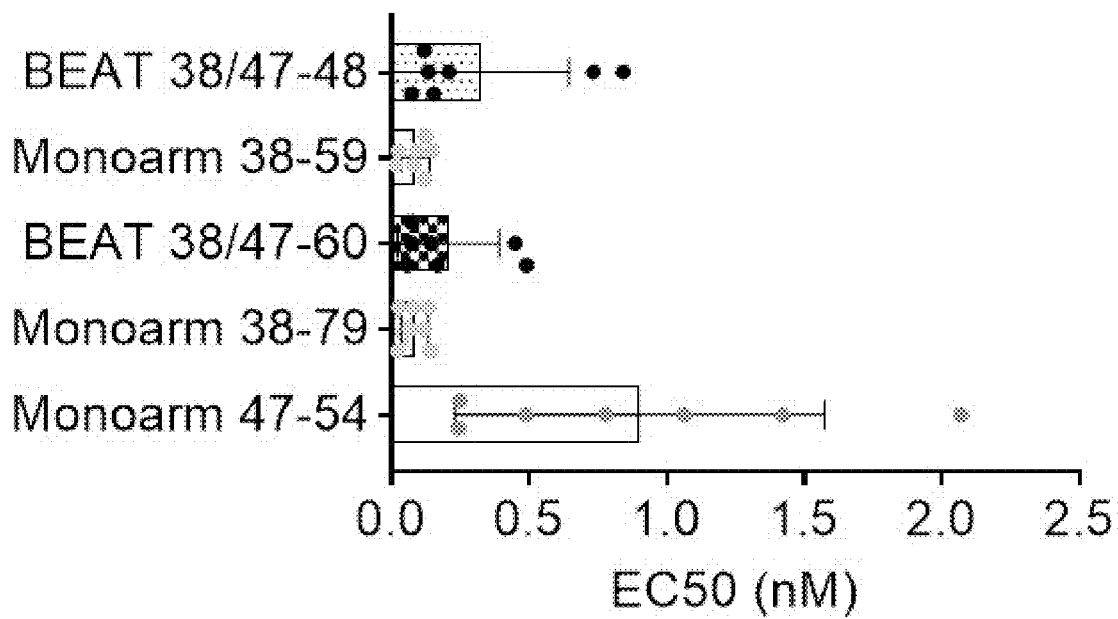

To assess whether co-targeting CD38 and CD47 improved functions of BEATs 38/47 as compared to single targeting anti-CD38 or anti-CD47, we analyzed the capacity of BEAT 38/47-48 and -60 to induce ADCP of tumor cells relative to their CD38 or CD47 mono arms (FIG. 14A). Both BEAT 38/47-48 and -60 showed enhanced ADCP of CD38$^{low}$ expressing tumor cells as measured their higher maximal phagocytosis as compared to Monoarm CD38-59 and -79 respectively (FIG. 14B). In addition, albeit Monoarm CD47-54 reached a similar or higher induction of phagocytosis of tumor cells as compared to that of BEAT 38/47-48 and -60 (in 3 out of 7 experiments) its potency to induce phagocytosis was lower than that of both BEAT 38/47-48 and -60 as measured by a higher EC50 (FIG. 14C and Table 15).

Altogether BEAT 38/47-48 and -60 show improved potency over their relatives anti-CD38 and anti-CD47 mono arms suggesting that BEAT format it is luckily to induce a better potency in patients as that induced by targeting single CD38 or CD47.

TABLE 15

Statistic values calculated in CD38$^{low}$ (KMS12-BM) tumor
cells using Tuckey's multiple comparison tests.

| Conditions | Max Phagocytosis | EC50 |
|---|---|---|
| BEAT 38/47-48 vs. Monoarm CD47-54 | >0.05 | >0.05 |
| BEAT 38/47-60 vs. Monoarm CD47-54 | >0.05 | >0.05 |
| BEAT 38/47-48 vs. Monoarm CD38-59 | >0.05 | >0.05 |
| BEAT 38/47-60 vs. Monoarm CD38-79 | >0.05 | >0.05 |

Example 6.5: BEAT38/47-48 and -60 Show Superior Killing of Tumor Cells Through Complement Dependent Cytotoxicity (CDC) as Compared to Clinical Benchmarks Material and Methods Tumor cells were labelled with 5 μM calcein AM and plated in 96-well plates with increasing concentration of test antibody and in presence of human serum for 4 h30 at 37° C., 5% CO2. In some experiments, either 2.8 ng/ml sCD38 or 500 M/ml red blood cells were added to each well in order to assess the impact of CD38 and CD47 antigen-sink.

Triton X-100 was used as a positive control for maximum tumor cell killing. After the completion of the assay, cells were centrifuged at 350 g for 5 minutes to pellet the cells. 100 μL of supernatant was then carefully transferred in a black flat bottom 96 wells plate, without transferring any cell. Fluorescence induced by the calcein release was read with a Synergy Plate reader using the following parameters:

Excitation wavelength: 485 nm
Emission wavelength: 515 nm
Specific killing was calculated according to the formula:

% Specific Killing = [(release in test condition − spontaneous release)/
(maximum release TritonX100 − spontaneous release)].

Results and Conclusions

Interaction of the Fc portion of a target bound antibody with C1q, the first subcomponent of the C1 complement system, activates the complement pathway and ultimately induces CDC. This is one of the mechanisms of action (MOA) of most clinically validated antibodies to kill tumor cells, including MM standard of care Darzalex. Tumor cells evolves and undergo several immune escape mechanisms, including escape to drug treatments (acquired escape mechanisms). Pertinent to MM, escape to CDC killing is one of the best-established mechanisms of resistance to Darzalex which eventually impact in the relapse of the disease. The acquired escape mechanisms to CDC is multifactorial and still need to be fully understood. However, several factors influence it, including antigen density per tumor cells (CD38 downregulation) as well as the overexpression of complement regulatory proteins (including CD46, CD55 and CD59). For these reasons, BEATs 38/47-48 and -60 were designed with having dedicated engineering of their Fc portions to enhance Fc effector functions, including CDC (as reported WO2011104604). In addition, as previously reported in this patent, both BEATs 38/47-48 and -60 in their 2+1 architectures, already enhanced CDC as compared to 1+1 architectures, most probably as a consequence of the enhancing CD38 clustering in the cell surface for optimal CDC killing (see Example 5, and FIG. 7).

Figure 15A:
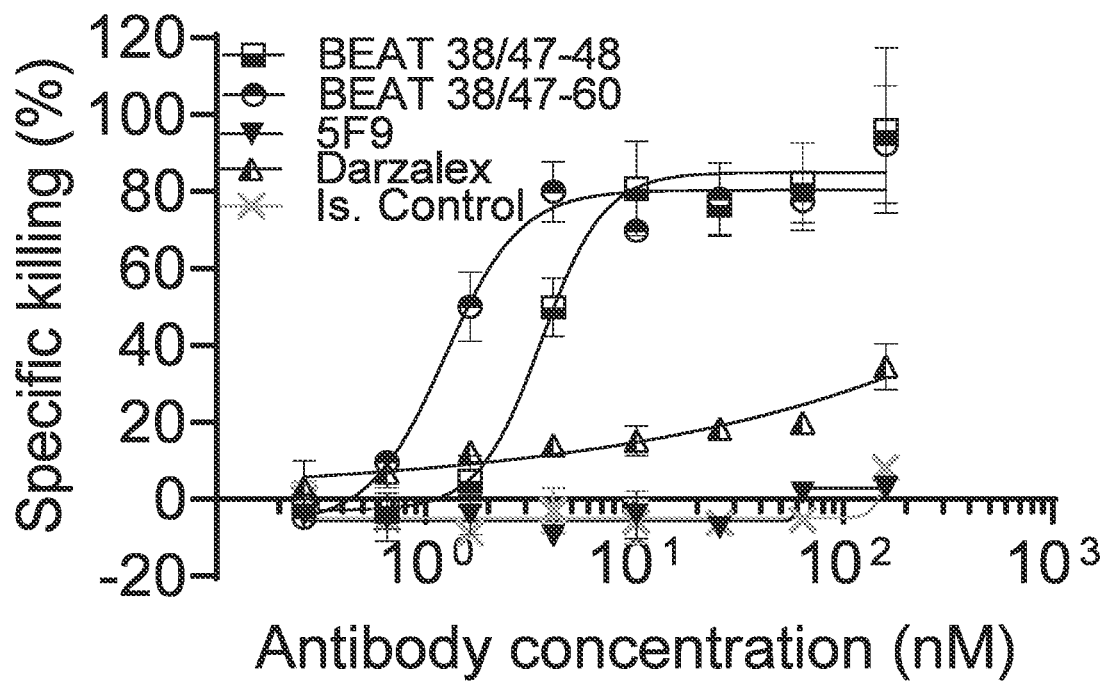
Figure 15B:
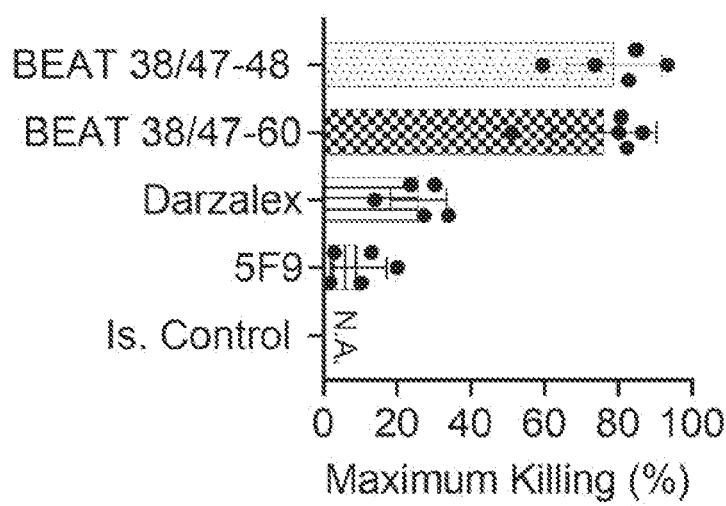
Figure 15C:
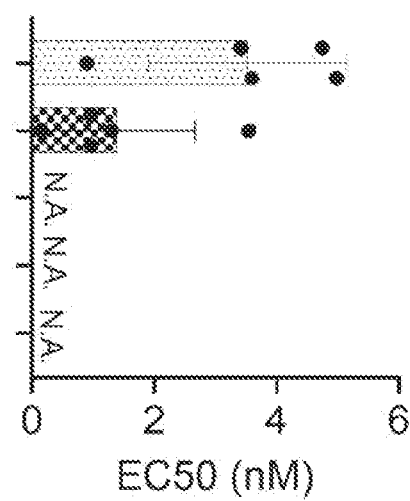

We assessed BEATs 38/47-48 and -60 potency against tumor cells to induce CDC as compared to clinical benchmarks. Both BEATs 38/47-48 and -60 showed a statistically significant higher tumor cells killing by CDC as compared to Darzalex (FIG. 15A). As expected, 5F9-like did not induce any detectable killing by CDC, in line with its low/absent IgG4 Fc effector format. When comparing our internal clinical candidates BEAT 38/47-48 and -60, we found that BEAT 38/47-60 showed a statistically significant difference in potency as measured by a lower CDC EC50 (FIG. 15C). No differences in Maximal killing between the two BEATs CD38/47 were found (FIG. 15B and Table 16).

These data suggest that, modulating Fc effector function with dedicated CDC enhancing mutations, improve potency as compared to using wild type (WT) IgG-1 class as in Darzalex. This improved potency against Darzalex is luckily to favor an enhanced activity in patients of BEATs 38/47 in context where CDC might be impaired.

TABLE 16

Statistics values calculated in CD38$^{high}$ (Daudi) tumor cells using using Tuckey's multiple comparison test (for Max Killing) and T-test (for EC50). NS = not significant.

| Conditions | Max Killing | EC50 |
| --- | --- | --- |
| BEAT 38/47-48 vs. Darzalex | >0.0005 | NS |
| BEAT 38/47-60 vs. Darzalex | >0.0005 | NS |
| BEAT 38/47-60 vs. BEAT 38/47-48 | NS | >0.005 |

Example 6.6: BEAT38/47-48 and -60 Show Superior Killing of CD38$^{low}$ Expressing Tumor Cells Through Antibody Dependent Cell Cytotoxicity (ADCC) as Compared to Clinical Benchmarks Material and Methods Tumor cells were first labelled with 1 μM eFluor670 and then plated in a 96-well plate with increasing concentrations of BEAT 38/47 or control antibodies. Purified NK cells were then added to make a final Effector:Target (E:T) ratio of 5:1. The plates were incubated at 37° C., 5% $CO_2$. After 4 h30 incubation, the plates were centrifugated. Cells were then resuspended in 100 μl FACS buffer containing either Sytox (1/2000) or Dapi (1/50000).

Flow-cytometric analysis was then performed with a Cytoflex (Beckman Coulter). Viable tumor cells were identified as positive for eFluor670 and negative for Sytox dead cell stain.

Absolute number of live tumor cells were then reported and % of Killing and % Specific ADCC were calculated with the following formulas:

% Specific Killing=
(1 − (Target Abs.count/well of sample/ Average of Target
Abs.count/well of Target only)) ∗ 100

% Specific ADCC = % Specific Killing of sample −
% Specific Killing of no Ab

Results and Conclusions

Interaction of the Fc portion of a target bound antibody Fcγ-Receptor III (CD16) activates NK cells and induces potent degranulation leading to ADCC of tumor cells. Together with CDC, ADCC is one of best characterized MOA of Fc competent antibodies to kill tumor cells and is considered one of the more prominent mechanism induced by Darzalex to kill MM cells.

Figure 16A:
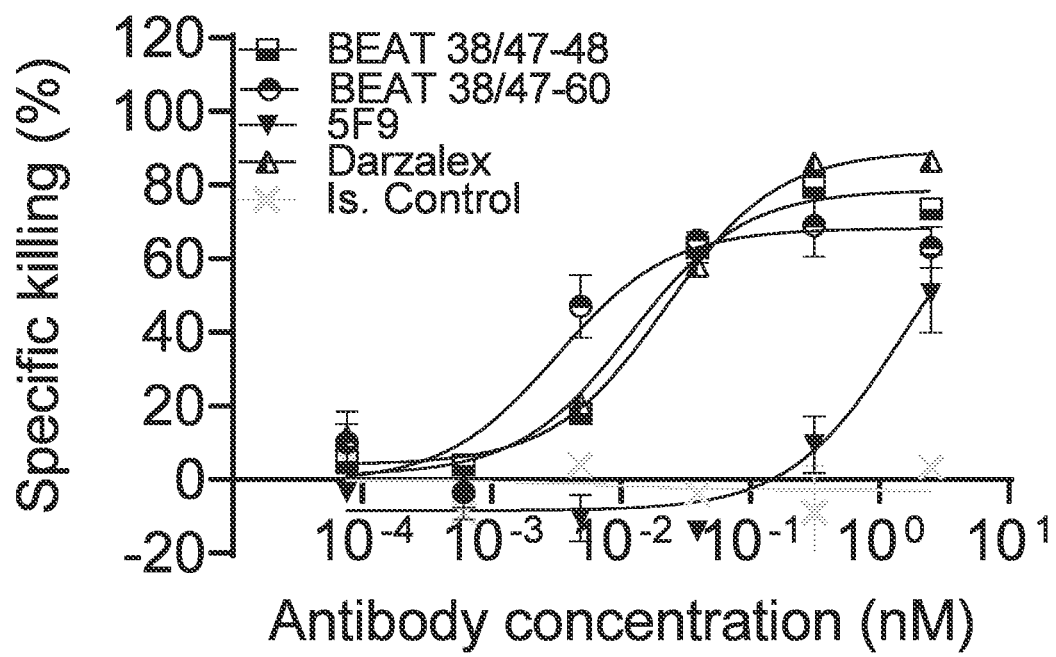
Figure 16B:
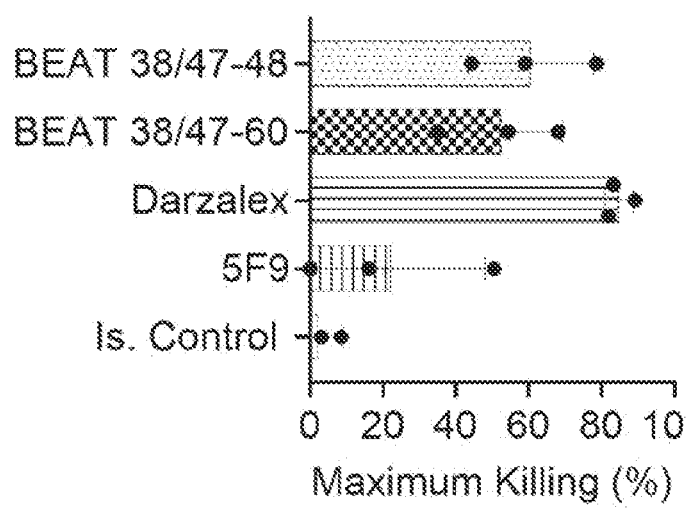
Figure 16C:
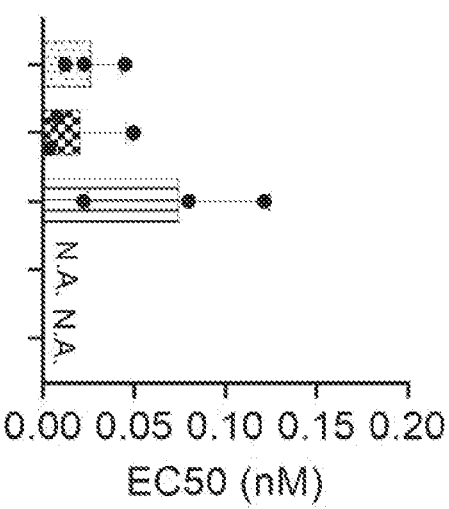

We assessed BEAT 38/47-48 and -60 ADCC potency against tumor cells as compared to clinical benchmarks (FIGS. 16A-16F and Table 17). Both BEATs 38/47-48 and -60 showed a comparable killing of CD38$^{high}$ expressing tumor cells as that induced by Darzalex (FIGS. 16A, 16B, and 16C). On the contrary, on CD38$^{low}$ expressing tumor cells, albeit reaching a similar maximal level of tumor cell killing as that of Darzalex (FIGS. 16D and 16E), both BEATs 38/47-48 and -60 showed a more prominent potency as measured by a statistical significant lower EC50 of killing (FIG. 16F). Similarly to what already shown with CDC, 5F9-like did not induce any detectable killing by ADCC, in line with its low/absent IgG4 Fc effector format. These data suggest that by having two bi-paratopic CD38 Fab arms in BEAT CD38/47-48 and -60, can improve the efficacy od ADCC when CD38 level are scarce on cell surface. When comparing our internal clinical candidates BEAT 38/47-48 and -60, we found no differences in their potency as measured by both Maximal killing or EC50 in either CD38$^{high}$ or CD38$^{low}$ expressing tumor cells.

The improved ADCC potency against Darzalex on CD38$^{low}$ expressing tumor cells is luckily to favor an enhanced activity in patients that show low expression of CD38 as a consequence of antigen down modulation due to Darzalex treatment as well as on MM clones having low CD38 due to acquired immune escape mechanisms.

TABLE 17

Statistics values calculated using Tuckey's multiple comparison tests in CD38$^{high}$ (Raji) or CD38$^{low-int}$ (NCI-H929) tumor cells. NS = not significant.

| | CD38$^{high}$ tumor cells | | CD38$^{low/int}$ tumor cells | |
| --- | --- | --- | --- | --- |
| Conditions | Max Phagocytosis | EC50 | Max Phagocytosis | EC50 |
| BEAT 38/47-48 vs. Darzalex | NS | NS | NS | >0.05 |
| BEAT 38/47-60 vs. Darzalex | NS | NS | NS | >0.05 |
| BEAT 38/47-60 vs. BEAT 38/47-48 | NS | NS | NS | NS |

Example 6.7: BEAT CD38/47-48 and BEAT CD38/47-60 Induce Killing of NCI-H929 MM Tumor Cells Measure by Multiple Mode of Action of Killing (MMoAK) Assay Material and Methods Peripheral Blood Mononuclear Cells (PMBCs) from Healthy Volunteers were harvested from buffy coats obtained from the La Chaux-de-Fonds Transfusion Center. For blood filter processing, buffy coats were diluted in 50 ml of PBS (1/2 dilution) and then transferred in 3 SepMate tubes previously loaded with Ficoll. Isolation was performed following manufacturer's instructions (centrifugation at 1200 g for 10 minutes with brake). The mononuclear layer was transferred into 50 ml falcon tubes, the PBMCs were washed 3 times in PBS (300 g for 10 min), counted and frozen at −80° C. The day before the assay, autologous PBMCs were thawed and incubated overnight at 37° C. in complete medium. Human monocytes were purified from frozen PBMCs and differentiated into macrophages by culturing them during 7 days in complete medium containing 50 ng/mL M-CSF.

MMoAK Assay

On the day of the experiment, 1×105 PBMCs+5000 autologous Monocyte-Derived-Macrophages were plated with tumor cells labelled with 5 µM eFluor 670 in presence of 50% human serum in ultra-low attachment 96-well plates. In some experiments (FIGS. 18A-18D), either 2.8 ng/ml sCD38 or 500 M/ml red blood cells were added to each well in order to assess the impact of CD38 and CD47 antigen-sink. Increasing concentration of test antibody and control antibodies was then added to the well and incubated for further 48 h at 37° C., 5% CO2. After completion of the assay, cells were centrifuged at 350 g for 10 minutes and resuspended in 100 µl FACS buffer containing either Sytox (1/2000) or Dapi (1/50000). Samples were acquired using Cytoflex flow cytometer and analyzed using Flowjo software (tree star).

Viable tumor cells were identified as positive for eFluor-670 and negative for Sytox dead cell stain. Absolute number of live tumor cells were then reported and % of Killing and % Specific Killing were calculated with the following formulas:

Killing capacity of BEAT 38/47 was quantified using the formula:

% Specific Killing=(1−(Target Abs·count/well of sample/Average of Target Abs·count/well of Target only))*100

Results and Conclusions

Figure 17A:
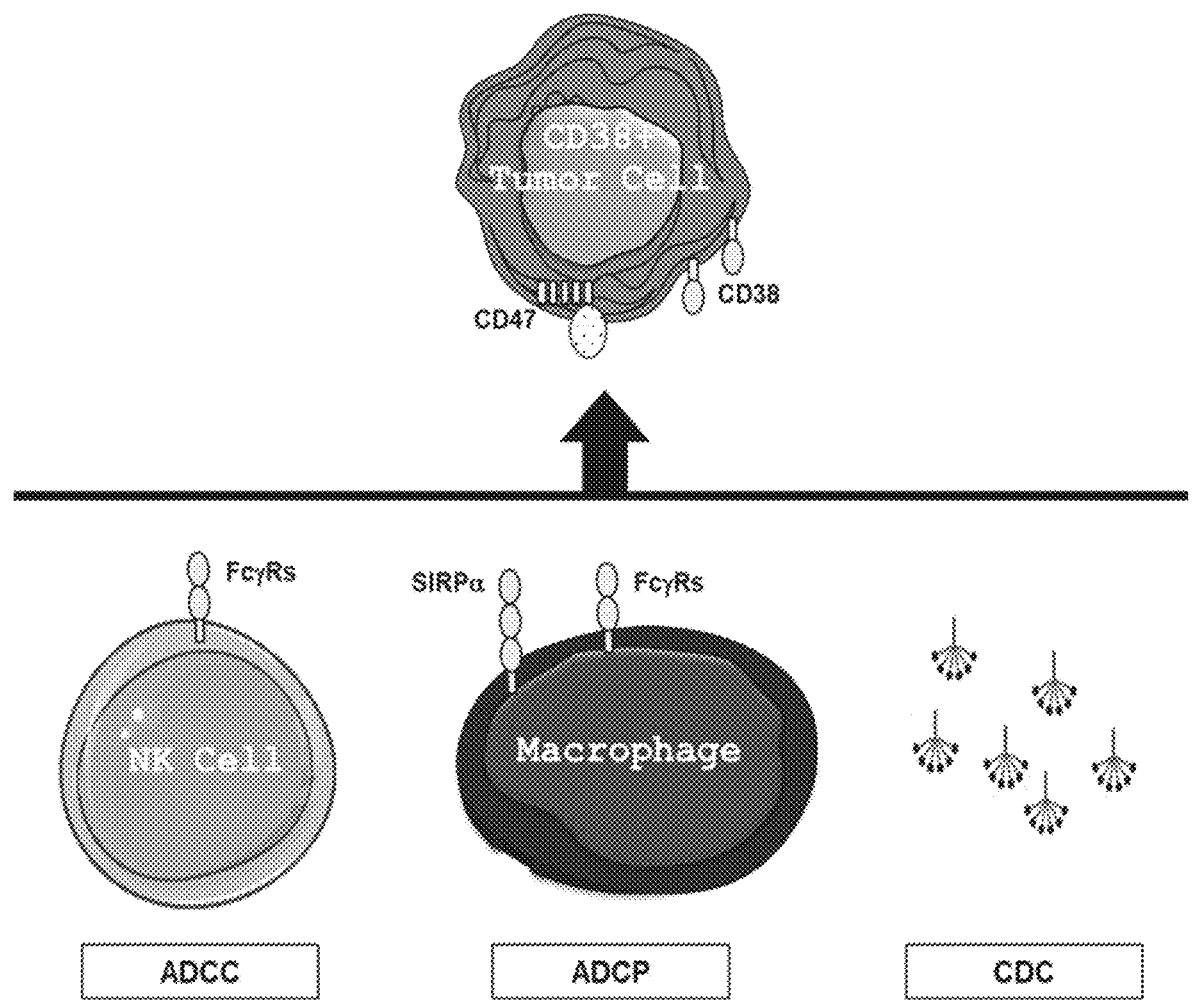

Physiologically, antibody dependent effector functions do not occur as separate entities but rather concomitantly. To accurately compare the potency of BEATs 38/47-48 and -60 and benchmarks, an optimized multiple mode of killing assay was established in vitro (FIG. 17A). It consists of a co-culture of human PBMCs stimulated with 100 U/ml of IL-2 with tumor cells in the presence of human serum and autologous monocyte-derived macrophages. With this approach, in the presence of test antibodies, tumor cells are killed through multiple mechanisms such as ADCC by IL-2 activated NK cells, Re-Directed Lysis (RDL) by T cells, CDC by complement and ADCP (mediated by the presence of phagocytes). Importantly, in MMoAK assays, human serum acts also as a source of human immunoglobulins (Igs), a key element to assess the potency of antibody-dependent effector functions in the presence of physiological levels of Igs. Hence, BEAT 38/47-48 and -60 killing potency can be quantified and accurately compared to benchmarks through this assay.

Figure 17B:
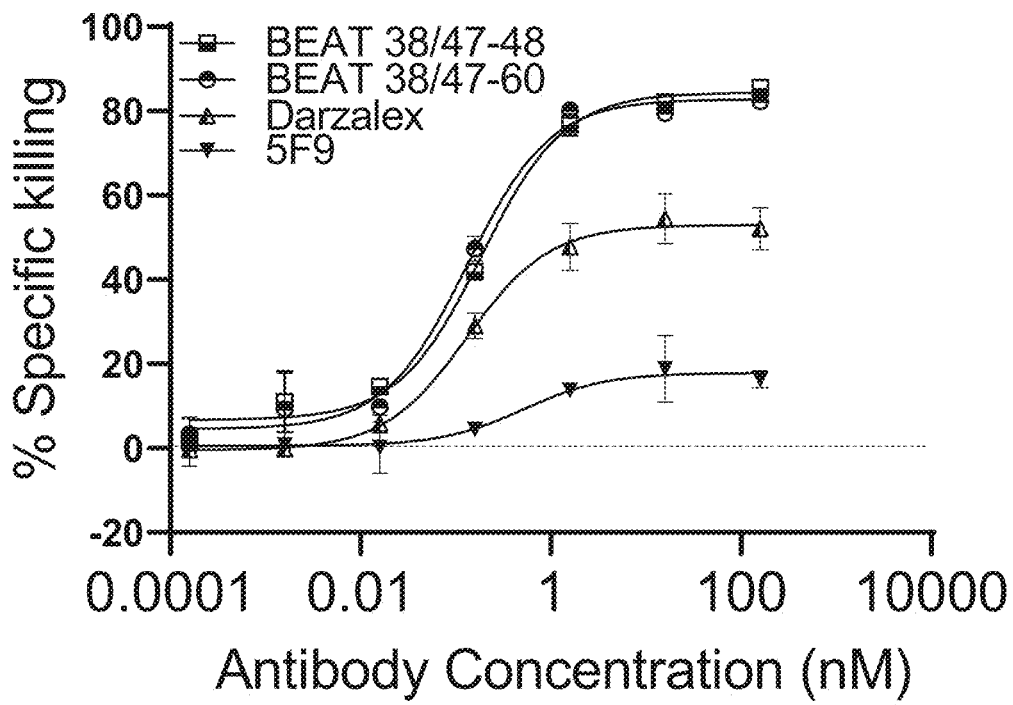
Figure 17C:
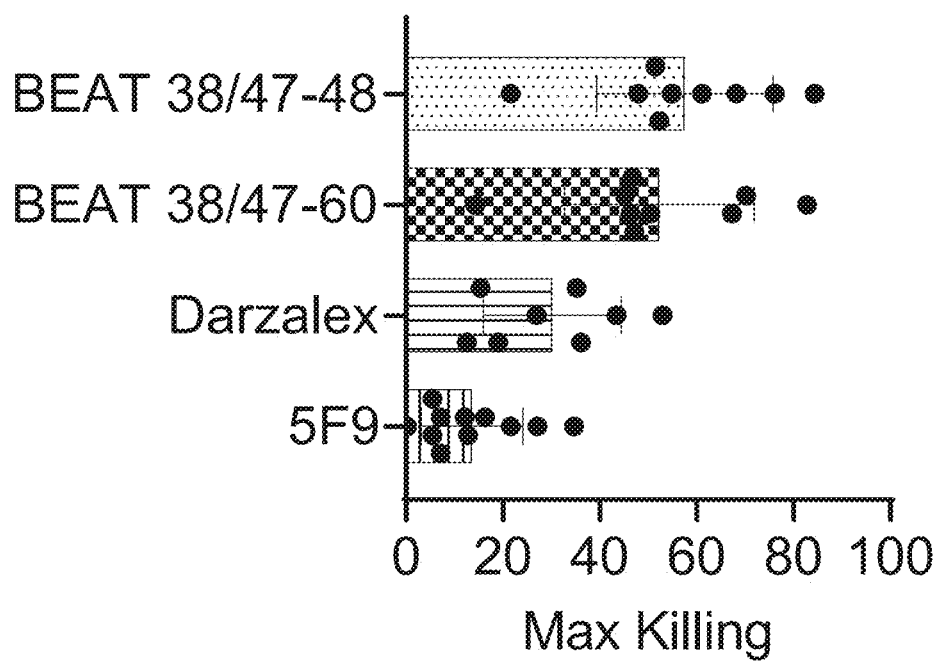
Figure 17D:
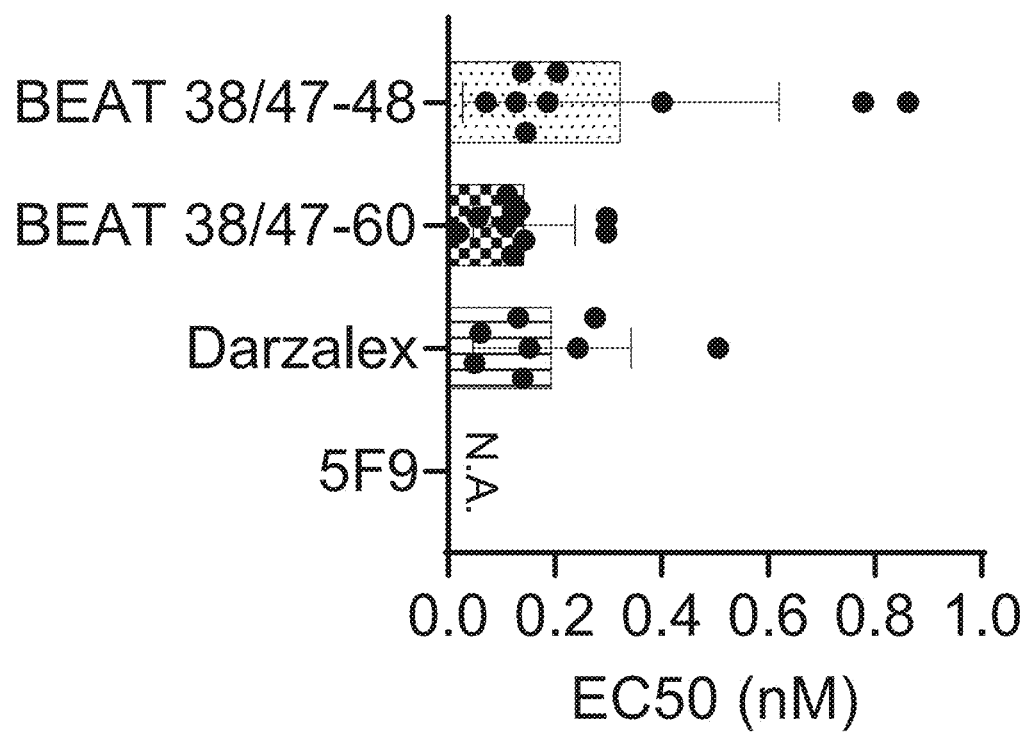

Under this condition, 5F9 failed to induce detectable level of tumor cells killing, most probably as a consequence of having an IgG4 Fc with minimal effector function thereby outcompeting for Fc receptors with Igs present in the serum. In marked contrast, BEAT 38/47-48 and -60 exhibited a prominent tumor cell killing which was twice as high as that induced by Darzalex (FIG. 17B). When comparing our internal clinical candidates, no differences in Maximal killing between the two BEATs CD38/47 were found, however, BEAT 38/47-60 showed a statistically significant difference in potency as measured by a lower EC50 in MMoAK (FIGS. 17C and 17D).

Figure 18A:
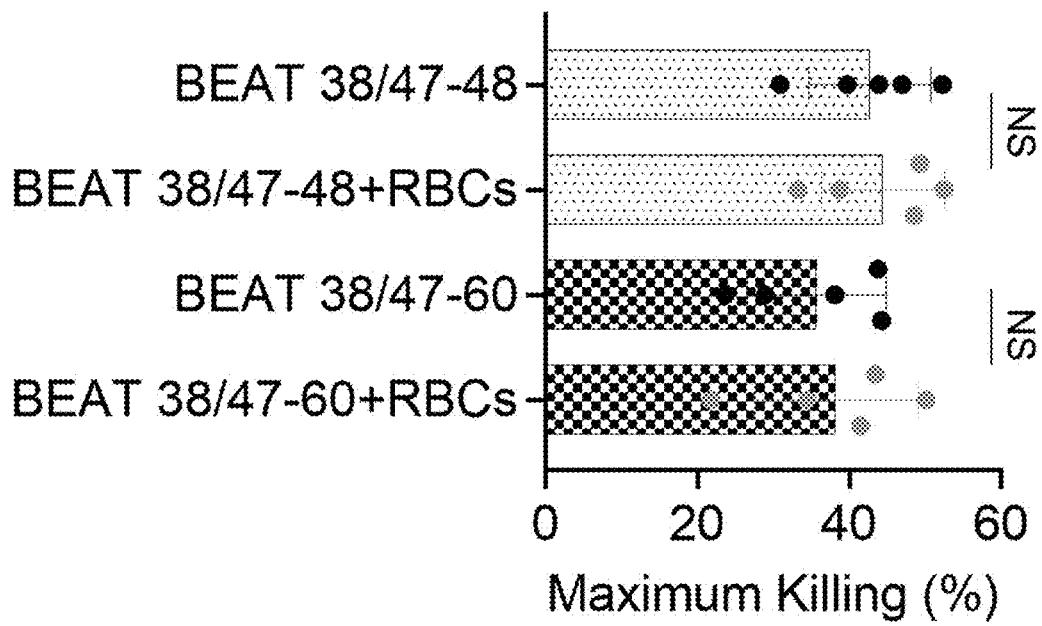
Figure 18B:
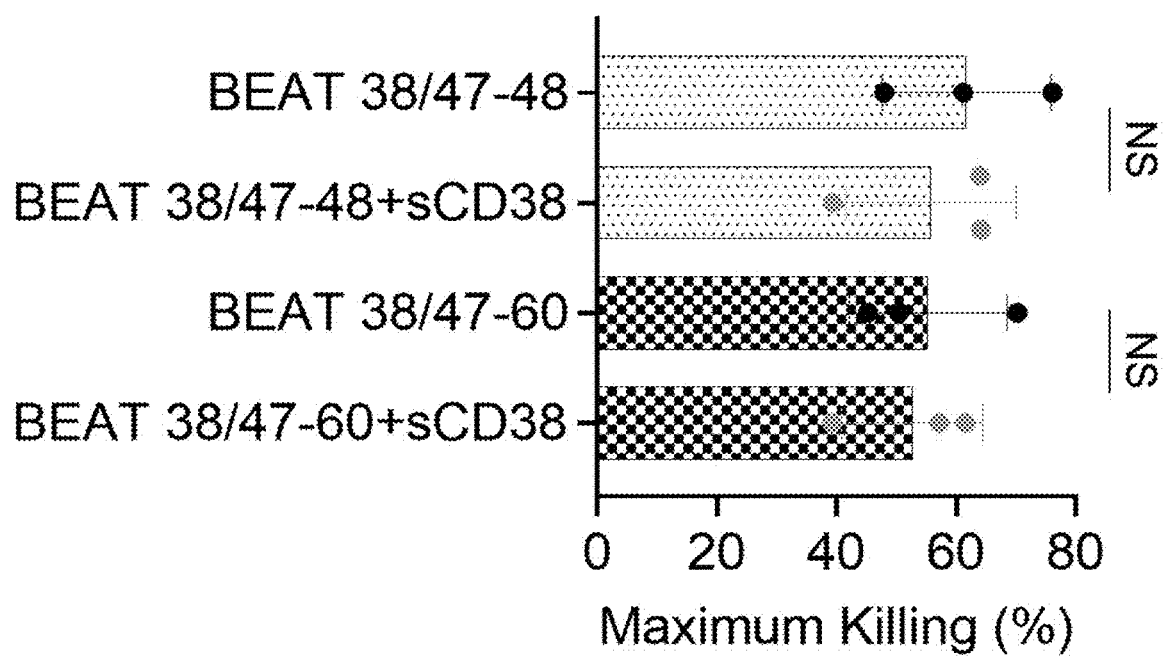
Figure 18C:
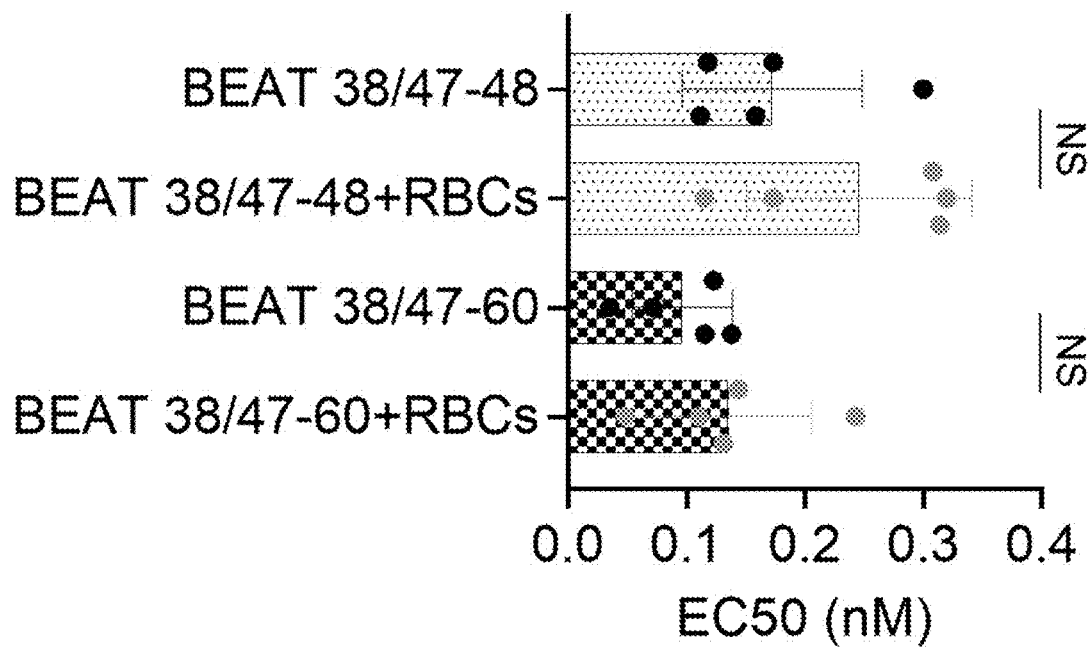
Figure 18D:
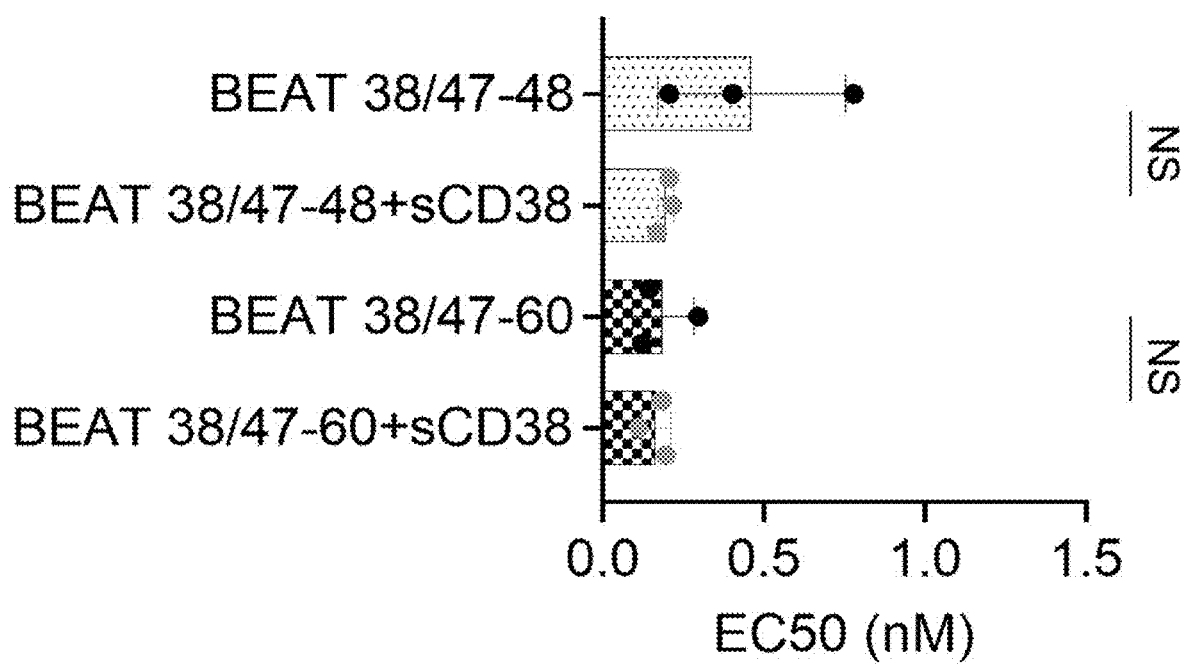

CD38 can be released in serum and the fraction of circulating soluble CD38 (sCD38) increases with disease stage in MM thereby potentially functioning as a sink for CD38 and thus limiting the efficacy of CD38 targeting therapies. Together with this, high number of circulating RBCs could be a second major antigen sink for BEATs 38/47-48 and -60 based on high level CD47 expression on RBCs. Thus, the impact of sCD38 and a high concentration of RBCs were evaluated in MMoAK to test whether antigen sink impact BEATs 38/47-48 and -60 potency in vitro. Presence or absence of sCD38 at 2.8 ng/ml (a concentration that is detected in patient bone marrow) did not impact BEATs 38/47-48 and -60 killing of tumor cells through MMoAK as measured by no difference in maximal killing or EC50 (FIGS. 18B and 18D and Table 18). Likewise, this mode of killing was not impacted by a high concentration of RBCs (500 million/ml) (FIGS. 18A and 18C).

Altogether, by using an in vitro assay that aim at recapitulating the complexity of the MOAs of Fc competent antibody in vivo, we found that BEAT 38/47-48 and -60 show important differentiations in terms of potency as compared to MM standard of care Darzalex. In addition, this assay remarks how critical is the correct activity of Fc functions, as in the presence of serum, 5F9 is completely abrogated in its capacity to phagocytose $CD38^{low}$ expressing tumor cells. Importantly, CD38 or CD47 antigen sink did not impact BEAT 38/47-48 and -60 potency in vitro. These findings and their translational relevance strongly support that BEAT 38/47-48 and -60 will have prominent activity in MM patients which is luckily to be superior as that of standard of care Darzalex. Based on all the parameters tested, both BEATs show no major differentiation in terms of potency in vitro. However, BEAT 38/47-60 showed enhanced potency compared to BEAT 38/47-48 in CDC and MMoAK and therefore it was prioritized over BEAT 38/47-48 as our clinical candidate.

TABLE 18

Statistics values calculated using One way Anova multiple comparison tests in CD38low-int (NCI-H929) tumor cells. NS = not significant. When killing curves do not reach comparable maximal level, comparing EC50 is not applicable (NA).

| Conditions | Max Killing | EC50 |
| --- | --- | --- |
| BEAT 38/47-48 vs. Darzalex | >0.01 | NS |
| BEAT 38/47-60 vs. Darzalex | >0.05 | NS |
| BEAT 38/47-48 vs. 5F9 | >0.0001 | NA |
| BEAT 38/47-60 vs. 5F9 | >0.0001 | NA |
| Darzalex vs 5F9 | NS | NA |
| BEAT 38/47-60 vs. BEAT 38/47-48 | NS | >0.05 |

Example 6.8: BEAT38/47-60 Show Higher Potency as Compared to Combination of Benchmark Darzalex and 5F9 In Vitro Material and Methods MMoAK performed as described in Example 6.7. For combination condition (Darzalex+5F9), Darzalex was tested in dose dependent fashion like BEAT 38/47-60 while 5F9 was used at saturating concentration (160 nM).

Results and Conclusions

Figure 19B:
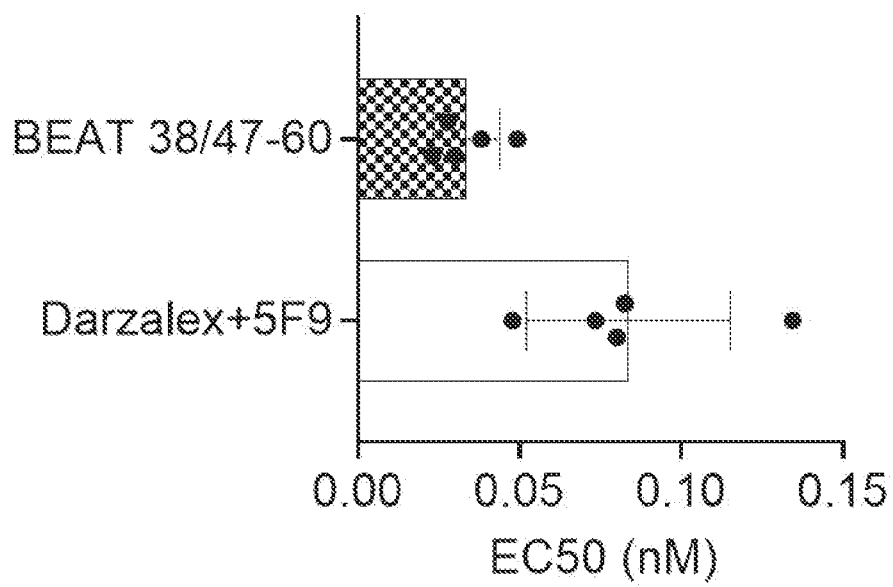
Figure 19C:
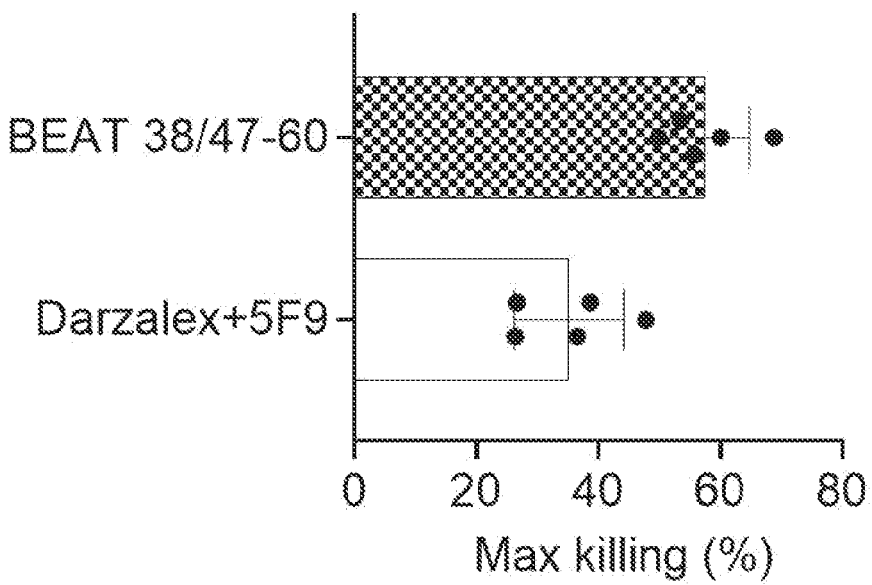

Darzalex is the standard of care in MM treatment and Magrolimab has successfully been used in combination with tumor targeting antibody (i.e. Rituximab) (MARK P. CHAO ET AL. Anti-CD47 Antibody Synergizes with Rituximab to Promote Phagocytosis and Eradicate Non-Hodgkin Lymphoma. Sep. 3, 2010. Cell 142, 699-713) to enhance phagocytosis of tumor cells. Therefore, a critical question to address was to understand whether the BEAT 38/47 concept would show a better efficacy against tumor cells as compared to a potential combination of Darzalex with a CD47 blocker. Indeed, such a combination has already been presented in the context of acute lymphoblastic leukemia where it was found to show improved efficacy as compared to monotherapy CD38 (FOTINI VOGIATZI, ET AL. Co-Targeting of CD38 and CD47 in T Cell Acute Lymphoblastic Leukemi 614. Acute lymphoblastic leukemia: therapy, excluding transplantation. Nov. 5, 2020. Blood (2020) 136 (Supplement 1): 39). We therefore assessed the potency of BEAT 38/47-60 against the combination of Darzalex with Magrolimab-like (5F9) in MMoAK assays in order to recapitulate all the effector functions as well as the competition of Fc Receptor with circulating Igs. To have a stringent comparison, Magrolimab-like was used at saturating doses in combination with Darzalex tested at different concentration as BEAT 38/47-60. In these settings, BEAT 38/47-60 showed a statistical significant higher killing of tumor cells as compared to that induced by combination of Darzalex with 5F9 (FIGS. 19A, 19B, and 19C and Table 19). These data suggest that, albeit having a lower affinity for CD47 in a single Fab arm, by blocking CD47 at the effector to target interface of the using a BEAT format by avidity-dependent crosslinking using high affinity anti-CD38 Fab arms, induce a higher potency of tumor cells as compared to the combination of high affinity anti-CD38 and anti-CD47 monoclonal antibodies.

TABLE 19

Statistics values calculated using Tuckey's multiple comparison tests in CD38high (Raji) or CD38low-int (NCI-H929) tumor cells. When killing curves do not reach comparable maximal level, comparing EC50 is not applicable (NA).

| Conditions | Max Phagocytosis | EC50 |
|---|---|---|
| BEAT 38/47-60 vs. (Darzalex + 5F9) | <0.01 | NA |

Figure 20A:
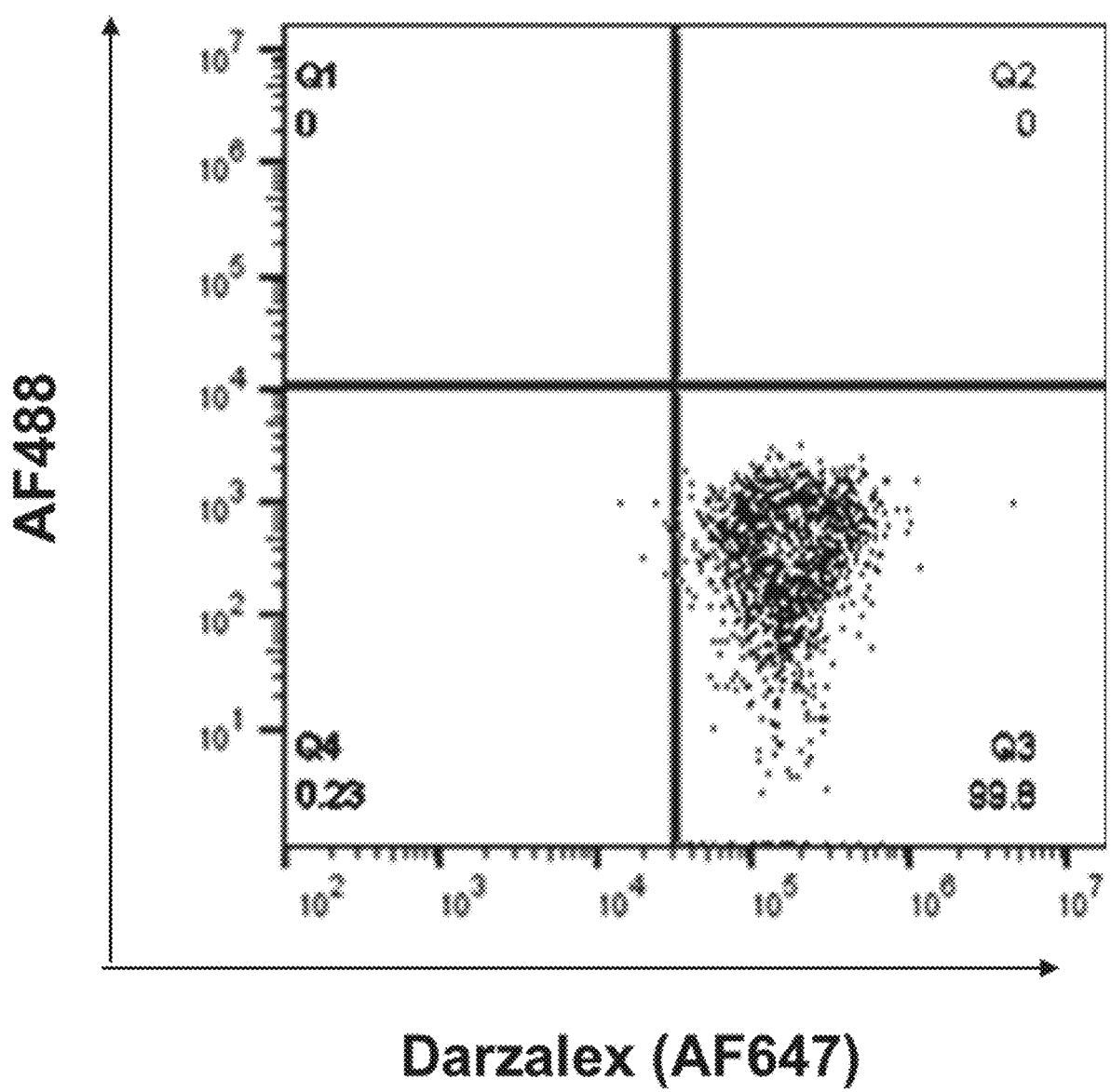
Figure 20B:
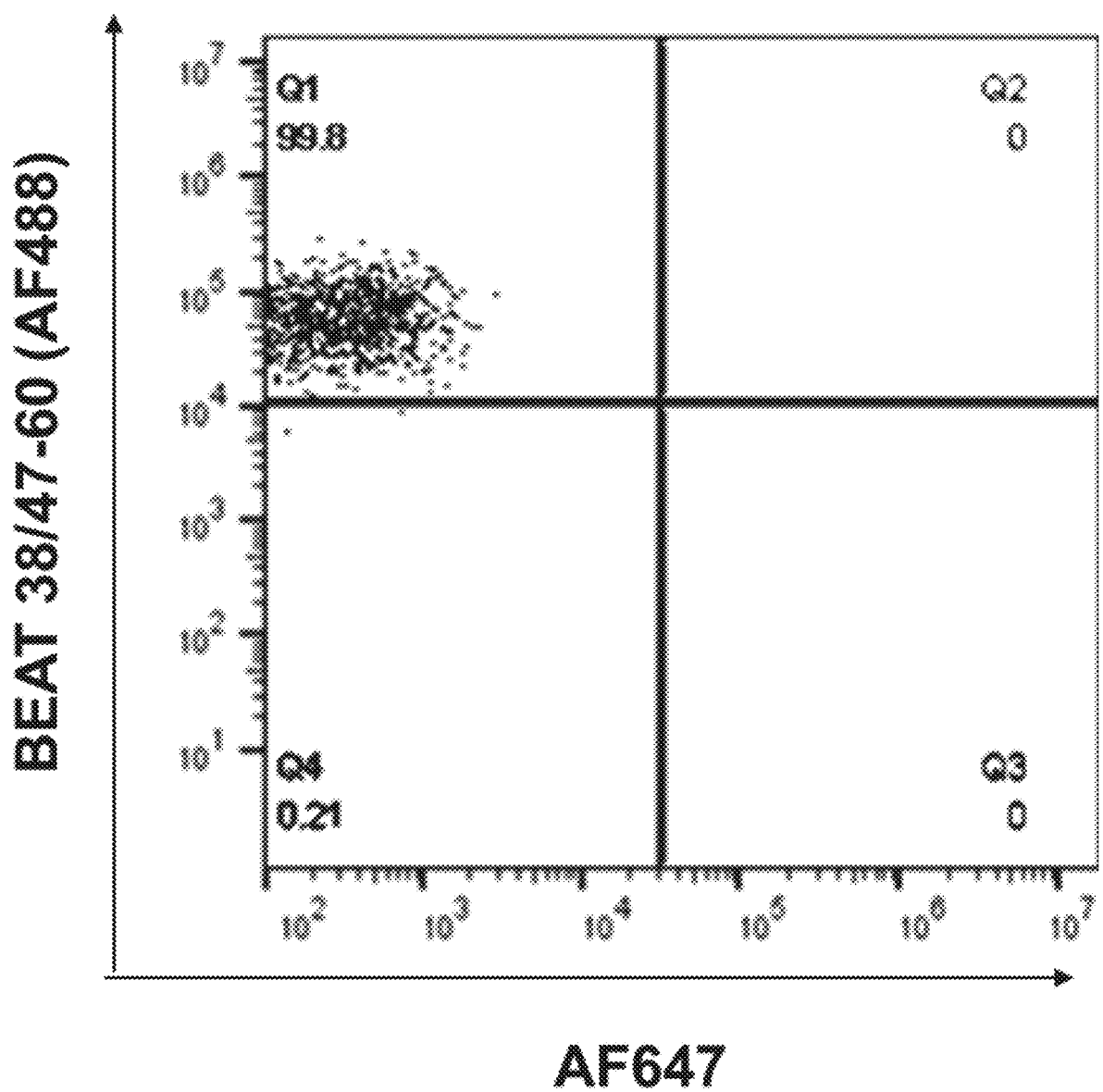
Figure 20C:
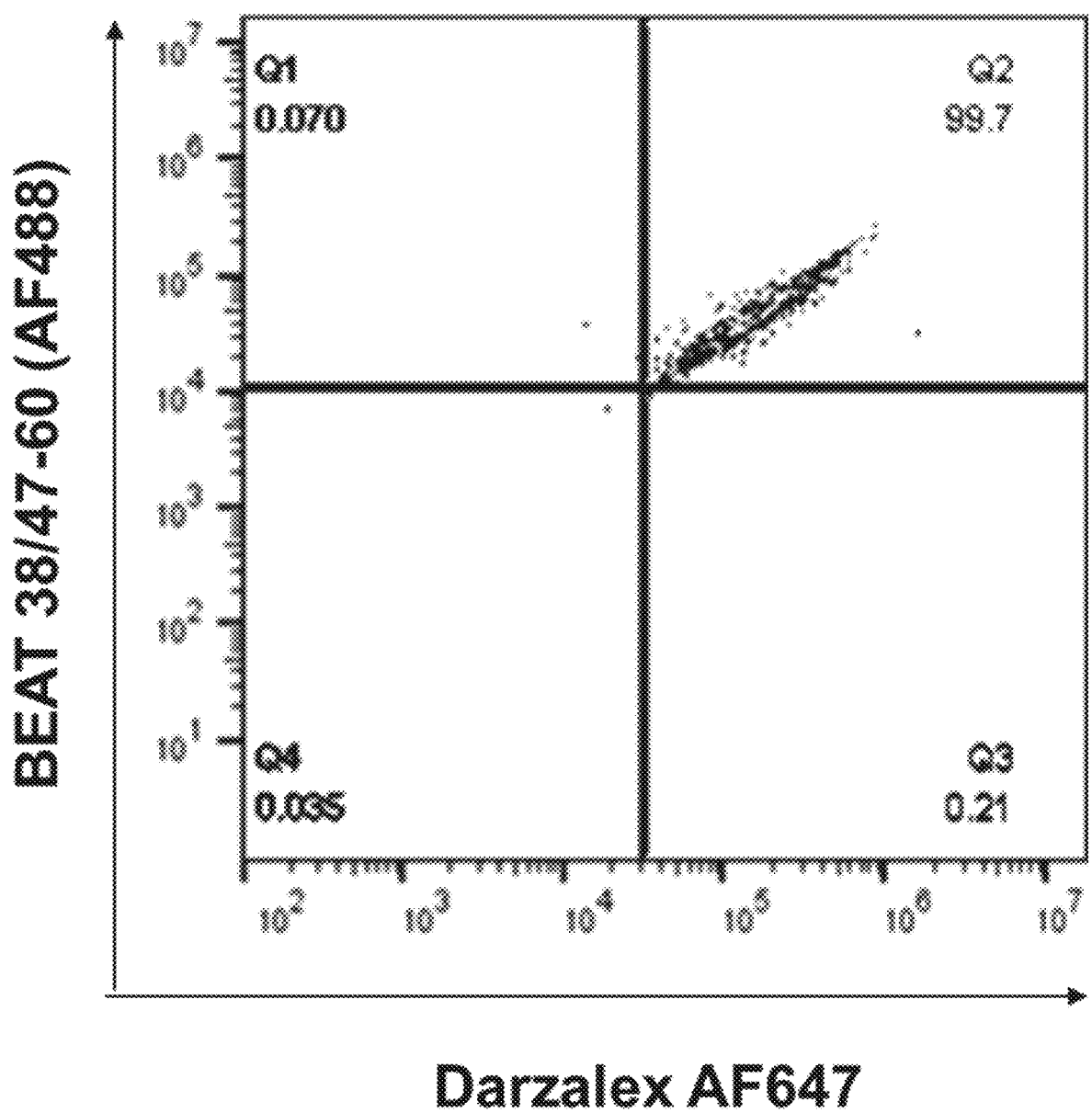

Example 6.9: BEAT38/47-60 do not Compete for Binding to CD38 with Darzalex on Cells and its Potency is not Impacted by Concomitant Darzalex Treatment In Vitro Materials and Methods Raji-CD47KO cells were incubated with saturating concentration of Darzalex-AF647 (FIG. 20A), BEAT 38/47-AF488 (FIG. 20B) or mix of Darzalex-AF647+BEAT 38/47-AF488 (FIG. 20C). After washing steps, fluorescence was analysed with a Cytoflex cytometer. FIGS. 20A, 20B, and 20C each show a representative Flow Cytometry Dot Plot.

Figure 20D:
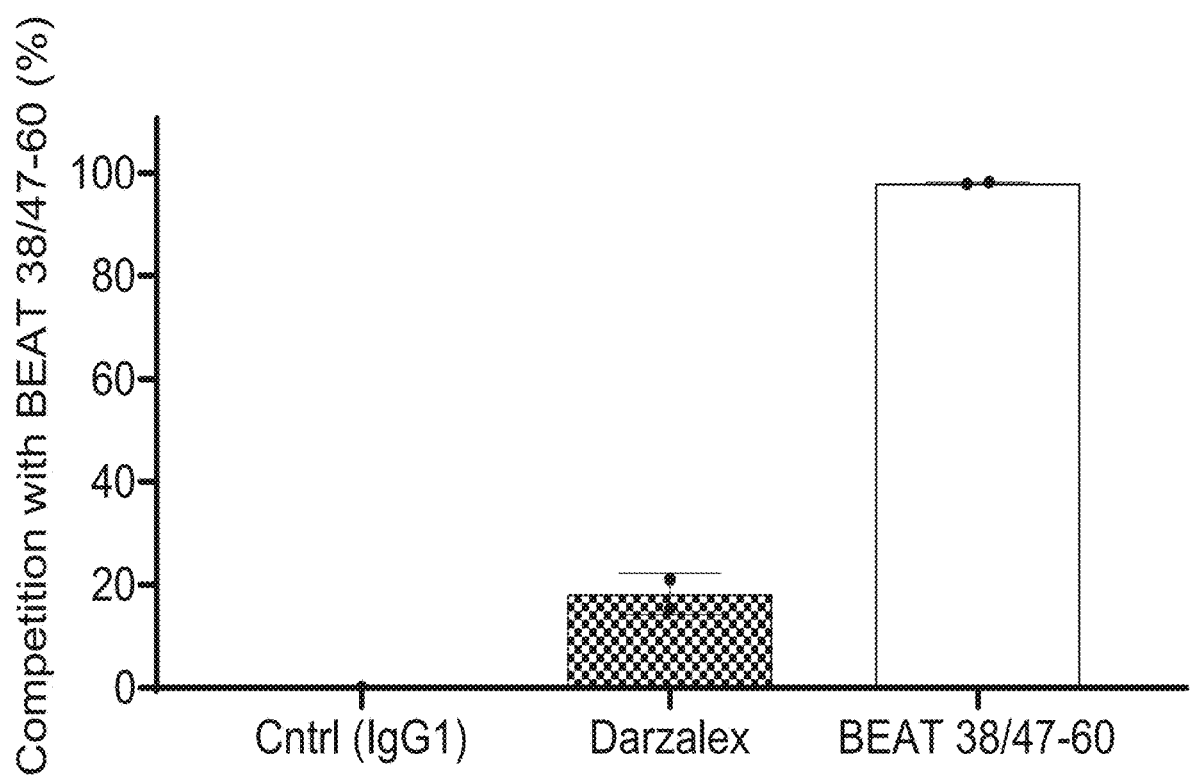

With regard to FIG. 20D, Raji-CD47KO cells were pre-incubated with saturating concentration of IgG1 control, Darzalex or BEAT 38/47 purified antibodies for 30 min at 4° C. before the addition of saturating concentration of BEAT 38/47-AF488. After washing steps, fluorescence was analysed with a Cytoflex cytometer and % of competition with BEAT 38/47-AF488 was then calculated. Mean of duplicates is represented here +/−Standard Deviations (SD).

MMoAK performed as described in Example 6.7. BEAT38/47+ Darzalex combination was performed with increasing doses of both BEAT 38/47 and Darzalex at the concentrations indicated in X axis of the figure.

Results and Conclusions

Figure 21A:
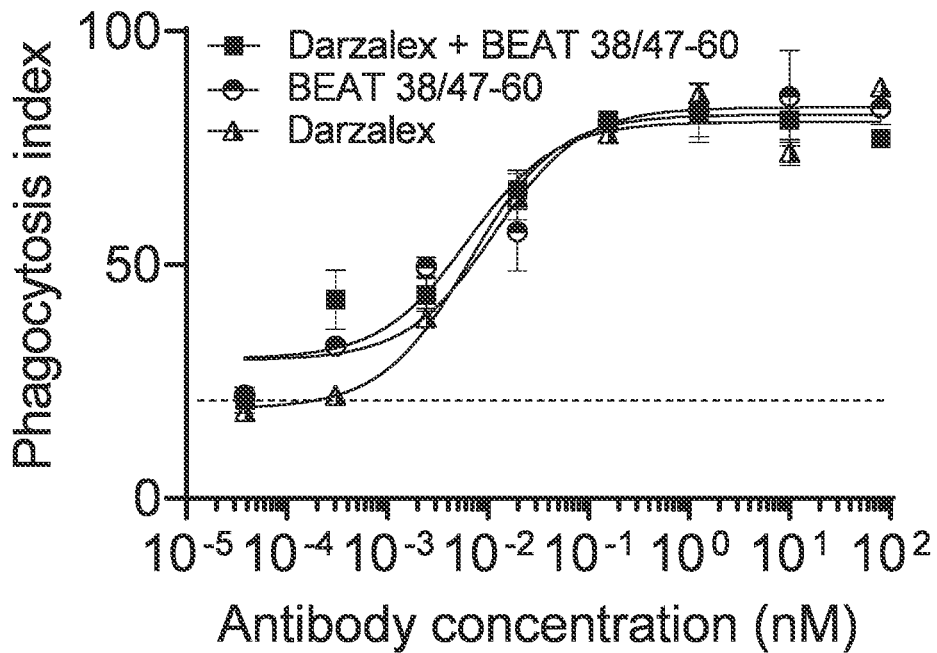
Figure 21B:
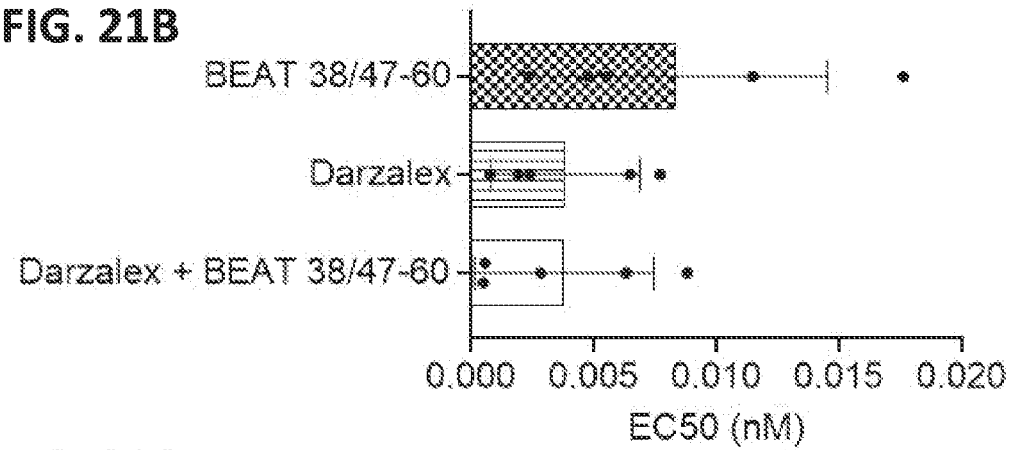
Figure 21C:
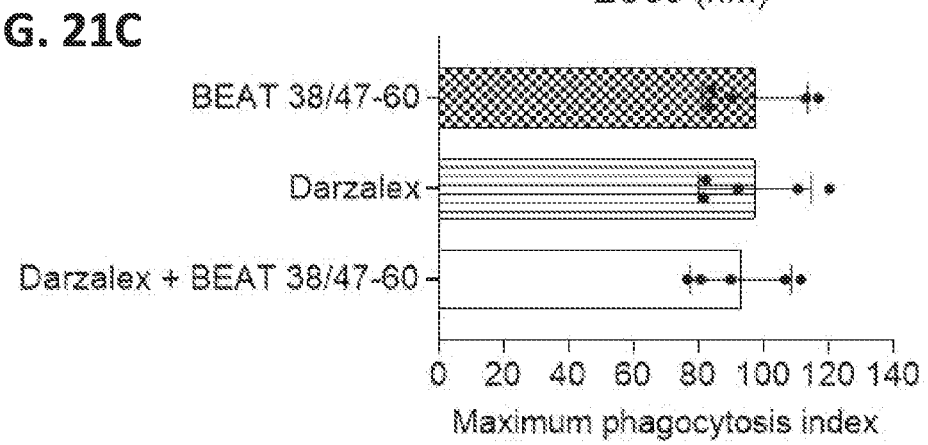
Figure 21D:
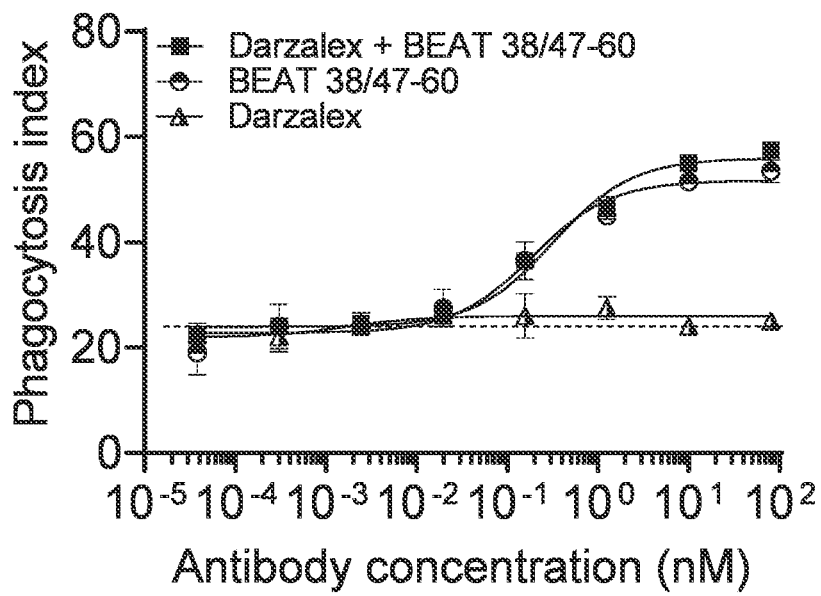
Figure 21E:
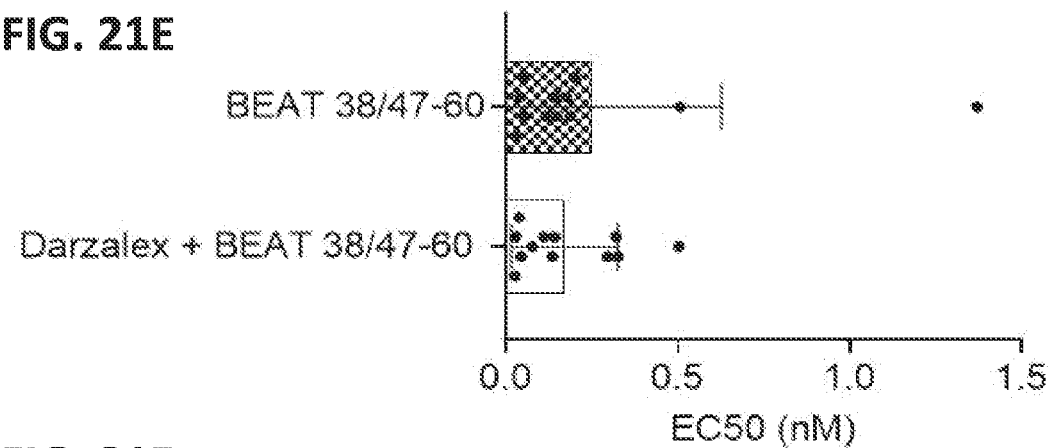
Figure 21F:
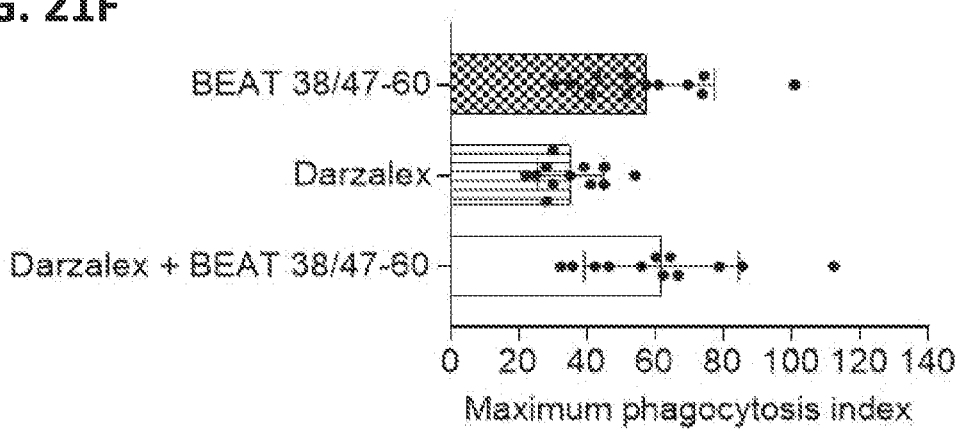
Figure 21G:
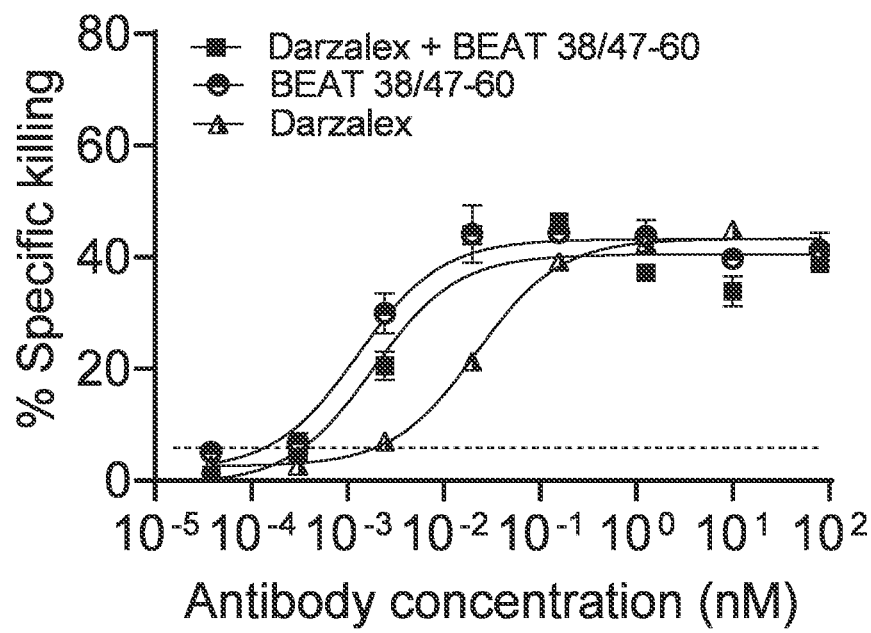
Figure 21H:
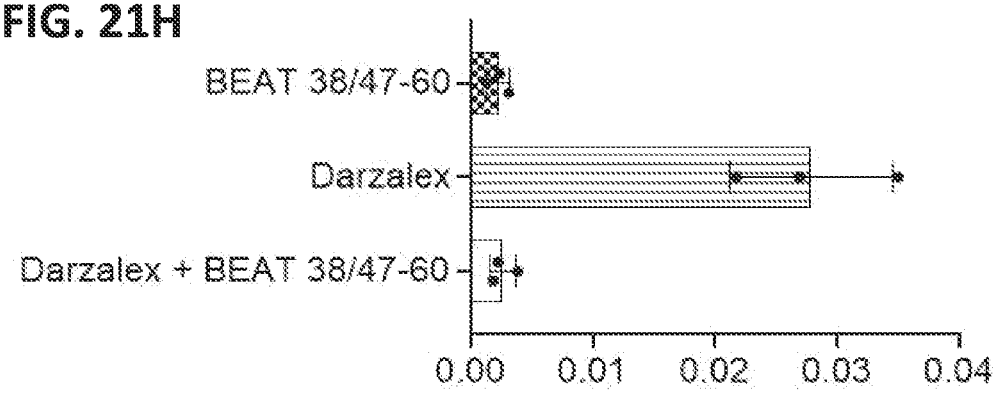
Figure 21I:
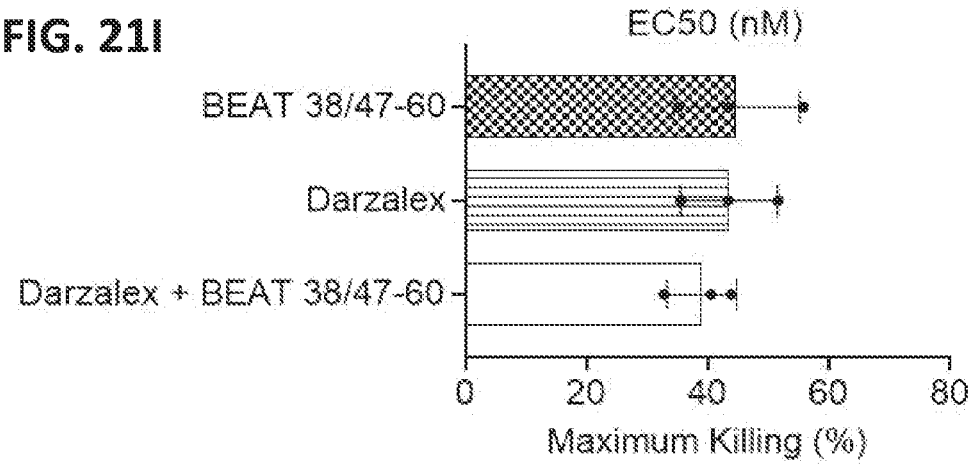
Figure 21J:
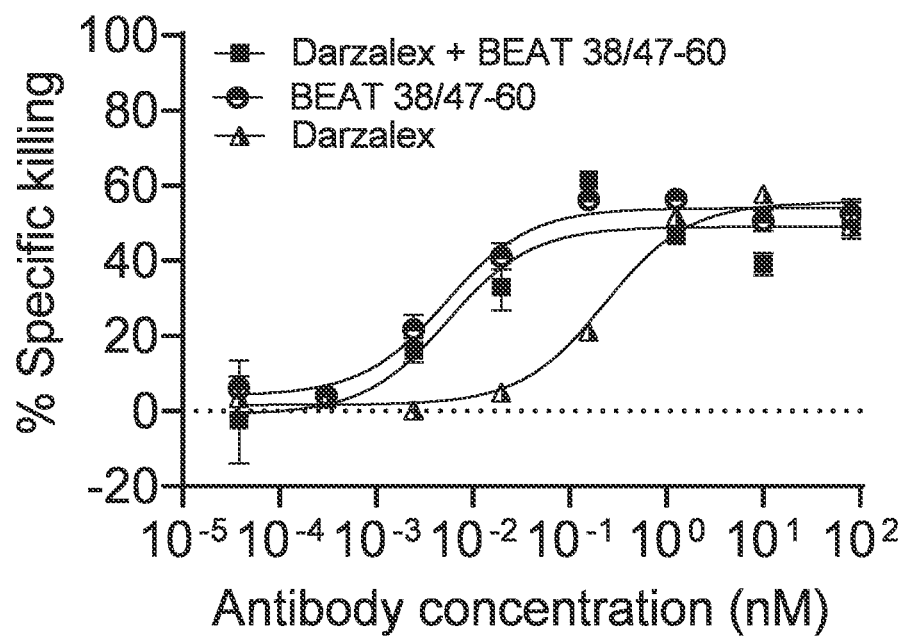
Figure 21K:
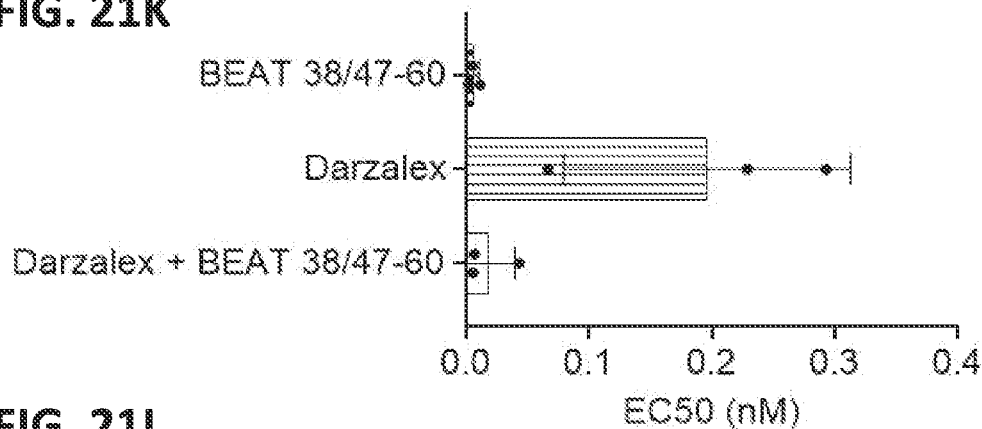
Figure 21L:
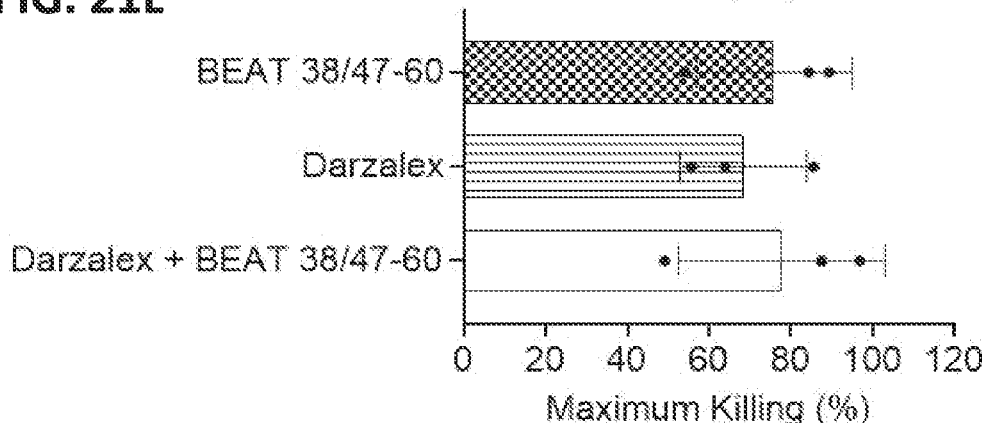
Figure 21M:
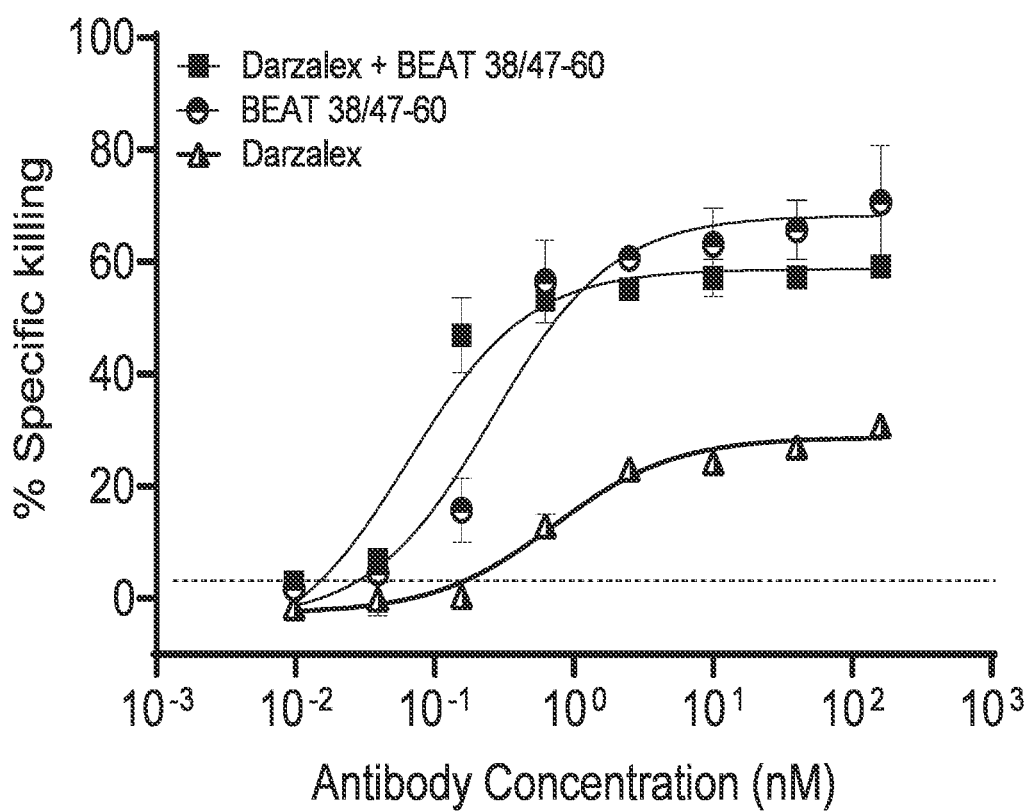

Darzalex is a standard of care for the treatment of multiple myeloma and BEAT 38/47-60 is envisioned to be used in relapsed refractory MM patients post Darzalex treatment. Therefore, we assessed if BEAT 38/47-60 is impacted for cell binding in the presence of Darzalex as well as whether Darzalex impact BEAT 38/47-60 potency against tumor cells in vitro. To precisely address competition for CD38, we used CD47-KO Raji tumor cells to avoid CD47 binding of BEAT 38/47-60. By concomitantly incubating CD47-KO Raji cells with BEAT 38/47-60 and Darzalex at 4° C., we found that Darzalex did not impact binding of BEAT 38/47-60 to CD47-KO Raji cells (FIG. 20C). In addition, we found only a low (20%) inhibition of BEAT 38/47-60 binding when Darzalex was incubated with to CD47-KO Raji tumor cells prior to BEAT 38/47-60 staining (FIG. 20D). To address whether the low competition mediated by Darzalex on cell binding was affecting BEAT 38/47-60 potency in vitro, we tested ADCP (FIGS. 21A, 21B, 21C, 21D, 21E, and 21F), ADCC and CDC activity (FIG. 21G, 21H, 21I, 21J, 21K, 21L, 21M, 21N, and 21O) of BEAT 38/47-60 in the presence of Darzalex. Overall, we found no impact in any of the effector function of BEAT 38/47-60 by concomitant treatment with Darzalex in vitro (FIGS. 21A-21O, and Table 20).

Altogether these data suggest that BEAT 38/47-60 can maintain its efficacy even in presence of bound Darzalex.

TABLE 20

Statistics values calculated using Tuckey's multiple comparison tests in indicated tumor cell lines. NS = Not significant. When killing curves do not reach comparable maximal level, comparing EC50 is not applicable (NA).

| | Conditions | Max Phagocytosis | EC50 |
|---|---|---|---|
| ADCP ($CD38^{high}$) | BEAT 38/47-60 vs. Darzalex | NS | NS |
| | BEAT 38/47-60 vs. (Darzalex + BEAT 38/47-60) | NS | NS |
| ADCP ($CD38^{low}$) | BEAT 38/47-60 vs. Darzalex | NA | NA |
| | BEAT 38/47-60 vs. (Darzalex + BEAT 38/47-60) | NS | NS |
| ADCC ($CD38^{high}$) | BEAT 38/47-60 vs. Darzalex | <0.001 | NS |
| | BEAT 38/47-60 vs. (Darzalex + BEAT 38/47-60) | NS | NS |
| ADCC ($CD38^{low}$) | BEAT 38/47-60 vs. Darzalex | <0.01 | NS |
| | BEAT 38/47-60 vs. (Darzalex + BEAT 38/47-60) | NS | NS |
| CDC ($CD38^{high}$) | BEAT 38/47-60 vs. Darzalex | <0.05 | NA |
| | BEAT 38/47-60 vs. (Darzalex + BEAT 38/47-60) | NS | <0.001 |

EXAMPLE 7: EX VIVO EVALUATION OF BEAT CD38/47-60 ON-TARGET PROFILES

CD47 is expressed ubiquitously and is upregulated in several hematological cancers. To test the on-target specificity of BEAT CD38/47-60 on non-tumor cells, we assessed their binding in RBCs and platelets that are known to expressed high level of CD47.

For the assessment of BEAT CD38/47-60 a different batch of molecule was used as clinical development batch. Albeit showing improved purity as compared to BEAT CD38/47-60 used for the examples before, both BEAT CD38/47-60 early and late development batches showed comparable functionality and potency against tumor cell lines.

Figure 22A:
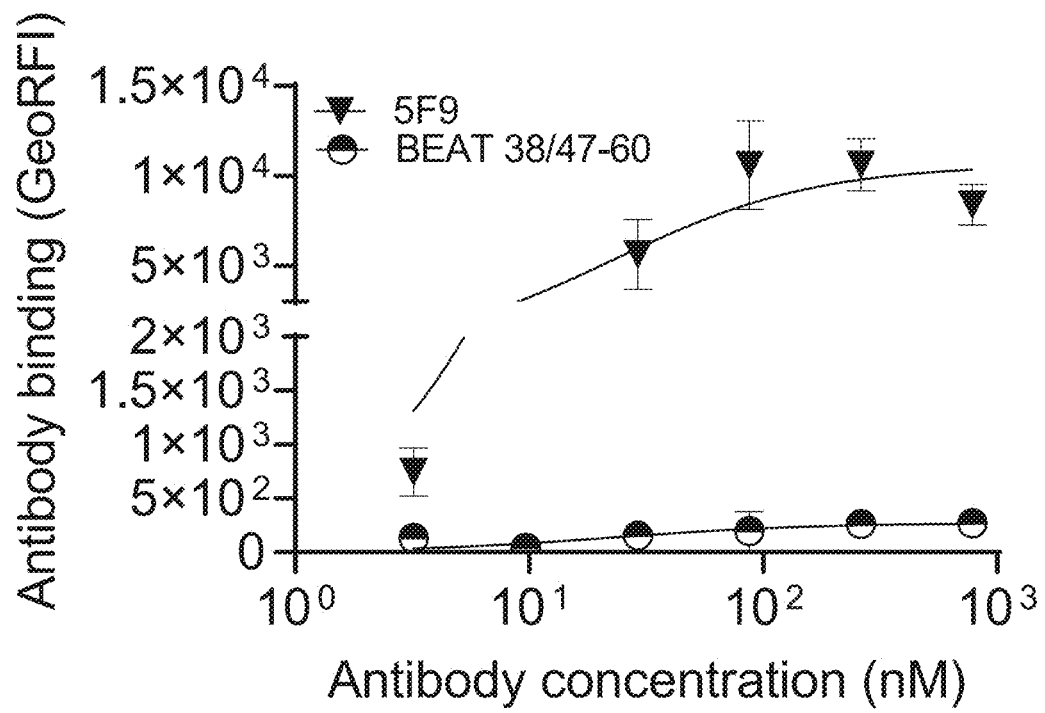

Example 7.1: BEAT38/47-60 Show Lower on Target/Off Tumor Activity in RBCs and Platelets as Compared to 5F9 In Vitro Materials and Methods Binding of BEAT 38/47 and 5F9 to Human RBCS (FIG. 22A)

Representative example of binding of BEAT 38/47 or 5F9 human red blood cells. The graphs in FIG. 22A show the overlay of nonlinear sigmoidal regression binding curves (Relative Geometric Mean Fluorescence Intensity) for a given donor. Binding was evaluated on six different human red blood cell donors. Staining of cells were performed as described in Example 6.1.

Ability of BEAT 38/47 to Induce Erythrocyte Agglutination (FIG. 228) was Evaluated Using an Indirect Coombs Assay Preparation of a 0.8% Blood Solution Fresh peripheral blood from healthy volunteers collected on EDTA K3 tubes were obtained from Bern Transfusion Center. 2 ml of fresh blood was added to 48 ml of sterile PBS in a 50 ml Falcon tube. The tubes were centrifuged for 10 min at 3500 G. Supernatant was gently removed with a 25 ml pipette. A 0.8% red blood cell suspension solution was prepared by adding 100 ul of packed red cells into 10 ml of ID-Diluent 2 in a new clean tube.

Indirect Coombs Test

Test and control antibodies were then prepared 3× concentrated in sterile PBS. 50 µl of blood from the 0.8% blood solution and 25 µl of each antibody dilution was then added in each column of the ID-card Coombs anti-IgG. The cards were incubated at 37° C. for 15 minutes and then were centrifuged in the ID-centrifuge. Each microtube of the ID-card contains anti-human globulin anti-IgG (rabbit) within a gel matrix. The gel column acts as a filter that traps agglutinated red blood cells as they pass through the gel column during the centrifugation of the card. The gel column separates agglutinated red blood cells from non-agglutinated red blood cells based on size. Any agglutinated red blood cells are captured at the top of or along the gel column, and non-agglutinated red blood cells descend to the bottom of the microtube forming a pellet. Extent of agglutination was scored from 0 (no agglutination) to 4 (complete agglutination).

Figure 22B:
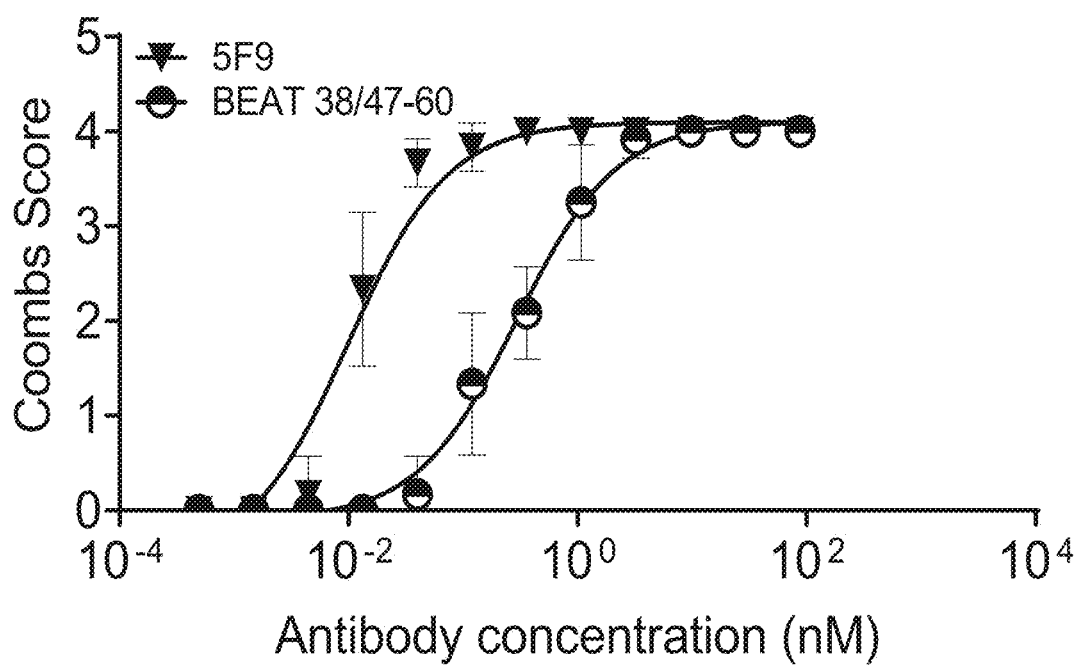
Figure 22C:
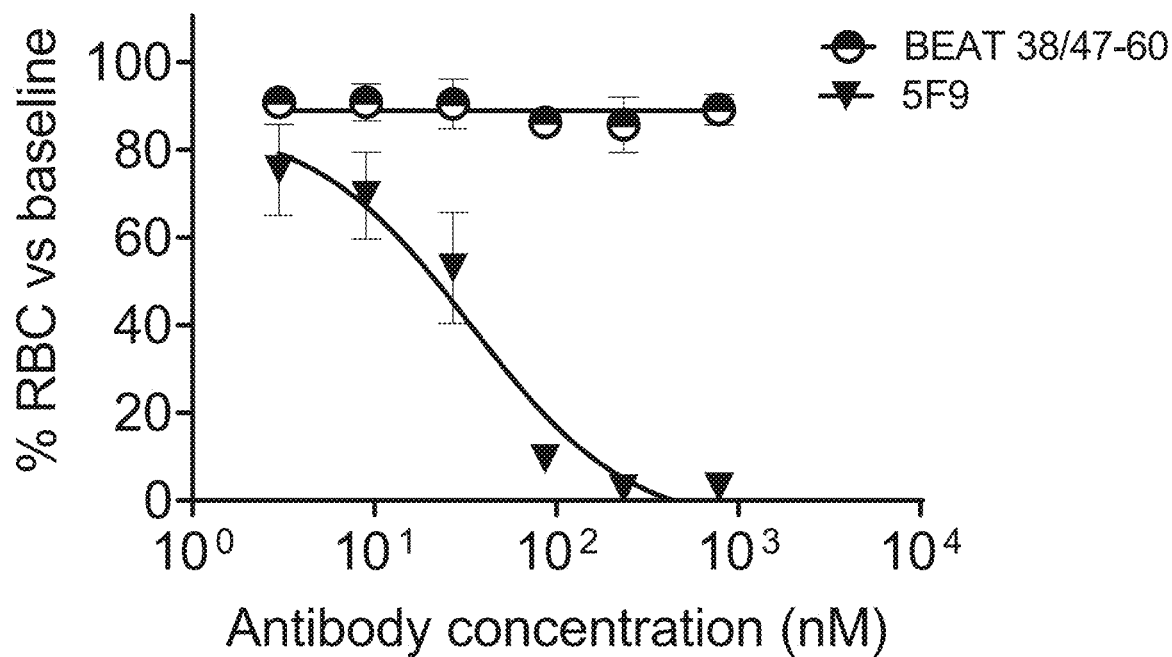

Red Blood Cell Depletion Assay (FIG. 22C)

Ability of BEAT 38/47 to induce red-blood cell loss was evaluated in-house using a hematology analyzer (Sigma 5H with human blood) (FIG. 22C). Fresh peripheral blood from healthy human volunteers collected on EDTA K3 tubes were obtained from Bern Transfusion Center.

Test and control antibodies were incubated 13× concentrated in 500 µl of complete peripheral blood for 1 h30 at 37° C. under gentle agitation (100 rpm). After incubation, blood cell counting was performed using Sigma 5H hematology Analyzer (SwissAvans). Red Blood cell concentration in fresh blood were then reported and analyzed in GraphPad Prism software.

Figure 22D:
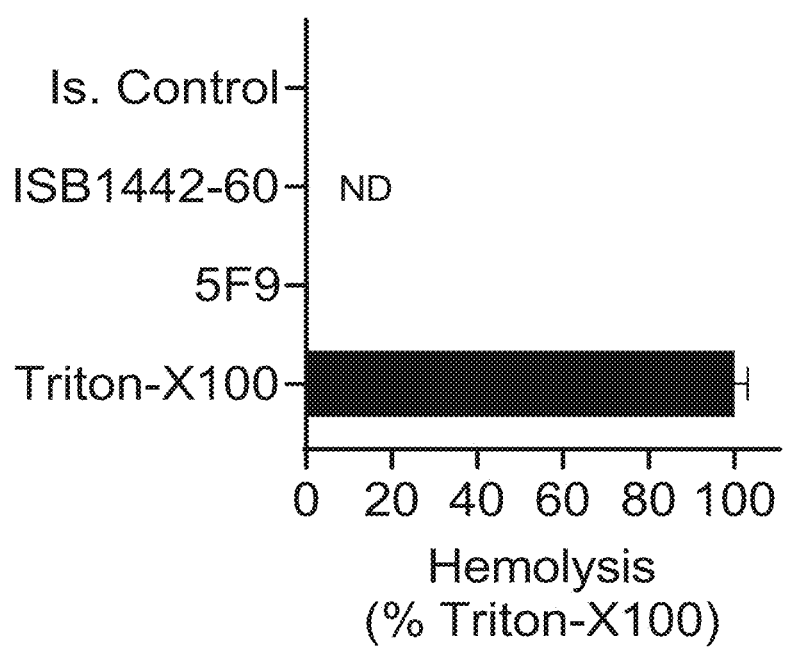

Hemolysis of RBCs (FIG. 22D)

Fresh peripheral blood from healthy volunteers collected on EDTA K3 tubes were obtained from Bern Transfusion Center. BEAT 38/47-induction of hemolysis (FIG. 22D) was tested in vitro by incubating test and control antibodies in fresh peripheral blood at 37° C. for 3 h30 and analysis the hemoglobin absorbance in plasma at 414 nm. Triton X-100 was used as a positive control for hemolysis. Samples were centrifuged and plasma was transferred into a clear bottom 96 well plate. Hemolysis was quantified by measuring the absorbance of plasma at 414 nm. Results were normalized in GraphPad Prism software to no antibody treatment condition (negative control) and triton X-100 (positive control).

Figure 22E:
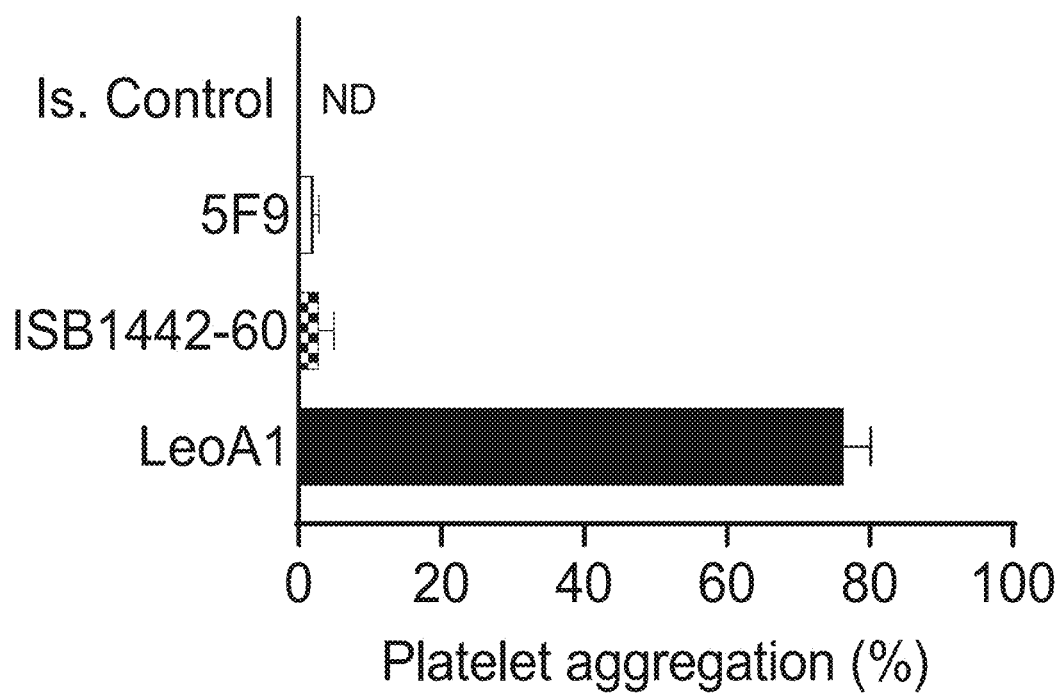

Platelet Aggregation (FIG. 22E)

Blood Collection and Preparation

Following written informed consent, blood was obtained by careful venepuncture, using a 19-gauge needle and 60 mL syringe, from six healthy volunteers who denied recent ingestion of non-steroidal anti-inflammatory agents or other drugs known to affect platelet function. Blood (total volume 50 mL) was dispensed into 10 mL graduated plastic tubes, each containing 3.13% (w/v) tri-sodium citrate dihydrate (1 part citrate to 9 parts blood), and inverted carefully 3 times to mix with the anticoagulant. After careful mixing, the blood was left to rest on the bench for 10 minutes before being centrifuged at 180×g for 10 min to prepare platelet rich plasma (PRP). The PRP was carefully aspirated using a plastic pipette, pooled into a sterile plastic 30 ml Universal container. Some of the residual blood was centrifuged further (3,000×g for 10 min) to obtain platelet poor plasma (PPP) that was required to set 100% light transmission aggregometry (LTA) on the aggregometer, AggRAM.

LTA Procedure

The AggRAM aggregometer was used according to the manufacturers' instructions. The instrument was pre-warmed to 37° C. prior to the start of the experiment. For each individual sample (aggregation curve) 100% optical transmission was set using a 250 µl sample of autologous PPP. Following this, 215 µL of PRP was added to the cuvette containing a stirrer bar and 25 µL of the test compounds or LeoA1 was added to the sample, which was then placed into the warming well of the AggRAM for 2 minutes without stirring. After 1 minute, the cuvette was moved to the optical well of the AggRAM with stirring, where light transmission was set to record for a further minute to establish the 0% transmission baseline prior to the addition of 10 µL of collagen, ADP or PBS. The aggregation response was recorded for a further 6 minutes. Aggregation traces, showing the changes in light transmission, and reports for each run were printed directly from the aggregometer. Hard copies of raw data for all individual volunteers were stored in a designated secure location within Platelet Services and can be provided upon request. The numerical output (AUC and % Max) was taken directly from the machine and is presented in tabulated form in Platelet Services' report and were displayed using GraphPad Prism software.

Results and Conclusions

CD38 and CD47, albeit upregulated in multiple myeloma cells, can be expressed at low level in other tissues and cellular compartments, including RBCs, platelets and several white blood cells. Specifically, Human RBCs are especially prone to be targeted by anti-CD47 based therapies due their high basal expression of CD47. Indeed, transient anemia in about 60% of the patients in phase I clinical trial was a major side effect of Magrolimab (SIKIC, B. I. ET AL. First-in-Human, First-in-Class Phase I Trial of the Anti-CD47 Antibody Hu5F9-G4 in Patients With Advanced Cancers. J Clin Oncol 37, 946-953, 2019). Based on this, BEAT 38/47-60 was designed to have a low affinity anti-CD47 Fab arm to risk mitigate RBCs on target induced by the anti-CD47 monotherapies like the high affinity anti-CD47 Magrolimab. We therefore addressed several on target/off tumor parameters of BEAT 38/47-60 in vitro, as compared to Magrolimab-like monoclonal antibody. We analysed binding to RBCs and whole blood cell subsets, induction of hemagglutination, RBCs depletion and hemolysis as well as platelet aggregation (FIGS. 22A-22E).

BEAT 38/47-60 showed a remarkably lower binding to RBCs as compared to Magrolimab (5F9) in whole blood incubated with increasing concentration of antibodies (FIG. 22A) suggesting a more favorable on target on RBCs. This is in line with its lower affinity against CD47 as compared to Magrolimab. To assess whether the lower binding RBCs resulted in a lower on target effect on RBCs, we assessed hemagglutination, hemolysis and RBCs depletion potentials of BEAT 38/47-60. To have a robust and reproducible measurement of RBCs agglutination in vitro, we set up the Coombs assay, a method that indirectly induces agglutination upon crosslinking of antibodies bound on RBCs. Using this method, Magrolimab induced prominent hemagglutination of RBCs in vitro while BEAT 38/47-60 induced a lower Coombs score as compared to it (FIG. 22B). In addition, using a hematoanalyser machine to count RBCs, we found that incubation of whole blood with BEAT 38/47-60 induce no detectable depletion of RBCs in whole blood (FIG. 22C). On the contrary, Magrolimab-like antibodies induced a dose-dependent depletion of RBCs in whole blood (FIG. 22C). Both BEAT 38/47-60 and Magrolimab-like antibodies did not induce a detectable of RBC lysis in vitro (FIG. 22D). Next, the impact of BEAT 38/47-60 on platelet aggregation in vitro was evaluated. Leao-1, a well-established antibody that induce platelet aggregation (JUDITH L. SCOTT at al. Characterization of a novel membrane glycoprotein involved in platelet activation. J Biol Chem. 1989 Aug. 15; 264(23):13475-82) was used as positive control. Accordingly, it induced high level of platelet aggregation (FIG. 22E). On the contrary, BEAT 38/47-60 or Magrolimab-like antibody failed to induce platelet aggregation (FIG. 22E).

Altogether these data suggest that BEAT 38/47-60 have a more favorable on target profile on RBCs as compared to anti-CD47 Magrolimab-like antibody.

TABLE 21

Statistics values calculated using Tuckey's multiple comparison tests in indicated conditions of Coombs score.

| | Conditions | EC50 |
|---|---|---|
| Coombs Score | BEAT 38/47-60 vs. 5F9 | <0.0001 |

Example 7.2: BEAT38/47-60 Show Lower on Target/Off Tumor Activity in RBCs and Platelets as Compared to 5F9 In Vitro Materials and Methods Binding was evaluated on six different human red blood cell donors. Staining of cells were performed as described in FIGS. 11A-11E.

Results and Conclusions

Figure 23A:
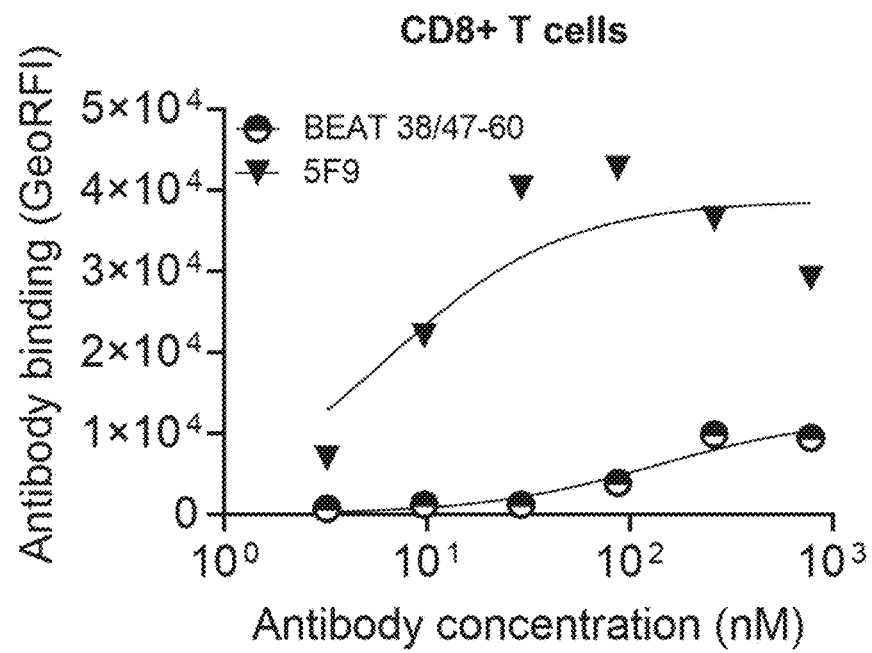
Figure 23B:
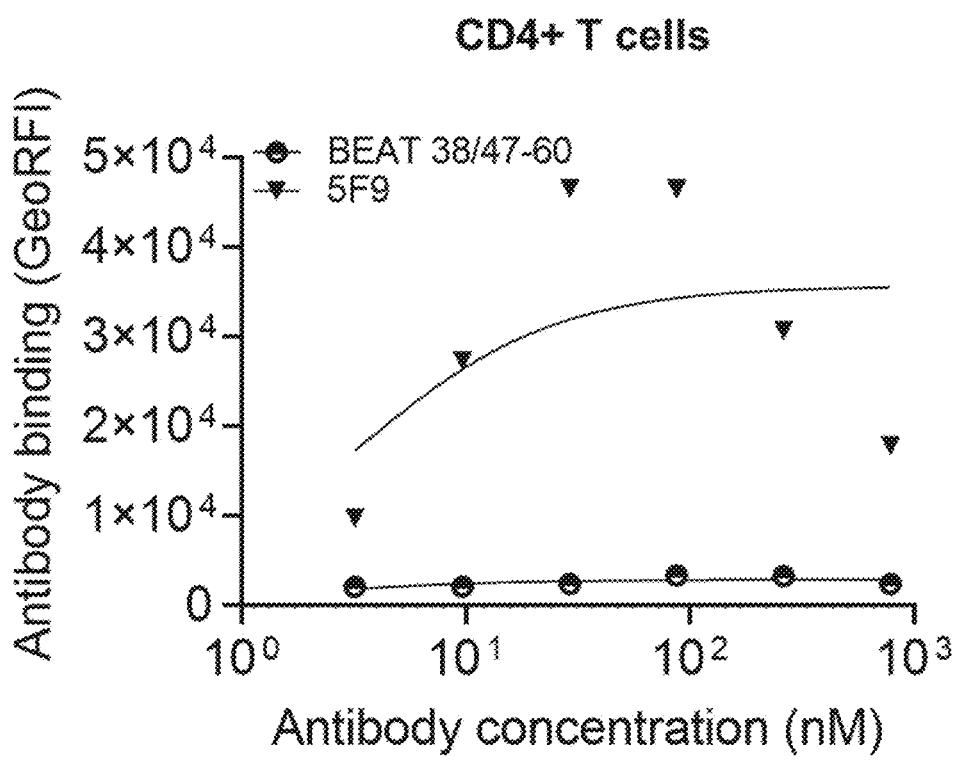
Figure 23C:
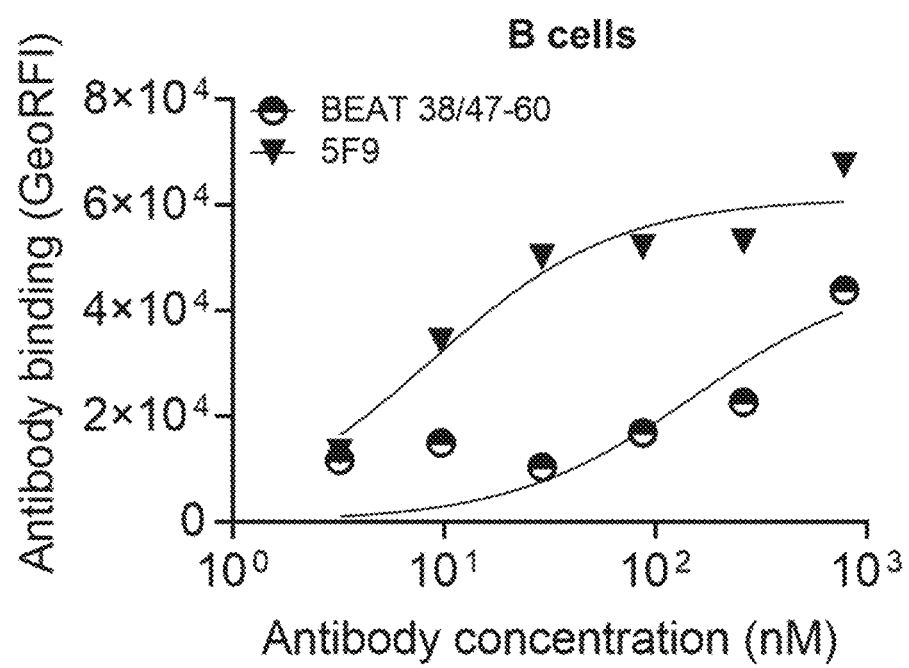
Figure 23D:
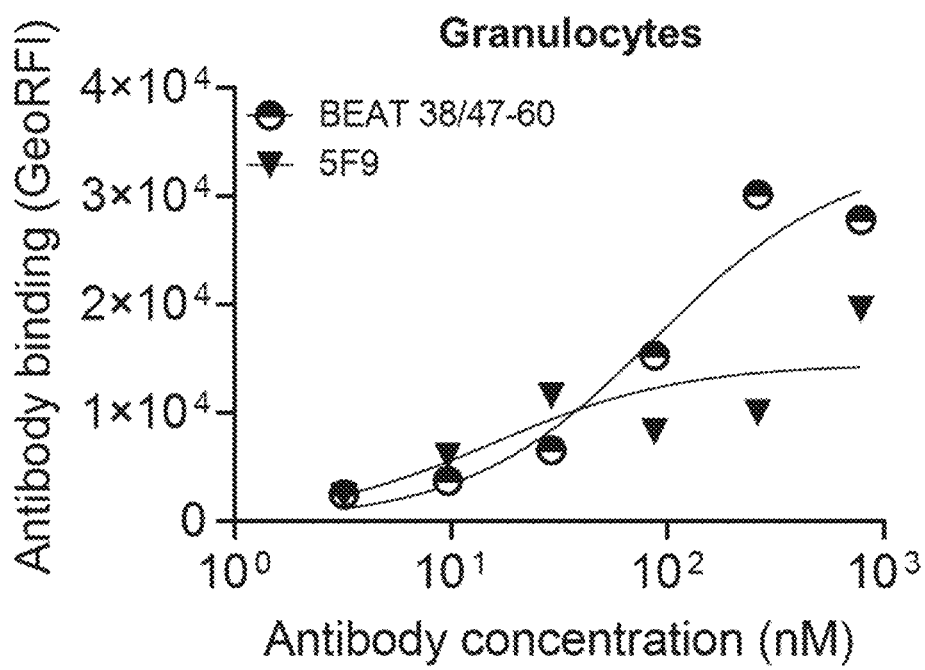
Figure 23E:
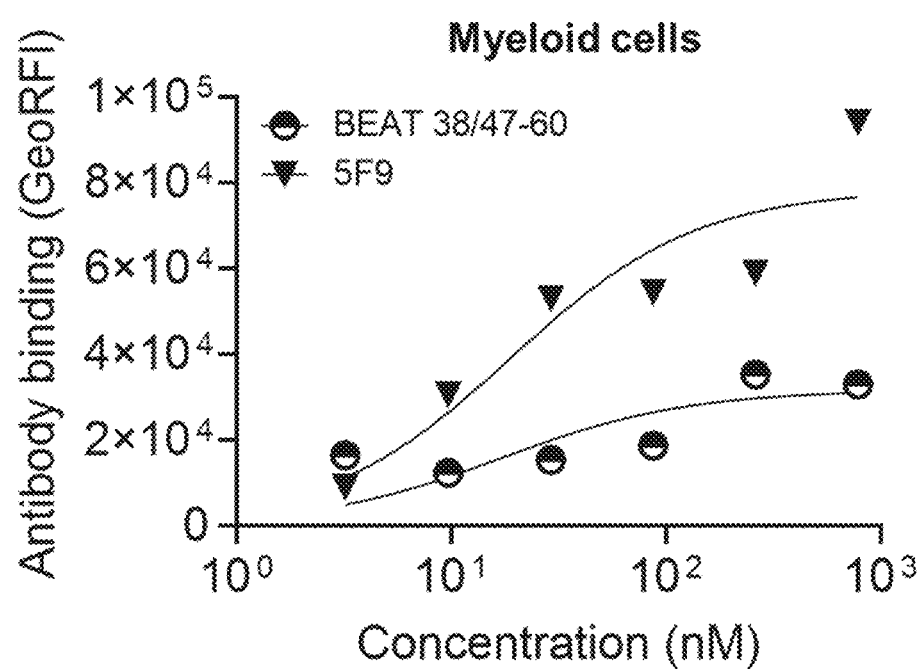

Next, we analyzed the binding level of BEAT 38/47-60 in whole blood as CD47 and CD38 can be expressed on multiple white blood cells subsets. The binding of BEAT 38/47-60 and Magrolimab-like antibody to immune cells was compared by flow cytometry following staining of whole blood from healthy donors. BEAT 38/47-60 showed a trend of lower binding to CD4 (FIG. 23B) and CD8 T cell (FIG. 23A) subsets, B cells (FIG. 23C) and NK cells (FIG. 23E) relative to 5F9. Binding to granulocytes was the only exception where BEAT 38/47-60 was showing a trend of higher binding at the highest concentrations tested (FIG. 23D).

Altogether these data suggest that BEAT 38/47-60 show no major liability as measured by its on target profile on whole blood as compared to anti-CD47 Magrolimab-like antibody.

EXAMPLE 8: EFFICACY OF BEAT CD38/CD47-48 AND BEAT CD38/CD47-60 IN VIVO MODELS

Example 8.1: Efficacy of BEAT CD38/CD47-48 and BEAT CD38/CD47-60 in an In Vivo Raji Tumor Mouse Model Expressing High Level of CD38

Material and Method

Animal Husbandry

In vivo experiments were performed in female 6-7-week-old immune-competent SCID mice from JANVIER LABS. All mice were maintained under standardized environmental conditions in rodent cages (20±1° C. room temperature, 50±10% relative humidity, 12 hours light dark cycle). Mice received irradiated food and bedding and 0.22 µm-filtered drinking water. Studies were performed in collaboration with Transcure company (FRANCE).

Raji Tumor Mouse Model CD38 High Expressing

Two experiments were conducted and were named respectively Raj_9 and Raj_10 studies.

Raj_9 study. Dose escalation of BEAT CD38/CD47-48 and BEAT CD38/CD47-60 in Raji tumors. SCID mice were xenograft subcutaneously with Raji tumor cells only at day 0 (5 mice per group; 8 groups; 40 mice total). 12 days after the xenograft, mice were randomized based on the tumor volume and were injected intravenously with PBS1×; BEAT CD38/CD47-48 molecules at 10, 1 and 0.1 mg/kg and BEAT CD38/CD47-60 molecules at 10, 1 and 0.1 mg/kg once per week for 3 weeks. No ex vivo analysis was performed on these animals. This experiment was done only once.

Raj_10 study. BEAT CD38/CD47-48 and BEAT CD38/CD47-60 efficacy study in Raji tumors. SCID mice were xenograft subcutaneously with Raji tumor cells only at day 0 (10 mice per group; 8 groups; 80 mice total). 12 days after the xenograft, mice were randomized based on the tumor volume and were injected intravenously with PBS1×; BEAT CD38/CD47-48 molecules; BEAT CD38/CD47-60 molecules; BEAT CD38/CD47-59 molecules; BEAT CD38/CD47-79 molecules once per week for 3 weeks. Darzalex was injected intravenously at 16 mg/kg twice per week for 3 weeks. Ex vivo analysis was performed on 5 animals per group at day 16. Mice serum and tumors were harvested for ex vivo analysis. Luminex was performed on mice serum and tumor supernatant samples. FACS analysis was performed on mice tumors. This experiment was done only once.

Tumor growth inhibition is calculated using the 1-Δt/Δc method (change in test tumor size divided by change in control tumor size) and expressed as a percentage. Averages for each group are used for this calculation):

$$TGI = (1 - (TreatmentV_{current} - TreatmentV_{start})/$$
$$(ControlV_{current} - ControlV_{start})) \times 100 \text{ as a \%}$$

Tumor regression was defined as achieving a negative Δt.

Mice Samples Preparation for Flow Cytometry

For tumor samples, tumors were harvested and dissociated with GentleMACS. Cell suspensions were filtered and centrifuged. Cells were then counted and stained for immune cell profiling. Staining with a complete antibody panel and the relative controls were prepared in FACS buffer. Samples were analyzed on the Northern lights instrument (CYTEK). Data were analyzed using FlowJo v10.7.1 and GraphPad Prism 8.

Mice Samples Preparation for Luminex Assay

Serum samples and tumor supernatant samples were assessed by Multiplex Luminex quantification according to the manufacturer's instructions. Beads, in-vivo samples and/or supernatants and diluted standards provided by the kit, were added to the plates, incubated overnight. The detection antibody was added to the plates and incubated for 30 minutes at room temperature. The plates were washed, and streptavidin-PE was added and incubated for 30 minutes at room temperature. The plates were washed, and the reading buffer was added and incubated at room temperature before reading with the Luminex 200 instrument. Luminex data were analyzed using ProcartaPlex 1.0 Analyst software. Cytokines concentration was normalized to the upper (ULOQ) and lower (LLOQ) limit of quantification. All data below LLOQ were set to the lowest point of the standard curves and considered like unanalyzable (for GraphPad Prism analysis no zero allowed). Data were analyzed using Excel and GraphPad Prism 8.

Statistical Analysis

Data were analyzed using GraphPad Prism 9 software. Statistical analysis performed: one-way analysis of variance (ANOVA) and if significant followed by Dunnett's with PBS control and Tukey's multiple comparison P<0.05 was considered as statistically significant. Level of significance is represented by asterisks. (** for <0.0001; * for 0.0001; ** for 0.001 and * for 0.05).

Results and Conclusions

BEAT CD38/CD47-48 and BEAT CD38/CD47-60 were evaluated in a dose response experiment in vivo in a Raji tumor cell line derived xenograft (CDX) model, this tumor cell line expresses high levels of CD38 and has been reported to respond to Darzalex (Y U et al, Novel anti-CD38 humanized mAb SG003 possessed enhanced cytotoxicity in lymphoma than Daratumumab via antibody-dependent cell-mediated cytotoxicity. BMC Biotechnology (2019) 19:28).

SCID mice were xenograft subcutaneously with Raji tumor cells only at day 0 (5 mice per group; 8 groups; 40 mice total). 12 days after the xenograft, mice were randomized based on the tumor volume and were injected intravenously with PBS, BEAT CD38/CD47-48 molecules at 10, 1 and 0.1 mg/kg and BEAT CD38/CD47-60 molecules at 10, 1 and 0.1 mg/kg once per week for 3 weeks. Tumor volumes at enrollment varied from 40-270 mm$^3$. 3 mice with no measurable tumor on D12 were excluded from further evaluation.

Figure 24A:
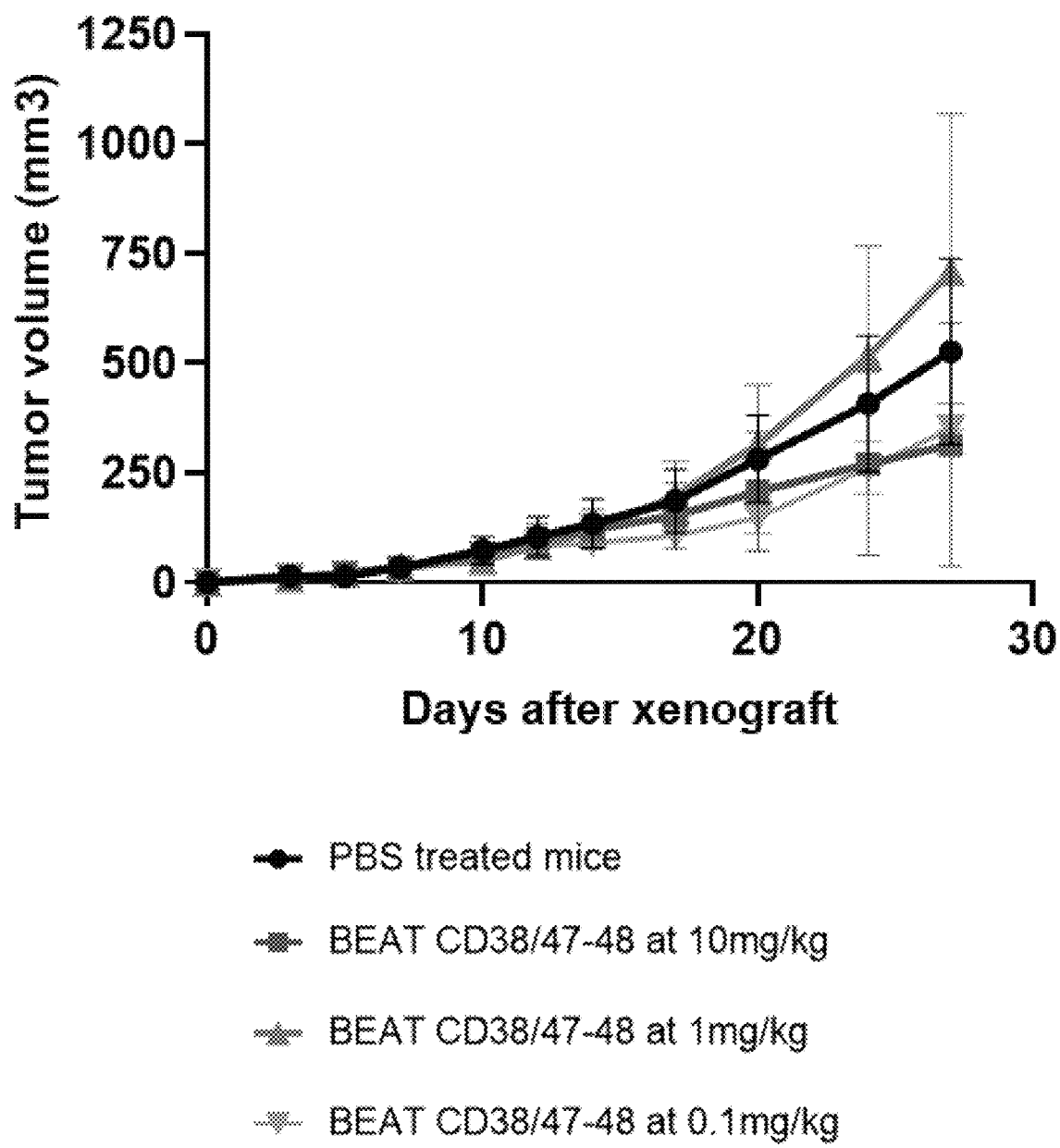
Figure 24B:
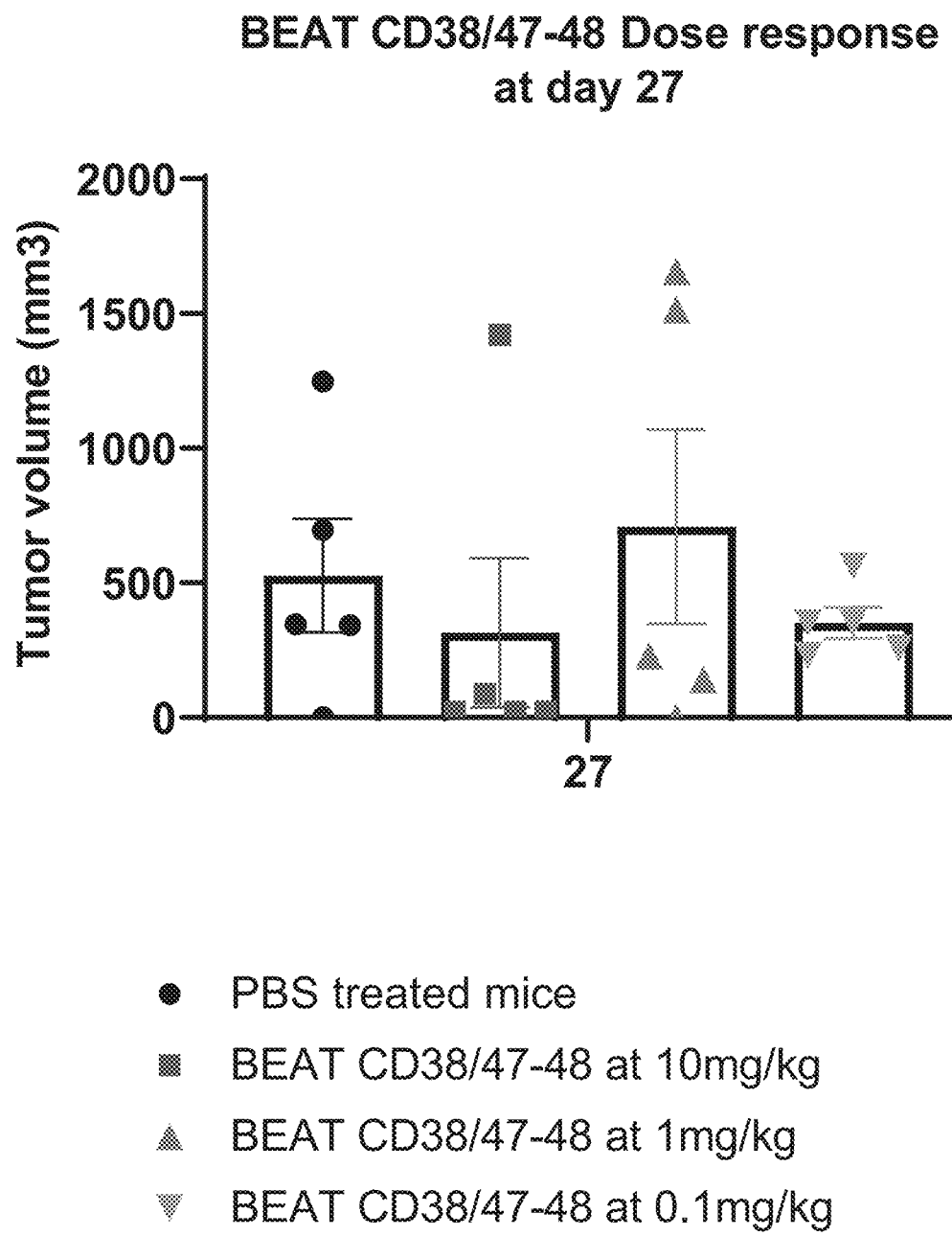
Figure 25A:
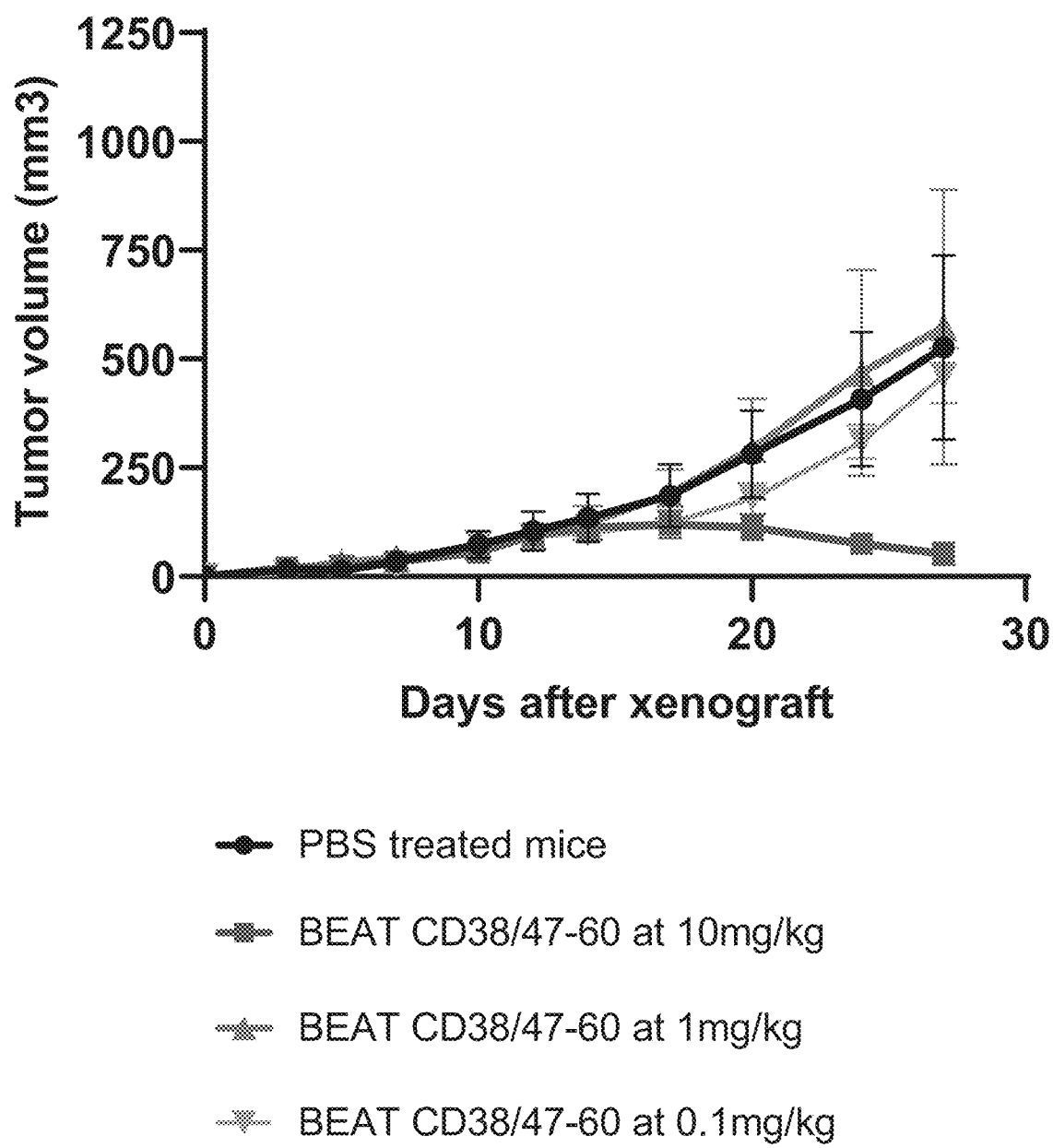
Figure 25B:
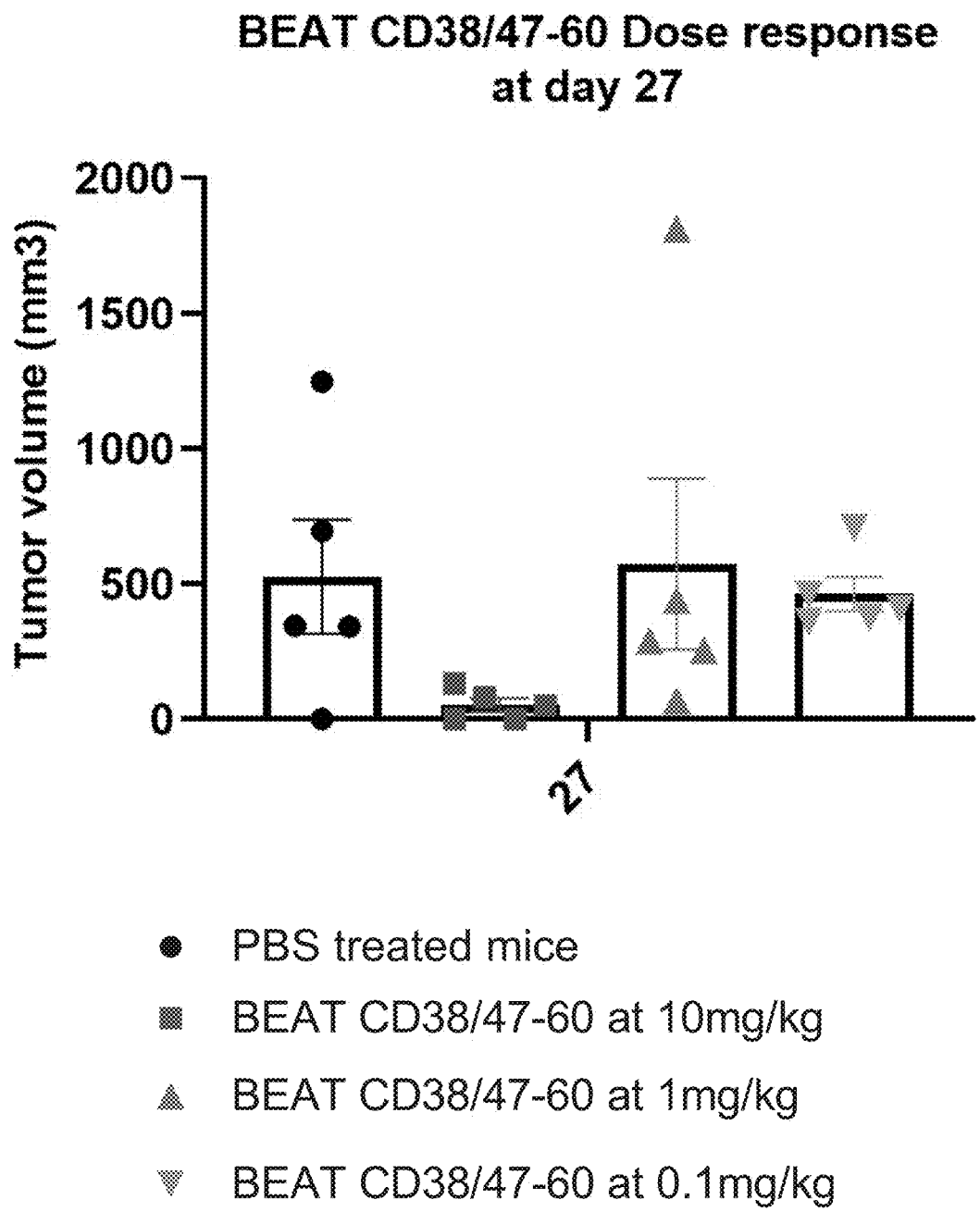

15 days after the start of treatment (27 days post xenograft) control tumors were reaching the ethical endpoint of 1000 mm3 and the study was halted. Tumor growth inhibition was evaluated for both molecules at all 3 doses. Tumor regression during treatment was observed for 3/5 mice treated with BEAT CD38/CD47-48 and 4/5 mice treated with BEAT CD38/CD47-60. Tumor growth is shown in FIG. 24A and FIG. 25A. Based on number of regressions 10 mg/kg was identified as the efficacious dose. One way ANOVA analysis on D27 was not significant due to high variability in tumor volumes and no post hoc test was conducted (FIG. 24B and FIG. 25B).

The efficacy of BEAT CD38/CD47-48 and BEAT CD38/CD47-60 at 10 mg/kg was tested in one further experiment in vivo in the Raji tumor model. SCID mice were xenograft subcutaneously with Raji tumor cells at day 0 (10 mice per group; 8 groups; 80 mice total). 12 days after the xenograft, mice were randomized based on the tumor volume and were injected intravenously with PBS1x; BEAT CD38/CD47-48 molecules; BEAT CD38/CD47-60 molecules; BEAT CD38/CD47-59 molecules (Single arm CD38 control for BEAT CD38/CD47-48) and BEAT CD38/CD47-79 molecules (Single arm CD38 control for BEAT CD38/CD47-60) once per week for 3 weeks. All BEAT molecules were injected at 10 mg/kg. Darzalex was injected intravenously at 16 mg/kg twice per week for 3 weeks. Ex vivo analysis were performed on 5 animals per group at day 16. Mice serum and tumors were harvested for ex vivo analysis. Luminex was performed on mice serum and tumor supernatant samples. FACS analysis was performed on mice tumors.

Figure 26A:
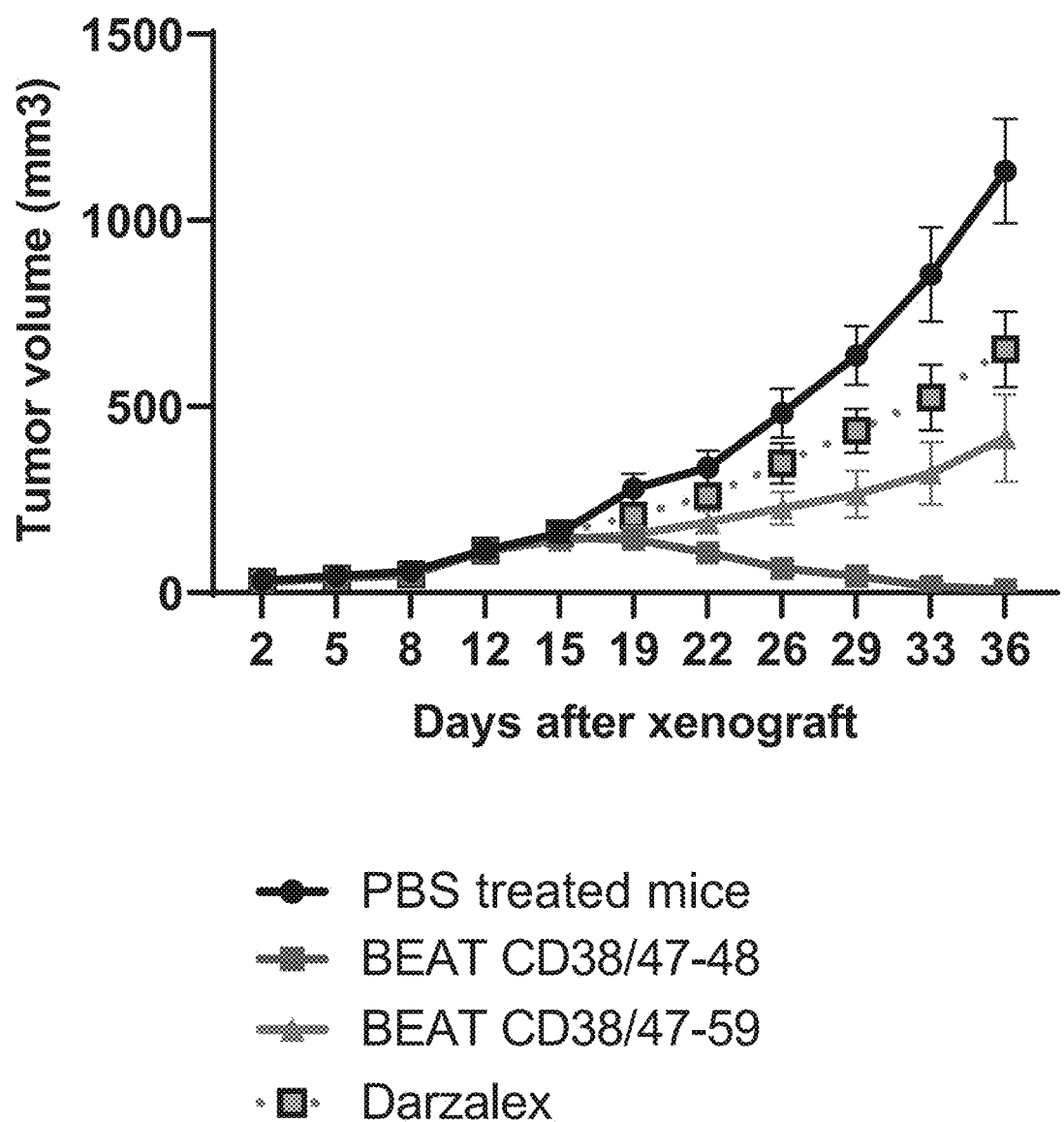
Figure 27A:
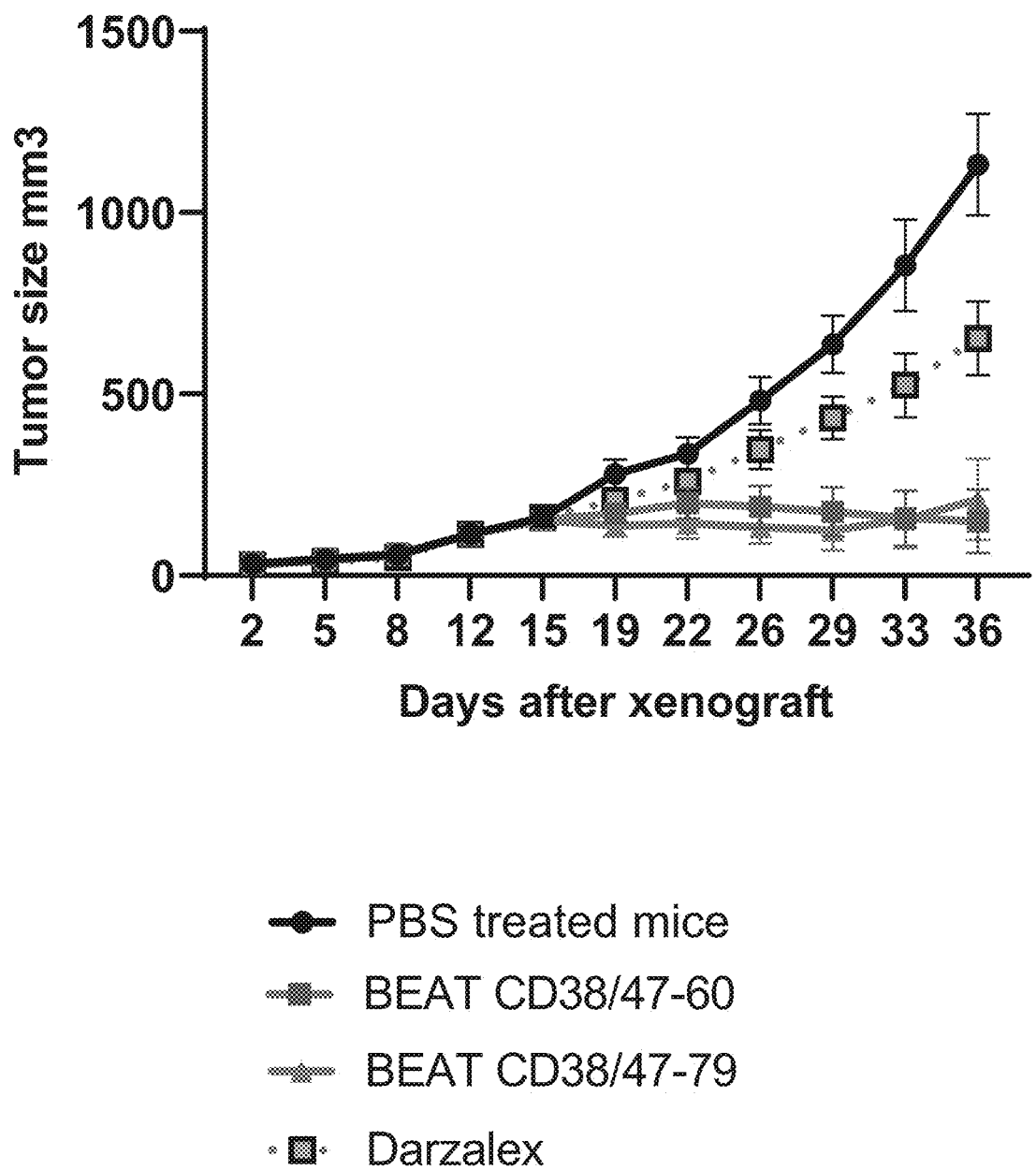
Figure 28A:
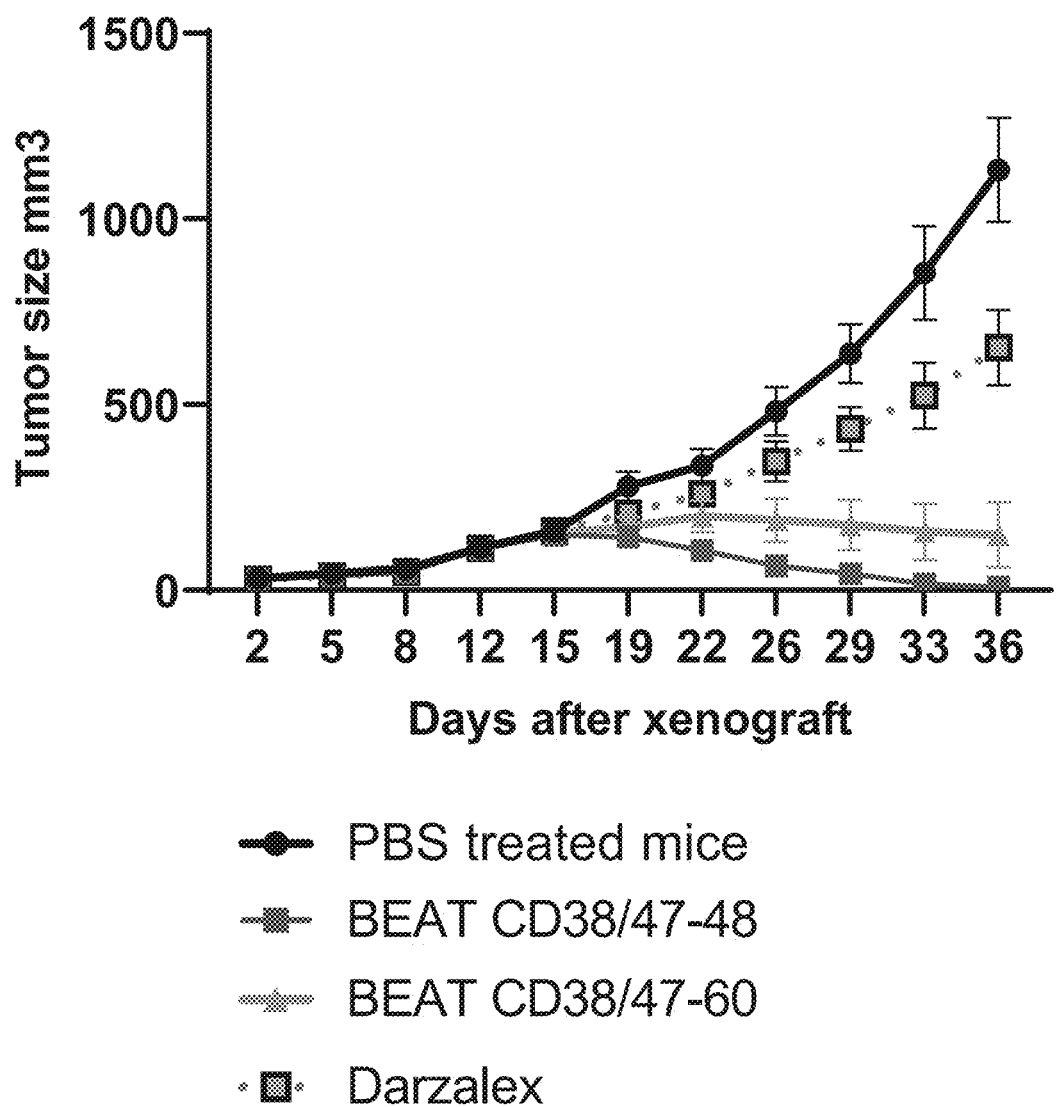

36 days after the xenograft control mice had tumors exceeding 1000 mm$^3$ and the study was terminated. Tumor growth inhibition (TGI) was calculated, all BEATs and Darzalex showed significant TGI ranging from 47% to 110% (regression) (Table 22). Both BEAT CD38/CD47-48 and BEAT CD38/CD47-60 showed a significant efficacy on tumor reduction (FIG. 26A, FIG. 27A and FIG. 28A, and Table 22).

TABLE 22

Figure 26B:
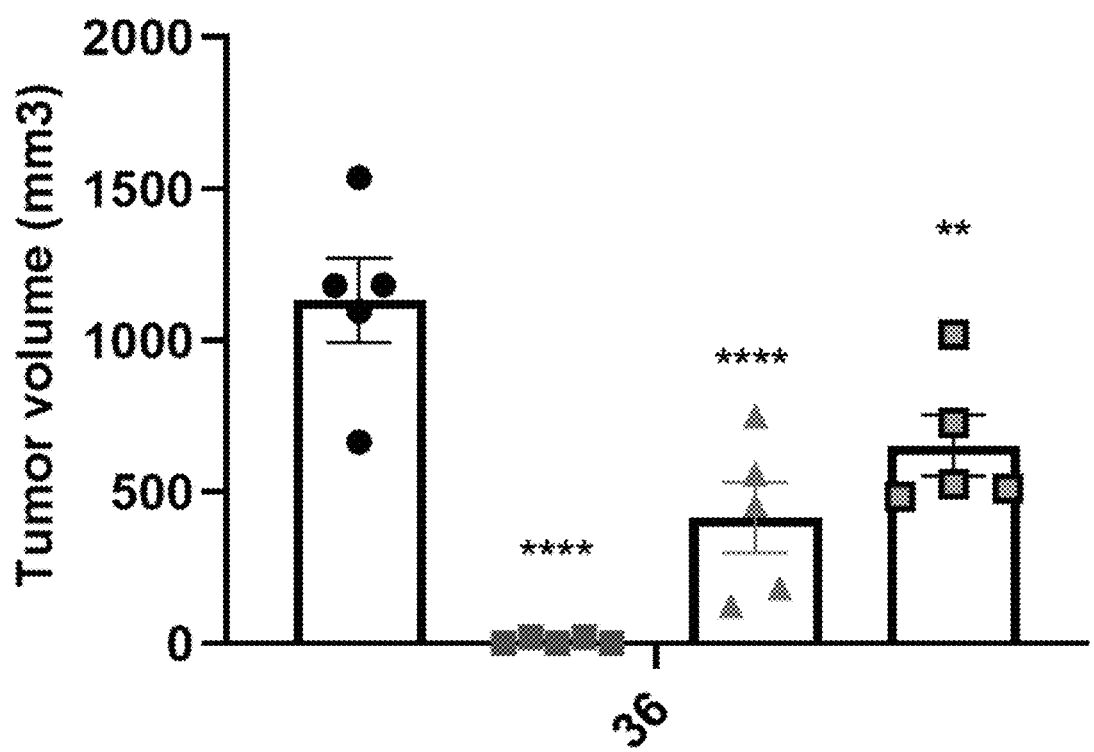
Figure 27B:
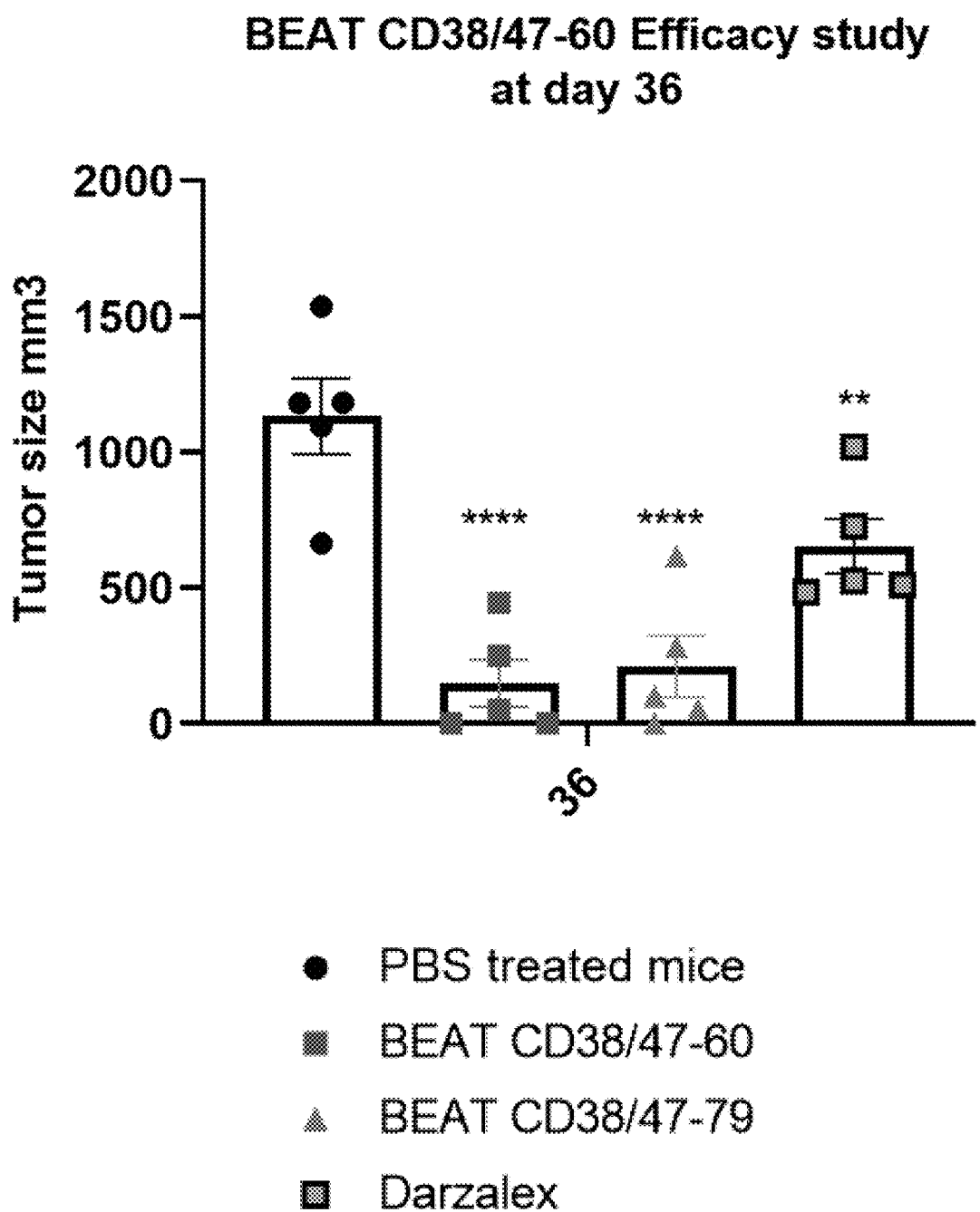
Figure 28B:
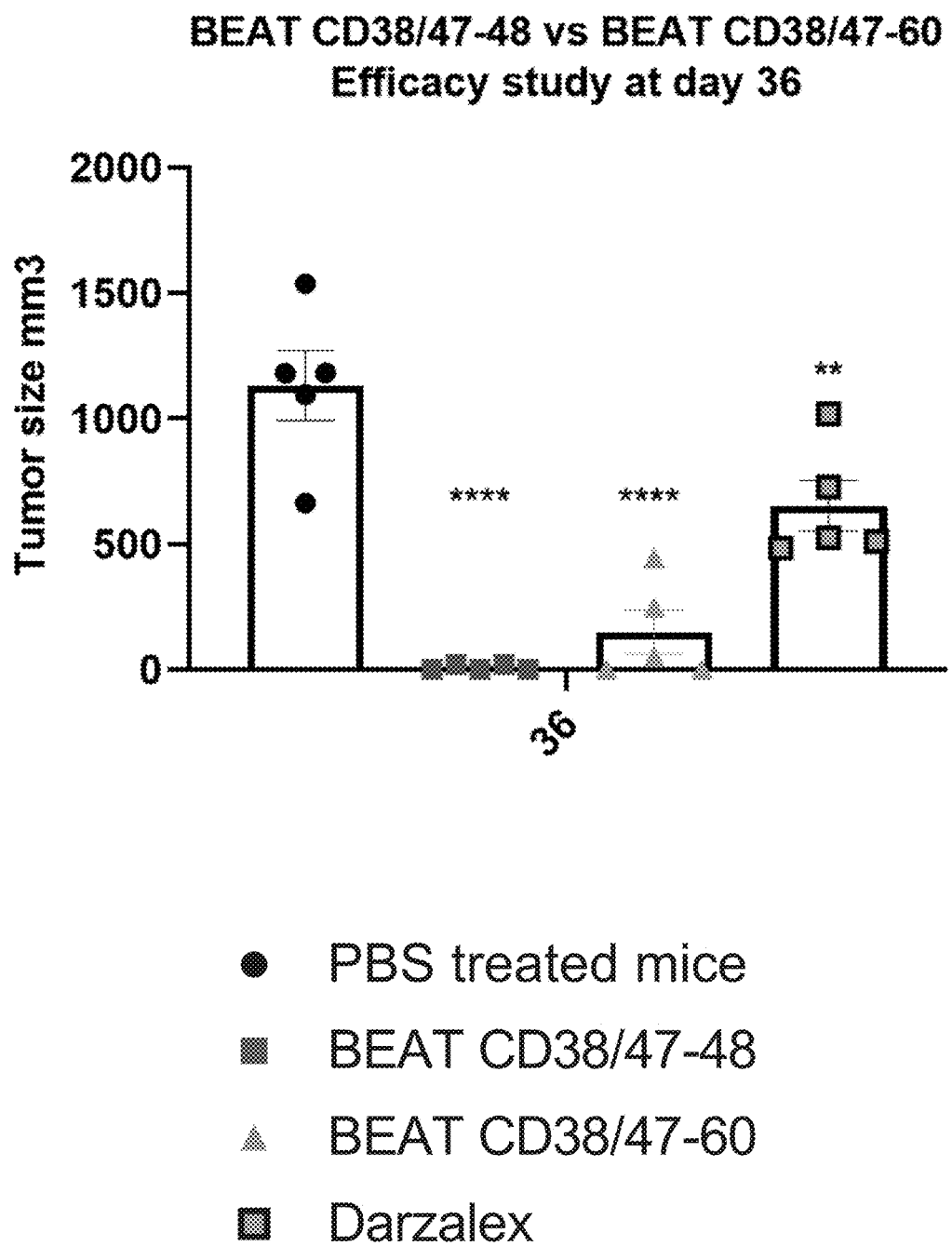

Statistical analysis at day 36 of FIG. 26B, FIG. 27B and FIG. 28B (one-way analysis of variance (ANOVA) followed by Dunnett's multiple comparison). TGI (tumor growth inhibition) is shown.

| Dunnett's multiple comparisons test | Mean Diff, | 95.00% CI of diff, | Significant? | Summary | Adjusted P Value | TGI |
|---|---|---|---|---|---|---|
| PBS treated mice vs. BEAT CD38/47-48 | 1124 | 775.1 to 1472 | Yes | **** | <0.0001 | 110% |
| PBS treated mice vs. BEAT CD38/47-59 | 716.6 | 368.1 to 1065 | Yes | **** | <0.0001 | 70% |
| PBS treated mice vs. BEAT CD38/47-60 | 982.8 | 634.3 to 1331 | Yes | **** | <0.0001 | 96% |
| PBS treated mice vs. BEAT CD38/47-79 | 922.2 | 573.7 to 1271 | Yes | **** | <0.0001 | 91% |
| PBS treated mice vs. Darzalex | 479 | 130.5 to 827.5 | Yes | ** | 0.0038 | 47% |

BEAT CD38/CD47-48 achieved regression in 5/5 mice; BEAT CD38/CD47-60 achieved regression in 3/5 mice while Darzalex showed regression in none and as shown in Table 23 Tukey's post hoc testing showed no difference between BEAT CD38/CD47-48 BEAT and CD38/CD47-60. At day 36, in this experiment design, BEAT CD38/CD47-48 and BEAT CD38/CD47-60 showed a better efficacy than Darzalex (respectively P=0.0003 and P=0.0076) (Table 23).

TABLE 23

Statistical analysis at day 36 of FIG. 26B, FIG. 27B and FIG. 28B (one-way analysis of variance (ANOVA) followed by Tukey's multiple comparison).

| Tukey's multiple comparisons test | Mean Diff. | 95.00% Cl of diff. | Significant? | Summary | Adjusted P Value |
|---|---|---|---|---|---|
| PBS treated mice vs. BEAT CD38/47-48 | 1124 | 714.9 to 1532 | Yes | **** | <0.0001 |
| PBS treated mice vs. BEAT CD38/47-59 | 716.6 | 307.9 to 1125 | Yes | **** | <0.0001 |
| PBS treated mice vs. BEAT CD38/47-60 | 982.8 | 574.1 to 1392 | Yes | **** | <0.0001 |
| PBS treated mice vs. BEAT CD38/47-79 | 922.2 | 513.5 to 1331 | Yes | **** | <0.0001 |
| PBS treated mice vs. Darzalex | 479 | 70.29 to 887.7 | Yes | * | 0.0127 |
| BEAT CD38/47-48 vs. BEAT CD38/47-59 | −407 | −815.7 to 1.713 | No | ns | 0.0516 |
| BEAT CD38/47-48 vs. BEAT CD38/47-60 | −140.8 | −549.5 to 267.9 | No | ns | 0.9485 |
| BEAT CD38/47-48 vs. BEAT CD38/47-79 | −201.4 | −610.1 to 207.3 | No | ns | 0.749 |
| BEAT CD38/47-48 vs. Darzalex | −644.6 | −1053 to −235.9 | Yes | *** | 0.0003 |
| BEAT CD38/47-59 vs. BEAT CD38/47-60 | 266.2 | −142.5 to 674.9 | No | ns | 0.4304 |
| BEAT CD38/47-59 vs. BEAT CD38/47-79 | 205.6 | −203.1 to 614.3 | No | ns | 0.7296 |
| BEAT CD38/47-59 vs. Darzalex | −237.6 | −646.3 to 171.1 | No | ns | 0.5715 |
| BEAT CD38/47-60 vs. BEAT CD38/47-79 | −60.6 | −469.3 to 348.1 | No | ns | 0.9997 |
| BEAT CD38/47-60 vs. Darzalex | −503.8 | −912.5 to −95.09 | Yes | ** | 0.0076 |
| BEAT CD38/47-79 vs. Darzalex | −443.2 | −851.9 to −34.49 | Yes | * | 0.026 |

Figure 29A:
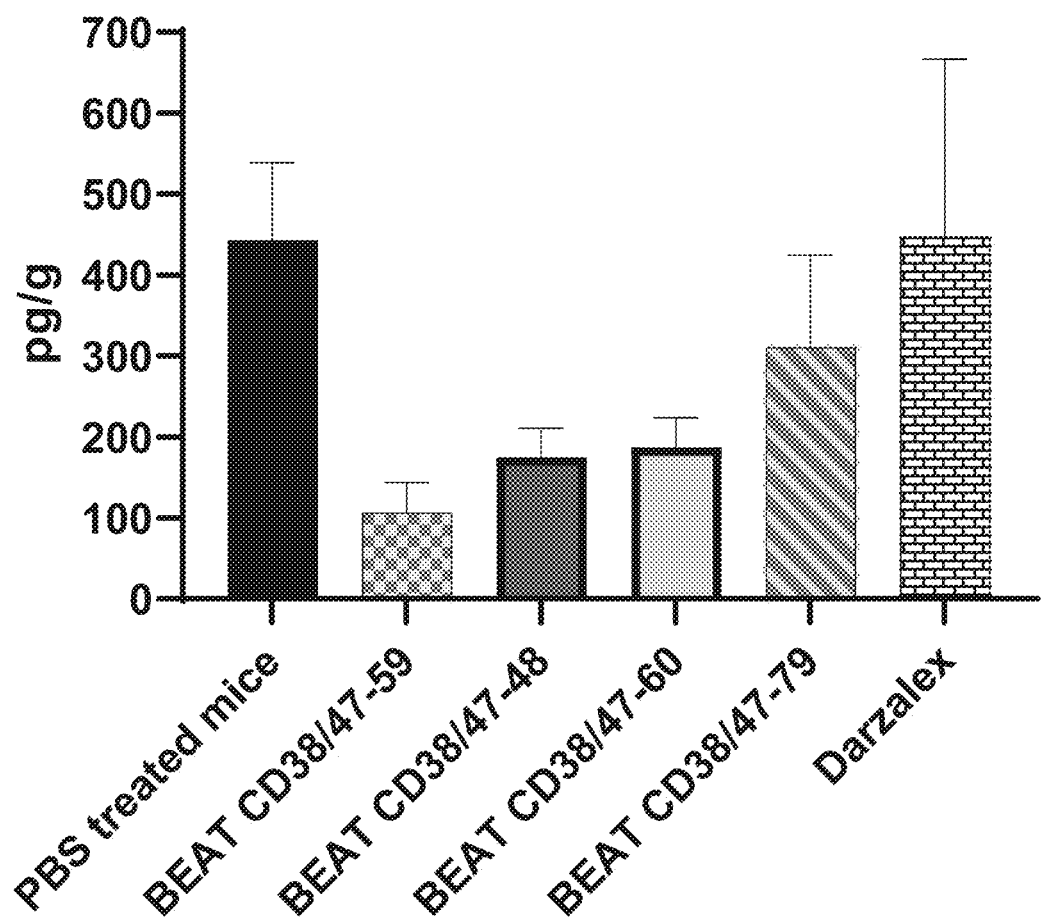

15 days after the xenograft (3 days after first treatment), 5 animals per group were sacrificed. Mice serum and tumors were harvested and analyzed ex vivo by Luminex and FACS. BEAT CD38/CD47-48 and BEAT CD38/CD47-60 showed a trend of IL-1b decrease level in the tumors (FIG. 29A). BEAT CD38/CD47-60 showed a significant decrease of MHCII+macrophages in the tumors (FIG. 29B, and Table 24).

TABLE 24

Figure 29B:
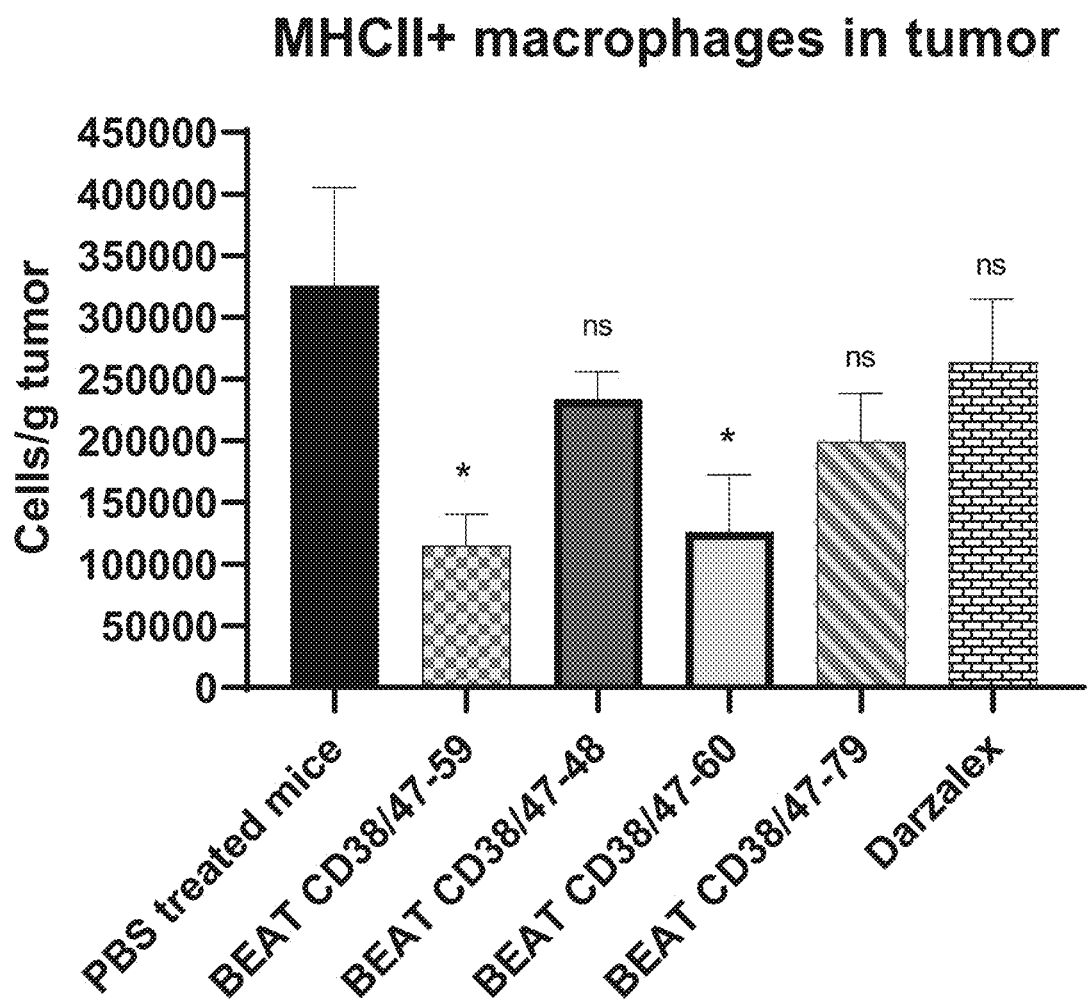

Statistical analysis of FIG. 29B (one-way analysis of variance (ANOVA) followed by Dunnett's multiple comparison).

| Dunnett's multiple comparisons test | Mean Diff. | 95.00% Cl of diff. | Significant? | Summary | Adjusted P Value |
|---|---|---|---|---|---|
| PBS treated mice vs. BEAT CD38/47-48 | 91691 | −79161 to 262544 | No | ns | 0.532 |
| PBS treated mice vs. BEAT CD38/47-59 | 210665 | 39812 to 381518 | Yes | * | 0.0106 |
| PBS treated mice vs. BEAT CD38/47-60 | 199452 | 28599 to 370305 | Yes | * | 0.0166 |
| PBS treated mice vs. BEAT CD38/47-79 | 126510 | −54707 to 307727 | No | ns | 0.2696 |
| PBS treated mice vs. Darzalex | 62652 | −108200 to 233505 | No | ns | 0.8491 |

In conclusion, BEAT CD38/CD47-48 and BEAT CD38/CD47-60 at 10 mg/kg showed a significant efficacy of tumor reduction in Raji xenografted mouse model. BEAT CD38/CD47-60 showed a corresponding activation of macrophages consistent with ADCP.

Example 8.2: Efficacy of BEAT CD38/CD47-48 and BEAT CD38/CD47-60 in an In Vivo KMS-12-BM Tumor Mouse Model Expressing Low Level of CD38

Material and Method

Animal Husbandry

In vivo experiments were performed in female 6-7-week-old immune-competent SCID mice from JANVIER LABS. All mice were maintained under standardized environmental conditions in rodent cages (20±1° C. room temperature, 50±10% relative humidity, 12 hours light dark cycle). Mice received irradiated food and bedding and 0.22 μm-filtered drinking water. Studies were performed in collaboration with Transcure company (FRANCE).

KMS-12-BM Tumor Mouse Model Darzalex Resistant

Once experiment was conducted and was named KMS_7 study.

KMS_7 study. Dose escalation of BEAT CD38/CD47-48 and BEAT CD38/CD47-60 in KMS-12-BM tumors. SCID mice were xenograft subcutaneously with KMS-12-BM tumor cells only at day 0 (5 mice per group; 9 groups; 45 mice total). 15 days after the xenograft, mice were randomized based on the tumor volume and were injected intravenously with PBS1×; BEAT CD38/CD47-48 molecules at 10, 1 and 0.1 mg/kg and BEAT CD38/CD47-60 molecules at 10, 1 and 0.1 mg/kg once per week for 3 weeks. Darzalex was injected intravenously at 16 mg/kg twice per week for 3 weeks. No ex vivo analysis was performed on these animals. This experiment was done only once.

Tumor growth inhibition is calculated using the 1-Δt/Δc method (change in test tumor size divided by change in control tumor size) and expressed as a percentage. Averages for each group are used for this calculation):

$$TGI = (1 - (TreatmentV_{current} - TreatmentV_{start}) / (ControlV_{current} - ControlV_{start})) \times 100 \text{ as a \%}$$

Tumor regression was defined as achieving a negative Δt (tumor smaller at end of study than beginning).

Statistical Analysis

Data were analyzed using GraphPad Prism 9 software. Statistical analysis performed: one-way analysis of variance (ANOVA) on the tumor growth and if significant followed by Dunnett's with PBS control and Tukey's multiple comparison $P<0.05$ was considered as statistically significant. Level of significance is represented by asterisks. (** for <0.0001; * for 0.0001; ** for 0.001 and * for 0.05).

Results and Conclusions

BEAT CD38/CD47-48 and BEAT CD38/CD47-60 were tested in one experiment in vivo in KMS-12-BM tumor model, which expresses low levels of CD38. SCID mice were xenografted subcutaneously with KMS-12-BM tumor cells at day 0 (5 mice per group; 9 groups; 45 mice total). 15 days after the xenograft, mice were randomized based on the tumor volume and were injected intravenously with PBS, BEAT CD38/CD47-48 molecules at 10, 1 and 0.1 mg/kg and BEAT CD38/CD47-60 molecules at 10, 1 and 0.1 mg/kg once per week for 3 weeks. Darzalex was injected intravenously at 16 mg/kg twice per week for 3 weeks.

Figure 30B:
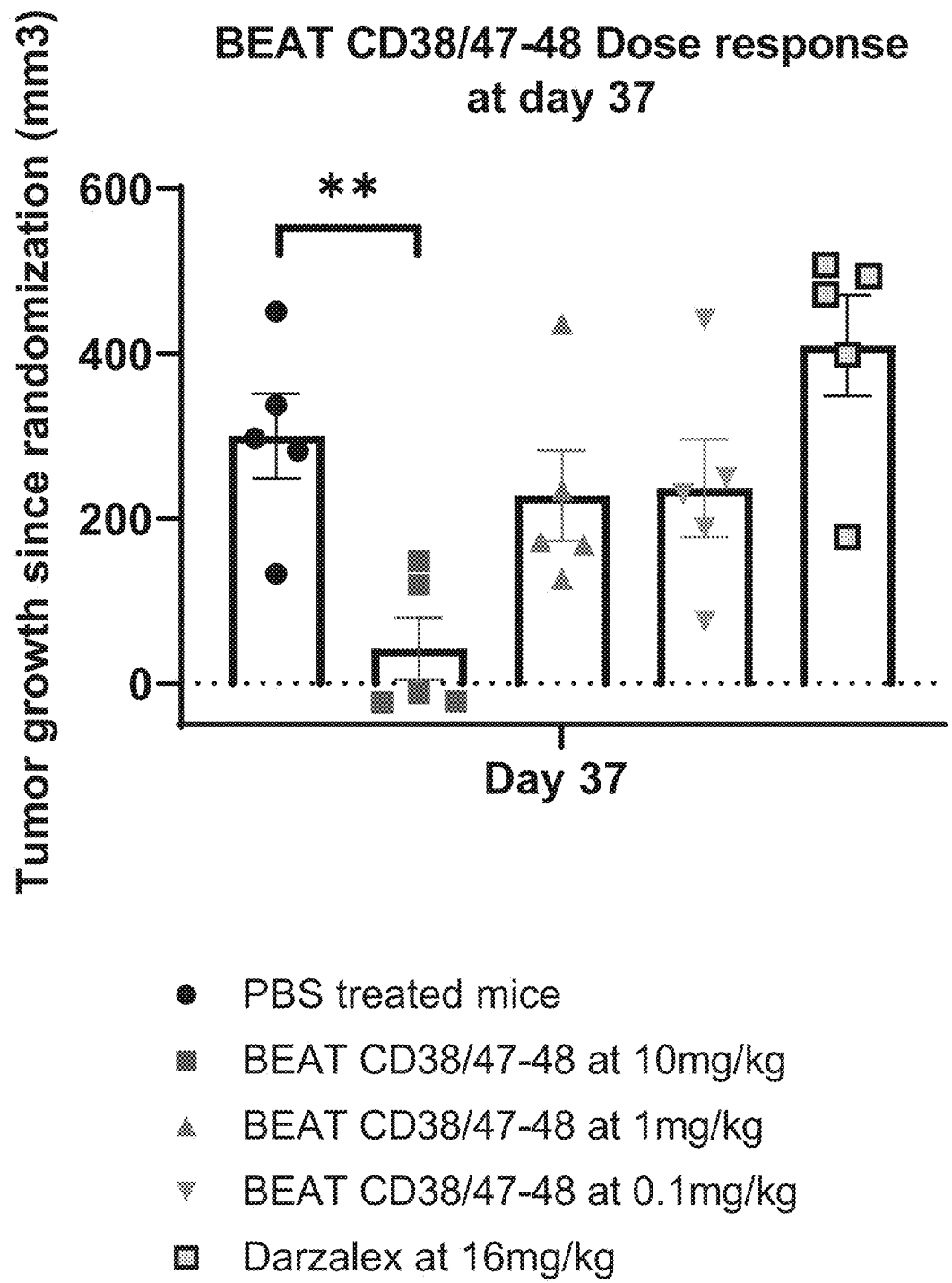
Figure 31B:
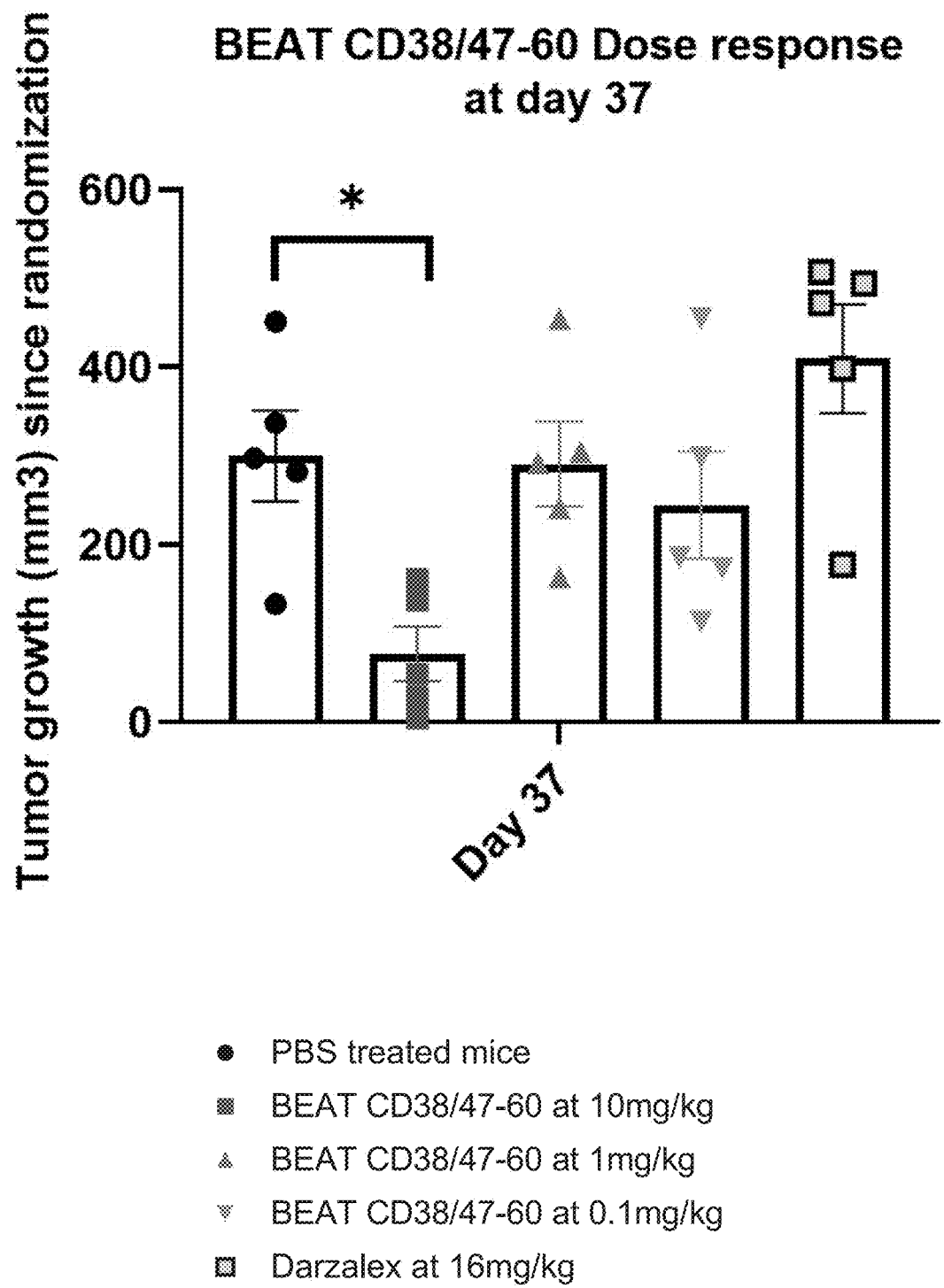

Tumor growth was monitored, and tumor growth inhibition assessed at the end of the planned 3 week treatment on Day 37 (FIG. 30B and FIG. 31B). Control tumors had grown an average of 300 mm³ and Tumor growth inhibition ranged from −37% (progression faster than control, though this was not significant) for Darzalex through to 86% tumor growth inhibition for BEAT CD38/CD47-48 at 10 mg/kg (Table 25). At the highest dose (10 mg/kg) both BEAT CD38/CD47-48 and BEAT CD38/CD47-60 were statistically superior to PBS and Darzalex treatment (Table 25 and Table 26). At Day 37 there was no statistical difference between BEAT CD38/CD47-48 and BEAT CD38/CD47-60 (Table 25 and Table 26).

TABLE 25

Statistical analysis at day 37 of FIG. 30B and FIG. 31B.

| Dunnett's multiple comparisons test | Mean Diff. | 95.00% CI of diff. | Significant | Summary | Adjusted P Value | TGI |
|---|---|---|---|---|---|---|
| PBS treated mice vs. BEAT CD38/47-48 at 10 mg/kg | 258 | 56.97 to 459.0 | Yes | ** | 0.0073 | 86% |
| PBS treated mice vs. BEAT CD38/47-48 at 1 mg/kg | 72.6 | −128.4 to 273.6 | No | ns | 0.856 | 24% |
| PBS treated mice vs. BEAT CD38/47-48 at 0.1 mg/kg | 63.4 | −137.6 to 264.4 | No | ns | 0.9169 | 21% |
| PBS treated mice vs. BEAT CD38/47-60 at 10 mg/kg | 223.2 | 22.17 to 424.2 | Yes | * | 0.0244 | 74% |
| PBS treated mice vs. BEAT CD38/47-60 at 1 mg/kg | 9.2 | −191.8 to 210.2 | No | ns | 0.9998 | 3% |
| PBS treated mice vs. BEAT CD38/47-60 at 0.1 mg/kg | 55.2 | −145.8 to 256.2 | No | ns | 0.9559 | 18% |

TABLE 25-continued

Statistical analysis at day 37 of FIG. 30B and FIG. 31B.

| Dunnett's multiple comparisons test | Mean Diff. | 95.00% CI of diff. | Significant | Summary | Adjusted P Value | TGI |
|---|---|---|---|---|---|---|
| PBS treated mice vs. Darzalex at 16 mg/kg | −109.6 | −310.6 to 91.43 | No | ns | 0.5143 | −37% |

At day 55, in this experiment design, BEAT CD38/CD47-48 showed a better efficacy than Darzalex (P=0.0478) (Table 26).

TABLE 26

Statistical analysis at day 55.

| Tukey's multiple comparisons test | Mean Diff. | 95.00% CI of diff. | Significant | Summary | Adjusted P Value |
|---|---|---|---|---|---|
| PBS treated mice vs. BEAT CD38/47-48 at 10 mg/kg | 258 | 22.21 to 493.8 | Yes | * | 0.024 |
| PBS treated mice vs. BEAT CD38/47-48 at 1 mg/kg | 72.6 | −163.2 to 308.4 | No | ns | 0.9715 |
| PBS treated mice vs. BEAT CD38/47-48 at 0.1 mg/kg | 63.4 | −172.4 to 299.2 | No | ns | 0.9867 |
| PBS treated mice vs. BEAT CD38/47-60 at 10 mg/kg | 223.2 | −12.59 to 459.0 | No | ns | 0.0741 |
| PBS treated mice vs. BEAT CD38/47-60 at 1 mg/kg | 9.2 | −226.6 to 245.0 | No | ns | >0.9999 |
| PBS treated mice vs. BEAT CD38/47-60 at 0.1 mg/kg | 55.2 | −180.6 to 291.0 | No | ns | 0.9941 |
| PBS treated mice vs. Darzalex at 16 mg/kg | −109.6 | −345.4 to 126.2 | No | ns | 0.7988 |
| BEAT CD38/47-48 at 10 mg/kg vs. BEAT CD38/47-48 at 1 mg/kg | −185.4 | −421.2 to 50.39 | No | ns | 0.2128 |
| BEAT CD38/47-48 at 10 mg/kg vs. BEAT CD38/47-48 at 0.1 mg/kg | −194.6 | −430.4 to 41.19 | No | ns | 0.1678 |
| BEAT CD38/47-48 at 10 mg/kg vs. BEAT CD38/47-60 at 10 mg/kg | −34.8 | −270.6 to 201.0 | No | ns | 0.9997 |
| BEAT CD38/47-48 at 10 mg/kg vs. BEAT CD38/47-60 at 1 mg/kg | −248.8 | −484.6 to −13.01 | Yes | * | 0.0327 |
| BEAT CD38/47-48 at 10 mg/kg vs. BEAT CD38/47-60 at 0.1 mg/kg | −202.8 | −438.6 to 32.99 | No | ns | 0.1343 |
| BEAT CD38/47-48 at 10 mg/kg vs. Darzalex at 16 mg/kg | −367.6 | −603.4 to −131.8 | Yes | *** | 0.0004 |
| BEAT CD38/47-48 at 1 mg/kg vs. BEAT CD38/47-48 at 0.1 mg/kg | −9.2 | −245.0 to 226.6 | No | ns | >0.9999 |
| BEAT CD38/47-48 at 1 mg/kg vs. BEAT CD38/47-60 at 10 mg/kg | 150.6 | −85.19 to 386.4 | No | ns | 0.455 |
| BEAT CD38/47-48 at 1 mg/kg vs. BEAT CD38/47-60 at 1 mg/kg | −63.4 | −299.2 to 172.4 | No | ns | 0.9867 |
| BEAT CD38/47-48 at 1 mg/kg vs. BEAT CD38/47-60 at 0.1 mg/kg | −17.4 | −253.2 to 218.4 | No | ns | >0.9999 |
| BEAT CD38/47-48 at 1 mg/kg vs. Darzalex at 16 mg/kg | −182.2 | −418.0 to 53.59 | No | ns | 0.2304 |
| BEAT CD38/47-48 at 0.1 mg/kg vs. BEAT CD38/47-60 at 10 mg/kg | 159.8 | −75.99 to 395.6 | No | ns | 0.3809 |
| BEAT CD38/47-48 at 0.1 mg/kg vs. BEAT CD38/47-60 at 1 mg/kg | −54.2 | −290.0 to 181.6 | No | ns | 0.9947 |
| BEAT CD38/47-48 at 0.1 mg/kg vs. BEAT CD38/47-60 at 0.1 mg/kg | −8.2 | −244.0 to 227.6 | No | ns | >0.9999 |
| BEAT CD38/47-48 at 0.1 mg/kg vs. Darzalex at 16 mg/kg | −173 | −408.8 to 62.79 | No | ns | 0.2865 |
| BEAT CD38/47-60 at 10 mg/kg vs. BEAT CD38/47-60 at 1 mg/kg | −214 | −449.8 to 21.79 | No | ns | 0.0975 |
| BEAT CD38/47-60 at 10 mg/kg vs. BEAT CD38/47-60 at 0.1 mg/kg | −168 | −403.8 to 67.79 | No | ns | 0.3204 |
| BEAT CD38/47-60 at 10 mg/kg vs. Darzalex at 16 mg/kg | −332.8 | −568.6 to −97.01 | Yes | ** | 0.0016 |
| BEAT CD38/47-60 at 1 mg/kg vs. BEAT CD38/47-60 at 0.1 mg/kg | 46 | −189.8 to 281.8 | No | ns | 0.9981 |
| BEAT CD38/47-60 at 1 mg/kg vs. Darzalex at 16 mg/kg | −118.8 | −354.6 to 117.0 | No | ns | 0.7281 |

TABLE 26-continued

Statistical analysis at day 55.

| Tukey's multiple comparisons test | Mean Diff. | 95.00% Cl of diff. | Significant | Summary | Adjusted P Value |
|---|---|---|---|---|---|
| BEAT CD38/47-60 at 0.1 mg/kg vs. Darzalex at 16 mg/kg | −164.8 | −400.6 to 70.99 | No | ns | 0.3433 |

In conclusion BEAT CD38/CD47-48 and BEAT CD38/CD47-60 at 10 mg/kg showed efficacy and tumor growth inhibition of 86% and 74% respectively vs. PBS control.

The invention claimed is:

1. A bispecific antibody comprising at least two antigen binding sites, at least one of which binds to human CD38 and comprises a heavy chain complementarity determining region (CDR) set comprising the heavy chain CDR1, CDR2, and CDR3 amino acid sequence sequences of SEQ ID NO: 117, SEQ ID NO: 177, and SEQ ID NO: 237, respectively, and at least one of which binds to human CD47 and comprises the heavy chain CDR set comprising the heavy chain CDR1, CDR2, and CDR3 amino acid sequences of SEQ ID NO: 75, SEQ ID NO: 135, and SEQ ID NO: 195, respectively, wherein the two antigen binding sites share a common light chain comprising a light chain CDR set comprising the light chain CDR1, CDR2, and CDR3 of the common light chain comprising SEQ ID NO: 10.

2. The bispecific antibody according to claim 1, comprising at least one antigen binding site which binds to human CD47 and at least two antigen binding sites which bind to human CD38.

3. The bispecific antibody according to claim 2, wherein said at least two CD38 antigen binding sites are biparatopic.

4. The bispecific antibody according to claim 1, wherein at least one of said antigen binding sites which binds to human CD47 can also bind to cynomologus CD47.

5. The bispecific antibody according to claim 1, wherein at least one of said antigen binding sites which binds to human CD38 can also bind to cynomologus CD38.

6. The bispecific antibody according to claim 1, wherein said bispecific antibody comprises an Fc region.

7. The bispecific antibody according to claim 6, wherein said Fc region is a variant which comprises at least one amino acid modification relative to the Fc region of the parent antibody, wherein the antibody comprising the variant Fc region exhibits altered effector function compared to the parent antibody, wherein said variant Fc region comprises at least one amino acid modification selected from the group consisting of S324N, K334E, K334A, E269D, S298A, S239D, I332E and E333A.

8. The bispecific antibody of claim 1, wherein said at least one antigen binding site which binds to human CD47 has an affinity to human CD47 lower than the affinity that said at least one antigen binding site which binds to human CD38 has to human CD38.

9. An isolated nucleic acid encoding the bispecific antibody of claim 1.

10. A host cell comprising the isolated nucleic acid of claim 9.

11. A method of treating a subject having a proliferative disorder, the method comprising administering to the subject a therapeutically effective amount of the bispecific antibody of claim 1, wherein the proliferative disorder is selected from the group consisting of multiple myeloma, acute lymphoblastic leukemia, chronic lymphocytic leukemia, acute myeloid leukemia, lymphoma, breast cancer such as Her2+ breast cancer, prostate cancer, cervical cancer, germinal center B-cell lymphoma or B-cell acute lymphoblastic leukemia, Chronic lymphocytic leukemia (CLL), myelodysplastic syndrome (MDS), Non-Hodgkin lymphoma, diffuse large B-cell lymphoma, non-small cell lung cancer (NSCLC), Hepatocellular carcinoma (HCC), High-grade serous ovarian carcinoma, and peritoneal cancer.

12. The bispecific antibody according to claim 2, wherein at least one of said antigen binding sites which binds to human CD47 can also bind to cynomologus CD47.

* * * * *

SEQUENCE LISTING

```
<160> NUMBER OF SEQ ID NOS: 303

<210> SEQ ID NO 1
<211> LENGTH: 264
<212> TYPE: PRT
<213> ORGANISM: Artificial Sequence
<220> FEATURE:
<223> OTHER INFORMATION: >SEQ ID NO: 1 - human CD38-ECD-C-His

<400> SEQUENCE: 1

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile His His His His His His
            260
```

<210> SEQ ID NO 2
<211> LENGTH: 264
<212> TYPE: PRT
<213> ORGANISM: Artificial Sequence
<220> FEATURE:
<223> OTHER INFORMATION: >SEQ ID NO: 2 - cynomolgus monkey CD38-ECD-C-His

<400> SEQUENCE: 2

Val Pro Arg Trp Arg Gln Gln Trp Ser Gly Ser Gly Thr Ser Arg
1               5                   10                  15

Phe Pro Glu Thr Val Leu Ala Arg Cys Val Lys Tyr Thr Glu Val His
            20                  25                  30

Pro Glu Met Arg His Val Asp Cys Gln Ser Val Trp Asp Ala Phe Lys
        35                  40                  45

Gly Ala Phe Ile Ser Lys Tyr Pro Cys Asn Ile Thr Glu Glu Asp Tyr
    50                  55                  60

Gln Pro Leu Val Lys Leu Gly Thr Gln Thr Val Pro Cys Asn Lys Thr
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Met Leu Leu Gly Tyr Leu Ala
            100                 105                 110

Asp Asp Leu Thr Trp Cys Gly Glu Phe Asn Thr Phe Glu Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Thr Ala Cys Gly
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Ala Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Arg Phe Phe Cys Lys Asn Ile Tyr Arg Pro Asp
225                 230                 235                 240

Lys Phe Leu Gln Cys Val Lys Asn Pro Glu Asp Ser Ser Cys Leu Ser
                245                 250                 255

Gly Ile His His His His His His
            260

<210> SEQ ID NO 3
<211> LENGTH: 157
<212> TYPE: PRT
<213> ORGANISM: Artificial Sequence
<220> FEATURE:
<223> OTHER INFORMATION: >SEQ ID NO: 3 - human CD47(C33S)-ECD-Avi-His

<400> SEQUENCE: 3

Gln Leu Leu Phe Asn Lys Thr Lys Ser Val Glu Phe Thr Phe Ser Asn
1               5                   10                  15

Asp Thr Val Val Ile Pro Cys Phe Val Thr Asn Met Glu Ala Gln Asn
            20                  25                  30

```
Thr Thr Glu Val Tyr Val Lys Trp Lys Phe Lys Gly Arg Asp Ile Tyr
         35                  40                  45

Thr Phe Asp Gly Ala Leu Asn Lys Ser Thr Val Pro Thr Asp Phe Ser
 50                  55                  60

Ser Ala Lys Ile Glu Val Ser Gln Leu Leu Lys Gly Asp Ala Ser Leu
 65                  70                  75                  80

Lys Met Asp Lys Ser Asp Ala Val Ser His Thr Gly Asn Tyr Thr Cys
                 85                  90                  95

Glu Val Thr Glu Leu Thr Arg Glu Gly Glu Thr Ile Ile Glu Leu Lys
                100                 105                 110

Tyr Arg Val Val Ser Trp Phe Ser Pro Asn Glu Gly Gly Gly Gly Thr
            115                 120                 125

Gly Gly Leu Asn Asp Ile Phe Glu Ala Gln Lys Ile Glu Trp His Glu
130                 135                 140

Gly Gly Gly His His His His His His His His
145                 150                 155
```

<210> SEQ ID NO 4
<211> LENGTH: 157
<212> TYPE: PRT
<213> ORGANISM: Artificial Sequence
<220> FEATURE:
<223> OTHER INFORMATION: >SEQ ID NO: 4 - cynomolgus monkey CD47(C33S)-
      ECD-Avi-His

<400> SEQUENCE: 4

```
Gln Leu Leu Phe Asn Lys Thr Lys Ser Val Glu Phe Thr Phe Ser Asn
 1               5                  10                  15

Asp Thr Val Val Ile Pro Cys Phe Val Thr Asn Met Glu Ala Gln Asn
                 20                  25                  30

Thr Thr Glu Val Tyr Val Lys Trp Lys Phe Lys Gly Arg Asp Ile Tyr
         35                  40                  45

Thr Phe Asp Gly Ala Leu Asn Lys Ser Thr Ala Pro Ala Asn Phe Ser
 50                  55                  60

Ser Ala Lys Ile Glu Val Ser Gln Leu Leu Lys Gly Asp Ala Ser Leu
 65                  70                  75                  80

Lys Met Asp Lys Ser Asp Ala Val Ser His Thr Gly Asn Tyr Thr Cys
                 85                  90                  95

Glu Val Thr Glu Leu Thr Arg Glu Gly Glu Thr Ile Ile Glu Leu Lys
                100                 105                 110

Tyr Arg Val Val Ser Trp Phe Ser Pro Asn Glu Gly Gly Gly Gly Thr
            115                 120                 125

Gly Gly Leu Asn Asp Ile Phe Glu Ala Gln Lys Ile Glu Trp His Glu
130                 135                 140

Gly Gly Gly His His His His His His His His
145                 150                 155
```

<210> SEQ ID NO 5
<211> LENGTH: 299
<212> TYPE: PRT
<213> ORGANISM: Macaca fascicularis
<220> FEATURE:
<221> NAME/KEY: MISC_FEATURE
<222> LOCATION: (1)..(299)
<223> OTHER INFORMATION: >SEQ ID NO: 5 - Full-length human CD38

<400> SEQUENCE: 5

```
Ala Asn Cys Glu Phe Ser Pro Val Ser Gly Asp Lys Pro Cys Cys Arg
 1               5                  10                  15
```

Leu Ser Arg Arg Ala Gln Leu Cys Leu Gly Val Ser Ile Leu Val Leu
            20                  25                  30

Ile Leu Val Val Val Leu Ala Val Val Pro Arg Trp Arg Gln Gln
            35                  40                  45

Trp Ser Gly Pro Gly Thr Thr Lys Arg Phe Pro Glu Thr Val Leu Ala
 50                  55                  60

Arg Cys Val Lys Tyr Thr Glu Ile His Pro Glu Met Arg His Val Asp
 65                  70                  75                  80

Cys Gln Ser Val Trp Asp Ala Phe Lys Gly Ala Phe Ile Ser Lys His
                 85                  90                  95

Pro Cys Asn Ile Thr Glu Glu Asp Tyr Gln Pro Leu Met Lys Leu Gly
                100                 105                 110

Thr Gln Thr Val Pro Cys Asn Lys Ile Leu Leu Trp Ser Arg Ile Lys
            115                 120                 125

Asp Leu Ala His Gln Phe Thr Gln Val Gln Arg Asp Met Phe Thr Leu
130                 135                 140

Glu Asp Thr Leu Leu Gly Tyr Leu Ala Asp Asp Leu Thr Trp Cys Gly
145                 150                 155                 160

Glu Phe Asn Thr Ser Lys Ile Asn Tyr Gln Ser Cys Pro Asp Trp Arg
                165                 170                 175

Lys Asp Cys Ser Asn Asn Pro Val Ser Val Phe Trp Lys Thr Val Ser
            180                 185                 190

Arg Arg Phe Ala Glu Ala Ala Cys Asp Val His Val Met Leu Asn
            195                 200                 205

Gly Ser Arg Ser Lys Ile Phe Asp Lys Asn Ser Thr Phe Gly Ser Val
210                 215                 220

Glu Val His Asn Leu Gln Pro Glu Lys Val Gln Thr Leu Glu Ala Trp
225                 230                 235                 240

Val Ile His Gly Gly Arg Glu Asp Ser Arg Asp Leu Cys Gln Asp Pro
                245                 250                 255

Thr Ile Lys Glu Leu Glu Ser Ile Ile Ser Lys Arg Asn Ile Gln Phe
            260                 265                 270

Ser Cys Lys Asn Ile Tyr Arg Pro Asp Lys Phe Leu Gln Cys Val Lys
            275                 280                 285

Asn Pro Glu Asp Ser Ser Cys Thr Ser Glu Ile
            290                 295

<210> SEQ ID NO 6
<211> LENGTH: 300
<212> TYPE: PRT
<213> ORGANISM: Artificial Sequence
<220> FEATURE:
<223> OTHER INFORMATION: >SEQ ID NO: 6 - Full-length cynomolgus monkey
      CD38

<400> SEQUENCE: 6

Ala Asn Cys Glu Phe Ser Pro Val Ser Gly Asp Lys Pro Cys Cys Arg
 1               5                  10                  15

Leu Ser Arg Arg Ala Gln Val Cys Leu Gly Val Cys Leu Leu Val Leu
            20                  25                  30

Leu Ile Leu Val Val Val Val Ala Val Val Leu Pro Arg Trp Arg Gln
            35                  40                  45

Gln Trp Ser Gly Ser Gly Thr Thr Ser Arg Phe Pro Glu Thr Val Leu
 50                  55                  60

Ala Arg Cys Val Lys Tyr Thr Glu Val His Pro Glu Met Arg His Val

```
                65                  70                  75                  80
Asp Cys Gln Ser Val Trp Asp Ala Phe Lys Gly Ala Phe Ile Ser Lys
                85                  90                  95

Tyr Pro Cys Asn Ile Thr Glu Glu Asp Tyr Gln Pro Leu Val Lys Leu
            100                 105                 110

Gly Thr Gln Thr Val Pro Cys Asn Lys Thr Leu Leu Trp Ser Arg Ile
            115                 120                 125

Lys Asp Leu Ala His Gln Phe Thr Gln Val Gln Arg Asp Met Phe Thr
        130                 135                 140

Leu Glu Asp Met Leu Leu Gly Tyr Leu Ala Asp Asp Leu Thr Trp Cys
145                 150                 155                 160

Gly Glu Phe Asn Thr Phe Glu Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Thr Ala Cys Gly Val Val His Val Met Leu
            195                 200                 205

Asn Gly Ser Arg Ser Lys Ile Phe Asp Lys Asn Ser Thr Phe Gly Ser
        210                 215                 220

Val Glu Val His Asn Leu Gln Pro Glu Lys Val Gln Ala Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Arg
            260                 265                 270

Phe Phe Cys Lys Asn Ile Tyr Arg Pro Asp Lys Phe Leu Gln Cys Val
            275                 280                 285

Lys Asn Pro Glu Asp Ser Ser Cys Leu Ser Gly Ile
        290                 295                 300

<210> SEQ ID NO 7
<211> LENGTH: 305
<212> TYPE: PRT
<213> ORGANISM: Homo sapiens
<220> FEATURE:
<221> NAME/KEY: MISC_FEATURE
<222> LOCATION: (1)..(305)
<223> OTHER INFORMATION: >SEQ ID NO: 7 - Full-length human CD47

<400> SEQUENCE: 7

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125
```

```
Ile Phe Pro Ile Phe Ala Ile Leu Leu Phe Trp Gly Gln Phe Gly Ile
        130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
                180                 185                 190

Gly Leu Ile Val Thr Ser Thr Gly Ile Leu Ile Leu Leu His Tyr Tyr
                195                 200                 205

Val Phe Ser Thr Ala Ile Gly Leu Thr Ser Phe Val Ile Ala Ile Leu
        210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
                260                 265                 270

Phe Val Ala Ser Asn Gln Lys Thr Ile Gln Pro Pro Arg Lys Ala Val
                275                 280                 285

Glu Glu Pro Leu Asn Ala Phe Lys Glu Ser Lys Gly Met Met Asn Asp
        290                 295                 300

Glu
305

<210> SEQ ID NO 8
<211> LENGTH: 305
<212> TYPE: PRT
<213> ORGANISM: Macaca fascicularis
<220> FEATURE:
<221> NAME/KEY: MISC_FEATURE
<222> LOCATION: (1)..(305)
<223> OTHER INFORMATION: >SEQ ID NO: 8 - Full-length cynomolgus CD47

<400> SEQUENCE: 8

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Ala Pro Ala Asn Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125

Ile Phe Pro Ile Phe Ala Ile Leu Leu Phe Trp Gly Gln Phe Gly Ile
        130                 135                 140

Lys Thr Leu Lys Tyr Arg Ser Gly Gly Met Asp Glu Lys Thr Ile Ala
145                 150                 155                 160
```

```
Leu Leu Val Ala Gly Leu Met Ile Thr Val Ile Val Ile Gly Ala
                165                 170                 175
Ile Leu Phe Val Pro Gly Glu Tyr Ser Leu Lys Asn Ala Thr Gly Leu
            180                 185                 190
Gly Leu Ile Val Thr Ser Thr Gly Ile Leu Ile Leu Leu His Tyr Tyr
            195                 200                 205
Val Phe Ser Thr Ala Ile Gly Leu Thr Ser Phe Val Ile Ala Ile Leu
            210                 215                 220
Val Ile Gln Val Ile Ala Tyr Ile Leu Ala Val Val Gly Leu Ser Leu
225                 230                 235                 240
Cys Ile Ala Ala Cys Ile Pro Met His Gly Pro Leu Leu Ile Ser Gly
                245                 250                 255
Leu Ser Ile Leu Ala Leu Ala Gln Leu Leu Gly Leu Val Tyr Met Lys
                260                 265                 270
Phe Val Ala Ser Asn Gln Lys Thr Ile Gln Pro Pro Arg Lys Ala Val
                275                 280                 285
Glu Glu Pro Leu Asn Ala Phe Lys Glu Ser Lys Gly Met Met Asn Asp
        290                 295                 300
Glu
305
```

<210> SEQ ID NO 9
<211> LENGTH: 322
<212> TYPE: PRT
<213> ORGANISM: Artificial Sequence
<220> FEATURE:
<223> OTHER INFORMATION: >SEQ ID NO: 9 - human SIRPa-v1-ECD(E31-H352)

<400> SEQUENCE: 9

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Ile Pro
            20                  25                  30
Val Gly Pro Ile Gln Trp Phe Arg Gly Ala Gly Pro Gly Arg Glu Leu
            35                  40                  45
Ile Tyr Asn Gln Lys Glu Gly His Phe Pro Arg Val Thr Thr Val Ser
        50                  55                  60
Asp Leu Thr Lys Arg Asn Asn Met Asp Phe Ser Ile Arg Ile Gly Asn
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Ala Pro Val Val Ser Gly Pro Ala Ala
            115                 120                 125
Arg Ala Thr Pro Gln His Thr Val Ser Phe Thr Cys Glu Ser His Gly
        130                 135                 140
Phe Ser Pro Arg Asp Ile Thr Leu Lys Trp Phe Lys Asn Gly Asn Glu
145                 150                 155                 160
Leu Ser Asp Phe Gln Thr Asn Val Asp Pro Val Gly Glu Ser Val Ser
                165                 170                 175
Tyr Ser Ile His Ser Thr Ala Lys Val Val Leu Thr Arg Glu Asp Val
                180                 185                 190
His Ser Gln Val Ile Cys Glu Val Ala His Val Thr Leu Gln Gly Asp
            195                 200                 205
```

```
Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
                275                 280                 285

Asn Val Ser Ala His Arg Asp Asp Val Lys Leu Thr Cys Gln Val Glu
            290                 295                 300

His Asp Gly Gln Pro Ala Val Ser Lys Ser His Asp Leu Lys Val Ser
305                 310                 315                 320

Ala His
```

<210> SEQ ID NO 10
<211> LENGTH: 214
<212> TYPE: PRT
<213> ORGANISM: Homo sapiens
<220> FEATURE:
<221> NAME/KEY: MISC_FEATURE
<222> LOCATION: (1)..(214)
<223> OTHER INFORMATION: >SEQ ID NO: 10 - Vk3-15/Jk1 light chain

<400> SEQUENCE: 10

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11

<211> LENGTH: 231
<212> TYPE: PRT
<213> ORGANISM: Artificial Sequence
<220> FEATURE:
<223> OTHER INFORMATION: >SEQ ID NO: 11 - anti-CD47-UCP01-A1 FAB heavy
      chain

<400> SEQUENCE: 11

```
Gln Val Gln Leu Val Gln Ser Gly Ala Glu Val Lys Pro Gly Ser
1               5                   10                  15

Ser Val Lys Val Ser Cys Lys Ala Ser Gly Gly Phe Phe Arg Leu Tyr
            20                  25                  30

Ala Phe Ser Trp Val Arg Gln Ala Pro Gly Gln Gly Leu Glu Trp Met
        35                  40                  45

Gly Gly Ile Ile Pro Thr Asp Gly Phe Val Gly Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Tyr Arg Pro Tyr Gly Glu Tyr Tyr Val Val Gly
            100                 105                 110

Tyr Gly Phe Ala Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys
225                 230
```

<210> SEQ ID NO 12
<211> LENGTH: 226
<212> TYPE: PRT
<213> ORGANISM: Artificial Sequence
<220> FEATURE:
<223> OTHER INFORMATION: >SEQ ID NO: 12 - anti-CD47-UCP01-G1 FAB heavy
      chain

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ala Trp Val Arg Gln Ala Pro Gly Lys Gly Leu Glu Trp Val
        35                  40                  45

Ser Val Ile Ser Val Glu Gly Gly Leu Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                    85                  90                  95

Ala Arg Gly Ser Arg Asp Ser Arg Gly Lys Tyr Gly Ala Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 13
<211> LENGTH: 226
<212> TYPE: PRT
<213> ORGANISM: Artificial Sequence
<220> FEATURE:
<223> OTHER INFORMATION: >SEQ ID NO: 13 - anti-CD47-UCP01-A2 FAB heavy
      chain

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Ala Met Gly Trp Val Arg Gln Ala Pro Gly Lys Gly Leu Glu Trp Val
        35                  40                  45

Ser Ile Ile Ser Pro Asn Gly His Val Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Ser Val Ser Ser Gln Gly Val Ala Phe Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val 195                 200                 205
Asn His Lys Pro Ser Asn Thr Lys Val Asp Lys Lys Val Glu Pro Lys
    210                 215                 220

Ser Cys
225

<210> SEQ ID NO 14
<211> LENGTH: 225
<212> TYPE: PRT
<213> ORGANISM: Artificial Sequence
<220> FEATURE:
<223> OTHER INFORMATION: >SEQ ID NO: 14 - anti-CD47-UCP01-G2 FAB heavy
      chain

<400> SEQUENCE: 14

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Asn Ser
            20                  25                  30

Tyr Met Thr Trp Val Arg Gln Ala Pro Gly Lys Gly Leu Glu Trp Val
        35                  40                  45

Ser Val Ile Tyr Lys Tyr Gly Lys Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Thr Val Ser Pro Tyr Trp Gly Gly Ala Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 15
<211> LENGTH: 226
<212> TYPE: PRT
<213> ORGANISM: Artificial Sequence
<220> FEATURE:
<223> OTHER INFORMATION: >SEQ ID NO: 15 - anti-CD47-UCP01-H2 FAB heavy
      chain

<400> SEQUENCE: 15

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn 20                  25                  30
Thr Met His Trp Val Arg Gln Ala Pro Gly Lys Gly Leu Glu Trp Val
            35                  40                  45
Ser Val Ile Tyr Gln Ser Gly Val Thr Arg Tyr Ala Asp Ser Val Lys
         50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Gly Arg Tyr Gly Val Ala Gly Pro Gly Tyr Ala Phe Asp Val
                100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
            210                 215                 220
Ser Cys
225

<210> SEQ ID NO 16
<211> LENGTH: 231
<212> TYPE: PRT
<213> ORGANISM: Artificial Sequence
<220> FEATURE:
<223> OTHER INFORMATION: >SEQ ID NO: 16 - anti-CD47-UCP01-A3 FAB heavy
      chain

<400> SEQUENCE: 16

Glu Val Gln Leu Val Glu Ser Gly Gly Gly Leu Ile Gln Pro Gly Gly
 1               5                  10                  15
Ser Leu Arg Leu Ser Cys Ala Ala Ser Gly Phe Thr Phe Thr Asn Ser
            20                  25                  30
Trp Met Ser Trp Val Arg Gln Ala Pro Gly Lys Gly Leu Glu Trp Val
            35                  40                  45
Ser Val Ile Tyr Lys Tyr Gly Phe Thr Glu Tyr Ala Asp Ser Val Lys
         50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Gly Ser Ser Ile Ala Ala Tyr Ala Tyr Ala Ala Pro Tyr Arg Gly
                100                 105                 110
Gly Trp Met Asp Val Trp Gly Gln Gly Thr Leu Val Thr Val Ser Ser
            115                 120                 125
Ala Ser Thr Lys Gly Pro Ser Val Phe Pro Leu Ala Pro Ser Ser Lys
            130                 135                 140

```
Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Leu Gly Thr Gln Thr
    195                 200                 205

Tyr Ile Cys Asn Val Asn His Lys Pro Ser Asn Thr Lys Val Asp Lys
    210                 215                 220

Lys Val Glu Pro Lys Ser Cys
225                 230
```

<210> SEQ ID NO 17
<211> LENGTH: 225
<212> TYPE: PRT
<213> ORGANISM: Artificial Sequence
<220> FEATURE:
<223> OTHER INFORMATION: >SEQ ID NO: 17 - anti-CD47-UCP01-B3 FAB heavy
      chain

<400> SEQUENCE: 17

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Asn Asn
            20                  25                  30

Tyr Met Ser Trp Val Arg Gln Ala Pro Gly Lys Gly Leu Glu Trp Val
        35                  40                  45

Ser Val Ile Tyr Lys Lys Gly Phe Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Ser Val Asp Lys Tyr Asp Gly Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 18
<211> LENGTH: 227
<212> TYPE: PRT
<213> ORGANISM: Artificial Sequence
<220> FEATURE:
<223> OTHER INFORMATION: >SEQ ID NO: 18 - anti-CD47-UCP02-C1 FAB heavy
      chain

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ala His
            20                  25                  30

Thr Ile Ser Trp Val Arg Gln Ala Pro Gly Gln Gly Leu Glu Trp Met
        35                  40                  45

Gly Arg Ile Thr Ala Val Arg Gly Val Pro Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Tyr Gly Gly Pro Arg Tyr Tyr Trp Asp Gly Leu Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 19
<211> LENGTH: 222
<212> TYPE: PRT
<213> ORGANISM: Artificial Sequence
<220> FEATURE:
<223> OTHER INFORMATION: >SEQ ID NO: 19 - anti-CD47-UCP02-C2 FAB heavy
      chain

<400> SEQUENCE: 19

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Val Ser Ser Asn
            20                  25                  30

Tyr Met Gly Trp Val Arg Gln Ala Pro Gly Lys Gly Leu Glu Trp Val
        35                  40                  45

Ser Leu Ile Asn Lys Asn Gly Gln Thr Gly Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

-continued

Arg Ser Tyr Ala Arg Ser Ser Tyr Gln Glu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
210                 215                 220

<210> SEQ ID NO 20
<211> LENGTH: 230
<212> TYPE: PRT
<213> ORGANISM: Artificial Sequence
<220> FEATURE:
<223> OTHER INFORMATION: >SEQ ID NO: 20 - anti-CD47-UCP02-B3 FAB heavy
      chain

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Arg Leu Tyr
            20                  25                  30

Gly Ile Asn Trp Val Arg Gln Ala Pro Gly Gln Gly Leu Glu Trp Met
        35                  40                  45

Gly Gly Ile Ser Pro Ile Asp Gly Tyr Ala Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Arg Pro Tyr Ser Ala Ser Ala Ser Tyr Pro Gly Tyr
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys

<210> SEQ ID NO 21
<211> LENGTH: 231
<212> TYPE: PRT
<213> ORGANISM: Artificial Sequence
<220> FEATURE:
<223> OTHER INFORMATION: >SEQ ID NO: 21 - anti-CD47-UCP02-H3 FAB heavy
      chain

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Arg Leu Tyr
            20                  25                  30

Ala Phe Ser Trp Val Arg Gln Ala Pro Gly Gln Gly Leu Glu Trp Met
        35                  40                  45

Gly Gly Ile Ile Pro Thr Asp Gly Phe Val Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Tyr Arg Pro Tyr Gly Glu Tyr Tyr Val Val Gly
            100                 105                 110

Tyr Gly Phe Ala Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys
225                 230

<210> SEQ ID NO 22
<211> LENGTH: 227
<212> TYPE: PRT
<213> ORGANISM: Artificial Sequence
<220> FEATURE:
<223> OTHER INFORMATION: >SEQ ID NO: 22 - anti-CD38-UCP01-B1 FAB heavy
      chain

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Asp Phe Asp Gln Tyr
            20                  25                  30

Tyr Ile Ser Trp Val Arg Gln Ala Pro Gly Gln Gly Leu Glu Trp Met
        35                  40                  45

Gly Arg Ile Ile Pro Thr Leu Gly Asp Ser Gln Tyr Ala Gln Lys Phe

```
                50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Val Ile Val Ser Pro Tyr Tyr Ile Tyr Val Phe Asp
                100                 105                 110

Val Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Val Glu Pro
            210                 215                 220

Lys Ser Cys
225

<210> SEQ ID NO 23
<211> LENGTH: 223
<212> TYPE: PRT
<213> ORGANISM: Artificial Sequence
<220> FEATURE:
<223> OTHER INFORMATION: >SEQ ID NO: 23 - anti-CD38-UCP01-D1 FAB heavy
      chain

<400> SEQUENCE: 23

Gln Val Gln Leu Val Gln Ser Gly Ala Glu Val Lys Lys Pro Gly Ser
 1               5                  10                  15

Ser Val Lys Val Ser Cys Lys Ala Ser Gly Ile Phe Asn Gly Tyr
             20                  25                  30

Leu Ile Ser Trp Val Arg Gln Ala Pro Gly Gln Gly Leu Glu Trp Met
             35                  40                  45

Gly Gly Ile Ile Pro Val Asn Gly Leu Ala Asp Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Ile Gly Arg Tyr Ile Ile Ala Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 24
<211> LENGTH: 224
<212> TYPE: PRT
<213> ORGANISM: Artificial Sequence
<220> FEATURE:
<223> OTHER INFORMATION: >SEQ ID NO: 24 - anti-CD38-UCP01-F1 FAB heavy
      chain

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Leu Tyr
            20                  25                  30

Thr Ile Thr Trp Val Arg Gln Ala Pro Gly Gln Gly Leu Glu Trp Met
        35                  40                  45

Gly Ser Ile Ile Pro Leu Leu Gly Asp Pro Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Pro Tyr Pro Tyr Gly Ser Lys Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 25
<211> LENGTH: 225
<212> TYPE: PRT
<213> ORGANISM: Artificial Sequence
<220> FEATURE:
<223> OTHER INFORMATION: >SEQ ID NO: 25 - anti-CD38-UCP01-G1 FAB heavy
      chain

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Ser Lys Tyr
            20                  25                  30

Phe Ile Thr Trp Val Arg Gln Ala Pro Gly Gln Gly Leu Glu Trp Met
            35                  40                  45

Gly Gly Val Ile Pro Lys Ile Gly Tyr Thr Ser Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Asp Asp Tyr Ala Ser Tyr Ser Pro Leu Asp Ser Trp
             100                 105                 110

Gly Gln Gly Thr Leu Val Thr Val Ser Ser Ala Ser Thr Lys Gly Pro
             115                 120                 125

Ser Val Phe Pro Leu Ala Pro Ser Ser Lys Ser Thr Ser Gly Gly Thr
 130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
             195                 200                 205

His Lys Pro Ser Asn Thr Lys Val Asp Lys Lys Val Glu Pro Lys Ser
210                 215                 220

Cys
225

<210> SEQ ID NO 26
<211> LENGTH: 220
<212> TYPE: PRT
<213> ORGANISM: Artificial Sequence
<220> FEATURE:
<223> OTHER INFORMATION: >SEQ ID NO: 26 - anti-CD38-UCP01-H1 FAB heavy
      chain

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Asp Phe Phe Ser Gly Tyr
            20                  25                  30

Ala Ile Asn Trp Val Arg Gln Ala Pro Gly Gln Gly Leu Glu Trp Met
            35                  40                  45

Gly Arg Ile Ile Pro Leu Leu Gly Asp Thr Tyr Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Ala Gly Trp Phe Ala Tyr Trp Gly Gln Gly Thr Leu
             100                 105                 110

Val Thr Val Ser Ser Ala Ser Thr Lys Gly Pro Ser Val Phe Pro Leu
             115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Val Glu Pro Lys Ser Cys
    210                 215                 220

<210> SEQ ID NO 27
<211> LENGTH: 219
<212> TYPE: PRT
<213> ORGANISM: Artificial Sequence
<220> FEATURE:
<223> OTHER INFORMATION: >SEQ ID NO: 27 - anti-CD38-UCP01-C2 FAB heavy
      chain

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Tyr Leu Gly Ile Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Glu Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Val Trp Trp Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215

<210> SEQ ID NO 28
<211> LENGTH: 226
<212> TYPE: PRT
<213> ORGANISM: Artificial Sequence
<220> FEATURE:
<223> OTHER INFORMATION: >SEQ ID NO: 28 - anti-CD38-UCP01-E2 FAB heavy
      chain

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Gly Trp Val Arg Gln Ala Pro Gly Gln Gly Leu Glu Trp Met
        35                  40                  45

Gly Arg Ile Ile Pro Val Phe Gly Ser Ala His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 29
<211> LENGTH: 226
<212> TYPE: PRT
<213> ORGANISM: Artificial Sequence
<220> FEATURE:
<223> OTHER INFORMATION: >SEQ ID NO: 29 - anti-CD38-UCP02-A7 FAB heavy
      chain

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Asp Met Ser Trp Val Arg Gln Ala Pro Gly Lys Gly Leu Glu Trp Val
        35                  40                  45

Ser Thr Ile Thr Leu His Gly Gly Asp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Tyr Ile Tyr Ser Thr Ser Gly Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly

```
                130             135             140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys
225

<210> SEQ ID NO 30
<211> LENGTH: 228
<212> TYPE: PRT
<213> ORGANISM: Artificial Sequence
<220> FEATURE:
<223> OTHER INFORMATION: >SEQ ID NO: 30 - anti-CD38-UCP02-B1 FAB heavy
      chain

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Gln Phe Ser Phe Tyr
            20                  25                  30

Ala Ile Asn Trp Val Arg Gln Ala Pro Gly Gln Gly Leu Glu Trp Met
        35                  40                  45

Gly Glu Ile Ile Pro Asp Tyr Gly Val Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Ser Tyr Thr Tyr Gly Ile Arg Tyr Tyr Lys Leu Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 31
<211> LENGTH: 225
```

```
<212> TYPE: PRT
<213> ORGANISM: Artificial Sequence
<220> FEATURE:
<223> OTHER INFORMATION: >SEQ ID NO: 31 - anti-CD38-UCP02-B7 FAB heavy
      chain

<400> SEQUENCE: 31

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Asn Glu Ala
            20                  25                  30

Trp Met Thr Trp Val Arg Gln Ala Pro Gly Lys Gly Leu Glu Trp Val
        35                  40                  45

Gly Arg Ile Lys Ser Tyr Ser Asp Gly Gly Tyr Thr Gly Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ser Pro Gly Ile Pro Tyr His Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 32
<211> LENGTH: 224
<212> TYPE: PRT
<213> ORGANISM: Artificial Sequence
<220> FEATURE:
<223> OTHER INFORMATION: >SEQ ID NO: 32 - anti-CD38-UCP02-C3 FAB heavy
      chain

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Asp Tyr Phe Asn Asn Tyr
            20                  25                  30

Ala Ile Asn Trp Val Arg Gln Ala Pro Gly Gln Gly Leu Glu Trp Met
        35                  40                  45

Gly Arg Ile Ile Pro Phe Leu Asp Asp Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ala Thr Ser Pro Leu Tyr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 33
<211> LENGTH: 227
<212> TYPE: PRT
<213> ORGANISM: Artificial Sequence
<220> FEATURE:
<223> OTHER INFORMATION: >SEQ ID NO: 33 - anti-CD38-UCP02-D1 FAB heavy chain

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Asp Phe Asp Gln Tyr
            20                  25                  30

Tyr Ile Ser Trp Val Arg Gln Ala Pro Gly Gln Gly Leu Glu Trp Met
        35                  40                  45

Gly Arg Ile Ile Pro Thr Leu Gly Asp Ser Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Val Ile Val Ser Pro Tyr Tyr Tyr Ile Tyr Val Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220
```

Lys Ser Cys
225

<210> SEQ ID NO 34
<211> LENGTH: 225
<212> TYPE: PRT
<213> ORGANISM: Artificial Sequence
<220> FEATURE:
<223> OTHER INFORMATION: >SEQ ID NO: 34 - anti-CD38-UCP02-D5 FAB heavy
      chain

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Val His
                20                  25                  30

Ala Ile His Trp Val Arg Gln Ala Pro Gly Gln Gly Leu Glu Trp Met
            35                  40                  45

Gly Glu Ile Ile Pro Val Ile Gly Glu Ala Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gln Tyr Tyr Tyr Ala Leu Gly Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 35
<211> LENGTH: 220
<212> TYPE: PRT
<213> ORGANISM: Artificial Sequence
<220> FEATURE:
<223> OTHER INFORMATION: >SEQ ID NO: 35 - anti-CD38-UCP02-E5 FAB heavy
      chain

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Gly Phe Arg His Tyr
                20                  25                  30

Phe Ile Ser Trp Val Arg Gln Ala Pro Gly Gln Gly Leu Glu Trp Met
            35                  40                  45

```
Gly Gly Ile Ile Pro Ala Ala Ala Thr Pro Tyr Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Trp His Trp Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys
210                 215                 220
```

<210> SEQ ID NO 36
<211> LENGTH: 224
<212> TYPE: PRT
<213> ORGANISM: Artificial Sequence
<220> FEATURE:
<223> OTHER INFORMATION: >SEQ ID NO: 36 - anti-CD38-UCP02-F2 FAB heavy chain

<400> SEQUENCE: 36

```
Gln Val Gln Leu Val Gln Ser Gly Ala Glu Val Lys Lys Pro Gly Ser
 1               5                  10                  15

Ser Val Lys Val Ser Cys Lys Ala Ser Gly Asp Val Phe Ser Leu Leu
                 20                  25                  30

Ala Ile Gly Trp Val Arg Gln Ala Pro Gly Gln Gly Leu Glu Trp Met
             35                  40                  45

Gly Arg Ile Ile Pro Ser Leu Asp Ala Thr His Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Asp Val Leu Arg Ser Tyr Tyr Phe Asp Ile Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                180             185             190
Pro Ser Ser Ser Leu Gly Thr Gln Thr Tyr Ile Cys Asn Val Asn His
            195             200             205
Lys Pro Ser Asn Thr Lys Val Asp Lys Lys Val Glu Pro Lys Ser Cys
            210             215             220
```

<210> SEQ ID NO 37
<211> LENGTH: 224
<212> TYPE: PRT
<213> ORGANISM: Artificial Sequence
<220> FEATURE:
<223> OTHER INFORMATION: >SEQ ID NO: 37 - anti-CD38-UCP02-F5 FAB heavy
      chain

<400> SEQUENCE: 37

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Val Phe Ser Tyr Tyr
            20                  25                  30
Thr Ile Ser Trp Val Arg Gln Ala Pro Gly Gln Gly Leu Glu Trp Met
        35                  40                  45
Gly Arg Ile Ile Pro Ser Leu Gly Ala Thr His Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Asp Ser Phe Tyr Tyr Ala Tyr Tyr Met Asp Leu Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
```

<210> SEQ ID NO 38
<211> LENGTH: 226
<212> TYPE: PRT
<213> ORGANISM: Artificial Sequence
<220> FEATURE:
<223> OTHER INFORMATION: >SEQ ID NO: 38 - anti-CD38-UCP02-F6 FAB heavy
      chain

<400> SEQUENCE: 38

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Phe Tyr
            20                  25                  30
Asp Met Ser Trp Val Arg Gln Ala Pro Gly Lys Gly Leu Glu Trp Val
```

```
                    35                  40                  45
Ser Ala Val Ser Leu Tyr Gly Asp Glu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Pro Val Ser Tyr Asp Tyr Tyr Gly Ser Tyr Phe Asp Tyr
                    100                 105                 110

Trp Gly Gln Gly Thr Leu Val Thr Val Ser Ser Ala Ser Thr Lys Gly
                    115                 120                 125

Pro Ser Val Phe Pro Leu Ala Pro Ser Ser Lys Ser Thr Ser Gly Gly
                    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                    180                 185                 190

Thr Val Pro Ser Ser Ser Leu Gly Thr Gln Thr Tyr Ile Cys Asn Val
                    195                 200                 205

Asn His Lys Pro Ser Asn Thr Lys Val Asp Lys Lys Val Glu Pro Lys
                    210                 215                 220

Ser Cys
225

<210> SEQ ID NO 39
<211> LENGTH: 223
<212> TYPE: PRT
<213> ORGANISM: Artificial Sequence
<220> FEATURE:
<223> OTHER INFORMATION: >SEQ ID NO: 39 - anti-CD38-UCP02-H1 FAB heavy
      chain

<400> SEQUENCE: 39

Gln Val Gln Leu Val Gln Ser Gly Ala Glu Val Lys Lys Pro Gly Ser
  1               5                  10                  15

Ser Val Lys Val Ser Cys Lys Ala Ser Gly Asp Lys Phe Asn Thr Tyr
                 20                  25                  30

Ala Ile Ser Trp Val Arg Gln Ala Pro Gly Gln Gly Leu Glu Trp Met
                 35                  40                  45

Gly Gly Ile Thr Pro Arg Tyr Asp Tyr Ala His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Ser Trp Gly Phe Arg Ala Gly Tyr Leu Asp Tyr Trp Gly Gln
                    100                 105                 110

Gly Thr Leu Val Thr Val Ser Ser Ala Ser Thr Lys Gly Pro Ser Val
                    115                 120                 125

Phe Pro Leu Ala Pro Ser Ser Lys Ser Thr Ser Gly Gly Thr Ala Ala
                    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220
```

<210> SEQ ID NO 40
<211> LENGTH: 224
<212> TYPE: PRT
<213> ORGANISM: Artificial Sequence
<220> FEATURE:
<223> OTHER INFORMATION: >SEQ ID NO: 40 - anti-CD38-UCP03-B3 FAB heavy chain

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Asp Phe Thr Leu Tyr
            20                  25                  30

Ser Ile Ser Trp Val Arg Gln Ala Pro Gly Gln Gly Leu Glu Trp Met
        35                  40                  45

Gly Arg Ile Ile Pro Thr Gly Ala Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Pro Ser Leu Gly Ser Gly Trp Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 41
<211> LENGTH: 224
<212> TYPE: PRT
<213> ORGANISM: Artificial Sequence
<220> FEATURE:
<223> OTHER INFORMATION: >SEQ ID NO: 41 - anti-CD38-UCP03-C3 FAB heavy chain

<400> SEQUENCE: 41

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Lys Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Gln Ile Gly Asp Ala Ala Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ala Ser Phe Leu Tyr Tyr Ser Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

<210> SEQ ID NO 42
<211> LENGTH: 218
<212> TYPE: PRT
<213> ORGANISM: Artificial Sequence
<220> FEATURE:
<223> OTHER INFORMATION: >SEQ ID NO: 42 - anti-CD38-UCP03-H5 FAB heavy
      chain

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Leu Phe Ser Phe Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Glu Pro Gln Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Ser Tyr Arg Phe Asp Val Trp Gly Gln Gly Thr Leu Val
            100                 105                 110

Thr Val Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
210                 215

<210> SEQ ID NO 43
<211> LENGTH: 224
<212> TYPE: PRT
<213> ORGANISM: Artificial Sequence
<220> FEATURE:
<223> OTHER INFORMATION: >SEQ ID NO: 43 - anti-CD38-UCP03-B6 FAB heavy
      chain

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Ile Ser Asn Ser
            20                  25                  30

Ala Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 44
<211> LENGTH: 225
<212> TYPE: PRT
<213> ORGANISM: Artificial Sequence
<220> FEATURE:
<223> OTHER INFORMATION: >SEQ ID NO: 44 - anti-CD38-UCP03-E3 FAB heavy
      chain

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asn Ser Gly Asp Thr Asp Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Tyr Asp Ser Tyr Gly Glu Ser Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys
225

<210> SEQ ID NO 45
<211> LENGTH: 224
<212> TYPE: PRT
<213> ORGANISM: Artificial Sequence
<220> FEATURE:
<223> OTHER INFORMATION: >SEQ ID NO: 45 - anti-CD38-UCP03-A6 FAB heavy
      chain

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Asp Phe Ser Leu Tyr
            20                  25                  30

Ala Ile Ser Trp Val Arg Gln Ala Pro Gly Gln Gly Leu Glu Trp Met
        35                  40                  45

Gly Gly Ile Ile Pro Leu Leu Gly Glu Pro Val Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Arg Val Tyr Ser Ser Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala 130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

<210> SEQ ID NO 46
<211> LENGTH: 225
<212> TYPE: PRT
<213> ORGANISM: Artificial Sequence
<220> FEATURE:
<223> OTHER INFORMATION: >SEQ ID NO: 46 - anti-CD38-UCP03-B1 FAB heavy
      chain

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Ser Lys Tyr
            20                  25                  30

Phe Ile Thr Trp Val Arg Gln Ala Pro Gly Gln Gly Leu Glu Trp Met
        35                  40                  45

Gly Gly Val Ile Pro Lys Ile Gly Tyr Thr Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Asp Asp Tyr Ala Ser Tyr Ser Pro Leu Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225

<210> SEQ ID NO 47
<211> LENGTH: 224
<212> TYPE: PRT
<213> ORGANISM: Artificial Sequence
<220> FEATURE:

<223> OTHER INFORMATION: >SEQ ID NO: 47 - anti-CD38-UCP03-C2 FAB heavy
chain

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ala Phe Gly Asp Ala Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Val Leu Tyr Tyr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 48
<211> LENGTH: 223
<212> TYPE: PRT
<213> ORGANISM: Artificial Sequence
<220> FEATURE:
<223> OTHER INFORMATION: >SEQ ID NO: 48 - anti-CD38-UCP03-H2 FAB heavy
chain

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Glu Phe Ser Ile Tyr
            20                  25                  30

Val Ile Ser Trp Val Arg Gln Ala Pro Gly Gln Gly Leu Glu Trp Met
        35                  40                  45

Gly Arg Val Ile Pro Ser Thr Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Ala Tyr Tyr Ser Gly Trp Leu Ala Ile Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220
```

<210> SEQ ID NO 49
<211> LENGTH: 218
<212> TYPE: PRT
<213> ORGANISM: Artificial Sequence
<220> FEATURE:
<223> OTHER INFORMATION: >SEQ ID NO: 49 - anti-CD38-UCP03-H3 FAB heavy
    chain

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Gln Phe
            20                  25                  30

Pro Ile Ser Trp Val Arg Gln Ala Pro Gly Gln Gly Leu Glu Trp Met
        35                  40                  45

Gly Gly Ile Ile Ala Gly Tyr Gly Ala Thr Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Gly Gly Ile Asp Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
210                 215
```

<210> SEQ ID NO 50
<211> LENGTH: 226
<212> TYPE: PRT
<213> ORGANISM: Artificial Sequence

```
<220> FEATURE:
<223> OTHER INFORMATION: >SEQ ID NO: 50 - anti-CD38-E2-UCP01-A10 FAB
      heavy chain

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Val Phe Gly Ser Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 51
<211> LENGTH: 226
<212> TYPE: PRT
<213> ORGANISM: Artificial Sequence
<220> FEATURE:
<223> OTHER INFORMATION: >SEQ ID NO: 51 - anti-CD38-E2-UCP02-E7 FAB
      heavy chain

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Gly Trp Val Arg Gln Ala Pro Gly Gln Gly Leu Glu Trp Met
        35                  40                  45

Gly Arg Ile Ile Pro Ala Leu Ala Ala Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Leu Gly Tyr Tyr Leu Tyr Ser Ser Tyr Phe Asp Ile
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys
225

<210> SEQ ID NO 52
<211> LENGTH: 226
<212> TYPE: PRT
<213> ORGANISM: Artificial Sequence
<220> FEATURE:
<223> OTHER INFORMATION: >SEQ ID NO: 52 - anti-CD38-E2-UCP02-F3 FAB
      heavy chain

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Gly Trp Val Arg Gln Ala Pro Gly Gln Gly Leu Glu Trp Met
            35                  40                  45

Gly Arg Ile Ile Pro Val Leu Asp Ala Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Phe Asp Ile
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys

Ser Cys
225

<210> SEQ ID NO 53
<211> LENGTH: 226
<212> TYPE: PRT
<213> ORGANISM: Artificial Sequence
<220> FEATURE:
<223> OTHER INFORMATION: >SEQ ID NO: 53 - anti-CD38-E2-UCP02-D6 FAB
      heavy chain

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 54
<211> LENGTH: 226
<212> TYPE: PRT
<213> ORGANISM: Artificial Sequence
<220> FEATURE:
<223> OTHER INFORMATION: >SEQ ID NO: 54 - anti-CD38-E2-UCP02-G8 FAB
      heavy chain

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Gly Trp Val Arg Gln Ala Pro Gly Gln Gly Leu Glu Trp Met

```
            35                  40                  45
Gly Arg Ile Ile Pro Ala Leu Gly Gly Val His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Leu Gly Tyr Tyr Leu Tyr Ser Ser Tyr Tyr Phe Asp Ile
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys
225

<210> SEQ ID NO 55
<211> LENGTH: 226
<212> TYPE: PRT
<213> ORGANISM: Artificial Sequence
<220> FEATURE:
<223> OTHER INFORMATION: >SEQ ID NO: 55 - anti-CD38-E2-UCP02-F8 FAB
      heavy chain

<400> SEQUENCE: 55

Gln Val Gln Leu Val Gln Ser Gly Ala Glu Val Lys Lys Pro Gly Ser
 1                   5                  10                  15

Ser Val Lys Val Ser Cys Lys Ala Ser Gly Gly Ser Phe Ser Asn Tyr
                 20                  25                  30

Ala Ile Gly Trp Val Arg Gln Ala Pro Gly Gln Gly Leu Glu Trp Met
             35                  40                  45

Gly Arg Ile Ile Pro Ser Leu Asp Ala Gly His Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Leu Gly Tyr Tyr Leu Tyr Ser Ser Tyr Tyr Phe Asp Ile
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 56
<211> LENGTH: 226
<212> TYPE: PRT
<213> ORGANISM: Artificial Sequence
<220> FEATURE:
<223> OTHER INFORMATION: >SEQ ID NO: 56 - anti-CD38-E2-UCP02-A5 FAB
      heavy chain

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Ile Gly Trp Val Arg Gln Ala Pro Gly Gln Gly Leu Glu Trp Met
        35                  40                  45

Gly Arg Ile Ile Pro Asp Leu Gly Ala Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 57
<211> LENGTH: 226
<212> TYPE: PRT
<213> ORGANISM: Artificial Sequence
<220> FEATURE:
<223> OTHER INFORMATION: >SEQ ID NO: 57 - anti-CD38-E2-RecA FAB heavy
      chain
```

<400> SEQUENCE: 57

```
Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```

<210> SEQ ID NO 58
<211> LENGTH: 226
<212> TYPE: PRT
<213> ORGANISM: Artificial Sequence
<220> FEATURE:
<223> OTHER INFORMATION: >SEQ ID NO: 58 - anti-CD38-E2-RecB FAB heavy
      chain

<400> SEQUENCE: 58

```
Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Ala Leu Ala Ala Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110
```

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 59
<211> LENGTH: 226
<212> TYPE: PRT
<213> ORGANISM: Artificial Sequence
<220> FEATURE:
<223> OTHER INFORMATION: >SEQ ID NO: 59 - anti-CD38-E2-RecC FAB heavy
      chain

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Val Leu Asp Ala Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys

<210> SEQ ID NO 60
<211> LENGTH: 226
<212> TYPE: PRT
<213> ORGANISM: Artificial Sequence
<220> FEATURE:
<223> OTHER INFORMATION: >SEQ ID NO: 60 - anti-CD38-E2-RecD FAB heavy chain

<400> SEQUENCE: 60

```
Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Ala Leu Gly Gly Val His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```

<210> SEQ ID NO 61
<211> LENGTH: 224
<212> TYPE: PRT
<213> ORGANISM: Artificial Sequence
<220> FEATURE:
<223> OTHER INFORMATION: >SEQ ID NO: 61 - anti-CD38-B6-MP01-D9 FAB heavy chain

<400> SEQUENCE: 61

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser His Tyr
            20                  25                  30

Ile Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
```

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 62
<211> LENGTH: 224
<212> TYPE: PRT
<213> ORGANISM: Artificial Sequence
<220> FEATURE:
<223> OTHER INFORMATION: >SEQ ID NO: 62 - anti-CD38-B6-MP01-B4 FAB heavy
      chain

<400> SEQUENCE: 62

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Glu Phe Asn Thr Tyr
             20                  25                  30

Ile Ile Asn Trp Val Arg Gln Ala Pro Gly Gln Gly Leu Glu Trp Met
         35                  40                  45

Gly Arg Val Ile Pro Val Ile Asp Asp Ala Tyr Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 63
<211> LENGTH: 224
<212> TYPE: PRT
<213> ORGANISM: Artificial Sequence
<220> FEATURE:
<223> OTHER INFORMATION: >SEQ ID NO: 63 - anti-CD38-B6-MP02-C1 FAB heavy
      chain

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Gln Leu Gly Lys
            20                  25                  30

Ile Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 64
<211> LENGTH: 224
<212> TYPE: PRT
<213> ORGANISM: Artificial Sequence
<220> FEATURE:
<223> OTHER INFORMATION: >SEQ ID NO: 64 - anti-CD38-B6-MP02-B10 FAB
      heavy chain

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Asn Leu Gly Lys
            20                  25                  30

Ile Ile Asn Trp Val Arg Gln Pro Pro Gly Gln Gly Leu Glu Trp Met
        35                  40                  45
```

Gly Arg Val Ile Pro Val Ile Asp Asp Ala Tyr Tyr Ala Gln Lys Phe
                50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Arg Gly Tyr Tyr Gly Ser Phe Tyr Phe Asp Ile Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

<210> SEQ ID NO 65
<211> LENGTH: 224
<212> TYPE: PRT
<213> ORGANISM: Artificial Sequence
<220> FEATURE:
<223> OTHER INFORMATION: >SEQ ID NO: 65 - anti-CD38-B6-MP01-H3a FAB
      heavy chain

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Asn Ala Asn
                20                  25                  30

Ile Val Asn Trp Ile Arg Gln Ala Pro Gly Gln Gly Leu Glu Trp Met
                35                  40                  45

Gly Arg Val Ile Pro Val Ile Asp Asp Ala Tyr Tyr Ala Gln Lys Phe
                50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Arg Gly Tyr Tyr Gly Ser Phe Tyr Phe Asp Ile Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 66
<211> LENGTH: 224
<212> TYPE: PRT
<213> ORGANISM: Artificial Sequence
<220> FEATURE:
<223> OTHER INFORMATION: >SEQ ID NO: 66 - anti-CD38-B6-MP01-H3b FAB
      heavy chain

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Gln Ser Asn
            20                  25                  30

Ile Val Asn Trp Ile Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 67
<211> LENGTH: 224
<212> TYPE: PRT
<213> ORGANISM: Artificial Sequence
<220> FEATURE:
<223> OTHER INFORMATION: >SEQ ID NO: 67 - anti-CD38-B6-MP01-A4 FAB heavy
      chain

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Asp Tyr
            20                  25                  30

Val Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

<210> SEQ ID NO 68
<211> LENGTH: 224
<212> TYPE: PRT
<213> ORGANISM: Artificial Sequence
<220> FEATURE:
<223> OTHER INFORMATION: >SEQ ID NO: 68 - anti-CD38-B6-MP01-C2 FAB heavy
      chain

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Asp Tyr
            20                  25                  30

Val Ile Ser Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

<210> SEQ ID NO 69
<211> LENGTH: 224
<212> TYPE: PRT
<213> ORGANISM: Artificial Sequence
<220> FEATURE:
<223> OTHER INFORMATION: >SEQ ID NO: 69 - anti-CD38-B6-MP02-C2 FAB heavy
      chain

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Gly Gln Gln Arg
            20                  25                  30

Ile Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 70
<211> LENGTH: 224
<212> TYPE: PRT
<213> ORGANISM: Artificial Sequence
<220> FEATURE:
<223> OTHER INFORMATION: >SEQ ID NO: 70 - anti-CD38-B6-MP02-G11 FAB
      heavy chain

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Thr Leu Pro Pro
            20                  25                  30

Ile Ile Asn Trp Val Arg Gln Ala Pro Gly Gln Gly Leu Glu Trp Met

```
                    35                  40                  45
Gly Arg Val Ile Pro Val Ile Asp Asp Ala Tyr Tyr Ala Gln Lys Phe
         50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Arg Gly Tyr Tyr Gly Ser Phe Tyr Phe Asp Ile Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220

<210> SEQ ID NO 71
<211> LENGTH: 10
<212> TYPE: PRT
<213> ORGANISM: Artificial Sequence
<220> FEATURE:
<223> OTHER INFORMATION: >SEQ ID NO: 71 - anti-CD47-UCP01-A1 CDRH1

<400> SEQUENCE: 71

Gly Gly Phe Phe Arg Leu Tyr Ala Phe Ser
1               5                   10

<210> SEQ ID NO 72
<211> LENGTH: 10
<212> TYPE: PRT
<213> ORGANISM: Artificial Sequence
<220> FEATURE:
<223> OTHER INFORMATION: >SEQ ID NO: 72 - anti-CD47-UCP01-G1 CDRH1

<400> SEQUENCE: 72

Gly Phe Thr Phe Ser Asn Tyr Ala Met Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: >SEQ ID NO: 73 - anti-CD47-UCP01-A2 CDRH1

<400> SEQUENCE: 73

Gly Phe Thr Phe Ser Arg Phe Ala Met Gly
1               5                   10

<210> SEQ ID NO 74
<211> LENGTH: 10
<212> TYPE: PRT
<213> ORGANISM: Artificial Sequence
```

```
<220> FEATURE:
<223> OTHER INFORMATION: >SEQ ID NO: 74 - anti-CD47-UCP01-G2 CDRH1

<400> SEQUENCE: 74

Gly Phe Thr Val Ser Asn Ser Tyr Met Thr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: >SEQ ID NO: 75 - anti-CD47-UCP01-H2 CDRH1

<400> SEQUENCE: 75

Gly Phe Thr Leu Ser Arg Asn Thr Met His
1               5                   10

<210> SEQ ID NO 76
<211> LENGTH: 10
<212> TYPE: PRT
<213> ORGANISM: Artificial Sequence
<220> FEATURE:
<223> OTHER INFORMATION: >SEQ ID NO: 76 - anti-CD47-UCP01-A3 CDRH1

<400> SEQUENCE: 76

Gly Phe Thr Phe Thr Asn Ser Trp Met Ser
1               5                   10

<210> SEQ ID NO 77
<211> LENGTH: 10
<212> TYPE: PRT
<213> ORGANISM: Artificial Sequence
<220> FEATURE:
<223> OTHER INFORMATION: >SEQ ID NO: 77 - anti-CD47-UCP01-B3 CDRH1

<400> SEQUENCE: 77

Gly Phe Thr Phe Ser Asn Asn Tyr Met Ser
1               5                   10

<210> SEQ ID NO 78
<211> LENGTH: 10
<212> TYPE: PRT
<213> ORGANISM: Artificial Sequence
<220> FEATURE:
<223> OTHER INFORMATION: >SEQ ID NO: 78 - anti-CD47-UCP02-C1 CDRH1

<400> SEQUENCE: 78

Gly Gly Phe Phe Ser Ala His Thr Ile Ser
1               5                   10

<210> SEQ ID NO 79
<211> LENGTH: 10
<212> TYPE: PRT
<213> ORGANISM: Artificial Sequence
<220> FEATURE:
<223> OTHER INFORMATION: >SEQ ID NO: 79 - anti-CD47-UCP02-C2 CDRH1

<400> SEQUENCE: 79

Gly Phe Ser Val Ser Ser Asn Tyr Met Gly
1               5                   10

<210> SEQ ID NO 80
<211> LENGTH: 10
<212> TYPE: PRT
<213> ORGANISM: Artificial Sequence
<220> FEATURE:
```

```
<223> OTHER INFORMATION: >SEQ ID NO: 80 - anti-CD47-UCP02-H3 CDRH1

<400> SEQUENCE: 80

Gly Gly Phe Phe Arg Leu Tyr Ala Phe Ser
1               5                   10

<210> SEQ ID NO 81
<211> LENGTH: 10
<212> TYPE: PRT
<213> ORGANISM: Artificial Sequence
<220> FEATURE:
<223> OTHER INFORMATION: >SEQ ID NO: 81 - anti-CD47-UCP02-B3 CDRH1

<400> SEQUENCE: 81

Gly Gly Arg Phe Arg Leu Tyr Gly Ile Asn
1               5                   10

<210> SEQ ID NO 82
<211> LENGTH: 10
<212> TYPE: PRT
<213> ORGANISM: Artificial Sequence
<220> FEATURE:
<223> OTHER INFORMATION: >SEQ ID NO: 82 - anti-CD38-UCP01-B1 CDRH1

<400> SEQUENCE: 82

Gly Gly Asp Phe Asp Gln Tyr Tyr Ile Ser
1               5                   10

<210> SEQ ID NO 83
<211> LENGTH: 10
<212> TYPE: PRT
<213> ORGANISM: Artificial Sequence
<220> FEATURE:
<223> OTHER INFORMATION: >SEQ ID NO: 83 - anti-CD38-UCP01-D1 CDRH1

<400> SEQUENCE: 83

Gly Gly Ile Phe Asn Gly Tyr Leu Ile Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: >SEQ ID NO: 84 - anti-CD38-UCP01-F1 CDRH1

<400> SEQUENCE: 84

Gly Gly Val Phe Ser Leu Tyr Thr Ile Thr
1               5                   10

<210> SEQ ID NO 85
<211> LENGTH: 10
<212> TYPE: PRT
<213> ORGANISM: Artificial Sequence
<220> FEATURE:
<223> OTHER INFORMATION: >SEQ ID NO: 85 - anti-CD38-UCP01-G1 CDRH1

<400> SEQUENCE: 85

Gly Gly Gly Phe Ser Lys Tyr Phe Ile Thr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: >SEQ ID NO: 86 - anti-CD38-UCP01-H1 CDRH1
```

```
<400> SEQUENCE: 86

Gly Asp Phe Phe Ser Gly Tyr Ala Ile Asn
1               5                   10

<210> SEQ ID NO 87
<211> LENGTH: 10
<212> TYPE: PRT
<213> ORGANISM: Artificial Sequence
<220> FEATURE:
<223> OTHER INFORMATION: >SEQ ID NO: 87 - anti-CD38-UCP01-C2 CDRH1

<400> SEQUENCE: 87

Gly Gly Tyr Leu Gly Ile Tyr Ala Ile Ser
1               5                   10

<210> SEQ ID NO 88
<211> LENGTH: 10
<212> TYPE: PRT
<213> ORGANISM: Artificial Sequence
<220> FEATURE:
<223> OTHER INFORMATION: >SEQ ID NO: 88 - anti-CD38-UCP01-E2 CDRH1

<400> SEQUENCE: 88

Gly Gly Ser Phe Ser Asn Tyr Ala Ile Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: >SEQ ID NO: 89 - anti-CD38-UCP02-A7 CDRH1

<400> SEQUENCE: 89

Gly Phe Thr Phe Ser Phe Tyr Asp Met Ser
1               5                   10

<210> SEQ ID NO 90
<211> LENGTH: 10
<212> TYPE: PRT
<213> ORGANISM: Artificial Sequence
<220> FEATURE:
<223> OTHER INFORMATION: >SEQ ID NO: 90 - anti-CD38-UCP02-B1 CDRH1

<400> SEQUENCE: 90

Gly Gly Gln Phe Ser Phe Tyr Ala Ile Asn
1               5                   10

<210> SEQ ID NO 91
<211> LENGTH: 10
<212> TYPE: PRT
<213> ORGANISM: Artificial Sequence
<220> FEATURE:
<223> OTHER INFORMATION: >SEQ ID NO: 91 - anti-CD38-UCP02-B7 CDRH1

<400> SEQUENCE: 91

Gly Phe Ser Phe Asn Glu Ala Trp Met Thr
1               5                   10

<210> SEQ ID NO 92
<211> LENGTH: 10
<212> TYPE: PRT
<213> ORGANISM: Artificial Sequence
<220> FEATURE:
<223> OTHER INFORMATION: >SEQ ID NO: 92 - anti-CD38-UCP02-C3 CDRH1
```

```
<400> SEQUENCE: 92

Gly Asp Tyr Phe Asn Asn Tyr Ala Ile Asn
1               5                   10

<210> SEQ ID NO 93
<211> LENGTH: 10
<212> TYPE: PRT
<213> ORGANISM: Artificial Sequence
<220> FEATURE:
<223> OTHER INFORMATION: >SEQ ID NO: 93 - anti-CD38-UCP02-D1 CDRH1

<400> SEQUENCE: 93

Gly Gly Asp Phe Asp Gln Tyr Tyr Ile Ser
1               5                   10

<210> SEQ ID NO 94
<211> LENGTH: 10
<212> TYPE: PRT
<213> ORGANISM: Artificial Sequence
<220> FEATURE:
<223> OTHER INFORMATION: >SEQ ID NO: 94 - anti-CD38-UCP02-D5 CDRH1

<400> SEQUENCE: 94

Gly Gly Ile Phe Ser Val His Ala Ile His
1               5                   10

<210> SEQ ID NO 95
<211> LENGTH: 10
<212> TYPE: PRT
<213> ORGANISM: Artificial Sequence
<220> FEATURE:
<223> OTHER INFORMATION: >SEQ ID NO: 95 - anti-CD38-UCP02-E5 CDRH1

<400> SEQUENCE: 95

Gly Gly Gly Phe Arg His Tyr Phe Ile Ser
1               5                   10

<210> SEQ ID NO 96
<211> LENGTH: 10
<212> TYPE: PRT
<213> ORGANISM: Artificial Sequence
<220> FEATURE:
<223> OTHER INFORMATION: >SEQ ID NO: 96 - anti-CD38-UCP02-F2 CDRH1

<400> SEQUENCE: 96

Gly Asp Val Phe Ser Leu Leu Ala Ile Gly
1               5                   10

<210> SEQ ID NO 97
<211> LENGTH: 10
<212> TYPE: PRT
<213> ORGANISM: Artificial Sequence
<220> FEATURE:
<223> OTHER INFORMATION: >SEQ ID NO: 97 - anti-CD38-UCP02-F5 CDRH1

<400> SEQUENCE: 97

Gly Gly Val Phe Ser Tyr Tyr Thr Ile Ser
1               5                   10

<210> SEQ ID NO 98
<211> LENGTH: 10
<212> TYPE: PRT
<213> ORGANISM: Artificial Sequence
<220> FEATURE:
<223> OTHER INFORMATION: >SEQ ID NO: 98 - anti-CD38-UCP02-F6 CDRH1

<400> SEQUENCE: 98
```

```
Gly Phe Thr Phe Ser Phe Tyr Asp Met Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: >SEQ ID NO: 99 - anti-CD38-UCP02-H1 CDRH1

<400> SEQUENCE: 99

Gly Asp Lys Phe Asn Thr Tyr Ala Ile Ser
1               5                   10

<210> SEQ ID NO 100
<211> LENGTH: 10
<212> TYPE: PRT
<213> ORGANISM: Artificial Sequence
<220> FEATURE:
<223> OTHER INFORMATION: >SEQ ID NO: 100 - anti-CD38-UCP03-B3 CDRH1

<400> SEQUENCE: 100

Gly Gly Asp Phe Thr Leu Tyr Ser Ile Ser
1               5                   10

<210> SEQ ID NO 101
<211> LENGTH: 10
<212> TYPE: PRT
<213> ORGANISM: Artificial Sequence
<220> FEATURE:
<223> OTHER INFORMATION: >SEQ ID NO: 101 - anti-CD38-UCP03-C3 CDRH1

<400> SEQUENCE: 101

Gly Gly Lys Phe Ser Asn Tyr Ala Ile Ser
1               5                   10

<210> SEQ ID NO 102
<211> LENGTH: 10
<212> TYPE: PRT
<213> ORGANISM: Artificial Sequence
<220> FEATURE:
<223> OTHER INFORMATION: >SEQ ID NO: 102 - anti-CD38-UCP03-H5 CDRH1

<400> SEQUENCE: 102

Gly Gly Leu Phe Ser Phe Tyr Ala Ile Ser
1               5                   10

<210> SEQ ID NO 103
<211> LENGTH: 10
<212> TYPE: PRT
<213> ORGANISM: Artificial Sequence
<220> FEATURE:
<223> OTHER INFORMATION: >SEQ ID NO: 103 - anti-CD38-UCP03-B6 CDRH1

<400> SEQUENCE: 103

Gly Gly His Ile Ser Asn Ser Ala Ile Asn
1               5                   10

<210> SEQ ID NO 104
<211> LENGTH: 10
<212> TYPE: PRT
<213> ORGANISM: Artificial Sequence
<220> FEATURE:
<223> OTHER INFORMATION: >SEQ ID NO: 104 - anti-CD38-UCP03-E3 CDRH1

<400> SEQUENCE: 104
```

```
Gly Gly Ser Phe Ser Ile Tyr Ala Ile Ser
1               5                   10
```

<210> SEQ ID NO 105
<211> LENGTH: 10
<212> TYPE: PRT
<213> ORGANISM: Artificial Sequence
<220> FEATURE:
<223> OTHER INFORMATION: >SEQ ID NO: 105 - anti-CD38-UCP03-A6 CDRH1

<400> SEQUENCE: 105

```
Gly Gly Asp Phe Ser Leu Tyr Ala Ile Ser
1               5                   10
```

<210> SEQ ID NO 106
<211> LENGTH: 10
<212> TYPE: PRT
<213> ORGANISM: Artificial Sequence
<220> FEATURE:
<223> OTHER INFORMATION: >SEQ ID NO: 106 - anti-CD38-UCP03-B1 CDRH1

<400> SEQUENCE: 106

```
Gly Gly Gly Phe Ser Lys Tyr Phe Ile Thr
1               5                   10
```

<210> SEQ ID NO 107
<211> LENGTH: 10
<212> TYPE: PRT
<213> ORGANISM: Artificial Sequence
<220> FEATURE:
<223> OTHER INFORMATION: >SEQ ID NO: 107 - anti-CD38-UCP03-C2 CDRH1

<400> SEQUENCE: 107

```
Gly Gly Thr Phe Ser Asn Tyr Ala Ile Ser
1               5                   10
```

<210> SEQ ID NO 108
<211> LENGTH: 10
<212> TYPE: PRT
<213> ORGANISM: Artificial Sequence
<220> FEATURE:
<223> OTHER INFORMATION: >SEQ ID NO: 108 - anti-CD38-UCP03-H2 CDRH1

<400> SEQUENCE: 108

```
Gly Gly Glu Phe Ser Ile Tyr Val Ile Ser
1               5                   10
```

<210> SEQ ID NO 109
<211> LENGTH: 10
<212> TYPE: PRT
<213> ORGANISM: Artificial Sequence
<220> FEATURE:
<223> OTHER INFORMATION: >SEQ ID NO: 109 - anti-CD38-UCP03-H3 CDRH1

<400> SEQUENCE: 109

```
Gly Gly Val Phe Ser Gln Phe Pro Ile Ser
1               5                   10
```

<210> SEQ ID NO 110
<211> LENGTH: 10
<212> TYPE: PRT
<213> ORGANISM: Artificial Sequence
<220> FEATURE:
<223> OTHER INFORMATION: >SEQ ID NO: 110 - anti-CD38-E2-UCP01-A10 CDRH1

<400> SEQUENCE: 110

```
Gly Leu Pro Asp Ala Thr Tyr Ala Ile Gly
```

```
1               5                   10

<210> SEQ ID NO 111
<211> LENGTH: 10
<212> TYPE: PRT
<213> ORGANISM: Artificial Sequence
<220> FEATURE:
<223> OTHER INFORMATION: >SEQ ID NO: 111 - anti-CD38-E2-UCP02-E7 CDRH1

<400> SEQUENCE: 111

Gly Gly Ser Phe Ser Asn Tyr Ala Ile Gly
1               5                   10

<210> SEQ ID NO 112
<211> LENGTH: 10
<212> TYPE: PRT
<213> ORGANISM: Artificial Sequence
<220> FEATURE:
<223> OTHER INFORMATION: >SEQ ID NO: 112 - anti-CD38-E2-UCP02-F3 CDRH1

<400> SEQUENCE: 112

Gly Gly Ser Phe Ser Asn Tyr Ala Ile Gly
1               5                   10

<210> SEQ ID NO 113
<211> LENGTH: 10
<212> TYPE: PRT
<213> ORGANISM: Artificial Sequence
<220> FEATURE:
<223> OTHER INFORMATION: >SEQ ID NO: 113 - anti-CD38-E2-UCP02-D6 CDRH1

<400> SEQUENCE: 113

Gly Gly Ser Phe Ser Asn Tyr Ala Ile Gly
1               5                   10

<210> SEQ ID NO 114
<211> LENGTH: 10
<212> TYPE: PRT
<213> ORGANISM: Artificial Sequence
<220> FEATURE:
<223> OTHER INFORMATION: >SEQ ID NO: 114 - anti-CD38-E2-UCP02-G8 CDRH1

<400> SEQUENCE: 114

Gly Gly Ser Phe Ser Asn Tyr Ala Ile Gly
1               5                   10

<210> SEQ ID NO 115
<211> LENGTH: 10
<212> TYPE: PRT
<213> ORGANISM: Artificial Sequence
<220> FEATURE:
<223> OTHER INFORMATION: >SEQ ID NO: 115 - anti-CD38-E2-UCP02-F8 CDRH1

<400> SEQUENCE: 115

Gly Gly Ser Phe Ser Asn Tyr Ala Ile Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: >SEQ ID NO: 116 - anti-CD38-E2-UCP02-A5 CDRH1

<400> SEQUENCE: 116

Gly Gly Ser Phe Ser Asn Tyr Ala Ile Gly
1               5                   10
```

```
<210> SEQ ID NO 117
<211> LENGTH: 10
<212> TYPE: PRT
<213> ORGANISM: Artificial Sequence
<220> FEATURE:
<223> OTHER INFORMATION: >SEQ ID NO: 117 - anti-CD38-E2-RecA CDRH1

<400> SEQUENCE: 117

Gly Leu Pro Asp Ala Thr Tyr Ala Ile Gly
1               5                   10

<210> SEQ ID NO 118
<211> LENGTH: 10
<212> TYPE: PRT
<213> ORGANISM: Artificial Sequence
<220> FEATURE:
<223> OTHER INFORMATION: >SEQ ID NO: 118 - anti-CD38-E2-RecB CDRH1

<400> SEQUENCE: 118

Gly Leu Pro Asp Ala Thr Tyr Ala Ile Gly
1               5                   10

<210> SEQ ID NO 119
<211> LENGTH: 10
<212> TYPE: PRT
<213> ORGANISM: Artificial Sequence
<220> FEATURE:
<223> OTHER INFORMATION: >SEQ ID NO: 119 - anti-CD38-E2-RecC CDRH1

<400> SEQUENCE: 119

Gly Leu Pro Asp Ala Thr Tyr Ala Ile Gly
1               5                   10

<210> SEQ ID NO 120
<211> LENGTH: 10
<212> TYPE: PRT
<213> ORGANISM: Artificial Sequence
<220> FEATURE:
<223> OTHER INFORMATION: >SEQ ID NO: 120 - anti-CD38-E2-RecD CDRH1

<400> SEQUENCE: 120

Gly Leu Pro Asp Ala Thr Tyr Ala Ile Gly
1               5                   10

<210> SEQ ID NO 121
<211> LENGTH: 10
<212> TYPE: PRT
<213> ORGANISM: Artificial Sequence
<220> FEATURE:
<223> OTHER INFORMATION: >SEQ ID NO: 121 - anti-CD38-B6-MP01-D9 CDRH1

<400> SEQUENCE: 121

Gly Gly Phe Phe Ser His Tyr Ile Ile Asn
1               5                   10

<210> SEQ ID NO 122
<211> LENGTH: 10
<212> TYPE: PRT
<213> ORGANISM: Artificial Sequence
<220> FEATURE:
<223> OTHER INFORMATION: >SEQ ID NO: 122 - anti-CD38-B6-MP01-B4 CDRH1

<400> SEQUENCE: 122

Gly Tyr Glu Phe Asn Thr Tyr Ile Ile Asn
1               5                   10
```

<210> SEQ ID NO 123
<211> LENGTH: 10
<212> TYPE: PRT
<213> ORGANISM: Artificial Sequence
<220> FEATURE:
<223> OTHER INFORMATION: >SEQ ID NO: 123 - anti-CD38-B6-MP02-C1 CDRH1

<400> SEQUENCE: 123

Gly Gly His Gln Leu Gly Lys Ile Ile Asn
1               5                   10

<210> SEQ ID NO 124
<211> LENGTH: 10
<212> TYPE: PRT
<213> ORGANISM: Artificial Sequence
<220> FEATURE:
<223> OTHER INFORMATION: >SEQ ID NO: 124 - anti-CD38-B6-MP02-B10 CDRH1

<400> SEQUENCE: 124

Gly Gly His Asn Leu Gly Lys Ile Ile Asn
1               5                   10

<210> SEQ ID NO 125
<211> LENGTH: 10
<212> TYPE: PRT
<213> ORGANISM: Artificial Sequence
<220> FEATURE:
<223> OTHER INFORMATION: >SEQ ID NO: 125 - anti-CD38-B6-MP01-H3a CDRH1

<400> SEQUENCE: 125

Gly Gly Pro Phe Asn Ala Asn Ile Val Asn
1               5                   10

<210> SEQ ID NO 126
<211> LENGTH: 10
<212> TYPE: PRT
<213> ORGANISM: Artificial Sequence
<220> FEATURE:
<223> OTHER INFORMATION: >SEQ ID NO: 126 - anti-CD38-B6-MP01-H3b CDRH1

<400> SEQUENCE: 126

Gly Gly Pro Phe Gln Ser Asn Ile Val Asn
1               5                   10

<210> SEQ ID NO 127
<211> LENGTH: 10
<212> TYPE: PRT
<213> ORGANISM: Artificial Sequence
<220> FEATURE:
<223> OTHER INFORMATION: >SEQ ID NO: 127 - anti-CD38-B6-MP01-A4 CDRH1

<400> SEQUENCE: 127

Gly Gly Pro Phe Ser Asp Tyr Val Ile Asn
1               5                   10

<210> SEQ ID NO 128
<211> LENGTH: 10
<212> TYPE: PRT
<213> ORGANISM: Artificial Sequence
<220> FEATURE:
<223> OTHER INFORMATION: >SEQ ID NO: 128 - anti-CD38-B6-MP01-C2 CDRH1

<400> SEQUENCE: 128

Gly Gly Ala Phe Ser Asp Tyr Val Ile Ser
1               5                   10

```
<210> SEQ ID NO 129
<211> LENGTH: 10
<212> TYPE: PRT
<213> ORGANISM: Artificial Sequence
<220> FEATURE:
<223> OTHER INFORMATION: >SEQ ID NO: 129 - anti-CD38-B6-MP02-C2 CDRH1

<400> SEQUENCE: 129

Gly Gly His Gly Gln Gln Arg Ile Ile Asn
1               5                   10

<210> SEQ ID NO 130
<211> LENGTH: 10
<212> TYPE: PRT
<213> ORGANISM: Artificial Sequence
<220> FEATURE:
<223> OTHER INFORMATION: >SEQ ID NO: 130 - anti-CD38-B6-MP02-G11 CDRH1

<400> SEQUENCE: 130

Gly Gly His Thr Leu Pro Ile Ile Asn
1               5                   10

<210> SEQ ID NO 131
<211> LENGTH: 10
<212> TYPE: PRT
<213> ORGANISM: Artificial Sequence
<220> FEATURE:
<223> OTHER INFORMATION: >SEQ ID NO: 131 - anti-CD47-UCP01-A1 CDRH2

<400> SEQUENCE: 131

Gly Ile Ile Pro Thr Asp Gly Phe Val Gly
1               5                   10

<210> SEQ ID NO 132
<211> LENGTH: 10
<212> TYPE: PRT
<213> ORGANISM: Artificial Sequence
<220> FEATURE:
<223> OTHER INFORMATION: >SEQ ID NO: 132 - anti-CD47-UCP01-G1 CDRH2

<400> SEQUENCE: 132

Val Ile Ser Val Glu Gly Gly Leu Thr Val
1               5                   10

<210> SEQ ID NO 133
<211> LENGTH: 10
<212> TYPE: PRT
<213> ORGANISM: Artificial Sequence
<220> FEATURE:
<223> OTHER INFORMATION: >SEQ ID NO: 133 - anti-CD47-UCP01-A2 CDRH2

<400> SEQUENCE: 133

Ile Ile Ser Pro Asn Gly His Val Thr Ala
1               5                   10

<210> SEQ ID NO 134
<211> LENGTH: 9
<212> TYPE: PRT
<213> ORGANISM: Artificial Sequence
<220> FEATURE:
<223> OTHER INFORMATION: >SEQ ID NO: 134 - anti-CD47-UCP01-G2 CDRH2

<400> SEQUENCE: 134

Val Ile Tyr Lys Tyr Gly Lys Thr Ser
1               5

<210> SEQ ID NO 135
```

```
<211> LENGTH: 9
<212> TYPE: PRT
<213> ORGANISM: Artificial Sequence
<220> FEATURE:
<223> OTHER INFORMATION: >SEQ ID NO: 135 - anti-CD47-UCP01-H2 CDRH2

<400> SEQUENCE: 135

Val Ile Tyr Gln Ser Gly Val Thr Arg
1               5

<210> SEQ ID NO 136
<211> LENGTH: 9
<212> TYPE: PRT
<213> ORGANISM: Artificial Sequence
<220> FEATURE:
<223> OTHER INFORMATION: >SEQ ID NO: 136 - anti-CD47-UCP01-A3 CDRH2

<400> SEQUENCE: 136

Val Ile Tyr Lys Tyr Gly Phe Thr Glu
1               5

<210> SEQ ID NO 137
<211> LENGTH: 9
<212> TYPE: PRT
<213> ORGANISM: Artificial Sequence
<220> FEATURE:
<223> OTHER INFORMATION: >SEQ ID NO: 137 - anti-CD47-UCP01-B3 CDRH2

<400> SEQUENCE: 137

Val Ile Tyr Lys Lys Gly Phe Thr Asn
1               5

<210> SEQ ID NO 138
<211> LENGTH: 10
<212> TYPE: PRT
<213> ORGANISM: Artificial Sequence
<220> FEATURE:
<223> OTHER INFORMATION: >SEQ ID NO: 138 - anti-CD47-UCP02-C1 CDRH2

<400> SEQUENCE: 138

Arg Ile Thr Ala Val Arg Gly Val Pro Thr
1               5                   10

<210> SEQ ID NO 139
<211> LENGTH: 10
<212> TYPE: PRT
<213> ORGANISM: Artificial Sequence
<220> FEATURE:
<223> OTHER INFORMATION: >SEQ ID NO: 139 - anti-CD47-UCP02-H3 CDRH2

<400> SEQUENCE: 139

Gly Ile Ile Pro Thr Asp Gly Phe Val Gly
1               5                   10

<210> SEQ ID NO 140
<211> LENGTH: 10
<212> TYPE: PRT
<213> ORGANISM: Artificial Sequence
<220> FEATURE:
<223> OTHER INFORMATION: >SEQ ID NO: 140 - anti-CD47-UCP02-B3 CDRH2

<400> SEQUENCE: 140

Gly Ile Ser Pro Ile Asp Gly Tyr Ala Ala
1               5                   10

<210> SEQ ID NO 141
<211> LENGTH: 9
```

```
<212> TYPE: PRT
<213> ORGANISM: Artificial Sequence
<220> FEATURE:
<223> OTHER INFORMATION: >SEQ ID NO: 141 - anti-CD47-UCP02-C2 CDRH2

<400> SEQUENCE: 141

Leu Ile Asn Lys Asn Gly Gln Thr Gly
1               5

<210> SEQ ID NO 142
<211> LENGTH: 10
<212> TYPE: PRT
<213> ORGANISM: Artificial Sequence
<220> FEATURE:
<223> OTHER INFORMATION: >SEQ ID NO: 142 - anti-CD38-UCP01-B1 CDRH2

<400> SEQUENCE: 142

Arg Ile Ile Pro Thr Leu Gly Asp Ser Gln
1               5                   10

<210> SEQ ID NO 143
<211> LENGTH: 10
<212> TYPE: PRT
<213> ORGANISM: Artificial Sequence
<220> FEATURE:
<223> OTHER INFORMATION: >SEQ ID NO: 143 - anti-CD38-UCP01-D1 CDRH2

<400> SEQUENCE: 143

Gly Ile Ile Pro Val Asn Gly Leu Ala Asp
1               5                   10

<210> SEQ ID NO 144
<211> LENGTH: 10
<212> TYPE: PRT
<213> ORGANISM: Artificial Sequence
<220> FEATURE:
<223> OTHER INFORMATION: >SEQ ID NO: 144 - anti-CD38-UCP01-F1 CDRH2

<400> SEQUENCE: 144

Ser Ile Ile Pro Leu Leu Gly Asp Pro Glu
1               5                   10

<210> SEQ ID NO 145
<211> LENGTH: 10
<212> TYPE: PRT
<213> ORGANISM: Artificial Sequence
<220> FEATURE:
<223> OTHER INFORMATION: >SEQ ID NO: 145 - anti-CD38-UCP01-G1 CDRH2

<400> SEQUENCE: 145

Gly Val Ile Pro Lys Ile Gly Tyr Thr Ser
1               5                   10

<210> SEQ ID NO 146
<211> LENGTH: 10
<212> TYPE: PRT
<213> ORGANISM: Artificial Sequence
<220> FEATURE:
<223> OTHER INFORMATION: >SEQ ID NO: 146 - anti-CD38-UCP01-H1 CDRH2

<400> SEQUENCE: 146

Arg Ile Ile Pro Leu Leu Gly Asp Thr Tyr
1               5                   10

<210> SEQ ID NO 147
<211> LENGTH: 10
<212> TYPE: PRT
```

```
<213> ORGANISM: Artificial Sequence
<220> FEATURE:
<223> OTHER INFORMATION: >SEQ ID NO: 147 - anti-CD38-UCP01-C2 CDRH2

<400> SEQUENCE: 147

Arg Ile Ile Pro Ile Leu Gly Glu Ala Asp
1               5                   10

<210> SEQ ID NO 148
<211> LENGTH: 10
<212> TYPE: PRT
<213> ORGANISM: Artificial Sequence
<220> FEATURE:
<223> OTHER INFORMATION: >SEQ ID NO: 148 - anti-CD38-UCP01-E2 CDRH2

<400> SEQUENCE: 148

Arg Ile Ile Pro Val Phe Gly Ser Ala His
1               5                   10

<210> SEQ ID NO 149
<211> LENGTH: 10
<212> TYPE: PRT
<213> ORGANISM: Artificial Sequence
<220> FEATURE:
<223> OTHER INFORMATION: >SEQ ID NO: 149 - anti-CD38-UCP02-A7 CDRH2

<400> SEQUENCE: 149

Thr Ile Thr Leu His Gly Gly Asp Thr Tyr
1               5                   10

<210> SEQ ID NO 150
<211> LENGTH: 10
<212> TYPE: PRT
<213> ORGANISM: Artificial Sequence
<220> FEATURE:
<223> OTHER INFORMATION: >SEQ ID NO: 150 - anti-CD38-UCP02-B1 CDRH2

<400> SEQUENCE: 150

Glu Ile Ile Pro Asp Tyr Gly Val Thr His
1               5                   10

<210> SEQ ID NO 151
<211> LENGTH: 12
<212> TYPE: PRT
<213> ORGANISM: Artificial Sequence
<220> FEATURE:
<223> OTHER INFORMATION: >SEQ ID NO: 151 - anti-CD38-UCP02-B7 CDRH2

<400> SEQUENCE: 151

Arg Ile Lys Ser Tyr Ser Asp Gly Gly Tyr Thr Gly
1               5                   10

<210> SEQ ID NO 152
<211> LENGTH: 10
<212> TYPE: PRT
<213> ORGANISM: Artificial Sequence
<220> FEATURE:
<223> OTHER INFORMATION: >SEQ ID NO: 152 - anti-CD38-UCP02-C3 CDRH2

<400> SEQUENCE: 152

Arg Ile Ile Pro Phe Leu Asp Asp Ala Asn
1               5                   10

<210> SEQ ID NO 153
<211> LENGTH: 10
<212> TYPE: PRT
<213> ORGANISM: Artificial Sequence
```

```
<220> FEATURE:
<223> OTHER INFORMATION: >SEQ ID NO: 153 - anti-CD38-UCP02-D1 CDRH2

<400> SEQUENCE: 153

Arg Ile Ile Pro Thr Leu Gly Asp Ser Gln
 1               5                  10

<210> SEQ ID NO 154
<211> LENGTH: 10
<212> TYPE: PRT
<213> ORGANISM: Artificial Sequence
<220> FEATURE:
<223> OTHER INFORMATION: >SEQ ID NO: 154 - anti-CD38-UCP02-D5 CDRH2

<400> SEQUENCE: 154

Glu Ile Ile Pro Val Ile Gly Glu Ala Asp
 1               5                  10

<210> SEQ ID NO 155
<211> LENGTH: 10
<212> TYPE: PRT
<213> ORGANISM: Artificial Sequence
<220> FEATURE:
<223> OTHER INFORMATION: >SEQ ID NO: 155 - anti-CD38-UCP02-E5 CDRH2

<400> SEQUENCE: 155

Gly Ile Ile Pro Ala Ala Ala Thr Pro Tyr
 1               5                  10

<210> SEQ ID NO 156
<211> LENGTH: 10
<212> TYPE: PRT
<213> ORGANISM: Artificial Sequence
<220> FEATURE:
<223> OTHER INFORMATION: >SEQ ID NO: 156 - anti-CD38-UCP02-F2 CDRH2

<400> SEQUENCE: 156

Arg Ile Ile Pro Ser Leu Asp Ala Thr His
 1               5                  10

<210> SEQ ID NO 157
<211> LENGTH: 10
<212> TYPE: PRT
<213> ORGANISM: Artificial Sequence
<220> FEATURE:
<223> OTHER INFORMATION: >SEQ ID NO: 157 - anti-CD38-UCP02-F5 CDRH2

<400> SEQUENCE: 157

Arg Ile Ile Pro Ser Leu Gly Ala Thr His
 1               5                  10

<210> SEQ ID NO 158
<211> LENGTH: 10
<212> TYPE: PRT
<213> ORGANISM: Artificial Sequence
<220> FEATURE:
<223> OTHER INFORMATION: >SEQ ID NO: 158 - anti-CD38-UCP02-F6 CDRH2

<400> SEQUENCE: 158

Ala Val Ser Leu Tyr Gly Asp Glu Thr Tyr
 1               5                  10

<210> SEQ ID NO 159
<211> LENGTH: 10
<212> TYPE: PRT
<213> ORGANISM: Artificial Sequence
<220> FEATURE:
```

```
<223> OTHER INFORMATION: >SEQ ID NO: 159 - anti-CD38-UCP02-H1 CDRH2

<400> SEQUENCE: 159

Gly Ile Thr Pro Arg Tyr Asp Tyr Ala His
1               5                   10

<210> SEQ ID NO 160
<211> LENGTH: 10
<212> TYPE: PRT
<213> ORGANISM: Artificial Sequence
<220> FEATURE:
<223> OTHER INFORMATION: >SEQ ID NO: 160 - anti-CD38-UCP03-B3 CDRH2

<400> SEQUENCE: 160

Arg Ile Ile Pro Thr Gly Ala Asn Ala Asn
1               5                   10

<210> SEQ ID NO 161
<211> LENGTH: 10
<212> TYPE: PRT
<213> ORGANISM: Artificial Sequence
<220> FEATURE:
<223> OTHER INFORMATION: >SEQ ID NO: 161 - anti-CD38-UCP03-C3 CDRH2

<400> SEQUENCE: 161

Arg Ile Ile Pro Gln Ile Gly Asp Ala Ala
1               5                   10

<210> SEQ ID NO 162
<211> LENGTH: 10
<212> TYPE: PRT
<213> ORGANISM: Artificial Sequence
<220> FEATURE:
<223> OTHER INFORMATION: >SEQ ID NO: 162 - anti-CD38-UCP03-H5 CDRH2

<400> SEQUENCE: 162

Gly Ile Ile Pro Phe Phe Gly Glu Pro Gln
1               5                   10

<210> SEQ ID NO 163
<211> LENGTH: 10
<212> TYPE: PRT
<213> ORGANISM: Artificial Sequence
<220> FEATURE:
<223> OTHER INFORMATION: >SEQ ID NO: 163 - anti-CD38-UCP03-B6 CDRH2

<400> SEQUENCE: 163

Arg Val Ile Pro Val Ile Asp Asp Ala Tyr
1               5                   10

<210> SEQ ID NO 164
<211> LENGTH: 10
<212> TYPE: PRT
<213> ORGANISM: Artificial Sequence
<220> FEATURE:
<223> OTHER INFORMATION: >SEQ ID NO: 164 - anti-CD38-UCP03-E3 CDRH2

<400> SEQUENCE: 164

Gly Ile Ile Pro Asn Ser Gly Asp Thr Asp
1               5                   10

<210> SEQ ID NO 165
<211> LENGTH: 10
<212> TYPE: PRT
<213> ORGANISM: Artificial Sequence
<220> FEATURE:
<223> OTHER INFORMATION: >SEQ ID NO: 165 - anti-CD38-UCP03-A6 CDRH2
```

```
<400> SEQUENCE: 165

Gly Ile Ile Pro Leu Leu Gly Glu Pro Val
1               5                   10

<210> SEQ ID NO 166
<211> LENGTH: 10
<212> TYPE: PRT
<213> ORGANISM: Artificial Sequence
<220> FEATURE:
<223> OTHER INFORMATION: >SEQ ID NO: 166 - anti-CD38-UCP03-B1 CDRH2

<400> SEQUENCE: 166

Gly Val Ile Pro Lys Ile Gly Tyr Thr Ser
1               5                   10

<210> SEQ ID NO 167
<211> LENGTH: 10
<212> TYPE: PRT
<213> ORGANISM: Artificial Sequence
<220> FEATURE:
<223> OTHER INFORMATION: >SEQ ID NO: 167 - anti-CD38-UCP03-C2 CDRH2

<400> SEQUENCE: 167

Gly Ile Ile Pro Ala Phe Gly Asp Ala Gly
1               5                   10

<210> SEQ ID NO 168
<211> LENGTH: 10
<212> TYPE: PRT
<213> ORGANISM: Artificial Sequence
<220> FEATURE:
<223> OTHER INFORMATION: >SEQ ID NO: 168 - anti-CD38-UCP03-H2 CDRH2

<400> SEQUENCE: 168

Arg Val Ile Pro Ser Thr Gly Asp Thr Asn
1               5                   10

<210> SEQ ID NO 169
<211> LENGTH: 10
<212> TYPE: PRT
<213> ORGANISM: Artificial Sequence
<220> FEATURE:
<223> OTHER INFORMATION: >SEQ ID NO: 169 - anti-CD38-UCP03-H3 CDRH2

<400> SEQUENCE: 169

Gly Ile Ile Ala Gly Tyr Gly Ala Thr Glu
1               5                   10

<210> SEQ ID NO 170
<211> LENGTH: 10
<212> TYPE: PRT
<213> ORGANISM: Artificial Sequence
<220> FEATURE:
<223> OTHER INFORMATION: >SEQ ID NO: 170 - anti-CD38-E2-UCP01-A10 CDRH2

<400> SEQUENCE: 170

Arg Ile Ile Pro Val Phe Gly Ser Ala His
1               5                   10

<210> SEQ ID NO 171
<211> LENGTH: 10
<212> TYPE: PRT
<213> ORGANISM: Artificial Sequence
<220> FEATURE:
<223> OTHER INFORMATION: >SEQ ID NO: 171 - anti-CD38-E2-UCP02-E7 CDRH2
```

```
<400> SEQUENCE: 171

Arg Ile Ile Pro Ala Leu Ala Ala Thr His
1               5                   10

<210> SEQ ID NO 172
<211> LENGTH: 10
<212> TYPE: PRT
<213> ORGANISM: Artificial Sequence
<220> FEATURE:
<223> OTHER INFORMATION: >SEQ ID NO: 172 - anti-CD38-E2-UCP02-F3 CDRH2

<400> SEQUENCE: 172

Arg Ile Ile Pro Val Leu Asp Ala Ala His
1               5                   10

<210> SEQ ID NO 173
<211> LENGTH: 10
<212> TYPE: PRT
<213> ORGANISM: Artificial Sequence
<220> FEATURE:
<223> OTHER INFORMATION: >SEQ ID NO: 173 - anti-CD38-E2-UCP02-D6 CDRH2

<400> SEQUENCE: 173

Arg Ile Ile Pro Arg Leu Asp Ala Glu His
1               5                   10

<210> SEQ ID NO 174
<211> LENGTH: 10
<212> TYPE: PRT
<213> ORGANISM: Artificial Sequence
<220> FEATURE:
<223> OTHER INFORMATION: >SEQ ID NO: 174 - anti-CD38-E2-UCP02-G8 CDRH2

<400> SEQUENCE: 174

Arg Ile Ile Pro Ala Leu Gly Gly Val His
1               5                   10

<210> SEQ ID NO 175
<211> LENGTH: 10
<212> TYPE: PRT
<213> ORGANISM: Artificial Sequence
<220> FEATURE:
<223> OTHER INFORMATION: >SEQ ID NO: 175 - anti-CD38-E2-UCP02-A5 CDRH2

<400> SEQUENCE: 175

Arg Ile Ile Pro Asp Leu Gly Ala Ala His
1               5                   10

<210> SEQ ID NO 176
<211> LENGTH: 10
<212> TYPE: PRT
<213> ORGANISM: Artificial Sequence
<220> FEATURE:
<223> OTHER INFORMATION: >SEQ ID NO: 176 - anti-CD38-E2-UCP02-F8 CDRH2

<400> SEQUENCE: 176

Arg Ile Ile Pro Ser Leu Asp Ala Gly His
1               5                   10

<210> SEQ ID NO 177
<211> LENGTH: 10
<212> TYPE: PRT
<213> ORGANISM: Artificial Sequence
<220> FEATURE:
<223> OTHER INFORMATION: >SEQ ID NO: 177 - anti-CD38-E2-RecA CDRH2

<400> SEQUENCE: 177
```

Arg Ile Ile Pro Arg Leu Asp Ala Glu His
1               5                   10

<210> SEQ ID NO 178
<211> LENGTH: 10
<212> TYPE: PRT
<213> ORGANISM: Artificial Sequence
<220> FEATURE:
<223> OTHER INFORMATION: >SEQ ID NO: 178 - anti-CD38-E2-RecB CDRH2

<400> SEQUENCE: 178

Arg Ile Ile Pro Ala Leu Ala Ala Thr His
1               5                   10

<210> SEQ ID NO 179
<211> LENGTH: 10
<212> TYPE: PRT
<213> ORGANISM: Artificial Sequence
<220> FEATURE:
<223> OTHER INFORMATION: >SEQ ID NO: 179 - anti-CD38-E2-RecC CDRH2

<400> SEQUENCE: 179

Arg Ile Ile Pro Val Leu Asp Ala Ala His
1               5                   10

<210> SEQ ID NO 180
<211> LENGTH: 10
<212> TYPE: PRT
<213> ORGANISM: Artificial Sequence
<220> FEATURE:
<223> OTHER INFORMATION: >SEQ ID NO: 180 - anti-CD38-E2-RecD CDRH2

<400> SEQUENCE: 180

Arg Ile Ile Pro Ala Leu Gly Gly Val His
1               5                   10

<210> SEQ ID NO 181
<211> LENGTH: 10
<212> TYPE: PRT
<213> ORGANISM: Artificial Sequence
<220> FEATURE:
<223> OTHER INFORMATION: >SEQ ID NO: 181 - anti-CD38-B6-MP01-D9 CDRH2

<400> SEQUENCE: 181

Arg Val Ile Pro Val Ile Asp Asp Ala Tyr
1               5                   10

<210> SEQ ID NO 182
<211> LENGTH: 10
<212> TYPE: PRT
<213> ORGANISM: Artificial Sequence
<220> FEATURE:
<223> OTHER INFORMATION: >SEQ ID NO: 182 - anti-CD38-B6-MP01-B4 CDRH2

<400> SEQUENCE: 182

Arg Val Ile Pro Val Ile Asp Asp Ala Tyr
1               5                   10

<210> SEQ ID NO 183
<211> LENGTH: 10
<212> TYPE: PRT
<213> ORGANISM: Artificial Sequence
<220> FEATURE:
<223> OTHER INFORMATION: >SEQ ID NO: 183 - anti-CD38-B6-MP02-C1 CDRH2

<400> SEQUENCE: 183

Arg Val Ile Pro Val Ile Asp Asp Ala Tyr
1               5                   10

<210> SEQ ID NO 184
<211> LENGTH: 10
<212> TYPE: PRT
<213> ORGANISM: Artificial Sequence
<220> FEATURE:
<223> OTHER INFORMATION: >SEQ ID NO: 184 - anti-CD38-B6-MP02-B10 CDRH2

<400> SEQUENCE: 184

Arg Val Ile Pro Val Ile Asp Asp Ala Tyr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: >SEQ ID NO: 185 - anti-CD38-B6-MP01-H3a CDRH2

<400> SEQUENCE: 185

Arg Val Ile Pro Val Ile Asp Asp Ala Tyr
1               5                   10

<210> SEQ ID NO 186
<211> LENGTH: 10
<212> TYPE: PRT
<213> ORGANISM: Artificial Sequence
<220> FEATURE:
<223> OTHER INFORMATION: >SEQ ID NO: 186 - anti-CD38-B6-MP01-H3b CDRH2

<400> SEQUENCE: 186

Arg Val Ile Pro Val Ile Asp Asp Ala Tyr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: >SEQ ID NO: 187 - anti-CD38-B6-MP01-A4 CDRH2

<400> SEQUENCE: 187

Arg Val Ile Pro Val Ile Asp Asp Ala Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: >SEQ ID NO: 188 - anti-CD38-B6-MP01-C2 CDRH2

<400> SEQUENCE: 188

Arg Val Ile Pro Val Ile Asp Asp Ala Tyr
1               5                   10

<210> SEQ ID NO 189
<211> LENGTH: 10
<212> TYPE: PRT
<213> ORGANISM: Artificial Sequence
<220> FEATURE:
<223> OTHER INFORMATION: >SEQ ID NO: 189 - anti-CD38-B6-MP02-C2 CDRH2

<400> SEQUENCE: 189

Arg Val Ile Pro Val Ile Asp Asp Ala Tyr

<210> SEQ ID NO 190
<211> LENGTH: 10
<212> TYPE: PRT
<213> ORGANISM: Artificial Sequence
<220> FEATURE:
<223> OTHER INFORMATION: >SEQ ID NO: 190 - anti-CD38-B6-MP02-G11 CDRH2

<400> SEQUENCE: 190

Arg Val Ile Pro Val Ile Asp Asp Ala Tyr
1               5                   10

<210> SEQ ID NO 191
<211> LENGTH: 21
<212> TYPE: PRT
<213> ORGANISM: Artificial Sequence
<220> FEATURE:
<223> OTHER INFORMATION: >SEQ ID NO: 191 - anti-CD47-UCP01-A1 CDRH3

<400> SEQUENCE: 191

Ala Arg Ser Arg Tyr Tyr Arg Pro Tyr Gly Glu Tyr Tyr Val Val Gly
1               5                   10                  15

Tyr Gly Phe Ala Tyr
            20

<210> SEQ ID NO 192
<211> LENGTH: 16
<212> TYPE: PRT
<213> ORGANISM: Artificial Sequence
<220> FEATURE:
<223> OTHER INFORMATION: >SEQ ID NO: 192 - anti-CD47-UCP01-G1 CDRH3

<400> SEQUENCE: 192

Ala Arg Gly Ser Arg Asp Ser Arg Gly Lys Tyr Gly Ala Phe Asp Val
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: >SEQ ID NO: 193 - anti-CD47-UCP01-A2 CDRH3

<400> SEQUENCE: 193

Ala Arg Asp Gly Leu Ser Val Ser Ser Gln Gly Val Ala Phe Asp Tyr
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: >SEQ ID NO: 194 - anti-CD47-UCP01-G2 CDRH3

<400> SEQUENCE: 194

Ala Arg Gly Leu Thr Val Ser Pro Tyr Trp Gly Gly Ala Phe Asp Tyr
1               5                   10                  15

<210> SEQ ID NO 195
<211> LENGTH: 17
<212> TYPE: PRT
<213> ORGANISM: Artificial Sequence
<220> FEATURE:
<223> OTHER INFORMATION: >SEQ ID NO: 195 - anti-CD47-UCP01-H2 CDRH3

<400> SEQUENCE: 195

```
Ala Arg Gly Arg Tyr Gly Val Ala Gly Gly Pro Gly Tyr Ala Phe Asp
1               5                   10                  15
Val
```

<210> SEQ ID NO 196
<211> LENGTH: 22
<212> TYPE: PRT
<213> ORGANISM: Artificial Sequence
<220> FEATURE:
<223> OTHER INFORMATION: >SEQ ID NO: 196 - anti-CD47-UCP01-A3 CDRH3

<400> SEQUENCE: 196

```
Ala Arg Gly Ser Ser Ile Ala Ala Tyr Ala Tyr Ala Ala Pro Tyr Arg
1               5                   10                  15
Gly Gly Trp Met Asp Val
            20
```

<210> SEQ ID NO 197
<211> LENGTH: 16
<212> TYPE: PRT
<213> ORGANISM: Artificial Sequence
<220> FEATURE:
<223> OTHER INFORMATION: >SEQ ID NO: 197 - anti-CD47-UCP01-B3 CDRH3

<400> SEQUENCE: 197

```
Ala Arg Gly Leu Ser Val Asp Lys Tyr Asp Gly Gly Pro Phe Asp Tyr
1               5                   10                  15
```

<210> SEQ ID NO 198
<211> LENGTH: 17
<212> TYPE: PRT
<213> ORGANISM: Artificial Sequence
<220> FEATURE:
<223> OTHER INFORMATION: >SEQ ID NO: 198 - anti-CD47-UCP02-C1 CDRH3

<400> SEQUENCE: 198

```
Ala Arg Ala Ser Tyr Gly Gly Pro Arg Tyr Tyr Trp Asp Gly Leu Asp
1               5                   10                  15
Ile
```

<210> SEQ ID NO 199
<211> LENGTH: 21
<212> TYPE: PRT
<213> ORGANISM: Artificial Sequence
<220> FEATURE:
<223> OTHER INFORMATION: >SEQ ID NO: 199 - anti-CD47-UCP02-H3 CDRH3

<400> SEQUENCE: 199

```
Ala Arg Ser Arg Tyr Tyr Arg Pro Tyr Gly Glu Tyr Tyr Val Val Gly
1               5                   10                  15
Tyr Gly Phe Ala Tyr
            20
```

<210> SEQ ID NO 200
<211> LENGTH: 20
<212> TYPE: PRT
<213> ORGANISM: Artificial Sequence
<220> FEATURE:
<223> OTHER INFORMATION: >SEQ ID NO: 200 - anti-CD47-UCP02-B3 CDRH3

<400> SEQUENCE: 200

```
Ala Arg Ser Arg Arg Pro Tyr Ser Ala Ser Ala Ser Tyr Pro Gly Tyr
1               5                   10                  15
```

Gly Met Asp Val
            20

<210> SEQ ID NO 201
<211> LENGTH: 13
<212> TYPE: PRT
<213> ORGANISM: Artificial Sequence
<220> FEATURE:
<223> OTHER INFORMATION: >SEQ ID NO: 201 - anti-CD47-UCP02-C2 CDRH3

<400> SEQUENCE: 201

Ala Arg Ser Tyr Ala Arg Ser Ser Tyr Gln Glu Asp Tyr
1               5                   10

<210> SEQ ID NO 202
<211> LENGTH: 17
<212> TYPE: PRT
<213> ORGANISM: Artificial Sequence
<220> FEATURE:
<223> OTHER INFORMATION: >SEQ ID NO: 202 - anti-CD38-UCP01-B1 CDRH3

<400> SEQUENCE: 202

Ala Arg Ala Val Ile Val Ser Pro Tyr Tyr Tyr Ile Tyr Val Phe Asp
1               5                   10                  15

Val

<210> SEQ ID NO 203
<211> LENGTH: 13
<212> TYPE: PRT
<213> ORGANISM: Artificial Sequence
<220> FEATURE:
<223> OTHER INFORMATION: >SEQ ID NO: 203 - anti-CD38-UCP01-D1 CDRH3

<400> SEQUENCE: 203

Ala Arg Thr Ile Gly Arg Tyr Ile Ile Ala Phe Asp Tyr
1               5                   10

<210> SEQ ID NO 204
<211> LENGTH: 14
<212> TYPE: PRT
<213> ORGANISM: Artificial Sequence
<220> FEATURE:
<223> OTHER INFORMATION: >SEQ ID NO: 204 - anti-CD38-UCP01-F1 CDRH3

<400> SEQUENCE: 204

Ala Arg Tyr Pro Tyr Pro Tyr Gly Ser Lys Tyr Phe Asp Ile
1               5                   10

<210> SEQ ID NO 205
<211> LENGTH: 15
<212> TYPE: PRT
<213> ORGANISM: Artificial Sequence
<220> FEATURE:
<223> OTHER INFORMATION: >SEQ ID NO: 205 - anti-CD38-UCP01-G1 CDRH3

<400> SEQUENCE: 205

Ala Arg Gly Ser Asp Asp Tyr Ala Ser Tyr Ser Pro Leu Asp Ser
1               5                   10                  15

<210> SEQ ID NO 206
<211> LENGTH: 10
<212> TYPE: PRT
<213> ORGANISM: Artificial Sequence
<220> FEATURE:
<223> OTHER INFORMATION: >SEQ ID NO: 206 - anti-CD38-UCP01-H1 CDRH3

<400> SEQUENCE: 206

-continued

Ala Arg Ser Ala Ala Gly Trp Phe Ala Tyr
1               5                   10

<210> SEQ ID NO 207
<211> LENGTH: 9
<212> TYPE: PRT
<213> ORGANISM: Artificial Sequence
<220> FEATURE:
<223> OTHER INFORMATION: >SEQ ID NO: 207 - anti-CD38-UCP01-C2 CDRH3

<400> SEQUENCE: 207

Ala Arg Gly Gly Val Trp Trp Asp Tyr
1               5

<210> SEQ ID NO 208
<211> LENGTH: 16
<212> TYPE: PRT
<213> ORGANISM: Artificial Sequence
<220> FEATURE:
<223> OTHER INFORMATION: >SEQ ID NO: 208 - anti-CD38-UCP01-E2 CDRH3

<400> SEQUENCE: 208

Ala Arg Gly Leu Gly Tyr Tyr Leu Tyr Ser Ser Tyr Tyr Phe Asp Ile
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: >SEQ ID NO: 209 - anti-CD38-UCP02-A7 CDRH3

<400> SEQUENCE: 209

Ala Arg Asp Pro Ser Tyr Ile Tyr Ser Thr Ser Gly Tyr Phe Asp Tyr
1               5                   10                  15

<210> SEQ ID NO 210
<211> LENGTH: 18
<212> TYPE: PRT
<213> ORGANISM: Artificial Sequence
<220> FEATURE:
<223> OTHER INFORMATION: >SEQ ID NO: 210 - anti-CD38-UCP02-B1 CDRH3

<400> SEQUENCE: 210

Ala Arg Trp Ser Tyr Thr Tyr Gly Ile Arg Tyr Tyr Tyr Lys Leu Phe
1               5                   10                  15

Asp Pro

<210> SEQ ID NO 211
<211> LENGTH: 13
<212> TYPE: PRT
<213> ORGANISM: Artificial Sequence
<220> FEATURE:
<223> OTHER INFORMATION: >SEQ ID NO: 211 - anti-CD38-UCP02-B7 CDRH3

<400> SEQUENCE: 211

Ala Arg Ser Pro Gly Ile Pro Tyr His Tyr Phe Asp Val
1               5                   10

<210> SEQ ID NO 212
<211> LENGTH: 14
<212> TYPE: PRT
<213> ORGANISM: Artificial Sequence
<220> FEATURE:
<223> OTHER INFORMATION: >SEQ ID NO: 212 - anti-CD38-UCP02-C3 CDRH3

```
<400> SEQUENCE: 212

Ala Arg Ala Thr Ser Pro Leu Tyr Ser Tyr Tyr Phe Asp Tyr
1               5                   10

<210> SEQ ID NO 213
<211> LENGTH: 17
<212> TYPE: PRT
<213> ORGANISM: Artificial Sequence
<220> FEATURE:
<223> OTHER INFORMATION: >SEQ ID NO: 213 - anti-CD38-UCP02-D1 CDRH3

<400> SEQUENCE: 213

Ala Arg Ala Val Ile Val Ser Pro Tyr Tyr Tyr Ile Tyr Val Phe Asp
1               5                   10                  15

Val

<210> SEQ ID NO 214
<211> LENGTH: 15
<212> TYPE: PRT
<213> ORGANISM: Artificial Sequence
<220> FEATURE:
<223> OTHER INFORMATION: >SEQ ID NO: 214 - anti-CD38-UCP02-D5 CDRH3

<400> SEQUENCE: 214

Ala Arg Glu Gln Tyr Tyr Tyr Ala Leu Gly Gly Gly Phe Asp Tyr
1               5                   10                  15

<210> SEQ ID NO 215
<211> LENGTH: 10
<212> TYPE: PRT
<213> ORGANISM: Artificial Sequence
<220> FEATURE:
<223> OTHER INFORMATION: >SEQ ID NO: 215 - anti-CD38-UCP02-E5 CDRH3

<400> SEQUENCE: 215

Ala Arg Gly Tyr Trp His Trp Phe Asp Tyr
1               5                   10

<210> SEQ ID NO 216
<211> LENGTH: 14
<212> TYPE: PRT
<213> ORGANISM: Artificial Sequence
<220> FEATURE:
<223> OTHER INFORMATION: >SEQ ID NO: 216 - anti-CD38-UCP02-F2 CDRH3

<400> SEQUENCE: 216

Ala Arg Gly Arg Asp Val Leu Arg Ser Tyr Tyr Phe Asp Ile
1               5                   10

<210> SEQ ID NO 217
<211> LENGTH: 14
<212> TYPE: PRT
<213> ORGANISM: Artificial Sequence
<220> FEATURE:
<223> OTHER INFORMATION: >SEQ ID NO: 217 - anti-CD38-UCP02-F5 CDRH3

<400> SEQUENCE: 217

Ala Arg Ser Asp Ser Phe Tyr Tyr Ala Tyr Tyr Met Asp Leu
1               5                   10

<210> SEQ ID NO 218
<211> LENGTH: 16
<212> TYPE: PRT
<213> ORGANISM: Artificial Sequence
<220> FEATURE:
<223> OTHER INFORMATION: >SEQ ID NO: 218 - anti-CD38-UCP02-F6 CDRH3
```

<400> SEQUENCE: 218

Ala Arg Glu Pro Val Ser Tyr Asp Tyr Tyr Gly Ser Tyr Phe Asp Tyr
1               5                   10                  15

<210> SEQ ID NO 219
<211> LENGTH: 13
<212> TYPE: PRT
<213> ORGANISM: Artificial Sequence
<220> FEATURE:
<223> OTHER INFORMATION: >SEQ ID NO: 219 - anti-CD38-UCP02-H1 CDRH3

<400> SEQUENCE: 219

Ala Arg Ser Trp Gly Phe Arg Ala Gly Tyr Leu Asp Tyr
1               5                   10

<210> SEQ ID NO 220
<211> LENGTH: 14
<212> TYPE: PRT
<213> ORGANISM: Artificial Sequence
<220> FEATURE:
<223> OTHER INFORMATION: >SEQ ID NO: 220 - anti-CD38-UCP03-B3 CDRH3

<400> SEQUENCE: 220

Ala Arg Ser Trp Pro Ser Leu Gly Ser Gly Trp Phe Asp Ile
1               5                   10

<210> SEQ ID NO 221
<211> LENGTH: 14
<212> TYPE: PRT
<213> ORGANISM: Artificial Sequence
<220> FEATURE:
<223> OTHER INFORMATION: >SEQ ID NO: 221 - anti-CD38-UCP03-C3 CDRH3

<400> SEQUENCE: 221

Ala Arg Ala Ser Phe Leu Tyr Tyr Ser Tyr Tyr Phe Asp Tyr
1               5                   10

<210> SEQ ID NO 222
<211> LENGTH: 9
<212> TYPE: PRT
<213> ORGANISM: Artificial Sequence
<220> FEATURE:
<223> OTHER INFORMATION: >SEQ ID NO: 222 - anti-CD38-UCP03-H5 CDRH3

<400> SEQUENCE: 222

Ala Arg Gly Ser Tyr Arg Phe Asp Val
1               5

<210> SEQ ID NO 223
<211> LENGTH: 14
<212> TYPE: PRT
<213> ORGANISM: Artificial Sequence
<220> FEATURE:
<223> OTHER INFORMATION: >SEQ ID NO: 223 - anti-CD38-UCP03-B6 CDRH3

<400> SEQUENCE: 223

Ala Arg Ser Arg Gly Tyr Tyr Gly Ser Phe Tyr Phe Asp Ile
1               5                   10

<210> SEQ ID NO 224
<211> LENGTH: 15
<212> TYPE: PRT
<213> ORGANISM: Artificial Sequence
<220> FEATURE:
<223> OTHER INFORMATION: >SEQ ID NO: 224 - anti-CD38-UCP03-E3 CDRH3

<400> SEQUENCE: 224

Ala Arg Gly Pro Tyr Asp Ser Tyr Gly Glu Ser Tyr Phe Asp Tyr
1               5                   10                  15

<210> SEQ ID NO 225
<211> LENGTH: 14
<212> TYPE: PRT
<213> ORGANISM: Artificial Sequence
<220> FEATURE:
<223> OTHER INFORMATION: >SEQ ID NO: 225 - anti-CD38-UCP03-A6 CDRH3

<400> SEQUENCE: 225

Ala Arg Gly His Arg Val Tyr Ser Ser Ser Pro Phe Asp Tyr
1               5                   10

<210> SEQ ID NO 226
<211> LENGTH: 15
<212> TYPE: PRT
<213> ORGANISM: Artificial Sequence
<220> FEATURE:
<223> OTHER INFORMATION: >SEQ ID NO: 226 - anti-CD38-UCP03-B1 CDRH3

<400> SEQUENCE: 226

Ala Arg Gly Ser Asp Asp Tyr Ala Ser Tyr Ser Pro Leu Asp Ser
1               5                   10                  15

<210> SEQ ID NO 227
<211> LENGTH: 14
<212> TYPE: PRT
<213> ORGANISM: Artificial Sequence
<220> FEATURE:
<223> OTHER INFORMATION: >SEQ ID NO: 227 - anti-CD38-UCP03-C2 CDRH3

<400> SEQUENCE: 227

Ala Arg Gly Arg Val Leu Tyr Tyr Ser Tyr Tyr Phe Asp Tyr
1               5                   10

<210> SEQ ID NO 228
<211> LENGTH: 13
<212> TYPE: PRT
<213> ORGANISM: Artificial Sequence
<220> FEATURE:
<223> OTHER INFORMATION: >SEQ ID NO: 228 - anti-CD38-UCP03-H2 CDRH3

<400> SEQUENCE: 228

Ala Arg Gly Lys Ala Tyr Tyr Ser Gly Trp Leu Ala Ile
1               5                   10

<210> SEQ ID NO 229
<211> LENGTH: 8
<212> TYPE: PRT
<213> ORGANISM: Artificial Sequence
<220> FEATURE:
<223> OTHER INFORMATION: >SEQ ID NO: 229 - anti-CD38-UCP03-H3 CDRH3

<400> SEQUENCE: 229

Ala Arg Val Tyr Gly Gly Ile Asp
1               5

<210> SEQ ID NO 230
<211> LENGTH: 16
<212> TYPE: PRT
<213> ORGANISM: Artificial Sequence
<220> FEATURE:
<223> OTHER INFORMATION: >SEQ ID NO: 230 - anti-CD38-E2-UCP01-A10 CDRH3

<400> SEQUENCE: 230

Ala Arg Gly Leu Gly Tyr Tyr Leu Tyr Ser Ser Tyr Tyr Phe Asp Ile
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: >SEQ ID NO: 231 - anti-CD38-E2-UCP02-E7 CDRH3

<400> SEQUENCE: 231

Ala Arg Gly Leu Gly Tyr Tyr Leu Tyr Ser Ser Tyr Tyr Phe Asp Ile
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: >SEQ ID NO: 232 - anti-CD38-E2-UCP02-F3 CDRH3

<400> SEQUENCE: 232

Ala Arg Gly Leu Gly Tyr Tyr Leu Tyr Ser Ser Tyr Tyr Phe Asp Ile
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: >SEQ ID NO: 233 - anti-CD38-E2-UCP02-D6 CDRH3

<400> SEQUENCE: 233

Ala Arg Gly Leu Gly Tyr Tyr Leu Tyr Ser Ser Tyr Tyr Phe Asp Ile
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: >SEQ ID NO: 234 - anti-CD38-E2-UCP02-G8 CDRH3

<400> SEQUENCE: 234

Ala Arg Gly Leu Gly Tyr Tyr Leu Tyr Ser Ser Tyr Tyr Phe Asp Ile
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: >SEQ ID NO: 235 - anti-CD38-E2-UCP02-F8 CDRH3

<400> SEQUENCE: 235

Ala Arg Gly Leu Gly Tyr Tyr Leu Tyr Ser Ser Tyr Tyr Phe Asp Ile
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: >SEQ ID NO: 236 - anti-CD38-E2-UCP02-A5 CDRH3

<400> SEQUENCE: 236

```
Ala Arg Gly Leu Gly Tyr Tyr Leu Tyr Ser Ser Tyr Tyr Phe Asp Ile
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: >SEQ ID NO: 237 - anti-CD38-E2-RecA CDRH3

<400> SEQUENCE: 237

Ala Arg Gly Leu Gly Tyr Tyr Leu Tyr Ser Ser Tyr Tyr Phe Asp Ile
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: >SEQ ID NO: 238 - anti-CD38-E2-RecB CDRH3

<400> SEQUENCE: 238

Ala Arg Gly Leu Gly Tyr Tyr Leu Tyr Ser Ser Tyr Tyr Phe Asp Ile
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: >SEQ ID NO: 239 - anti-CD38-E2-RecC CDRH3

<400> SEQUENCE: 239

Ala Arg Gly Leu Gly Tyr Tyr Leu Tyr Ser Ser Tyr Tyr Phe Asp Ile
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: >SEQ ID NO: 240 - anti-CD38-E2-RecD CDRH3

<400> SEQUENCE: 240

Ala Arg Gly Leu Gly Tyr Tyr Leu Tyr Ser Ser Tyr Tyr Phe Asp Ile
1               5                   10                  15

<210> SEQ ID NO 241
<211> LENGTH: 14
<212> TYPE: PRT
<213> ORGANISM: Artificial Sequence
<220> FEATURE:
<223> OTHER INFORMATION: >SEQ ID NO: 241 - anti-CD38-B6-MP01-D9 CDRH3

<400> SEQUENCE: 241

Ala Arg Ser Arg Gly Tyr Tyr Gly Ser Phe Tyr Phe Asp Ile
1               5                   10

<210> SEQ ID NO 242
<211> LENGTH: 14
<212> TYPE: PRT
<213> ORGANISM: Artificial Sequence
<220> FEATURE:
<223> OTHER INFORMATION: >SEQ ID NO: 242 - anti-CD38-B6-MP01-B4 CDRH3

<400> SEQUENCE: 242

Ala Arg Ser Arg Gly Tyr Tyr Gly Ser Phe Tyr Phe Asp Ile
```

```
1               5                   10

<210> SEQ ID NO 243
<211> LENGTH: 14
<212> TYPE: PRT
<213> ORGANISM: Artificial Sequence
<220> FEATURE:
<223> OTHER INFORMATION: >SEQ ID NO: 243 - anti-CD38-B6-MP02-C1 CDRH3

<400> SEQUENCE: 243

Ala Arg Ser Arg Gly Tyr Tyr Gly Ser Phe Tyr Phe Asp Ile
1               5                   10

<210> SEQ ID NO 244
<211> LENGTH: 14
<212> TYPE: PRT
<213> ORGANISM: Artificial Sequence
<220> FEATURE:
<223> OTHER INFORMATION: >SEQ ID NO: 244 - anti-CD38-B6-MP02-B10 CDRH3

<400> SEQUENCE: 244

Ala Arg Ser Arg Gly Tyr Tyr Gly Ser Phe Tyr Phe Asp Ile
1               5                   10

<210> SEQ ID NO 245
<211> LENGTH: 14
<212> TYPE: PRT
<213> ORGANISM: Artificial Sequence
<220> FEATURE:
<223> OTHER INFORMATION: >SEQ ID NO: 245 - anti-CD38-B6-MP01-H3a CDRH3

<400> SEQUENCE: 245

Ala Arg Ser Arg Gly Tyr Tyr Gly Ser Phe Tyr Phe Asp Ile
1               5                   10

<210> SEQ ID NO 246
<211> LENGTH: 14
<212> TYPE: PRT
<213> ORGANISM: Artificial Sequence
<220> FEATURE:
<223> OTHER INFORMATION: >SEQ ID NO: 246 - anti-CD38-B6-MP01-H3b CDRH3

<400> SEQUENCE: 246

Ala Arg Ser Arg Gly Tyr Tyr Gly Ser Phe Tyr Phe Asp Ile
1               5                   10

<210> SEQ ID NO 247
<211> LENGTH: 14
<212> TYPE: PRT
<213> ORGANISM: Artificial Sequence
<220> FEATURE:
<223> OTHER INFORMATION: >SEQ ID NO: 247 - anti-CD38-B6-MP01-A4 CDRH3

<400> SEQUENCE: 247

Ala Arg Ser Arg Gly Tyr Tyr Gly Ser Phe Tyr Phe Asp Ile
1               5                   10

<210> SEQ ID NO 248
<211> LENGTH: 14
<212> TYPE: PRT
<213> ORGANISM: Artificial Sequence
<220> FEATURE:
<223> OTHER INFORMATION: >SEQ ID NO: 248 - anti-CD38-B6-MP01-C2 CDRH3

<400> SEQUENCE: 248

Ala Arg Ser Arg Gly Tyr Tyr Gly Ser Phe Tyr Phe Asp Ile
1               5                   10
```

```
<210> SEQ ID NO 249
<211> LENGTH: 14
<212> TYPE: PRT
<213> ORGANISM: Artificial Sequence
<220> FEATURE:
<223> OTHER INFORMATION: >SEQ ID NO: 249 - anti-CD38-B6-MP02-C2 CDRH3

<400> SEQUENCE: 249

Ala Arg Ser Arg Gly Tyr Tyr Gly Ser Phe Tyr Phe Asp Ile
1               5                   10

<210> SEQ ID NO 250
<211> LENGTH: 14
<212> TYPE: PRT
<213> ORGANISM: Artificial Sequence
<220> FEATURE:
<223> OTHER INFORMATION: >SEQ ID NO: 250 - anti-CD38-B6-MP02-G11 CDRH3

<400> SEQUENCE: 250

Ala Arg Ser Arg Gly Tyr Tyr Gly Ser Phe Tyr Phe Asp Ile
1               5                   10

<210> SEQ ID NO 251
<211> LENGTH: 10
<212> TYPE: PRT
<213> ORGANISM: Artificial Sequence
<220> FEATURE:
<223> OTHER INFORMATION: >SEQ ID NO: 251 - anti-CD38-E2 derivatives
      CDRH1 consensus

<400> SEQUENCE: 251

Gly Leu Pro Asp Ala Thr Tyr Ala Ile Gln
1               5                   10

<210> SEQ ID NO 252
<211> LENGTH: 10
<212> TYPE: PRT
<213> ORGANISM: Artificial Sequence
<220> FEATURE:
<223> OTHER INFORMATION: >SEQ ID NO: 252 - anti-CD38-E2 derivatives
      CDRH2 consensus
<220> FEATURE:
<221> NAME/KEY: VARIANT
<222> LOCATION: (5)..(5)
<223> OTHER INFORMATION: Where X at position 5 can be V, A, S, D, or R.
<220> FEATURE:
<221> NAME/KEY: VARIANT
<222> LOCATION: (7)..(7)
<223> OTHER INFORMATION: Where X at position 7 can be A, G, or D.
<220> FEATURE:
<221> NAME/KEY: VARIANT
<222> LOCATION: (8)..(8)
<223> OTHER INFORMATION: Where X at position 8 can be A or G.
<220> FEATURE:
<221> NAME/KEY: VARIANT
<222> LOCATION: (9)..(9)
<223> OTHER INFORMATION: Where X at position 9 can be V, A, G, T, or E.

<400> SEQUENCE: 252

Arg Ile Ile Pro Xaa Phe Xaa Xaa Xaa His
1               5                   10

<210> SEQ ID NO 253
<211> LENGTH: 16
<212> TYPE: PRT
<213> ORGANISM: Artificial Sequence
<220> FEATURE:
<223> OTHER INFORMATION: >SEQ ID NO: 253 - anti-CD38-E2 derivatives
      CDRH3 consensus
```

<400> SEQUENCE: 253

Ala Arg Gly Leu Gly Tyr Tyr Leu Tyr Ser Ser Tyr Tyr Phe Asp Ile
1               5                   10                  15

<210> SEQ ID NO 254
<211> LENGTH: 10
<212> TYPE: PRT
<213> ORGANISM: Artificial Sequence
<220> FEATURE:
<223> OTHER INFORMATION: >SEQ ID NO: 254 - anti-CD38-B6 derivatives
      CDRH1 consensus
<220> FEATURE:
<221> NAME/KEY: VARIANT
<222> LOCATION: (2)..(2)
<223> OTHER INFORMATION: Where X at position 2 can be G or Y.
<220> FEATURE:
<221> NAME/KEY: VARIANT
<222> LOCATION: (3)..(3)
<223> OTHER INFORMATION: Where X at position 3 can be F, A, P, H, or E.
<220> FEATURE:
<221> NAME/KEY: VARIANT
<222> LOCATION: (4)..(4)
<223> OTHER INFORMATION: Where X at position 4 can be F, G, T, Q, or N.
<220> FEATURE:
<221> NAME/KEY: VARIANT
<222> LOCATION: (5)..(5)
<223> OTHER INFORMATION: Where X at position 5 can be L, S, Q, or N.
<220> FEATURE:
<221> NAME/KEY: VARIANT
<222> LOCATION: (6)..(6)
<223> OTHER INFORMATION: Where X at position 6 can be A, G, T, S, P, H,
      Q, or D.
<220> FEATURE:
<221> NAME/KEY: VARIANT
<222> LOCATION: (7)..(7)
<223> OTHER INFORMATION: Where X at position 7 can be Y, P, N, K, or R.
<220> FEATURE:
<221> NAME/KEY: VARIANT
<222> LOCATION: (8)..(8)
<223> OTHER INFORMATION: Where X at position 8 can be I or V.
<220> FEATURE:
<221> NAME/KEY: VARIANT
<222> LOCATION: (9)..(9)
<223> OTHER INFORMATION: Where X at position 9 can be I or V.
<220> FEATURE:
<221> NAME/KEY: VARIANT
<222> LOCATION: (10)..(10)
<223> OTHER INFORMATION: Where X at position 10 can be S or N.

<400> SEQUENCE: 254

Gly Xaa Xaa Xaa Xaa Xaa Xaa Xaa Xaa Xaa
1               5                   10

<210> SEQ ID NO 255
<211> LENGTH: 10
<212> TYPE: PRT
<213> ORGANISM: Artificial Sequence
<220> FEATURE:
<223> OTHER INFORMATION: >SEQ ID NO: 255 - anti-CD38-B6 derivatives
      CDRH2 consensus

<400> SEQUENCE: 255

Arg Val Ile Pro Val Ile Asp Asp Ala Tyr
1               5                   10

<210> SEQ ID NO 256
<211> LENGTH: 14
<212> TYPE: PRT
<213> ORGANISM: Artificial Sequence
<220> FEATURE:
<223> OTHER INFORMATION: >SEQ ID NO: 256 - anti-CD38-B6 derivatives
      CDRH3 consensus

<400> SEQUENCE: 256

Ala Arg Ser Arg Gly Tyr Tyr Gly Ser Phe Tyr Phe Asp Ile
1               5                   10

<210> SEQ ID NO 257
<211> LENGTH: 226
<212> TYPE: PRT
<213> ORGANISM: Artificial Sequence
<220> FEATURE:
<223> OTHER INFORMATION: >SEQ ID NO: 257 - BEAT (A) Fc

<400> SEQUENCE: 257

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Ala Val
        115                 120                 125

Tyr Thr Leu Pro Pro Ser Arg Glu Glu Met Thr Lys Asn Gln Val Lys
    130                 135                 140

Leu Val Cys Leu Val Thr Gly Phe Tyr Pro Ser Asp Ile Ala Val Glu
145                 150                 155                 160

Trp Glu Ser Ser Gly Gln Pro Glu Asn Asn Tyr Tyr Thr Thr Pro Pro
                165                 170                 175

Met Leu Asp Ser Asp Gly Ser Phe Ser Leu Val Ser Trp Leu Asn Val
            180                 185                 190

Asp Lys Ser Arg Trp Gln Gln Gly Asn Ile Phe Ser Cys Ser Val Met
        195                 200                 205

His Glu Ala Leu His Asn Arg Phe Thr Gln Lys Ser Leu Ser Leu Ser
    210                 215                 220

Pro Gly
225

<210> SEQ ID NO 258
<211> LENGTH: 226
<212> TYPE: PRT
<213> ORGANISM: Artificial Sequence
<220> FEATURE:
<223> OTHER INFORMATION: >SEQ ID NO: 258 -?? BEAT (B) Fc

<400> SEQUENCE: 258

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

```
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Glu Val
                115                 120                 125

Ala Thr Phe Pro Pro Ser Arg Asp Glu Leu Thr Lys Asn Gln Val Thr
130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Gln Gly Ser Phe Ala Leu Ser Ser Arg Leu Arg Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
210                 215                 220

Pro Gly
225

<210> SEQ ID NO 259
<211> LENGTH: 452
<212> TYPE: PRT
<213> ORGANISM: Artificial Sequence
<220> FEATURE:
<223> OTHER INFORMATION: >SEQ ID NO: 259 -?? BEAT CD38/CD47-3, -6, -19,
      -38 BEAT (A) Hc

<400> SEQUENCE: 259

Glu Val Gln Leu Val Glu Ser Gly Gly Gly Leu Ile Gln Pro Gly Gly
1                   5                  10                  15

Ser Leu Arg Leu Ser Cys Ala Ala Ser Gly Phe Thr Leu Ser Arg Asn
                 20                  25                  30

Thr Met His Trp Val Arg Gln Ala Pro Gly Lys Gly Leu Glu Trp Val
                 35                  40                  45

Ser Val Ile Tyr Gln Ser Gly Val Thr Arg Tyr Ala Asp Ser Val Lys
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Arg Tyr Gly Val Ala Gly Gly Pro Gly Tyr Ala Phe Asp Val
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Val Glu Pro Lys
        210                 215                 220
Ser Cys Asp Lys Thr His Thr Cys Pro Cys Pro Ala Pro Glu Leu
225                 230                 235                 240
Leu Gly Gly Pro Ser Val Phe Leu Phe Pro Pro Lys Pro Lys Asp Thr
            245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
            290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Ala Val Tyr Thr Leu Pro Pro Ser Arg Glu Glu Met Thr Lys Asn Gln
            355                 360                 365
Val Lys Leu Val Cys Leu Val Thr Gly Phe Tyr Pro Ser Asp Ile Ala
        370                 375                 380
Val Glu Trp Glu Ser Ser Gly Gln Pro Glu Asn Asn Tyr Tyr Thr Thr
385                 390                 395                 400
Pro Pro Met Leu Asp Ser Asp Gly Ser Phe Ser Leu Val Ser Trp Leu
                405                 410                 415
Asn Val Asp Lys Ser Arg Trp Gln Gln Gly Asn Ile Phe Ser Cys Ser
            420                 425                 430
Val Met His Glu Ala Leu His Asn Arg Phe Thr Gln Lys Ser Leu Ser
            435                 440                 445
Leu Ser Pro Gly
    450

<210> SEQ ID NO 260
<211> LENGTH: 452
<212> TYPE: PRT
<213> ORGANISM: Artificial Sequence
<220> FEATURE:
<223> OTHER INFORMATION: >SEQ ID NO: 260 -?? BEAT CD38/CD47-3 BEAT (B)
      Hc

<400> SEQUENCE: 260

Gln Val Gln Leu Val Gln Ser Gly Ala Glu Val Lys Lys Pro Gly Ser
1               5                   10                  15
Ser Val Lys Val Ser Cys Lys Ala Ser Gly Gly Ser Phe Ser Asn Tyr
            20                  25                  30
Ala Ile Gly Trp Val Arg Gln Ala Pro Gly Gln Gly Leu Glu Trp Met
        35                  40                  45
Gly Arg Ile Ile Pro Val Leu Asp Ala Ala His Tyr Ala Gln Lys Phe
    50                  55                  60
```

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Glu Val Ala Thr Phe Pro Pro Ser Arg Asp Glu Leu Thr Lys Asn Gln
        355                 360                 365

Val Thr Leu Val Cys Leu Val Thr Gly Phe Tyr Pro Ser Asp Ile Ala
370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 261
<211> LENGTH: 452
<212> TYPE: PRT

<213> ORGANISM: Artificial Sequence
<220> FEATURE:
<223> OTHER INFORMATION: >SEQ ID NO: 261 ?? BEAT CD38/CD47-6 BEAT (B) Hc

<400> SEQUENCE: 261

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Gly | Ser | Phe | Ser | Asn | Tyr |
| | | | 20 | | | | | 25 | | | | | 30 | | |
| Ala | Ile | Gly | Trp | Val | Arg | Gln | Ala | Pro | Gly | Gln | Gly | Leu | Glu | Trp | Met |
| | | | 35 | | | | | 40 | | | | | 45 | | |
| Gly | Arg | Ile | Ile | Pro | Ser | Leu | Asp | Ala | Gly | His | Tyr | Ala | Gln | Lys | Phe |
| | 50 | | | | | 55 | | | | | 60 | | | | |
| Gln | Gly | Arg | Val | Thr | Ile | Thr | Ala | Asp | Glu | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Leu | Gly | Tyr | Tyr | Leu | Tyr | Ser | Ser | Tyr | Tyr | Phe | Asp | Ile |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | 195 | | | | | 200 | | | | | 205 | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | | 275 | | | | | 280 | | | | | 285 | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Glu | Val | Ala | Thr | Phe | Pro | Pro | Ser | Arg | Asp | Glu | Leu | Thr | Lys | Asn | Gln |
| | | | 355 | | | | | 360 | | | | | 365 | | |
| Val | Thr | Leu | Val | Cys | Leu | Val | Thr | Gly | Phe | Tyr | Pro | Ser | Asp | Ile | Ala |
| | 370 | | | | | 375 | | | | | 380 | | | | |
| Val | Glu | Trp | Glu | Ser | Asn | Gly | Gln | Pro | Glu | Asn | Asn | Tyr | Lys | Thr | Asp |

```
                385                 390                 395                 400
Pro Pro Leu Leu Glu Ser Gln Gly Ser Phe Ala Leu Ser Ser Arg Leu
                    405                 410                 415

Arg Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
        450

<210> SEQ ID NO 262
<211> LENGTH: 452
<212> TYPE: PRT
<213> ORGANISM: Artificial Sequence
<220> FEATURE:
<223> OTHER INFORMATION: >SEQ ID NO: 262 -?? BEAT CD38/CD47-19 BEAT (B)
      Hc

<400> SEQUENCE: 262

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Ala Thr Phe Pro Pro Ser Arg Asp Glu Leu Thr Lys Asn Gln
        355                 360                 365

Val Thr Leu Val Cys Leu Val Thr Gly Phe Tyr Pro Ser Asp Ile Ala
370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
450

<210> SEQ ID NO 263
<211> LENGTH: 450
<212> TYPE: PRT
<213> ORGANISM: Artificial Sequence
<220> FEATURE:
<223> OTHER INFORMATION: >SEQ ID NO: 263 -?? Trastuzumab Hc

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 264
<211> LENGTH: 214
<212> TYPE: PRT
<213> ORGANISM: Artificial Sequence
<220> FEATURE:
<223> OTHER INFORMATION: >SEQ ID NO: 264 -?? Trastuzumab Lc

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

-continued

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 265
<211> LENGTH: 214
<212> TYPE: PRT
<213> ORGANISM: Artificial Sequence
<220> FEATURE:
<223> OTHER INFORMATION: >SEQ ID NO: 265 - ABC IgG1 Lc

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 266
<211> LENGTH: 446

```
<212> TYPE: PRT
<213> ORGANISM: Artificial Sequence
<220> FEATURE:
<223> OTHER INFORMATION: >SEQ ID NO: 266 - ABC IgG1 Hc

<400> SEQUENCE: 266

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Tyr Gly Ala Phe Asp Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 267
<211> LENGTH: 444
<212> TYPE: PRT
<213> ORGANISM: Artificial Sequence
<220> FEATURE:
<223> OTHER INFORMATION: >SEQ ID NO: 267 - 5F9-G4 Hc

<400> SEQUENCE: 267

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 268
<211> LENGTH: 219
<212> TYPE: PRT
<213> ORGANISM: Artificial Sequence
<220> FEATURE:
<223> OTHER INFORMATION: >SEQ ID NO: 268 - 5F9-G4 Lc

<400> SEQUENCE: 268

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
                20                  25                  30

Asn Gly Asn Thr Tyr Leu Gly Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 269
<211> LENGTH: 308
<212> TYPE: PRT
<213> ORGANISM: Artificial Sequence
<220> FEATURE:
<223> OTHER INFORMATION: >SEQ ID NO: 269 - human FcRn-Avi-His

<400> SEQUENCE: 269

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Ser Pro Ala Lys
            260                 265                 270

Ser Ser Gly Gly Gly Gly Thr Gly Gly Leu Asn Asp Ile Phe Glu Ala
        275                 280                 285

Gln Lys Ile Glu Trp His Glu Gly Gly His His His His His
    290                 295                 300

His His His His
305

<210> SEQ ID NO 270
<211> LENGTH: 99
<212> TYPE: PRT
<213> ORGANISM: Artificial Sequence
<220> FEATURE:
<223> OTHER INFORMATION: >SEQ ID NO: 270 - human beta 2-microglobulin

<400> SEQUENCE: 270
```

```
Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 271
<211> LENGTH: 185
<212> TYPE: PRT
<213> ORGANISM: Artificial Sequence
<220> FEATURE:
<223> OTHER INFORMATION: >SEQ ID NO: 271 - human FcgR2a-C-10His

<400> SEQUENCE: 271

Gln Ala Ala Pro Pro Lys Ala Val Leu Lys Leu Glu Pro Pro Trp
1               5                   10                  15

Ile Asn Val Leu Gln Glu Asp Ser Val Thr Leu Thr Cys Gln Gly Ala
                20                  25                  30

Arg Ser Pro Glu Ser Asp Ser Ile Gln Trp Phe His Asn Gly Asn Leu
            35                  40                  45

Ile Pro Thr His Thr Gln Pro Ser Tyr Arg Phe Lys Ala Asn Asn Asn
50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Met Leu Arg Cys His Ser
            100                 105                 110

Trp Lys Asp Lys Pro Leu Val Lys Val Thr Phe Phe Gln Asn Gly Lys
        115                 120                 125

Ser Gln Lys Phe Ser Arg Leu Asp Pro Thr Phe Ser Ile Pro Gln Ala
    130                 135                 140

Asn His Ser His Ser Gly Asp Tyr His Cys Thr Gly Asn Ile Gly Tyr
145                 150                 155                 160

Thr Leu Phe Ser Ser Lys Pro Val Thr Ile Thr Val Gln Val Pro His
                165                 170                 175

His His His His His His His His
            180                 185

<210> SEQ ID NO 272
<211> LENGTH: 178
<212> TYPE: PRT
<213> ORGANISM: Artificial Sequence
<220> FEATURE:
<223> OTHER INFORMATION: >SEQ ID NO: 272 - human FcgR2b-C-His

<400> SEQUENCE: 272

Ala Pro Pro Lys Ala Val Leu Lys Leu Glu Pro Gln Trp Ile Asn Val
1               5                   10                  15
```

```
Leu Gln Glu Asp Ser Val Thr Leu Thr Cys Arg Gly Thr His Ser Pro
             20                  25                  30

Glu Ser Asp Ser Ile Gln Trp Phe His Asn Gly Asn Leu Ile Pro Thr
         35                  40                  45

His Thr Gln Pro Ser Tyr Arg Phe Lys Ala Asn Asn Asn Asp Ser Gly
 50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                 85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
            115                 120                 125

Phe Ser Arg Ser Asp Pro Asn Phe Ser Ile Pro Gln Ala Asn His Ser
130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro His His His His
                165                 170                 175

His His

<210> SEQ ID NO 273
<211> LENGTH: 185
<212> TYPE: PRT
<213> ORGANISM: Artificial Sequence
<220> FEATURE:
<223> OTHER INFORMATION: >SEQ ID NO: 273 - human FcgR3a-C-His

<400> SEQUENCE: 273

Gly Met Arg Thr Glu Asp Leu Pro Lys Ala Val Val Phe Leu Glu Pro
1               5                  10                  15

Gln Trp Tyr Arg Val Leu Glu Lys Asp Ser Val Thr Leu Lys Cys Gln
             20                  25                  30

Gly Ala Tyr Ser Pro Glu Asp Asn Ser Thr Gln Trp Phe His Asn Glu
         35                  40                  45

Ser Leu Ile Ser Ser Gln Ala Ser Ser Tyr Phe Ile Asp Ala Ala Thr
 50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                 85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
            115                 120                 125

Gly Lys Gly Arg Lys Tyr Phe His His Asn Ser Asp Phe Tyr Ile Pro
            130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Ser Ala His His His His His His
                180                 185
```

<210> SEQ ID NO 274
<211> LENGTH: 452
<212> TYPE: PRT
<213> ORGANISM: Artificial Sequence
<220> FEATURE:
<223> OTHER INFORMATION: >SEQ ID NO: 274 -?? BEAT CD38/CD47-21 BEAT (A) Hc

<400> SEQUENCE: 274

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn
            20                  25                  30

Thr Met His Trp Val Arg Gln Ala Pro Gly Lys Gly Leu Glu Trp Val
        35                  40                  45

Ser Val Ile Tyr Gln Ser Gly Val Thr Arg Tyr Ala Asp Ser Val Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Gly Val Ala Gly Gly Pro Gly Tyr Ala Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Cys Pro Ala Pro Glu Leu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Glu Thr Ile Ser Lys Ala Lys Gly Gln Pro Arg Glu Pro
            340                 345                 350

Ala Val Tyr Thr Leu Pro Pro Ser Arg Glu Glu Met Thr Lys Asn Gln
        355                 360                 365
```

```
Val Lys Leu Val Cys Leu Val Thr Gly Phe Tyr Pro Ser Asp Ile Ala
        370                 375                 380

Val Glu Trp Glu Ser Ser Gly Gln Pro Glu Asn Asn Tyr Tyr Thr Thr
385                 390                 395                 400

Pro Pro Met Leu Asp Ser Asp Gly Ser Phe Ser Leu Val Ser Trp Leu
                405                 410                 415

Asn Val Asp Lys Ser Arg Trp Gln Gln Gly Asn Ile Phe Ser Cys Ser
                420                 425                 430

Val Met His Glu Ala Leu His Asn Arg Phe Thr Gln Lys Ser Leu Ser
                435                 440                 445

Leu Ser Pro Gly
        450

<210> SEQ ID NO 275
<211> LENGTH: 452
<212> TYPE: PRT
<213> ORGANISM: Artificial Sequence
<220> FEATURE:
<223> OTHER INFORMATION: >SEQ ID NO: 275 - BEAT CD38/CD47-21 BEAT (B) Hc

<400> SEQUENCE: 275

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Glu Thr Ile Ser Lys Ala Lys Gly Gln Pro Arg Glu Pro
            340                 345                 350

Glu Val Ala Thr Phe Pro Pro Ser Arg Asp Glu Leu Thr Lys Asn Gln
                355                 360                 365

Val Thr Leu Val Cys Leu Val Thr Gly Phe Tyr Pro Ser Asp Ile Ala
    370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
                435                 440                 445

Leu Ser Pro Gly
    450

<210> SEQ ID NO 276
<211> LENGTH: 452
<212> TYPE: PRT
<213> ORGANISM: Artificial Sequence
<220> FEATURE:
<223> OTHER INFORMATION: >SEQ ID NO: 276 -?? BEAT CD38/CD47-22 BEAT (A)
      Hc

<400> SEQUENCE: 276

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn
            20                  25                  30

Thr Met His Trp Val Arg Gln Ala Pro Gly Lys Gly Leu Glu Trp Val
        35                  40                  45

Ser Val Ile Tyr Gln Ser Gly Val Thr Arg Tyr Ala Asp Ser Val Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Gly Val Ala Gly Gly Pro Gly Tyr Ala Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
            165                 170                 175
Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Lys Thr Ile Ser Lys Ala Lys Gly Gln Pro Arg Glu Pro
                340                 345                 350

Ala Val Tyr Thr Leu Pro Pro Ser Arg Glu Glu Met Thr Lys Asn Gln
                355                 360                 365

Val Lys Leu Val Cys Leu Val Thr Gly Phe Tyr Pro Ser Asp Ile Ala
            370                 375                 380

Val Glu Trp Glu Ser Ser Gly Gln Pro Glu Asn Asn Tyr Tyr Thr Thr
385                 390                 395                 400

Pro Pro Met Leu Asp Ser Asp Gly Ser Phe Ser Leu Val Ser Trp Leu
                405                 410                 415

Asn Val Asp Lys Ser Arg Trp Gln Gln Gly Asn Ile Phe Ser Cys Ser
                420                 425                 430

Val Met His Glu Ala Leu His Asn Arg Phe Thr Gln Lys Ser Leu Ser
            435                 440                 445

Leu Ser Pro Gly
        450

<210> SEQ ID NO 277
<211> LENGTH: 452
<212> TYPE: PRT
<213> ORGANISM: Artificial Sequence
<220> FEATURE:
<223> OTHER INFORMATION: >SEQ ID NO: 277 -?? BEAT CD38/CD47-22, -42 BEAT
      (B) Hc

<400> SEQUENCE: 277

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Lys Thr Ile Ser Lys Ala Lys Gly Gln Pro Arg Glu Pro
            340                 345                 350

Glu Val Ala Thr Phe Pro Pro Ser Arg Asp Glu Leu Thr Lys Asn Gln
        355                 360                 365

Val Thr Leu Val Cys Leu Val Thr Gly Phe Tyr Pro Ser Asp Ile Ala
370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 278
<211> LENGTH: 452
<212> TYPE: PRT

<213> ORGANISM: Artificial Sequence
<220> FEATURE:
<223> OTHER INFORMATION: >SEQ ID NO: 278 -?? BEAT CD38/CD47-24, -34, -40 BEAT (A) Hc

<400> SEQUENCE: 278

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Ile | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Leu | Ser | Arg | Asn |
| | | | 20 | | | | | 25 | | | | | 30 | | |
| Thr | Met | His | Trp | Val | Arg | Gln | Ala | Pro | Gly | Lys | Gly | Leu | Glu | Trp | Val |
| | | 35 | | | | | 40 | | | | | 45 | | | |
| Ser | Val | Ile | Tyr | Gln | Ser | Gly | Val | Thr | Arg | Tyr | Ala | Asp | Ser | Val | Lys |
| | 50 | | | | | 55 | | | | | 60 | | | | |
| Ser | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |
| Arg | Gly | Arg | Tyr | Gly | Val | Ala | Gly | Gly | Pro | Gly | Tyr | Ala | Phe | Asp | Val |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Asp | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ala |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Asn | Asn | Lys | Ala | Leu | Pro | Ala |
| | | | | 325 | | | | | 330 | | | | | 335 | |
| Pro | Ile | Glu | Ala | Thr | Ile | Ser | Lys | Ala | Lys | Gly | Gln | Pro | Arg | Glu | Pro |
| | | | 340 | | | | | 345 | | | | | 350 | | |
| Ala | Val | Tyr | Thr | Leu | Pro | Pro | Ser | Arg | Glu | Glu | Met | Thr | Lys | Asn | Gln |
| | | | | 355 | | | | | 360 | | | | | 365 | |
| Val | Lys | Leu | Val | Cys | Leu | Val | Thr | Gly | Phe | Tyr | Pro | Ser | Asp | Ile | Ala |
| | 370 | | | | | 375 | | | | | 380 | | | | |

```
Val Glu Trp Glu Ser Ser Gly Gln Pro Glu Asn Asn Tyr Tyr Thr Thr
385                 390                 395                 400

Pro Pro Met Leu Asp Ser Asp Gly Ser Phe Ser Leu Val Ser Trp Leu
            405                 410                 415

Asn Val Asp Lys Ser Arg Trp Gln Gln Gly Asn Ile Phe Ser Cys Ser
        420                 425                 430

Val Met His Glu Ala Leu His Asn Arg Phe Thr Gln Lys Ser Leu Ser
        435                 440                 445

Leu Ser Pro Gly
        450

<210> SEQ ID NO 279
<211> LENGTH: 452
<212> TYPE: PRT
<213> ORGANISM: Artificial Sequence
<220> FEATURE:
<223> OTHER INFORMATION: >SEQ ID NO: 279 -?? BEAT CD38/CD47-24 BEAT (B)
      Hc

<400> SEQUENCE: 279

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Asp Asp Pro Glu Val Lys Phe Asn Trp Tyr Val Asp Gly Val
        275                 280                 285
```

```
Glu Val His Asn Ala Lys Thr Lys Pro Arg Glu Gln Tyr Asn Ala
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Ala Thr Ile Ser Lys Ala Lys Gly Gln Pro Arg Glu Pro
            340                 345                 350

Glu Val Ala Thr Phe Pro Pro Ser Arg Asp Glu Leu Thr Lys Asn Gln
            355                 360                 365

Val Thr Leu Val Cys Leu Val Thr Gly Phe Tyr Pro Ser Asp Ile Ala
370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450
```

<210> SEQ ID NO 280
<211> LENGTH: 452
<212> TYPE: PRT
<213> ORGANISM: Artificial Sequence
<220> FEATURE:
<223> OTHER INFORMATION: >SEQ ID NO: 280 -?? BEAT CD38/CD47-42, -48, -60
    BEAT (A) Hc

<400> SEQUENCE: 280

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn
            20                  25                  30

Thr Met His Trp Val Arg Gln Ala Pro Gly Lys Gly Leu Glu Trp Val
        35                  40                  45

Ser Val Ile Tyr Gln Ser Gly Val Thr Arg Tyr Ala Asp Ser Val Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Gly Val Ala Gly Gly Pro Gly Tyr Ala Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                      180                 185                 190
        Thr Val Pro Ser Ser Leu Gly Thr Gln Thr Tyr Ile Cys Asn Val
                    195                 200                 205

Asn His Lys Pro Ser Asn Thr Lys Val Asp Lys Val Glu Pro Lys
                    210                 215                 220

Ser Cys Asp Lys Thr His Thr Cys Pro Pro Cys Pro Ala Pro Glu Leu
        225                 230                 235                 240

Leu Gly Gly Pro Asp Val Phe Leu Phe Pro Pro Lys Pro Lys Asp Thr
                        245                 250                 255

Leu Met Ile Ser Arg Thr Pro Glu Val Thr Cys Val Val Val Asp Val
                    260                 265                 270

Ser His Glu Asp Pro Glu Val Lys Phe Asn Trp Tyr Val Asp Gly Val
                    275                 280                 285

Glu Val His Asn Ala Lys Thr Lys Pro Arg Glu Glu Gln Tyr Asn Ser
                    290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Asn Asn Lys Ala Leu Pro Ala
                        325                 330                 335

Pro Glu Glu Lys Thr Ile Ser Lys Ala Lys Gly Gln Pro Arg Glu Pro
                    340                 345                 350

Ala Val Tyr Thr Leu Pro Pro Ser Arg Glu Glu Met Thr Lys Asn Gln
                    355                 360                 365

Val Lys Leu Val Cys Leu Val Thr Gly Phe Tyr Pro Ser Asp Ile Ala
        370                 375                 380

Val Glu Trp Glu Ser Ser Gly Gln Pro Glu Asn Asn Tyr Tyr Thr Thr
        385                 390                 395                 400

Pro Pro Met Leu Asp Ser Asp Gly Ser Phe Ser Leu Val Ser Trp Leu
                        405                 410                 415

Asn Val Asp Lys Ser Arg Trp Gln Gln Gly Asn Ile Phe Ser Cys Ser
                    420                 425                 430

Val Met His Glu Ala Leu His Asn Arg Phe Thr Gln Lys Ser Leu Ser
                    435                 440                 445

Leu Ser Pro Gly
                    450

<210> SEQ ID NO 281
<211> LENGTH: 452
<212> TYPE: PRT
<213> ORGANISM: Artificial Sequence
<220> FEATURE:
<223> OTHER INFORMATION: >SEQ ID NO: 281 -?? BEAT CD38/CD47-23, -32, -39
      BEAT (A) Hc

<400> SEQUENCE: 281

Glu Val Gln Leu Val Glu Ser Gly Gly Gly Leu Ile Gln Pro Gly Gly
        1               5                   10                  15

Ser Leu Arg Leu Ser Cys Ala Ala Ser Gly Phe Thr Leu Ser Arg Asn
                    20                  25                  30

Thr Met His Trp Val Arg Gln Ala Pro Gly Lys Gly Leu Glu Trp Val
                    35                  40                  45

Ser Val Ile Tyr Gln Ser Gly Val Thr Arg Tyr Ala Asp Ser Val Lys
                50                  55                  60

Ser Arg Phe Thr Ile Ser Arg Asp Asn Ser Lys Asn Thr Leu Tyr Leu
        65                  70                  75                  80
```

```
Gln Met Asn Ser Leu Arg Ala Glu Asp Thr Ala Val Tyr Tyr Cys Ala
             85                  90                  95

Arg Gly Arg Tyr Gly Val Ala Gly Pro Gly Tyr Ala Phe Asp Val
        100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Asp Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ala
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Ala Lys Thr Ile Ser Lys Ala Lys Gly Gln Pro Arg Glu Pro
                340                 345                 350

Ala Val Tyr Thr Leu Pro Pro Ser Arg Glu Glu Met Thr Lys Asn Gln
        355                 360                 365

Val Lys Leu Val Cys Leu Val Thr Gly Phe Tyr Pro Ser Asp Ile Ala
        370                 375                 380

Val Glu Trp Glu Ser Ser Gly Gln Pro Glu Asn Asn Tyr Tyr Thr Thr
385                 390                 395                 400

Pro Pro Met Leu Asp Ser Asp Gly Ser Phe Ser Leu Val Ser Trp Leu
                405                 410                 415

Asn Val Asp Lys Ser Arg Trp Gln Gln Gly Asn Ile Phe Ser Cys Ser
                420                 425                 430

Val Met His Glu Ala Leu His Asn Arg Phe Thr Gln Lys Ser Leu Ser
        435                 440                 445

Leu Ser Pro Gly
    450

<210> SEQ ID NO 282
<211> LENGTH: 452
<212> TYPE: PRT
<213> ORGANISM: Artificial Sequence
<220> FEATURE:
<223> OTHER INFORMATION: >SEQ ID NO: 282 -?? BEAT CD38/CD47-23 BEAT (B)
```

Hc

<400> SEQUENCE: 282

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Asp Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ala
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Ala Lys Thr Ile Ser Lys Ala Lys Gly Gln Pro Arg Glu Pro
            340                 345                 350

Gln Val Ala Thr Phe Pro Pro Ser Arg Asp Glu Leu Thr Lys Asn Gln
        355                 360                 365

Val Thr Leu Val Cys Leu Val Thr Gly Phe Tyr Pro Ser Asp Ile Ala
    370                 375                 380

Val Glu Trp Glu Ser Asn Gly Gln Pro Glu Asn Asn Tyr Lys Thr Asp
385                 390                 395                 400

```
Pro Pro Leu Leu Glu Ser Gln Gly Ser Phe Ala Leu Ser Ser Arg Leu
            405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
        450

<210> SEQ ID NO 283
<211> LENGTH: 452
<212> TYPE: PRT
<213> ORGANISM: Artificial Sequence
<220> FEATURE:
<223> OTHER INFORMATION: >SEQ ID NO: 283 -?? BEAT CD38/CD47-25 BEAT (A)
      Hc

<400> SEQUENCE: 283

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn
            20                  25                  30

Thr Met His Trp Val Arg Gln Ala Pro Gly Lys Gly Leu Glu Trp Val
        35                  40                  45

Ser Val Ile Tyr Gln Ser Gly Val Thr Arg Tyr Ala Asp Ser Val Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Arg Tyr Gly Val Ala Gly Pro Gly Tyr Ala Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ala
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Ala Lys Thr Ile Ser Lys Ala Lys Gly Gln Pro Arg Glu Pro
            340                 345                 350

Ala Val Tyr Thr Leu Pro Pro Ser Arg Glu Glu Met Thr Lys Asn Gln
            355                 360                 365

Val Lys Leu Val Cys Leu Val Thr Gly Phe Tyr Pro Ser Asp Ile Ala
370                 375                 380

Val Glu Trp Glu Ser Ser Gly Gln Pro Glu Asn Asn Tyr Tyr Thr Thr
385                 390                 395                 400

Pro Pro Met Leu Asp Ser Asp Gly Ser Phe Ser Leu Val Ser Trp Leu
                405                 410                 415

Asn Val Asp Lys Ser Arg Trp Gln Gln Gly Asn Ile Phe Ser Cys Ser
                420                 425                 430

Val Met His Glu Ala Leu His Asn Arg Phe Thr Gln Lys Ser Leu Ser
            435                 440                 445

Leu Ser Pro Gly
    450

<210> SEQ ID NO 284
<211> LENGTH: 452
<212> TYPE: PRT
<213> ORGANISM: Artificial Sequence
<220> FEATURE:
<223> OTHER INFORMATION: >SEQ ID NO: 284 -?? BEAT CD38/CD47-25 BEAT (B)
      Hc

<400> SEQUENCE: 284

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
                20                  25                  30

Ala Ile Gly Trp Val Arg Gln Ala Pro Gly Gln Gly Leu Glu Trp Met
            35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val

```
                195                 200                 205
Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ala
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Ala Lys Thr Ile Ser Lys Ala Lys Gly Gln Pro Arg Glu Pro
            340                 345                 350

Glu Val Ala Thr Phe Pro Pro Ser Arg Asp Glu Leu Thr Lys Asn Gln
        355                 360                 365

Val Thr Leu Val Cys Leu Val Thr Gly Phe Tyr Pro Ser Asp Ile Ala
    370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415

Arg Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 285
<211> LENGTH: 452
<212> TYPE: PRT
<213> ORGANISM: Artificial Sequence
<220> FEATURE:
<223> OTHER INFORMATION: >SEQ ID NO: 285 -?? BEAT CD38/CD47-26 BEAT (A)
      Hc

<400> SEQUENCE: 285

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn
            20                  25                  30

Thr Met His Trp Val Arg Gln Ala Pro Gly Lys Gly Leu Glu Trp Val
        35                  40                  45

Ser Val Ile Tyr Gln Ser Gly Val Thr Arg Tyr Ala Asp Ser Val Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Gly Arg Tyr Gly Val Ala Gly Pro Gly Tyr Ala Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ala
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Ala Thr Ile Ser Lys Ala Lys Gly Gln Pro Arg Glu Pro
            340                 345                 350

Ala Val Tyr Thr Leu Pro Pro Ser Arg Glu Glu Met Thr Lys Asn Gln
        355                 360                 365

Val Lys Leu Val Cys Leu Val Thr Gly Phe Tyr Pro Ser Asp Ile Ala
370                 375                 380

Val Glu Trp Glu Ser Ser Gly Gln Pro Glu Asn Asn Tyr Tyr Thr Thr
385                 390                 395                 400

Pro Pro Met Leu Asp Ser Asp Gly Ser Phe Ser Leu Val Ser Trp Leu
                405                 410                 415

Asn Val Asp Lys Ser Arg Trp Gln Gln Gly Asn Ile Phe Ser Cys Ser
            420                 425                 430

Val Met His Glu Ala Leu His Asn Arg Phe Thr Gln Lys Ser Leu Ser
        435                 440                 445

Leu Ser Pro Gly
    450

<210> SEQ ID NO 286
<211> LENGTH: 452
<212> TYPE: PRT
<213> ORGANISM: Artificial Sequence
<220> FEATURE:
<223> OTHER INFORMATION: >SEQ ID NO: 286 -?? BEAT CD38/CD47-26 BEAT (B)
      Hc

<400> SEQUENCE: 286

```
Gln Val Gln Leu Val Gln Ser Gly Ala Glu Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
                100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ala
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Asn Asn Lys Ala Leu Pro Ala
                325                 330                 335

Pro Ile Glu Ala Thr Ile Ser Lys Ala Lys Gly Gln Pro Arg Glu Pro
                340                 345                 350

Glu Val Ala Thr Phe Pro Pro Ser Arg Asp Glu Leu Thr Lys Asn Gln
                355                 360                 365

Val Thr Leu Val Cys Leu Val Thr Gly Phe Tyr Pro Ser Asp Ile Ala
                370                 375                 380

Val Glu Trp Glu Ser Asn Gly Gln Pro Glu Asn Asn Tyr Lys Thr Asp
385                 390                 395                 400

Pro Pro Leu Leu Glu Ser Gln Gly Ser Phe Ala Leu Ser Ser Arg Leu
                405                 410                 415
```

-continued

Arg Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
        450

<210> SEQ ID NO 287
<211> LENGTH: 693
<212> TYPE: PRT
<213> ORGANISM: Artificial Sequence
<220> FEATURE:
<223> OTHER INFORMATION: >SEQ ID NO: 287 -?? BEAT CD38/CD47-32 BEAT (B)
      Hc

<400> SEQUENCE: 287

Gln Val Gln Leu Val Gln Ser Gly Ala Glu Val Lys Lys Pro Gly Ser
1               5                   10                  15

Ser Val Lys Val Ser Cys Lys Ala Ser Gly Leu Pro Asp Ala Thr Tyr
            20                  25                  30

Ala Ile Gly Trp Val Arg Gln Ala Pro Gly Gln Gly Leu Glu Trp Met
        35                  40                  45

Gly Arg Ile Ile Pro Arg Leu Asp Ala Glu His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Tyr Leu Tyr Ser Ser Tyr Tyr Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Gly Gly Gly Gly Ser Gly Gly Gly Ser Gly Gly Gly Gly
225                 230                 235                 240

Ser Gln Val Gln Leu Val Gln Ser Gly Ala Glu Val Lys Lys Pro Gly
                245                 250                 255

Ser Ser Val Lys Val Ser Cys Lys Ala Ser Gly Leu Pro Asp Ala Thr
            260                 265                 270

Tyr Ala Ile Gly Trp Val Arg Gln Ala Pro Gly Gln Gly Leu Glu Trp
        275                 280                 285

Met Gly Arg Ile Ile Pro Arg Leu Asp Ala Glu His Tyr Ala Gln Lys
    290                 295                 300

Phe Gln Gly Arg Val Thr Ile Thr Ala Asp Glu Ser Thr Ser Thr Ala
305                 310                 315                 320

```
Tyr Met Glu Leu Ser Ser Leu Arg Ser Glu Asp Thr Ala Val Tyr Tyr
            325                 330                 335

Cys Ala Arg Gly Leu Gly Tyr Tyr Leu Tyr Ser Ser Tyr Tyr Phe Asp
            340                 345                 350

Ile Trp Gly Gln Gly Thr Leu Val Thr Val Ser Ser Ala Ser Thr Lys
            355                 360                 365

Gly Pro Ser Val Phe Pro Leu Ala Pro Ser Ser Lys Ser Thr Ser Gly
            370                 375                 380

Gly Thr Ala Ala Leu Gly Cys Leu Val Lys Asp Tyr Phe Pro Glu Pro
385                 390                 395                 400

Val Thr Val Ser Trp Asn Ser Gly Ala Leu Thr Ser Gly Val His Thr
            405                 410                 415

Phe Pro Ala Val Leu Gln Ser Ser Gly Leu Tyr Ser Leu Ser Ser Val
            420                 425                 430

Val Thr Val Pro Ser Ser Ser Leu Gly Thr Gln Thr Tyr Ile Cys Asn
            435                 440                 445

Val Asn His Lys Pro Ser Asn Thr Lys Val Asp Lys Lys Val Glu Pro
        450                 455                 460

Lys Ser Cys Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
            485                 490                 495

Thr Leu Met Ile Ser Arg Thr Pro Glu Val Thr Cys Val Val Val Asp
            500                 505                 510

Val Ser His Asp Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ala Thr Tyr Arg Val Val Ser Val Leu Thr Val Leu His Gln Asp Trp
545                 550                 555                 560

Leu Asn Gly Lys Glu Tyr Lys Cys Lys Val Asn Asn Lys Ala Leu Pro
            565                 570                 575

Ala Pro Ile Ala Lys Thr Ile Ser Lys Ala Lys Gly Gln Pro Arg Glu
            580                 585                 590

Pro Glu Val Ala Thr Phe Pro Pro Ser Arg Asp Glu Leu Thr Lys Asn
            595                 600                 605

Gln Val Thr Leu Val Cys Leu Val Thr Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Asp Pro Pro Leu Leu Glu Ser Gln Gly Ser Phe Ala Leu Ser Ser Arg
            645                 650                 655

Leu Arg Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
            675                 680                 685

Ser Leu Ser Pro Gly
        690

<210> SEQ ID NO 288
<211> LENGTH: 693
<212> TYPE: PRT
<213> ORGANISM: Artificial Sequence
<220> FEATURE:
```

<223> OTHER INFORMATION: >SEQ ID NO: 288 -?? BEAT CD38/CD47-34 BEAT (B) Hc

<400> SEQUENCE: 288

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Leu | Pro | Asp | Ala | Thr | Tyr |
| | | | 20 | | | | | 25 | | | | | 30 | | |
| Ala | Ile | Gly | Trp | Val | Arg | Gln | Ala | Pro | Gly | Gln | Gly | Leu | Glu | Trp | Met |
| | | 35 | | | | | 40 | | | | | 45 | | | |
| Gly | Arg | Ile | Ile | Pro | Arg | Leu | Asp | Ala | Glu | His | Tyr | Ala | Gln | Lys | Phe |
| | 50 | | | | | 55 | | | | | 60 | | | | |
| Gln | Gly | Arg | Val | Thr | Ile | Thr | Ala | Asp | Glu | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Leu | Gly | Tyr | Tyr | Leu | Tyr | Ser | Ser | Tyr | Tyr | Phe | Asp | Ile |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Gly | Gly | Gly | Gly | Ser | Gly | Gly | Gly | Gly | Ser | Gly | Gly | Gly | Gly |
| 225 | | | | | 230 | | | | | 235 | | | | | 240 |
| Ser | Gln | Val | Gln | Leu | Val | Gln | Ser | Gly | Ala | Glu | Val | Lys | Lys | Pro | Gly |
| | | | | 245 | | | | | 250 | | | | | 255 | |
| Ser | Ser | Val | Lys | Val | Ser | Cys | Lys | Ala | Ser | Gly | Leu | Pro | Asp | Ala | Thr |
| | | | 260 | | | | | 265 | | | | | 270 | | |
| Tyr | Ala | Ile | Gly | Trp | Val | Arg | Gln | Ala | Pro | Gly | Gln | Gly | Leu | Glu | Trp |
| | | 275 | | | | | 280 | | | | | 285 | | | |
| Met | Gly | Arg | Ile | Ile | Pro | Arg | Leu | Asp | Ala | Glu | His | Tyr | Ala | Gln | Lys |
| | 290 | | | | | 295 | | | | | 300 | | | | |
| Phe | Gln | Gly | Arg | Val | Thr | Ile | Thr | Ala | Asp | Glu | Ser | Thr | Ser | Thr | Ala |
| 305 | | | | | 310 | | | | | 315 | | | | | 320 |
| Tyr | Met | Glu | Leu | Ser | Ser | Leu | Arg | Ser | Glu | Asp | Thr | Ala | Val | Tyr | Tyr |
| | | | | 325 | | | | | 330 | | | | | 335 | |
| Cys | Ala | Arg | Gly | Leu | Gly | Tyr | Tyr | Leu | Tyr | Ser | Ser | Tyr | Tyr | Phe | Asp |
| | | | 340 | | | | | 345 | | | | | 350 | | |
| Ile | Trp | Gly | Gln | Gly | Thr | Leu | Val | Thr | Val | Ser | Ser | Ala | Ser | Thr | Lys |
| | | 355 | | | | | 360 | | | | | 365 | | | |
| Gly | Pro | Ser | Val | Phe | Pro | Leu | Ala | Pro | Ser | Ser | Lys | Ser | Thr | Ser | Gly |
| | 370 | | | | | 375 | | | | | 380 | | | | |
| Gly | Thr | Ala | Ala | Leu | Gly | Cys | Leu | Val | Lys | Asp | Tyr | Phe | Pro | Glu | Pro |
| 385 | | | | | 390 | | | | | 395 | | | | | 400 |

```
Val Thr Val Ser Trp Asn Ser Gly Ala Leu Thr Ser Gly Val His Thr
                405                 410                 415

Phe Pro Ala Val Leu Gln Ser Ser Gly Leu Tyr Ser Leu Ser Ser Val
            420                 425                 430

Val Thr Val Pro Ser Ser Leu Gly Thr Gln Thr Tyr Ile Cys Asn
        435                 440                 445

Val Asn His Lys Pro Ser Asn Thr Lys Val Asp Lys Val Glu Pro
    450                 455                 460

Lys Ser Cys Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Asp Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ala Thr Tyr Arg Val Val Ser Val Leu Thr Val Leu His Gln Asp Trp
545                 550                 555                 560

Leu Asn Gly Lys Glu Tyr Lys Cys Lys Val Asn Asn Lys Ala Leu Pro
                565                 570                 575

Ala Pro Ile Glu Ala Thr Ile Ser Lys Ala Lys Gly Gln Pro Arg Glu
            580                 585                 590

Pro Glu Val Ala Thr Phe Pro Pro Ser Arg Asp Glu Leu Thr Lys Asn
        595                 600                 605

Gln Val Thr Leu Val Cys Leu Val Thr Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Asp Pro Pro Leu Leu Glu Ser Gln Gly Ser Phe Ala Leu Ser Ser Arg
                645                 650                 655

Leu Arg Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly
    690

<210> SEQ ID NO 289
<211> LENGTH: 691
<212> TYPE: PRT
<213> ORGANISM: Artificial Sequence
<220> FEATURE:
<223> OTHER INFORMATION: >SEQ ID NO: 289 -?? BEAT CD38/CD47-38 BEAT (B)
      Hc

<400> SEQUENCE: 289

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Ile Ser Asn Ser
            20                  25                  30

Ala Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
```

```
            50                  55                  60
Gln Gly Arg Val Thr Ile Thr Ala Asp Glu Ser Thr Ser Thr Ala Tyr
 65                      70                  75                  80

Met Glu Leu Ser Ser Leu Arg Ser Glu Asp Thr Ala Val Tyr Tyr Cys
                     85                  90                  95

Ala Arg Ser Arg Gly Tyr Tyr Gly Ser Phe Tyr Phe Asp Ile Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Gly Gly Gly Gly Ser Gly Gly Gly Gly Ser Gly Gly Gly Gly Ser Gln
225                 230                 235                 240

Val Gln Leu Val Gln Ser Gly Ala Glu Val Lys Lys Pro Gly Ser Ser
                245                 250                 255

Val Lys Val Ser Cys Lys Ala Ser Gly Leu Pro Asp Ala Thr Tyr Ala
                260                 265                 270

Ile Gly Trp Val Arg Gln Ala Pro Gly Gln Gly Leu Glu Trp Met Gly
                275                 280                 285

Arg Ile Ile Pro Arg Leu Asp Ala Glu His Tyr Ala Gln Lys Phe Gln
            290                 295                 300

Gly Arg Val Thr Ile Thr Ala Asp Glu Ser Thr Ser Thr Ala Tyr Met
305                 310                 315                 320

Glu Leu Ser Ser Leu Arg Ser Glu Asp Thr Ala Val Tyr Tyr Cys Ala
                325                 330                 335

Arg Gly Leu Gly Tyr Tyr Leu Tyr Ser Ser Tyr Tyr Phe Asp Ile Trp
                340                 345                 350

Gly Gln Gly Thr Leu Val Thr Val Ser Ser Ala Ser Thr Lys Gly Pro
                355                 360                 365

Ser Val Phe Pro Leu Ala Pro Ser Ser Lys Ser Thr Ser Gly Gly Thr
            370                 375                 380

Ala Ala Leu Gly Cys Leu Val Lys Asp Tyr Phe Pro Glu Pro Val Thr
385                 390                 395                 400

Val Ser Trp Asn Ser Gly Ala Leu Thr Ser Gly Val His Thr Phe Pro
                405                 410                 415

Ala Val Leu Gln Ser Ser Gly Leu Tyr Ser Leu Ser Ser Val Val Thr
                420                 425                 430

Val Pro Ser Ser Ser Leu Gly Thr Gln Thr Tyr Ile Cys Asn Val Asn
                435                 440                 445

His Lys Pro Ser Asn Thr Lys Val Asp Lys Lys Val Glu Pro Lys Ser
            450                 455                 460

Cys Asp Lys Thr His Thr Cys Pro Pro Cys Pro Ala Pro Glu Leu Leu
465                 470                 475                 480
```

```
Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
        515                 520                 525

Val His Asn Ala Lys Thr Lys Pro Arg Glu Glu Gln Tyr Asn Ser Thr
    530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Pro Ala Pro
                565                 570                 575

Ile Glu Lys Thr Ile Ser Lys Ala Lys Gly Gln Pro Arg Glu Pro Glu
            580                 585                 590

Val Ala Thr Phe Pro Pro Ser Arg Asp Glu Leu Thr Lys Asn Gln Val
        595                 600                 605

Thr Leu Val Cys Leu Val Thr Gly Phe Tyr Pro Ser Asp Ile Ala Val
    610                 615                 620

Glu Trp Glu Ser Asn Gly Gln Pro Glu Asn Asn Tyr Lys Thr Asp Pro
625                 630                 635                 640

Pro Leu Leu Glu Ser Gln Gly Ser Phe Ala Leu Ser Ser Arg Leu Arg
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
        675                 680                 685

Ser Pro Gly
    690

<210> SEQ ID NO 290
<211> LENGTH: 691
<212> TYPE: PRT
<213> ORGANISM: Artificial Sequence
<220> FEATURE:
<223> OTHER INFORMATION: >SEQ ID NO: 290 -?? BEAT CD38/CD47-39 BEAT (B)
      Hc

<400> SEQUENCE: 290

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Ile Ser Asn Ser
            20                  25                  30

Ala Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
              130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Gly Gly Gly Gly Ser Gly Gly Gly Gly Ser Gly Gly Gly Gly Ser Gln
225                 230                 235                 240

Val Gln Leu Val Gln Ser Gly Ala Glu Val Lys Lys Pro Gly Ser Ser
                245                 250                 255

Val Lys Val Ser Cys Lys Ala Ser Gly Leu Pro Asp Ala Thr Tyr Ala
                260                 265                 270

Ile Gly Trp Val Arg Gln Ala Pro Gly Gln Gly Leu Glu Trp Met Gly
                275                 280                 285

Arg Ile Ile Pro Arg Leu Asp Ala Glu His Tyr Ala Gln Lys Phe Gln
290                 295                 300

Gly Arg Val Thr Ile Thr Ala Asp Glu Ser Thr Ser Thr Ala Tyr Met
305                 310                 315                 320

Glu Leu Ser Ser Leu Arg Ser Glu Asp Thr Ala Val Tyr Tyr Cys Ala
                325                 330                 335

Arg Gly Leu Gly Tyr Tyr Leu Tyr Ser Ser Tyr Tyr Phe Asp Ile Trp
                340                 345                 350

Gly Gln Gly Thr Leu Val Thr Val Ser Ser Ala Ser Thr Lys Gly Pro
                355                 360                 365

Ser Val Phe Pro Leu Ala Pro Ser Ser Lys Ser Thr Ser Gly Gly Thr
                370                 375                 380

Ala Ala Leu Gly Cys Leu Val Lys Asp Tyr Phe Pro Glu Pro Val Thr
385                 390                 395                 400

Val Ser Trp Asn Ser Gly Ala Leu Thr Ser Gly Val His Thr Phe Pro
                405                 410                 415

Ala Val Leu Gln Ser Ser Gly Leu Tyr Ser Leu Ser Ser Val Val Thr
                420                 425                 430

Val Pro Ser Ser Ser Leu Gly Thr Gln Thr Tyr Ile Cys Asn Val Asn
                435                 440                 445

His Lys Pro Ser Asn Thr Lys Val Asp Lys Lys Val Glu Pro Lys Ser
450                 455                 460

Cys Asp Lys Thr His Thr Cys Pro Pro Cys Pro Ala Pro Glu Leu Leu
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
                500                 505                 510

His Asp Asp Pro Glu Val Lys Phe Asn Trp Tyr Val Asp Gly Val Glu
                515                 520                 525

Val His Asn Ala Lys Thr Lys Pro Arg Glu Glu Gln Tyr Asn Ala Thr
                530                 535                 540

Tyr Arg Val Val Ser Val Leu Thr Val Leu His Gln Asp Trp Leu Asn
545                 550                 555                 560
```

```
Gly Lys Glu Tyr Lys Cys Lys Val Asn Asn Lys Ala Leu Pro Ala Pro
                565                 570                 575

Ile Ala Lys Thr Ile Ser Lys Ala Lys Gly Gln Pro Arg Glu Pro Glu
            580                 585                 590

Val Ala Thr Phe Pro Pro Ser Arg Asp Glu Leu Thr Lys Asn Gln Val
            595                 600                 605

Thr Leu Val Cys Leu Val Thr Gly Phe Tyr Pro Ser Asp Ile Ala Val
            610                 615                 620

Glu Trp Glu Ser Asn Gly Gln Pro Glu Asn Asn Tyr Lys Thr Asp Pro
625                 630                 635                 640

Pro Leu Leu Glu Ser Gln Gly Ser Phe Ala Leu Ser Ser Arg Leu Arg
                645                 650                 655

Val Asp Lys Ser Arg Trp Gln Gln Gly Asn Val Phe Ser Cys Ser Val
                660                 665                 670

Met His Glu Ala Leu His Asn His Tyr Thr Gln Lys Ser Leu Ser Leu
                675                 680                 685

Ser Pro Gly
        690

<210> SEQ ID NO 291
<211> LENGTH: 691
<212> TYPE: PRT
<213> ORGANISM: Artificial Sequence
<220> FEATURE:
<223> OTHER INFORMATION: >SEQ ID NO: 291 -?? BEAT CD38/CD47-40 BEAT (B)
      Hc

<400> SEQUENCE: 291

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Ile Ser Asn Ser
            20                  25                  30

Ala Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

```
            210                 215                 220
Gly Gly Gly Gly Ser Gly Gly Gly Ser Gly Gly Gly Ser Gln
225                 230                 235                 240

Val Gln Leu Val Gln Ser Gly Ala Glu Val Lys Lys Pro Gly Ser Ser
                        245                 250                 255

Val Lys Val Ser Cys Lys Ala Ser Gly Leu Pro Asp Ala Thr Tyr Ala
                    260                 265                 270

Ile Gly Trp Val Arg Gln Ala Pro Gly Gln Gly Leu Glu Trp Met Gly
                275                 280                 285

Arg Ile Ile Pro Arg Leu Asp Ala Glu His Tyr Ala Gln Lys Phe Gln
            290                 295                 300

Gly Arg Val Thr Ile Thr Ala Asp Glu Ser Thr Ser Thr Ala Tyr Met
305                 310                 315                 320

Glu Leu Ser Ser Leu Arg Ser Glu Asp Thr Ala Val Tyr Tyr Cys Ala
                        325                 330                 335

Arg Gly Leu Gly Tyr Tyr Leu Tyr Ser Ser Tyr Tyr Phe Asp Ile Trp
                    340                 345                 350

Gly Gln Gly Thr Leu Val Thr Val Ser Ser Ala Ser Thr Lys Gly Pro
                355                 360                 365

Ser Val Phe Pro Leu Ala Pro Ser Ser Lys Ser Thr Ser Gly Gly Thr
            370                 375                 380

Ala Ala Leu Gly Cys Leu Val Lys Asp Tyr Phe Pro Glu Pro Val Thr
385                 390                 395                 400

Val Ser Trp Asn Ser Gly Ala Leu Thr Ser Gly Val His Thr Phe Pro
                        405                 410                 415

Ala Val Leu Gln Ser Ser Gly Leu Tyr Ser Leu Ser Ser Val Val Thr
                    420                 425                 430

Val Pro Ser Ser Ser Leu Gly Thr Gln Thr Tyr Ile Cys Asn Val Asn
                435                 440                 445

His Lys Pro Ser Asn Thr Lys Val Asp Lys Lys Val Glu Pro Lys Ser
            450                 455                 460

Cys Asp Lys Thr His Thr Cys Pro Pro Cys Pro Ala Pro Glu Leu Leu
465                 470                 475                 480

Gly Gly Pro Ser Val Phe Leu Phe Pro Pro Lys Pro Lys Asp Thr Leu
                        485                 490                 495

Met Ile Ser Arg Thr Pro Glu Val Thr Cys Val Val Val Asp Val Ser
                    500                 505                 510

His Asp Asp Pro Glu Val Lys Phe Asn Trp Tyr Val Asp Gly Val Glu
                515                 520                 525

Val His Asn Ala Lys Thr Lys Pro Arg Glu Glu Gln Tyr Asn Ala Thr
            530                 535                 540

Tyr Arg Val Val Ser Val Leu Thr Val Leu His Gln Asp Trp Leu Asn
545                 550                 555                 560

Gly Lys Glu Tyr Lys Cys Lys Val Asn Asn Lys Ala Leu Pro Ala Pro
                        565                 570                 575

Ile Glu Ala Thr Ile Ser Lys Ala Lys Gly Gln Pro Arg Glu Pro Glu
                    580                 585                 590

Val Ala Thr Phe Pro Pro Ser Arg Asp Glu Leu Thr Lys Asn Gln Val
                595                 600                 605

Thr Leu Val Cys Leu Val Thr Gly Phe Tyr Pro Ser Asp Ile Ala Val
            610                 615                 620

Glu Trp Glu Ser Asn Gly Gln Pro Glu Asn Asn Tyr Lys Thr Asp Pro
625                 630                 635                 640
```

-continued

```
Pro Leu Leu Glu Ser Gln Gly Ser Phe Ala Leu Ser Ser Arg Leu Arg
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
            675                 680                 685

Ser Pro Gly
    690

<210> SEQ ID NO 292
<211> LENGTH: 691
<212> TYPE: PRT
<213> ORGANISM: Artificial Sequence
<220> FEATURE:
<223> OTHER INFORMATION: >SEQ ID NO: 292 -?? BEAT CD38/CD47-48 BEAT (B)
      Hc

<400> SEQUENCE: 292

Gln Val Gln Leu Val Gln Ser Gly Ala Glu Val Lys Lys Pro Gly Ser
1               5                   10                  15

Ser Val Lys Val Ser Cys Lys Ala Ser Gly Gly His Ile Ser Asn Ser
            20                  25                  30

Ala Ile Asn Trp Val Arg Gln Ala Pro Gly Gln Gly Leu Glu Trp Met
        35                  40                  45

Gly Arg Val Ile Pro Val Ile Asp Asp Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Gly Gly Gly Gly Ser Gly Gly Gly Gly Ser Gly Gly Gly Gly Ser Gln
225                 230                 235                 240

Val Gln Leu Val Gln Ser Gly Ala Glu Val Lys Lys Pro Gly Ser Ser
                245                 250                 255

Val Lys Val Ser Cys Lys Ala Ser Gly Leu Pro Asp Ala Thr Tyr Ala
            260                 265                 270

Ile Gly Trp Val Arg Gln Ala Pro Gly Gln Gly Leu Glu Trp Met Gly
        275                 280                 285

Arg Ile Ile Pro Arg Leu Asp Ala Glu His Tyr Ala Gln Lys Phe Gln
```

```
                290                 295                 300
Gly Arg Val Thr Ile Thr Ala Asp Glu Ser Thr Ser Thr Ala Tyr Met
305                 310                 315                 320
Glu Leu Ser Ser Leu Arg Ser Glu Asp Thr Ala Val Tyr Tyr Cys Ala
                325                 330                 335
Arg Gly Leu Gly Tyr Tyr Leu Tyr Ser Ser Tyr Tyr Phe Asp Ile Trp
                340                 345                 350
Gly Gln Gly Thr Leu Val Thr Val Ser Ser Ala Ser Thr Lys Gly Pro
                355                 360                 365
Ser Val Phe Pro Leu Ala Pro Ser Ser Lys Ser Thr Ser Gly Gly Thr
370                 375                 380
Ala Ala Leu Gly Cys Leu Val Lys Asp Tyr Phe Pro Glu Pro Val Thr
385                 390                 395                 400
Val Ser Trp Asn Ser Gly Ala Leu Thr Ser Gly Val His Thr Phe Pro
                405                 410                 415
Ala Val Leu Gln Ser Ser Gly Leu Tyr Ser Leu Ser Ser Val Val Thr
                420                 425                 430
Val Pro Ser Ser Ser Leu Gly Thr Gln Thr Tyr Ile Cys Asn Val Asn
                435                 440                 445
His Lys Pro Ser Asn Thr Lys Val Asp Lys Lys Val Glu Pro Lys Ser
        450                 455                 460
Cys Asp Lys Thr His Thr Cys Pro Pro Cys Pro Ala Pro Glu Leu Leu
465                 470                 475                 480
Gly Gly Pro Ser Val Phe Leu Phe Pro Pro Lys Pro Lys Asp Thr Leu
                485                 490                 495
Met Ile Ser Arg Thr Pro Glu Val Thr Cys Val Val Val Asp Val Ser
                500                 505                 510
His Glu Asp Pro Glu Val Lys Phe Asn Trp Tyr Val Asp Gly Val Glu
        515                 520                 525
Val His Asn Ala Lys Thr Lys Pro Arg Glu Glu Gln Tyr Asn Ser Thr
        530                 535                 540
Tyr Arg Val Val Ser Val Leu Thr Val Leu His Gln Asp Trp Leu Asn
545                 550                 555                 560
Gly Lys Glu Tyr Lys Cys Lys Val Asn Asn Lys Ala Leu Pro Ala Pro
                565                 570                 575
Ile Glu Lys Thr Ile Ser Lys Ala Lys Gly Gln Pro Arg Glu Pro Glu
                580                 585                 590
Val Ala Thr Phe Pro Pro Ser Arg Asp Glu Leu Thr Lys Asn Gln Val
                595                 600                 605
Thr Leu Val Cys Leu Val Thr Gly Phe Tyr Pro Ser Asp Ile Ala Val
        610                 615                 620
Glu Trp Glu Ser Asn Gly Gln Pro Glu Asn Asn Tyr Lys Thr Asp Pro
625                 630                 635                 640
Pro Leu Leu Glu Ser Gln Gly Ser Phe Ala Leu Ser Ser Arg Leu Arg
                645                 650                 655
Val Asp Lys Ser Arg Trp Gln Gln Gly Asn Val Phe Ser Cys Ser Val
                660                 665                 670
Met His Glu Ala Leu His Asn His Tyr Thr Gln Lys Ser Leu Ser Leu
        675                 680                 685
Ser Pro Gly
    690

<210> SEQ ID NO 293
```

<211> LENGTH: 691
<212> TYPE: PRT
<213> ORGANISM: Artificial Sequence
<220> FEATURE:
<223> OTHER INFORMATION: >SEQ ID NO: 293 -?? BEAT CD38/CD47-60 BEAT (B) Hc

<400> SEQUENCE: 293

```
Gln Val Gln Leu Val Gln Ser Gly Ala Glu Val Lys Pro Gly Ser
1               5                   10                  15

Ser Val Lys Val Ser Cys Lys Ala Ser Gly Phe Phe Ser His Tyr
                20                  25                  30

Ile Ile Asn Trp Val Arg Gln Ala Pro Gly Gln Gly Leu Glu Trp Met
            35                  40                  45

Gly Arg Val Ile Pro Val Ile Asp Asp Ala Tyr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Tyr Tyr Gly Ser Phe Tyr Phe Asp Ile Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Gly Gly Gly Gly Ser Gly Gly Gly Gly Ser Gly Gly Gly Gly Ser Gln
225                 230                 235                 240

Val Gln Leu Val Gln Ser Gly Ala Glu Val Lys Pro Gly Ser Ser
                245                 250                 255

Val Lys Val Ser Cys Lys Ala Ser Gly Leu Pro Asp Ala Thr Tyr Ala
            260                 265                 270

Ile Gly Trp Val Arg Gln Ala Pro Gly Gln Gly Leu Glu Trp Met Gly
        275                 280                 285

Arg Ile Ile Pro Arg Leu Asp Ala Glu His Tyr Ala Gln Lys Phe Gln
290                 295                 300

Gly Arg Val Thr Ile Thr Ala Asp Glu Ser Thr Ser Thr Ala Tyr Met
305                 310                 315                 320

Glu Leu Ser Ser Leu Arg Ser Glu Asp Thr Ala Val Tyr Tyr Cys Ala
                325                 330                 335

Arg Gly Leu Gly Tyr Tyr Leu Tyr Ser Ser Tyr Tyr Phe Asp Ile Trp
            340                 345                 350

Gly Gln Gly Thr Leu Val Thr Val Ser Ser Ala Ser Thr Lys Gly Pro
        355                 360                 365

Ser Val Phe Pro Leu Ala Pro Ser Ser Lys Ser Thr Ser Gly Gly Thr
```

```
                370             375             380
Ala Ala Leu Gly Cys Leu Val Lys Asp Tyr Phe Pro Glu Pro Val Thr
385             390             395             400

Val Ser Trp Asn Ser Gly Ala Leu Thr Ser Gly Val His Thr Phe Pro
                405             410             415

Ala Val Leu Gln Ser Ser Gly Leu Tyr Ser Leu Ser Ser Val Val Thr
            420             425             430

Val Pro Ser Ser Ser Leu Gly Thr Gln Thr Tyr Ile Cys Asn Val Asn
            435             440             445

His Lys Pro Ser Asn Thr Lys Val Asp Lys Lys Val Glu Pro Lys Ser
        450             455             460

Cys Asp Lys Thr His Thr Cys Pro Pro Cys Pro Ala Pro Glu Leu Leu
465             470             475             480

Gly Gly Pro Ser Val Phe Leu Phe Pro Pro Lys Pro Lys Asp Thr Leu
                485             490             495

Met Ile Ser Arg Thr Pro Glu Val Thr Cys Val Val Val Asp Val Ser
            500             505             510

His Glu Asp Pro Glu Val Lys Phe Asn Trp Tyr Val Asp Gly Val Glu
        515             520             525

Val His Asn Ala Lys Thr Lys Pro Arg Glu Glu Gln Tyr Asn Ser Thr
    530             535             540

Tyr Arg Val Val Ser Val Leu Thr Val Leu His Gln Asp Trp Leu Asn
545             550             555             560

Gly Lys Glu Tyr Lys Cys Lys Val Asn Asn Lys Ala Leu Pro Ala Pro
                565             570             575

Ile Glu Lys Thr Ile Ser Lys Ala Lys Gly Gln Pro Arg Glu Pro Glu
            580             585             590

Val Ala Thr Phe Pro Pro Ser Arg Asp Glu Leu Thr Lys Asn Gln Val
            595             600             605

Thr Leu Val Cys Leu Val Thr Gly Phe Tyr Pro Ser Asp Ile Ala Val
        610             615             620

Glu Trp Glu Ser Asn Gly Gln Pro Glu Asn Asn Tyr Lys Thr Asp Pro
625             630             635             640

Pro Leu Leu Glu Ser Gln Gly Ser Phe Ala Leu Ser Ser Arg Leu Arg
                645             650             655

Val Asp Lys Ser Arg Trp Gln Gln Gly Asn Val Phe Ser Cys Ser Val
            660             665             670

Met His Glu Ala Leu His Asn His Tyr Thr Gln Lys Ser Leu Ser Leu
            675             680             685

Ser Pro Gly
        690

<210> SEQ ID NO 294
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: >SEQ ID NO: 294 - human CD38 isoform P28907-2

<400> SEQUENCE: 294

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30
```

```
Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
 50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
             100                 105                 110

Gly Thr Gln Thr Val Pro Cys Asn Lys Lys
             115                 120

<210> SEQ ID NO 295
<211> LENGTH: 300
<212> TYPE: PRT
<213> ORGANISM: Homo sapiens
<220> FEATURE:
<221> NAME/KEY: MISC_FEATURE
<222> LOCATION: (1)..(300)
<223> OTHER INFORMATION: >SEQ ID NO: 295 - human CD38 isoform P28907-1

<400> SEQUENCE: 295

Met Ala Asn Cys Glu Phe Ser Pro Val Ser Gly Asp Lys Pro Cys Cys
 1               5                  10                  15

Arg Leu Ser Arg Arg Ala Gln Leu Cys Leu Gly Val Ser Ile Leu Val
                 20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
 50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
             100                 105                 110

Gly Thr Gln Thr Val Pro Cys Asn Lys Ile Leu Leu Trp Ser Arg Ile
             115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255
```

```
Pro Thr Ile Lys Glu Leu Glu Ser Ile Ile Ser Lys Arg Asn Ile Gln
        260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
        290                 295                 300

<210> SEQ ID NO 296
<211> LENGTH: 300
<212> TYPE: PRT
<213> ORGANISM: Homo sapiens
<220> FEATURE:
<221> NAME/KEY: MISC_FEATURE
<222> LOCATION: (1)..(300)
<223> OTHER INFORMATION: >SEQ ID NO: 296- human CD38 isoform P28907-E

<400> SEQUENCE: 296

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65              70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300
```

<210> SEQ ID NO 297
<211> LENGTH: 4
<212> TYPE: PRT
<213> ORGANISM: Artificial Sequence
<220> FEATURE:
<223> OTHER INFORMATION: >SEQ ID NO: 297- 4G T linker

<400> SEQUENCE: 297

Gly Gly Gly Thr
1

<210> SEQ ID NO 298
<211> LENGTH: 15
<212> TYPE: PRT
<213> ORGANISM: Artificial Sequence
<220> FEATURE:
<223> OTHER INFORMATION: >SEQ ID NO: 298- 4GS linker

<400> SEQUENCE: 298

Gly Gly Gly Gly Ser Gly Gly Gly Ser Gly Gly Gly Gly Ser
1               5                   10                  15

<210> SEQ ID NO 299
<211> LENGTH: 226
<212> TYPE: PRT
<213> ORGANISM: Artificial Sequence
<220> FEATURE:
<223> OTHER INFORMATION: FAB Anti-CD47-H2 with G65S mutation

<400> SEQUENCE: 299

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Ser Arg Asn
            20                  25                  30

Thr Met His Trp Val Arg Gln Ala Pro Gly Lys Gly Leu Glu Trp Val
        35                  40                  45

Ser Val Ile Tyr Gln Ser Gly Val Thr Arg Tyr Ala Asp Ser Val Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Gly Val Ala Gly Pro Gly Tyr Ala Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 300
<211> LENGTH: 323
<212> TYPE: PRT
<213> ORGANISM: Artificial Sequence
<220> FEATURE:
<223> OTHER INFORMATION: Human CD47 Isoform OA3-323

<400> SEQUENCE: 300

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 301
<211> LENGTH: 292
<212> TYPE: PRT
<213> ORGANISM: Artificial Sequence
<220> FEATURE:

<223> OTHER INFORMATION: Human CD47 Isoform OA3-293

<400> SEQUENCE: 301

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val
    290

<210> SEQ ID NO 302
<211> LENGTH: 305
<212> TYPE: PRT
<213> ORGANISM: Artificial Sequence
<220> FEATURE:
<223> OTHER INFORMATION: Human CD47Isoform OA3-305

<400> SEQUENCE: 302

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
                35                  40                  45

-continued

```
Gln Asn Thr Thr Glu Val Tyr Val Lys Trp Lys Phe Lys Gly Arg Asp
     50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305

<210> SEQ ID NO 303
<211> LENGTH: 311
<212> TYPE: PRT
<213> ORGANISM: Artificial Sequence
<220> FEATURE:
<223> OTHER INFORMATION: Human CD47 Isoform OA3-312

<400> SEQUENCE: 303

Met Trp Pro Leu Val Ala Ala Leu Leu Leu Gly Ser Ala Cys Cys Gly
 1               5                  10                  15

Ser Ala Gln Leu Leu Phe Asn Lys Thr Lys Ser Val Glu Phe Thr Phe
             20                  25                  30

Cys Asn Asp Thr Val Val Ile Pro Cys Phe Val Thr Asn Met Glu Ala
         35                  40                  45

Gln Asn Thr Thr Glu Val Tyr Val Lys Trp Lys Phe Lys Gly Arg Asp
     50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95
```

-continued

```
Ser Leu Lys Met Asp Lys Ser Asp Ala Val Ser His Thr Gly Asn Tyr
            100             105             110

Thr Cys Glu Val Thr Glu Leu Thr Arg Glu Gly Glu Thr Ile Ile Glu
            115             120             125

Leu Lys Tyr Arg Val Val Ser Trp Phe Ser Pro Asn Glu Asn Ile Leu
    130             135             140

Ile Val Ile Phe Pro Ile Phe Ala Ile Leu Leu Phe Trp Gly Gln Phe
145             150             155             160

Gly Ile Lys Thr Leu Lys Tyr Arg Ser Gly Gly Met Asp Glu Lys Thr
                165             170             175

Ile Ala Leu Leu Val Ala Gly Leu Val Ile Thr Val Ile Val Ile Val
            180             185             190

Gly Ala Ile Leu Phe Val Pro Gly Glu Tyr Ser Leu Lys Asn Ala Thr
            195             200             205

Gly Leu Gly Leu Ile Val Thr Ser Thr Gly Ile Leu Ile Leu Leu His
    210             215             220

Tyr Tyr Val Phe Ser Thr Ala Ile Gly Leu Thr Ser Phe Val Ile Ala
225             230             235             240

Ile Leu Val Ile Gln Val Ile Ala Tyr Ile Leu Ala Val Val Gly Leu
                245             250             255

Ser Leu Cys Ile Ala Ala Cys Ile Pro Met His Gly Pro Leu Leu Ile
            260             265             270

Ser Gly Leu Ser Ile Leu Ala Leu Ala Gln Leu Leu Gly Leu Val Tyr
    275             280             285

Met Lys Phe Val Ala Ser Asn Gln Lys Thr Ile Gln Pro Pro Arg Lys
    290             295             300

Ala Val Glu Glu Pro Leu Asn
305             310
```